US012599490B2

(12) United States Patent
Sirhan et al.

(10) Patent No.: US 12,599,490 B2
(45) Date of Patent: Apr. 14, 2026

(54) UNCAGING STENT

(71) Applicant: Elixir Medical Corporation, Milpitas, CA (US)

(72) Inventors: Motasim Sirhan, Los Altos, CA (US); John Yan, Los Gatos, CA (US); Vinayak Bhat, Cupertino, CA (US); Joseph Paraschac, Campbell, CA (US); Brett Cryer, Fremont, CA (US); Benjamyn Serna, Gilroy, CA (US)

(73) Assignee: Elixir Medical Corporation, Milpitas, CA (US)

( * ) Notice: Subject to any disclaimer, the term of this patent is extended or adjusted under 35 U.S.C. 154(b) by 0 days.

(21) Appl. No.: 18/178,377

(22) Filed: Mar. 3, 2023

(65) Prior Publication Data

US 2023/0201014 A1     Jun. 29, 2023

Related U.S. Application Data

(63) Continuation of application No. 16/786,736, filed on Feb. 10, 2020, now Pat. No. 11,622,872, which is a
(Continued)

(51) Int. Cl.
*A61F 2/89*          (2013.01)
*A61F 2/90*          (2013.01)
(Continued)

(52) U.S. Cl.
CPC ................. *A61F 2/89* (2013.01); *A61F 2/90* (2013.01); *A61F 2/915* (2013.01); *A61F 2002/075* (2013.01); *A61F 2/2442* (2013.01);

*A61F 2002/825* (2013.01); *A61F 2002/91558* (2013.01); *A61F 2002/91566* (2013.01);
(Continued)

(58) Field of Classification Search
CPC .... A61F 2/89; A61F 2/90; A61F 2/915; A61F 2/2442
See application file for complete search history.

(56) References Cited

U.S. PATENT DOCUMENTS 3,867,190 A     2/1975 Schmitt et al.
5,298,276 A     3/1994 Jayaraman et al.
(Continued)

FOREIGN PATENT DOCUMENTS

CN     1328853 A     1/2002
CN     1569270 A     1/2005
(Continued)

OTHER PUBLICATIONS

Co-pending U.S. Appl. No. 18/629,632, inventors Sirhan; Motasim et al., filed Apr. 8, 2024.
(Continued)

*Primary Examiner* — Alvin J Stewart
(74) *Attorney, Agent, or Firm* — Wilson Sonsini Goodrich & Rosati

(57) ABSTRACT

A stent (scaffold) or other luminal prosthesis comprising circumferential structural elements which provide high strength after deployment and allows for scaffold to uncage, and/or allow for scaffold or luminal expansion thereafter. The circumferential scaffold is typically formed from non-degradable material and will be modified to expand and/or uncage after deployment.

27 Claims, 41 Drawing Sheets

Related U.S. Application Data continuation of application No. PCT/US2018/046561, filed on Aug. 13, 2018, which is a continuation-in-part of application No. 16/039,194, filed on Jul. 18, 2018, now Pat. No. 10,271,976, which is a continuation of application No. 15/921,508, filed on Mar. 14, 2018, now Pat. No. 10,076,431, which is a continuation of application No. 15/605,601, filed on May 25, 2017, now Pat. No. 9,943,426.

(60) Provisional application No. 62/622,741, filed on Jan. 26, 2018, provisional application No. 62/577,624, filed on Oct. 26, 2017, provisional application No. 62/558,273, filed on Sep. 13, 2017, provisional application No. 62/544,682, filed on Aug. 11, 2017.

(51) Int. Cl.

| | |
|---|---|
| *A61F 2/915* | (2013.01) |
| *A61F 2/07* | (2013.01) |
| *A61F 2/24* | (2006.01) |
| *A61F 2/82* | (2013.01) |

(52) U.S. Cl.
CPC .............. *A61F 2002/91575* (2013.01); *A61F 2002/91591* (2013.01); *A61F 2210/0004* (2013.01); *A61F 2210/0014* (2013.01); *A61F 2210/0076* (2013.01); *A61F 2220/0033* (2013.01); *A61F 2220/0091* (2013.01); *A61F 2230/0006* (2013.01); *A61F 2230/0008* (2013.01); *A61F 2230/001* (2013.01); *A61F 2230/0069* (2013.01); *A61F 2250/0031* (2013.01); *A61F 2250/0036* (2013.01); *A61F 2250/0048* (2013.01); *A61F 2250/0067* (2013.01); *A61F 2250/0071* (2013.01)

(56) References Cited

U.S. PATENT DOCUMENTS

| | | | |
|---|---|---|---|
| 5,306,286 A | 4/1994 | Stack et al. |
| 5,383,926 A | 1/1995 | Lock et al. |
| 5,441,483 A | 8/1995 | Avitall et al. |
| 5,441,515 A | 8/1995 | Khosravi et al. |
| 5,447,724 A | 9/1995 | Helmus et al. |
| 5,449,384 A | 9/1995 | Johnson et al. |
| 5,500,013 A | 3/1996 | Buscemi et al. |
| 5,556,413 A | 9/1996 | Lam |
| 5,607,466 A | 3/1997 | Imbert et al. |
| 5,670,161 A | 9/1997 | Healy et al. |
| 5,674,286 A | 10/1997 | D'Alessio et al. |
| 5,695,516 A | 12/1997 | Fischell et al. |
| 5,741,293 A | 4/1998 | Wijay |
| 5,741,329 A | 4/1998 | Agrawal et al. |
| 5,766,237 A | 6/1998 | Cragg |
| 5,797,951 A | 8/1998 | Mueller |
| 5,824,053 A | 10/1998 | Khosravi et al. |
| 5,824,059 A | 10/1998 | Wijay |
| 5,843,172 A | 12/1998 | Yan |
| 5,902,333 A | 5/1999 | Roberts et al. |
| 5,922,020 A | 7/1999 | Klein et al. |
| 5,935,119 A | 8/1999 | Guy et al. |
| 5,957,975 A | 9/1999 | Lafont et al. |
| 5,961,545 A | 10/1999 | Lentz et al. |
| 5,964,798 A | 10/1999 | Imran et al. |
| 5,980,564 A | 11/1999 | Stinson et al. |
| 6,022,371 A | 2/2000 | Killion |
| 6,027,526 A | 2/2000 | Limon et al. |
| 6,039,755 A | 3/2000 | Edwin et al. |
| 6,120,847 A | 9/2000 | Yang et al. |
| 6,190,405 B1 | 2/2001 | Culombo et al. |
| 6,224,803 B1 | 5/2001 | Tiernan et al. |
| 6,245,103 B1 | 6/2001 | Stinson et al. |
| 6,251,134 B1 | 6/2001 | Alt et al. |
| 6,258,117 B1 | 7/2001 | Camrud et al. |
| 6,322,847 B1 | 11/2001 | Zhong et al. |
| 6,323,256 B1 | 11/2001 | Delmain et al. |
| 6,325,825 B1 | 12/2001 | Kula et al. |
| 6,395,326 B1 | 5/2002 | Castro et al. |
| 6,409,754 B1 | 6/2002 | Smith et al. |
| 6,485,510 B1 | 11/2002 | Camrud et al. |
| 6,537,312 B2 | 3/2003 | Datta et al. |
| 6,540,777 B2 | 4/2003 | Stenzel |
| 6,547,814 B2 | 4/2003 | Edwin et al. |
| 6,565,599 B1 | 5/2003 | Hong et al. |
| 6,585,755 B2 | 7/2003 | Jackson et al. |
| 6,599,314 B2 | 7/2003 | Mathis |
| 6,602,282 B1 | 8/2003 | Yan |
| 6,626,939 B1 | 9/2003 | Burnside et al. |
| 6,652,582 B1 | 11/2003 | Stinson |
| 6,719,934 B2 | 4/2004 | Stinson |
| 6,726,701 B2 | 4/2004 | Gilson et al. |
| 6,761,784 B1 | 7/2004 | Hage et al. |
| 6,773,455 B2 | 8/2004 | Allen et al. |
| 6,774,278 B1 | 8/2004 | Ragheb et al. |
| 6,776,796 B2 | 8/2004 | Falotico et al. |
| 6,805,898 B1 | 10/2004 | Wu et al. |
| 6,863,757 B1 | 3/2005 | Gonzalez et al. |
| 6,896,695 B2 | 5/2005 | Mueller et al. |
| 6,920,677 B2 | 7/2005 | Dolan et al. |
| 6,945,995 B2 | 9/2005 | Nicholas |
| 6,964,677 B2 | 11/2005 | Osypka |
| 6,997,948 B2 | 2/2006 | Stinson |
| 7,001,421 B2 | 2/2006 | Cheng et al. |
| 7,011,678 B2 | 3/2006 | Tenerz et al. |
| 7,108,714 B1 | 9/2006 | Becker |
| 7,108,716 B2 | 9/2006 | Burnside et al. |
| 7,128,023 B2 | 10/2006 | Otsuji et al. |
| 7,141,063 B2 | 11/2006 | White et al. |
| 7,144,420 B2 | 12/2006 | Lenz |
| 7,153,322 B2 | 12/2006 | Alt et al. |
| 7,169,173 B2 | 1/2007 | Hossainy et al. |
| 7,175,654 B2 | 2/2007 | Bonsignore et al. |
| 7,235,093 B2 | 6/2007 | Gregorich |
| 7,258,697 B1 | 8/2007 | Cox et al. |
| 7,279,005 B2 | 10/2007 | Stinson |
| 7,285,304 B1 | 10/2007 | Hossainy et al. |
| 7,291,166 B2 | 11/2007 | Cheng et al. |
| 7,329,366 B1 | 2/2008 | Gale et al. |
| 7,354,450 B2 | 4/2008 | Bicek et al. |
| 7,377,939 B2 | 5/2008 | Williams et al. |
| 7,390,333 B2 | 6/2008 | Dutta et al. |
| 7,402,168 B2 | 7/2008 | Acosta et al. |
| 7,455,687 B2 | 11/2008 | Saunders et al. |
| 7,550,005 B2 | 6/2009 | Bates et al. |
| 7,563,277 B2 | 7/2009 | Case et al. |
| 7,572,287 B2 | 8/2009 | Stinson |
| 7,594,928 B2 | 9/2009 | Headley et al. |
| 7,618,448 B2 | 11/2009 | Schmitz et al. |
| 7,622,070 B2 | 11/2009 | Atladottir et al. |
| 7,645,409 B2 | 1/2010 | Saunders et al. |
| 7,666,342 B2 | 2/2010 | Limon et al. |
| 7,722,662 B2 | 5/2010 | Steinke et al. |
| 7,731,890 B2 | 6/2010 | Gale et al. |
| 7,758,636 B2 | 7/2010 | Shanley et al. |
| 7,763,065 B2 | 7/2010 | Schmid et al. |
| 7,789,906 B2 | 9/2010 | Blank et al. |
| 7,824,601 B1 | 11/2010 | Stankus et al. |
| 7,829,008 B2 | 11/2010 | Gueriguian et al. |
| 7,829,273 B2 | 11/2010 | Roof et al. |
| 7,833,260 B2 | 11/2010 | Cottone et al. |
| 7,875,233 B2 | 1/2011 | Huang et al. |
| 7,892,273 B2 | 2/2011 | George et al. |
| 7,947,071 B2 | 5/2011 | Schmid et al. |
| 7,964,136 B2 | 6/2011 | Sabaria |
| 7,967,998 B2 | 6/2011 | Gale et al. |
| 7,971,333 B2 | 7/2011 | Gale et al. |
| 8,002,818 B2 | 8/2011 | Bregulla |
| 8,025,694 B2 | 9/2011 | Strauss et al. |
| 8,043,553 B1 | 10/2011 | Durcan et al. |
| 8,052,743 B2 | 11/2011 | Weber et al. |
| 8,057,534 B2 | 11/2011 | Boismier et al. |
| 8,062,465 B1 | 11/2011 | Huang et al. |

(56) References Cited

U.S. PATENT DOCUMENTS

| | | | |
|---|---|---|---|
| 8,070,794 B2 | 12/2011 | Issenmann |
| 8,128,679 B2 | 3/2012 | Casey |
| 8,157,855 B2 | 4/2012 | Eidenschink et al. |
| 8,172,897 B2 | 5/2012 | Gale et al. |
| 8,173,062 B1 | 5/2012 | Durcan et al. |
| 8,182,890 B2 | 5/2012 | Zheng et al. |
| 8,202,313 B2 | 6/2012 | Shanley et al. |
| 8,241,554 B1 | 8/2012 | Abbate et al. |
| 8,268,228 B2 | 9/2012 | Huang et al. |
| 8,292,944 B2 | 10/2012 | Schmid et al. |
| 8,323,760 B2 | 12/2012 | Zheng et al. |
| 8,414,638 B2 | 4/2013 | Pacetti et al. |
| 8,425,587 B2 | 4/2013 | Trollsas et al. |
| 8,435,281 B2 | 5/2013 | Weber |
| 8,460,364 B2 | 6/2013 | Cottone et al. |
| 8,501,079 B2 | 8/2013 | Glauser et al. |
| 8,545,546 B2 | 10/2013 | Wang et al. |
| 8,562,666 B2 | 10/2013 | Bonsignore |
| 8,562,670 B2 | 10/2013 | Pacetti et al. |
| 8,568,469 B1 | 10/2013 | Gale et al. |
| 8,636,792 B2 | 1/2014 | Zheng et al. |
| 8,636,793 B2 | 1/2014 | Hoerstrup et al. |
| 8,652,192 B2 | 2/2014 | St. Germain et al. |
| 8,652,198 B2 | 2/2014 | Andreas et al. |
| 8,663,311 B2 | 3/2014 | Besselink et al. |
| 8,709,071 B1 | 4/2014 | Huang et al. |
| 8,740,839 B2 | 6/2014 | Eaton et al. |
| 8,778,256 B1 | 7/2014 | Huang et al. |
| 8,795,030 B2 | 8/2014 | Huang et al. |
| 8,801,770 B2 | 8/2014 | Takayuki et al. |
| 8,814,930 B2 | 8/2014 | Zheng et al. |
| 8,834,556 B2 | 9/2014 | Papp et al. |
| 8,840,660 B2 | 9/2014 | Weber et al. |
| 8,852,263 B2 | 10/2014 | Wang et al. |
| 8,870,940 B2 | 10/2014 | Venturelli et al. |
| 8,872,062 B2 | 10/2014 | Chen et al. |
| 8,900,292 B2 | 12/2014 | Gregorich et al. |
| 8,956,403 B2 | 2/2015 | Gregorich et al. |
| 8,961,585 B2 | 2/2015 | Ma et al. |
| 9,004,182 B2 | 4/2015 | O'Connor et al. |
| 9,005,276 B2 | 4/2015 | Fox et al. |
| 9,056,157 B2 | 6/2015 | Cho et al. |
| 9,119,905 B2 | 9/2015 | Zheng et al. |
| 9,149,378 B2 | 10/2015 | Morris et al. |
| 9,180,005 B1 | 11/2015 | Lashinski et al. |
| 9,192,471 B2 | 11/2015 | Bolling |
| 9,192,494 B2 | 11/2015 | Limon et al. |
| 9,259,339 B1 | 2/2016 | Yan et al. |
| 9,265,866 B2 | 2/2016 | Kramer-Brown et al. |
| 9,295,570 B2 | 3/2016 | Schwager et al. |
| 9,314,354 B2 | 4/2016 | Morris et al. |
| 9,375,329 B2 | 6/2016 | Takayuki et al. |
| 9,433,519 B2 | 9/2016 | Osypka et al. |
| 9,439,788 B2 | 9/2016 | Gale et al. |
| 9,445,924 B2 | 9/2016 | Wolf et al. |
| 9,480,588 B2 | 11/2016 | Yan et al. |
| 9,566,371 B2 | 2/2017 | Zheng et al. |
| 9,730,819 B2 | 8/2017 | Yan et al. |
| 9,943,426 B2 | 4/2018 | Sirhan et al. |
| 10,076,431 B2 | 9/2018 | Sirhan et al. |
| 10,271,976 B2 | 4/2019 | Sirhan et al. |
| 10,383,750 B1 | 8/2019 | Sirhan et al. |
| 10,786,374 B2 | 9/2020 | Sirhan et al. |
| 10,842,654 B2 | 11/2020 | Kim et al. |
| 10,905,573 B2 | 2/2021 | Neuss et al. |
| 10,918,505 B2 | 2/2021 | Sirhan et al. |
| 11,622,872 B2 | 4/2023 | Sirhan et al. |
| 12,011,378 B2 | 6/2024 | Sirhan et al. |
| 2001/0016729 A1 | 8/2001 | Divino et al. |
| 2001/0016769 A1 | 8/2001 | Hojeibane et al. |
| 2001/0047199 A1 | 11/2001 | Wijay |
| 2001/0053929 A1 | 12/2001 | Vonesh et al. |
| 2002/0007209 A1 | 1/2002 | Scheerder et al. |
| 2002/0026230 A1 | 2/2002 | Moll et al. |
| 2002/0038146 A1 | 3/2002 | Harry et al. |
| 2002/0107563 A1 | 8/2002 | Shanley |
| 2002/0120323 A1 | 8/2002 | Thompson et al. |
| 2002/0128706 A1 | 9/2002 | Osypka |
| 2002/0161430 A1 | 10/2002 | Jang et al. |
| 2002/0165597 A1 | 11/2002 | Clerc et al. |
| 2002/0183581 A1 | 12/2002 | Yoe et al. |
| 2002/0188347 A1 | 12/2002 | Mathis |
| 2002/0193336 A1 | 12/2002 | Elkins et al. |
| 2003/0033007 A1 | 2/2003 | Sirhan et al. |
| 2003/0050687 A1 | 3/2003 | Schwade et al. |
| 2003/0050692 A1 | 3/2003 | Sirhan et al. |
| 2003/0064097 A1 | 4/2003 | Patel et al. |
| 2003/0088307 A1 | 5/2003 | Shulze et al. |
| 2003/0093143 A1 | 5/2003 | Zhao et al. |
| 2003/0105513 A1 | 6/2003 | Moriuchi et al. |
| 2003/0135266 A1 | 7/2003 | Chew et al. |
| 2003/0139798 A1 | 7/2003 | Brown et al. |
| 2003/0144726 A1 | 7/2003 | Majercak et al. |
| 2003/0153971 A1 | 8/2003 | Chandrasekaran |
| 2003/0195609 A1 | 10/2003 | Berenstein et al. |
| 2003/0199993 A1 | 10/2003 | Gellman et al. |
| 2003/0236320 A1 | 12/2003 | Martin et al. |
| 2004/0006382 A1 | 1/2004 | Sohier et al. |
| 2004/0073290 A1 | 4/2004 | Chouinard et al. |
| 2004/0147999 A1 | 7/2004 | Udipi et al. |
| 2004/0167610 A1 | 8/2004 | Fleming |
| 2004/0186551 A1 | 9/2004 | Kao et al. |
| 2004/0199242 A1 | 10/2004 | Hong et al. |
| 2004/0260389 A1 | 12/2004 | Case et al. |
| 2005/0031704 A1 | 2/2005 | Ahn et al. |
| 2005/0033399 A1 | 2/2005 | Richter |
| 2005/0060020 A1 | 3/2005 | Jenson et al. |
| 2005/0070991 A1 | 3/2005 | Pienknagura et al. |
| 2005/0070996 A1 | 3/2005 | Dinh et al. |
| 2005/0075625 A1 | 4/2005 | Dao et al. |
| 2005/0075716 A1 | 4/2005 | Yan et al. |
| 2005/0123588 A1 | 6/2005 | Zhu et al. |
| 2005/0171595 A1 | 8/2005 | Feldman et al. |
| 2005/0182479 A1 | 8/2005 | Bonsignore et al. |
| 2005/0187615 A1 | 8/2005 | Williams et al. |
| 2005/0203607 A1 | 9/2005 | Scherrible |
| 2005/0216074 A1 | 9/2005 | Sahatjian et al. |
| 2005/0222671 A1 | 10/2005 | Schaeffer et al. |
| 2005/0228486 A1 | 10/2005 | Case et al. |
| 2005/0232964 A1 | 10/2005 | Fennimore et al. |
| 2005/0283229 A1 | 12/2005 | Dugan et al. |
| 2006/0025852 A1 | 2/2006 | Armstrong et al. |
| 2006/0030932 A1 | 2/2006 | Kantor et al. |
| 2006/0069424 A1 | 3/2006 | Acosta et al. |
| 2006/0100695 A1 | 5/2006 | Peacock, III et al. |
| 2006/0111485 A1 | 5/2006 | Laghi et al. |
| 2006/0122694 A1 | 6/2006 | Stinson et al. |
| 2006/0136048 A1 | 6/2006 | Pacetti et al. |
| 2006/0147538 A1 | 7/2006 | Craig et al. |
| 2006/0173527 A1 | 8/2006 | Scherrible |
| 2006/0193892 A1 | 8/2006 | Furst et al. |
| 2006/0229711 A1 | 10/2006 | Yan et al. |
| 2006/0251618 A1 | 11/2006 | Dennis et al. |
| 2006/0271170 A1 | 11/2006 | Gale et al. |
| 2006/0287710 A1 | 12/2006 | Lendlein et al. |
| 2007/0023974 A1 | 2/2007 | Wu |
| 2007/0100431 A1 | 5/2007 | Bonsignore et al. |
| 2007/0129789 A1 | 6/2007 | Cottone, Jr. et al. |
| 2007/0135904 A1 | 6/2007 | Eidenschink et al. |
| 2007/0213810 A1 | 9/2007 | Newhauser et al. |
| 2007/0219613 A1 | 9/2007 | Kao et al. |
| 2007/0231365 A1 | 10/2007 | Wang et al. |
| 2007/0239264 A1 | 10/2007 | Fliedner |
| 2007/0253999 A1 | 11/2007 | Huang et al. |
| 2007/0259099 A1 | 11/2007 | Van Sciver |
| 2007/0271763 A1 | 11/2007 | Huang et al. |
| 2007/0278250 A1 | 12/2007 | Wang et al. |
| 2007/0281117 A1 | 12/2007 | Kaplan et al. |
| 2007/0282426 A1 | 12/2007 | Wang et al. |
| 2007/0282434 A1 | 12/2007 | Wang et al. |
| 2007/0290412 A1 | 12/2007 | Capek et al. |
| 2007/0299505 A1 | 12/2007 | Gregorich et al. |
| 2008/0051866 A1 | 2/2008 | Chen et al. |
| 2008/0081063 A1 | 4/2008 | Wang et al. |

(56)  References Cited

U.S. PATENT DOCUMENTS

| | | |
|---|---|---|
| 2008/0097571 A1 | 4/2008 | Denison et al. |
| 2008/0097580 A1 | 4/2008 | Dave et al. |
| 2008/0103584 A1 | 5/2008 | Su et al. |
| 2008/0147165 A1 | 6/2008 | Hossainy et al. |
| 2008/0177373 A1 | 7/2008 | Huang et al. |
| 2008/0183275 A1 | 7/2008 | Schmid et al. |
| 2008/0243243 A1 | 10/2008 | Williams et al. |
| 2008/0249608 A1 | 10/2008 | Dave et al. |
| 2008/0262628 A1 | 10/2008 | Laitenberger et al. |
| 2008/0306579 A1 | 12/2008 | Dolan et al. |
| 2009/0030507 A1 | 1/2009 | Klocke et al. |
| 2009/0076584 A1 | 3/2009 | Mao et al. |
| 2009/0082848 A1 | 3/2009 | Mori et al. |
| 2009/0095715 A1 | 4/2009 | Sabaria et al. |
| 2009/0096137 A1 | 4/2009 | Williams et al. |
| 2009/0099639 A1 | 4/2009 | Sabaria et al. |
| 2009/0099644 A1 | 4/2009 | Biadillah et al. |
| 2009/0105800 A1 | 4/2009 | Sabaria et al. |
| 2009/0208555 A1 | 8/2009 | Kuttler et al. |
| 2009/0216309 A1 | 8/2009 | Granada et al. |
| 2009/0228094 A1 | 9/2009 | Yan et al. |
| 2009/0234429 A1 | 9/2009 | Lau |
| 2009/0234432 A1 | 9/2009 | Pacetti et al. |
| 2009/0264979 A1 | 10/2009 | Kao et al. |
| 2010/0010622 A1 | 1/2010 | Lowe et al. |
| 2010/0036478 A1 | 2/2010 | Wang et al. |
| 2010/0038822 A1 | 2/2010 | Wang et al. |
| 2010/0049300 A1 | 2/2010 | Harder et al. |
| 2010/0094405 A1 | 4/2010 | Cottone |
| 2010/0198331 A1 | 8/2010 | Rapoza et al. |
| 2010/0217370 A1 | 8/2010 | Scheuermann et al. |
| 2010/0234936 A1 | 9/2010 | Schlun |
| 2010/0244329 A1 | 9/2010 | Hossainy et al. |
| 2010/0252965 A1 | 10/2010 | Wang et al. |
| 2010/0256741 A1 | 10/2010 | Hansen |
| 2010/0256744 A1 | 10/2010 | Laborde et al. |
| 2010/0262224 A1 | 10/2010 | Kleiner et al. |
| 2010/0292773 A1 | 11/2010 | Schmid et al. |
| 2010/0324657 A1 | 12/2010 | Bogert et al. |
| 2011/0022163 A1 | 1/2011 | Wang et al. |
| 2011/0054591 A1 | 3/2011 | Sahatjian et al. |
| 2011/0130822 A1 | 6/2011 | Cottone |
| 2011/0152997 A1 | 6/2011 | Kelly et al. |
| 2011/0160757 A1 | 6/2011 | Ferrera et al. |
| 2011/0190861 A1 | 8/2011 | Pericevic et al. |
| 2011/0215505 A1 | 9/2011 | Kleiner et al. |
| 2011/0224777 A1 | 9/2011 | Von Oepen et al. |
| 2011/0238158 A1 | 9/2011 | Heringes et al. |
| 2011/0238162 A1 | 9/2011 | Busold et al. |
| 2011/0260352 A1 | 10/2011 | Tang et al. |
| 2011/0260358 A1 | 10/2011 | Wang et al. |
| 2012/0071962 A1 | 3/2012 | Huang et al. |
| 2012/0187606 A1 | 7/2012 | Zheng et al. |
| 2012/0191177 A1 | 7/2012 | Costa et al. |
| 2012/0290070 A1 | 11/2012 | Wang et al. |
| 2012/0290071 A1 | 11/2012 | Wang et al. |
| 2013/0046373 A1 | 2/2013 | Cartledge et al. |
| 2013/0084322 A1 | 4/2013 | Wu et al. |
| 2013/0085564 A1 | 4/2013 | Papp et al. |
| 2013/0150943 A1 | 6/2013 | Zheng et al. |
| 2013/0178926 A1 | 7/2013 | Denison et al. |
| 2013/0190676 A1 | 7/2013 | Dickinson et al. |
| 2013/0211499 A1 | 8/2013 | Bonsignore et al. |
| 2014/0004312 A1 | 1/2014 | Foreman et al. |
| 2014/0012362 A1 | 1/2014 | Gale et al. |
| 2014/0018903 A1 | 1/2014 | Eli et al. |
| 2014/0025161 A1 | 1/2014 | Stankus et al. |
| 2014/0081381 A1 | 3/2014 | Kim et al. |
| 2014/0114398 A1 | 4/2014 | Hossainy et al. |
| 2014/0121294 A1 | 5/2014 | Huang et al. |
| 2014/0188243 A1 | 7/2014 | Zheng et al. |
| 2014/0252683 A1 | 9/2014 | Huang et al. |
| 2014/0277373 A1 | 9/2014 | Huang et al. |
| 2014/0296961 A1 | 10/2014 | Blaser et al. |
| 2014/0350659 A1 | 11/2014 | Zheng et al. |
| 2014/0364935 A1 | 12/2014 | Eli et al. |
| 2015/0073536 A1 | 3/2015 | Rapoza et al. |
| 2015/0374521 A1 | 12/2015 | Zheng et al. |
| 2016/0067068 A1 | 3/2016 | Denison et al. |
| 2016/0166414 A1 | 6/2016 | Yan et al. |
| 2016/0206450 A1 | 7/2016 | Mitsudo et al. |
| 2016/0213499 A1 | 7/2016 | Zheng et al. |
| 2016/0278952 A1 | 9/2016 | Ngo et al. |
| 2016/0278953 A1 | 9/2016 | Zheng et al. |
| 2017/0128245 A1 | 5/2017 | Minami |
| 2017/0156899 A1 | 6/2017 | Zheng et al. |
| 2017/0216067 A1 | 8/2017 | LeBlanc et al. |
| 2017/0266024 A1 | 9/2017 | Kumazawa et al. |
| 2017/0348121 A1 | 12/2017 | Yamamoto |
| 2018/0078392 A1 | 3/2018 | Kito |
| 2020/0253757 A1 | 8/2020 | Sirhan et al. |
| 2020/0405513 A1 | 12/2020 | Sirhan et al. |
| 2022/0361874 A1 | 11/2022 | Shelton, IV et al. |
| 2023/0145447 A1 | 5/2023 | Bhat et al. |

FOREIGN PATENT DOCUMENTS

| | | |
|---|---|---|
| CN | 101868195 A | 10/2010 |
| CN | 103249380 A | 8/2013 |
| CN | 103764076 A | 4/2014 |
| DE | 10103000 A1 | 8/2002 |
| DE | 10105160 A1 | 8/2002 |
| DE | 10103000 B4 | 8/2007 |
| DE | 102004027108 B4 | 1/2009 |
| DE | 202009012562 U1 | 12/2009 |
| DE | 202011003403 U1 | 5/2011 |
| DE | 202012002340 U1 | 4/2012 |
| EP | 1563806 A1 | 8/2005 |
| EP | 2229919 A2 | 9/2010 |
| EP | 2229919 B1 | 1/2015 |
| EP | 3263073 A1 | 1/2018 |
| EP | 3664752 A1 | 6/2020 |
| JP | H11512626 A | 11/1999 |
| JP | 2000202032 A | 7/2000 |
| JP | 2003500101 A | 1/2003 |
| JP | 2003047662 A | 2/2003 |
| JP | 2004149692 A | 5/2004 |
| JP | 2005298617 A | 10/2005 |
| JP | 2005334632 A | 12/2005 |
| JP | 2006192111 A | 7/2006 |
| JP | 2006223860 A | 8/2006 |
| JP | 2009082245 A | 4/2009 |
| JP | 2009530060 A | 8/2009 |
| JP | 2011502195 A | 1/2011 |
| JP | 2018516735 A | 6/2018 |
| WO | WO-9204393 A1 | 3/1992 |
| WO | WO-0195834 A1 | 12/2001 |
| WO | WO-02091956 A1 | 11/2002 |
| WO | WO-03034940 A2 | 5/2003 |
| WO | WO-2004052420 A2 | 6/2004 |
| WO | WO-2004080332 A2 | 9/2004 |
| WO | WO-2004110315 A1 | 12/2004 |
| WO | WO-2004110515 A1 | 12/2004 |
| WO | WO-2004080332 A3 | 4/2005 |
| WO | WO-2005067816 A1 | 7/2005 |
| WO | WO-2005096992 A1 | 10/2005 |
| WO | WO-2005115277 A2 | 12/2005 |
| WO | WO-2007013102 A1 | 2/2007 |
| WO | WO-2005115277 A3 | 5/2007 |
| WO | WO-2007126599 A2 | 11/2007 |
| WO | WO-2007146354 A2 | 12/2007 |
| WO | WO-2008002479 A2 | 1/2008 |
| WO | WO-2008002636 A2 | 1/2008 |
| WO | WO-2008005390 A1 | 1/2008 |
| WO | WO-2008008416 A1 | 1/2008 |
| WO | WO-2008011048 A2 | 1/2008 |
| WO | WO-2007146354 A3 | 2/2008 |
| WO | WO-2008016667 A2 | 2/2008 |
| WO | WO-2008016696 A2 | 2/2008 |
| WO | WO-2008016696 A3 | 3/2008 |
| WO | WO-2008033263 A2 | 3/2008 |
| WO | WO-2008002636 A3 | 4/2008 |
| WO | WO-2008051867 A2 | 5/2008 |
| WO | WO-2007126599 A3 | 7/2008 |

(56) References Cited

FOREIGN PATENT DOCUMENTS

| | | |
|---|---|---|
| WO | WO-2008089434 A2 | 7/2008 |
| WO | WO-2008051867 A3 | 8/2008 |
| WO | WO-2008098434 A1 | 8/2008 |
| WO | WO-2008002479 A3 | 9/2008 |
| WO | WO-2008016667 A3 | 11/2008 |
| WO | WO-2008137821 A1 | 11/2008 |
| WO | WO-2008011048 A3 | 3/2009 |
| WO | WO-2008033263 A3 | 4/2009 |
| WO | WO-2009041664 A1 | 4/2009 |
| WO | WO-2011025945 A1 | 3/2011 |
| WO | WO-2014045068 A1 | 3/2014 |
| WO | WO-2014091438 A2 | 6/2014 |
| WO | WO-2015045101 A1 | 4/2015 |
| WO | WO-2016136375 A1 | 9/2016 |
| WO | WO-2016193449 A1 | 12/2016 |
| WO | WO-2017200956 A1 | 11/2017 |
| WO | WO-2019033121 | 2/2019 |

OTHER PUBLICATIONS

U.S. Appl. No. 18/187,583 Notice of Allowance dated Jan. 8, 2024.
U.S. Appl. No. 18/187,583 Notice of Allowance dated May 14, 2024.
U.S. Appl. No. 18/187,583 Office Action dated May 18, 2023.
Abstracts—Oral and Poster Presentations. 21 Annual Meeting. The Society for Cardiac Angiography and Interventions. May 13-16, 1998; Le Sheraton Centre, Montreal, Quebec, Canada. pp. 106-127.
Bae, et al. Drug delivery. Fundamentals and methods of tissue engineering. From 'Frontiers in Tissue Engineering' edited by Patrick et al. Feb. 20, 1998; Ch II. 14:263-272.
Breiby, et al. Quantification of preferential orientation in conjugated polymers using X-ray diffraction. J. Polymer Science Part B: Polymer Physics. 2003; 41(20):2375-2393.
Cruz, et al. Quantitative mapping of the orientation of fibroin beta-sheets in B. mori cocoon fibers by scanning transmission X-ray microscopy. Biomacromolecules. Mar. 2006;7(3):836-43.
Donald, et al. Electron Microscopy of Banded Structures in Oriented Thermotropic Polymers. J. Materials Science. 1983; 18:1143-1150.
EP17799967.9 The Extended European Search Report dated Jan. 3, 2020.
EP18843510.1 Extended European Search Report dated Feb. 8, 2021.
EP18843510.1 Extended Search Report dated Feb. 8, 2021.
EP21150336.2 Extended Search Report dated Jul. 12, 2021.
European search report and search opinion dated Feb. 18, 2015 for EP Application No. 12804895.6.
European search report and search opinion dated Dec. 20, 2012 for Application No. 8727927.9.
Ewert, et al. Early and mid-term results with the Growth Stent—a possible concept for transcatheter treatment of aortic coarctation from infancy to adulthood by stent implantation? Catheter Cardiovasc Interv. Jan. 1, 2008;71(1):120-6.
Ewert, et al. Novel growth stent for the permanent treatment of vessel stenosis in growing children: an experimental study. Catheter Cardiovasc Interv. Aug. 2004;62(4):506-10.
Fuhrman, et al. Central nervous system. From 'Tissue Engineering: From Lab to Clinic' edited by Pallua et al. 2010; Ch12:221-244.
Hacker, et al. Synthetic polymers. From 'Principles of Regenerative Medicine 2nd ed.' Edited by Atala et al. 2011; Ch 33:587-622.
Hara. Ion-containing polymers and their biological interactions. Polyelectrolytes Science and Technology. 1993; Ch 6:321-325.
Hombreiro-Perez, et al. Non-degradable microparticles containing a hydrophilic and/or a lipophilic drug: preparation, characterization and drug release modeling. J Control Release. Mar. 26, 2003;88(3):413-28.
International search report and written opinion dated Apr. 13, 2015 for PCT/US2015/012780.
International search report and written opinion dated Aug. 1, 2008 for PCT/US2008/051479.

International search report and written opinion dated Aug. 1, 2008 for PCT/US2008/051497.
International search report and written opinion dated Aug. 7, 2017 for PCT Application No. PCT/US2017/032748.
International search report and written opinion dated Aug. 25, 2016 for PCT Application No. PCT/US2016/026821.
International search report and written opinion dated Sep. 25, 2012 for PCT/US2012/44736.
International search report and written opinion dated Oct. 7, 2014 for PCT Application No. PCT/US2014/038508.
Kucharavy, et al. Application of S-Shaped Curves. TRIZ—Future Conference 2007: Current Scientific and Industrial Reality, Nov. 2007, Frankfurt, Germany. pp. 81-88, 2007.hal-00282758.
Lamberti, et al. Real-time orientation and crystallinity measurements during the isotactic polypropylene film-casting process. J. Polymer Science Part B: Polymer Physics. 2003; 41(9):998-1008.
Lee, et al. Retardation of enzymatic degradation of microbial polyesters using surface chemistry: effect of addition of non-degradable polymers. Surface Science. 2003; 542(3):235-243.
Ma, et al. Scaffolding in Tissue Engineering. 2005; pp. 78-80.
Majoros, et al. Poly(amidoamine) dendrimer synthesis and characterization. Dendrimer-based Nanomedicine. 2008; Ch 3:35-57.
Mullins, et al. Cardiac Catheterization in Congenital Heart Disease: Pediatric and Adult. John Wiley & Sons, Apr. 15, 2008. Chapter 22 Intravascular stents—general information; p. 582.583.
Notice of allowance dated Apr. 18, 2017 for U.S. Appl. No. 14/800,536.
Notice of allowance dated May 12, 2014 for U.S. Appl. No. 13/897,302.
Notice of Allowance dated Jun. 4, 2018 for U.S. Appl. No. 15/921,508.
Notice of allowance dated Jul. 15, 2015 for U.S. Appl. No. 14/461,159.
Notice of allowance dated Sep. 8, 2016 for U.S. Appl. No. 14/697,537.
Notice of allowance dated Oct. 27, 2017 for U.S. Appl. No. 15/605,601.
Notice of allowance dated Dec. 13, 2013 for U.S. Appl. No. 13/539,770.
Notice of allowance dated Dec. 13, 2016 for U.S. Appl. No. 14/804,415.
Notice of allowance dated Dec. 23, 2015 for U.S. Appl. No. 14/682,014.
Office action dated Feb. 16, 2017 for U.S. Appl. No. 14/800,536.
Office action dated Feb. 16, 2017 for U.S. Appl. No. 15/043,331.
Office action dated Mar. 2, 2010 for U.S. Appl. No. 12/016,077.
Office action dated Mar. 10, 2016 for U.S. Appl. No. 14/611,043.
Office action dated Mar. 10, 2017 for U.S. Appl. No. 14/604,621.
Office action dated Mar. 28, 2016 for U.S. Appl. No. 14/697,537.
Office action dated Mar. 30, 2011 for U.S. Appl. No. 12/016,085.
Office action dated Apr. 1, 2011 for U.S. Appl. No. 12/016,077.
Office action dated Apr. 24, 2015 for U.S. Appl. No. 14/461,159.
Office action dated Jul. 1, 2016 for U.S. Appl. No. 14/604,621.
Office action dated Jul. 2, 2013 for U.S. Appl. No. 12/016,077.
Office action dated Jul. 12, 2012 for U.S. Appl. No. 13/473,354.
Office action dated Jul. 15, 2015 for U.S. Appl. No. 14/682,014.
Office action dated Jul. 17, 2013 for U.S. Appl. No. 13/539,770.
Office action dated Aug. 1, 2014 for U.S. Appl. No. 14/097,087.
Office action dated Aug. 10, 2016 for U.S. Appl. No. 14/804,415.
Office action dated Aug. 10, 2017 for U.S. Appl. No. 15/605,601.
Office action dated Aug. 21, 2017 for U.S. Appl. No. 15/420,615.
Office action dated Oct. 4, 2012 for U.S. Appl. No. 13/539,770.
Office action dated Oct. 27, 2011 for U.S. Appl. No. 12/016,077.
Office action dated Nov. 4, 2016 for U.S. Appl. No. 15/178,506.
Office action dated Nov. 10, 2010 for U.S. Appl. No. 12/016,077.
Office action dated Nov. 14, 2014 for U.S. Appl. No. 14/461,159.
Office action dated Nov. 21, 2016 for U.S. Appl. No. 14/800,536.
Office action dated Dec. 5, 2012 for U.S. Appl. No. 12/016,077.
Office action dated Dec. 15, 2011 for U.S. Appl. No. 12/016,085.
Office action dated Dec. 18, 2013 for U.S. Appl. No. 13/897,302.
PCT/US18/46561 International Search Report and Written Opinion dated Oct. 25, 2018.
Qin, et al. Synthesis and Characterization of Unsaturated Thermotropic Polyesters Prepared via Acyclic Diene Metathesis Polymerization. Macromolecules. 2004; 37:5239-5249.

(56) References Cited

OTHER PUBLICATIONS

Rao, S. Future Directions in the Management of Aortic Coarctation in Young Patients. Pediat Therapeut. 2014; 4:e125. doi:10.4172/2161-0665.1000e125.

Sanders. Controlled delivery systems for peptides. From 'Peptide and protein drug delivery' Edited by Vincent Lee, Advances in Parenteral science vol. 4. 1990; Ch 19:785-806.

Seal, et al. Polymeric biomaterials for tissue and organ regeneration. Materials Science and Engineering. R34. 2001; 147-230.

Shashtri. Non-degradable biocompatible polymers in medicine: past, present, and future. Current Pharmaceutical Biotechnology. 2003; 4:331-337.

Sigler, et al. Breakable stent for interventions in infants and neonates: an animal study and histopathological findings. Heart. Feb. 2006; 92(2): 245-248.

Tanimoto, et al. Comparison of in vivo acute stent recoil between the bioabsorbable everolimus-eluting coronary stent and the everolimus-eluting cobalt chromium coronary stent: insights from the Absorb and Spirit trials. Catheter Cardiovasc Interv. Oct. 1, 2007;70(4):515-23.

U.S. Appl. No. 15/605,601 Notice of Allowance dated Feb. 21, 2018.

U.S. Appl. No. 16/518,657 Notice of Allowance dated May 28, 2020.

U.S. Appl. No. 16/786,736 Corrected Notice of Allowability dated Jan. 19, 2023.

U.S. Appl. No. 16/786,736 Notice of Allowance dated Nov. 25, 2022.

U.S. Appl. No. 16/786,736 Office Action dated Aug. 15, 2022.

U.S. Appl. No. 16/786,736 Office Action dated May 5, 2022.

U.S. Appl. No. 17/017,544 Notice of Allowance dated Dec. 9, 2020.

U.S. Appl. No. 16/039,194 Notice of Allowance dated Dec. 6, 2018.

U.S. Appl. No. 16/039,194 Office Action dated Sep. 11, 2018.

U.S. Appl. No. 16/356,933 Notice of Allowance dated Jun. 18, 2019.

U.S. Appl. No. 16/518,657 Office Action dated Sep. 26, 2019.

Valimaa, et al. Viscoelastic memory and self-expansion of self-reinforced bioabsorbable stents. Biomaterials. Sep. 2002;23(17):3575-82.

Weir, et al. Processing, Annealing and Sterilisation of Poly-L-Lactide. Biomaterials. 2004; 25:3939-3949.

EP20240185571.7 Extended European Search Report dated Jan. 8, 2025.

2460

2462

2462

2464

2466

2466

2468

2460

2462

2466

2466

2464

2464

2468

R

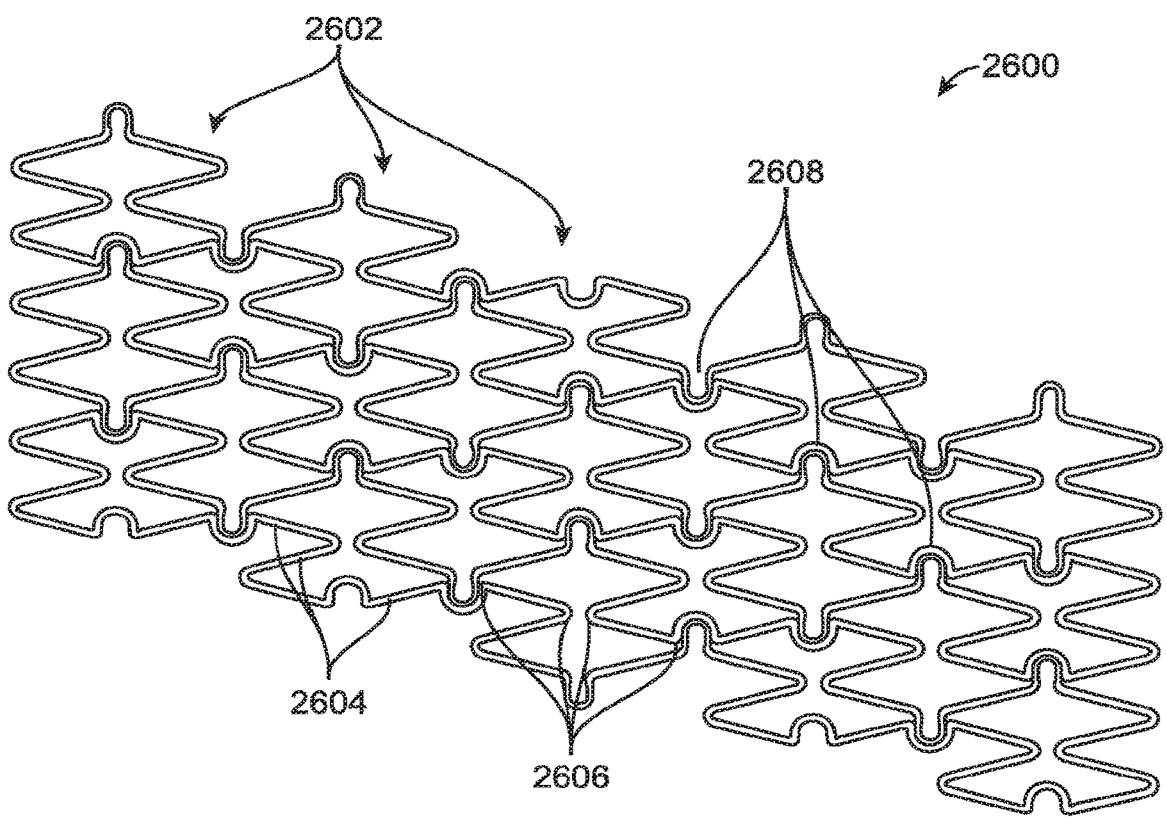
FIG. 35A
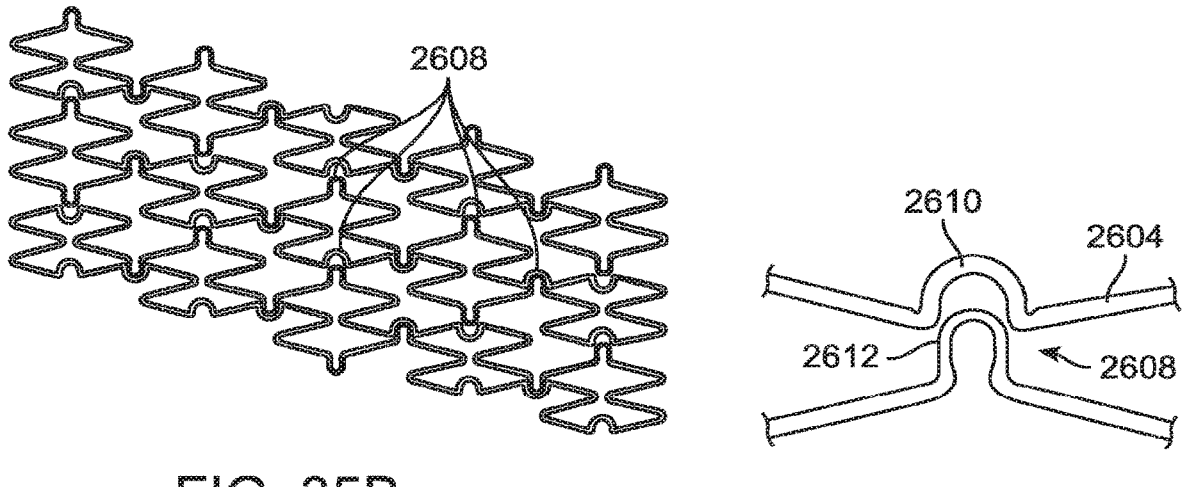
FIG. 35B
FIG. 35C

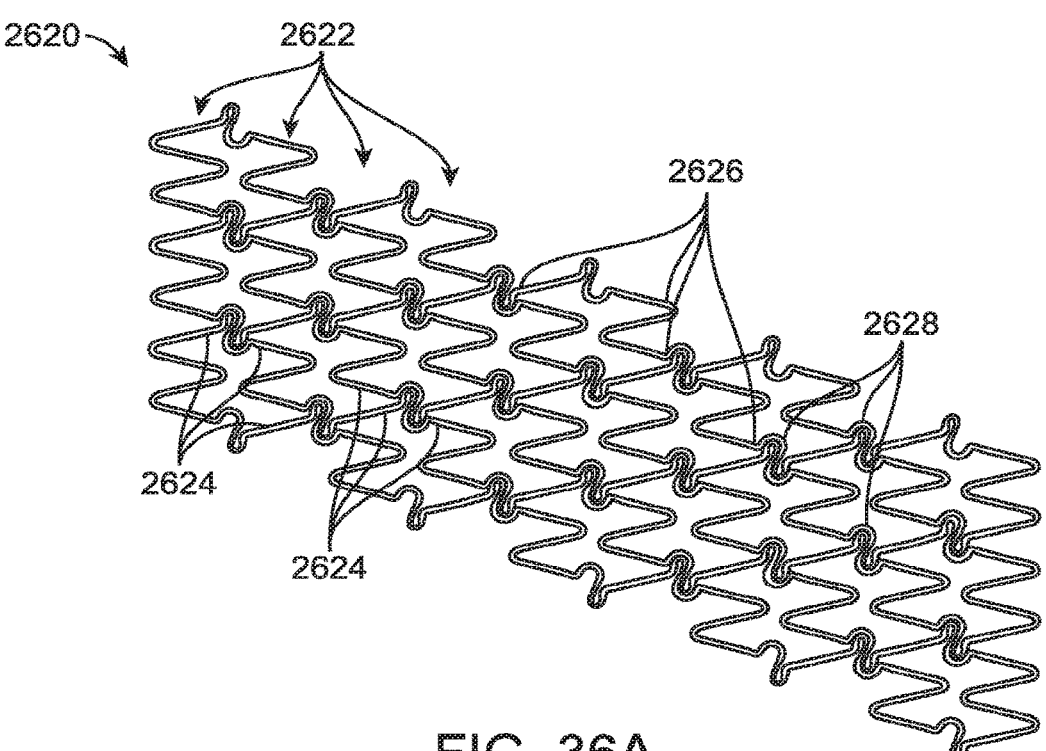
FIG. 36A
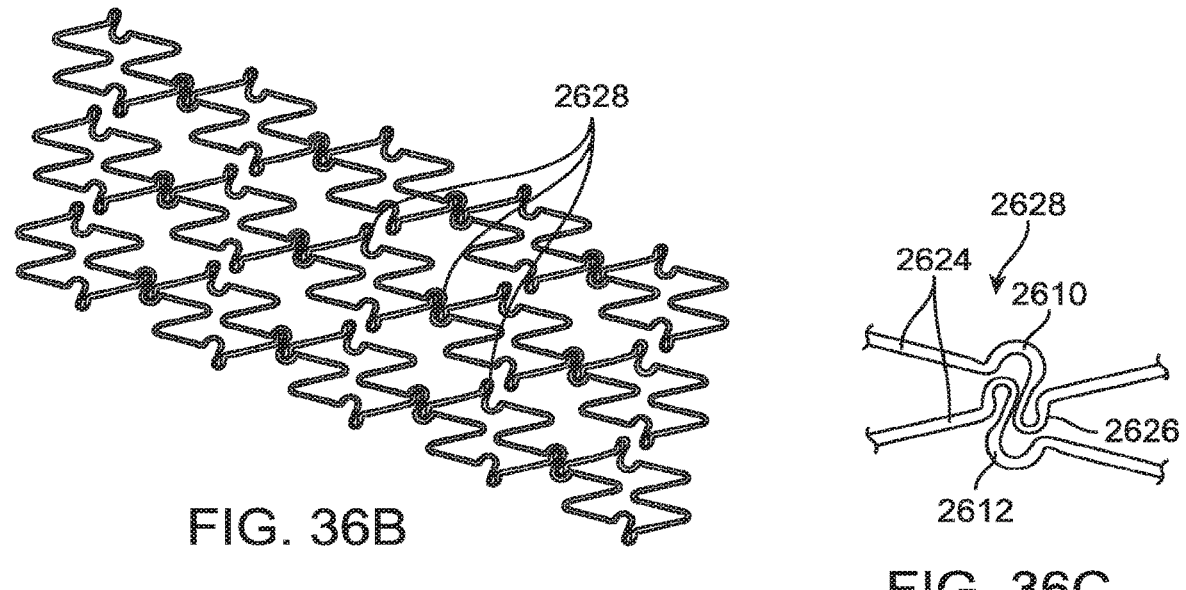
FIG. 36B
FIG. 36C

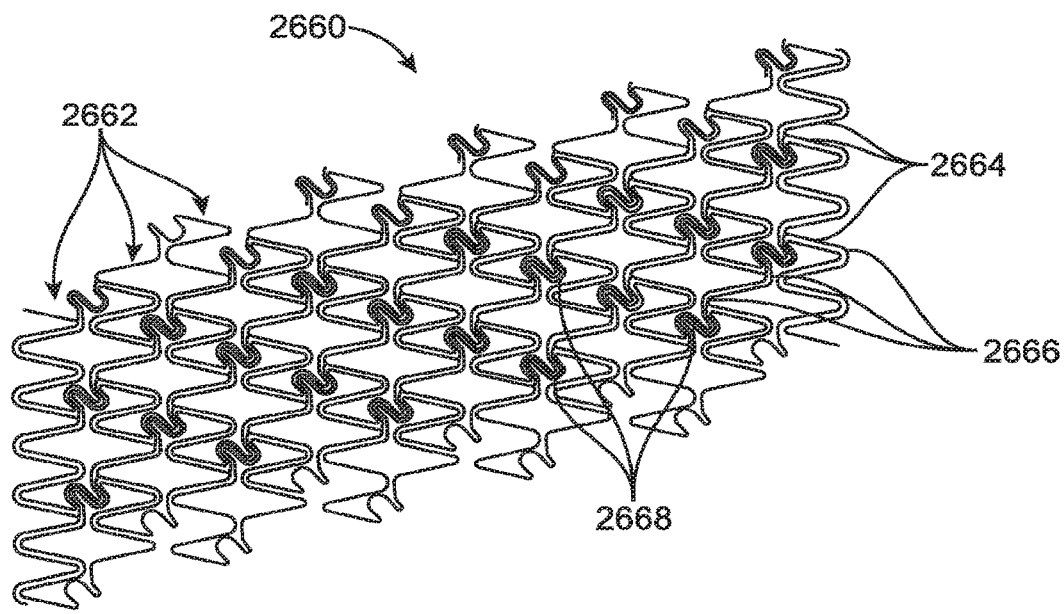
FIG. 38A
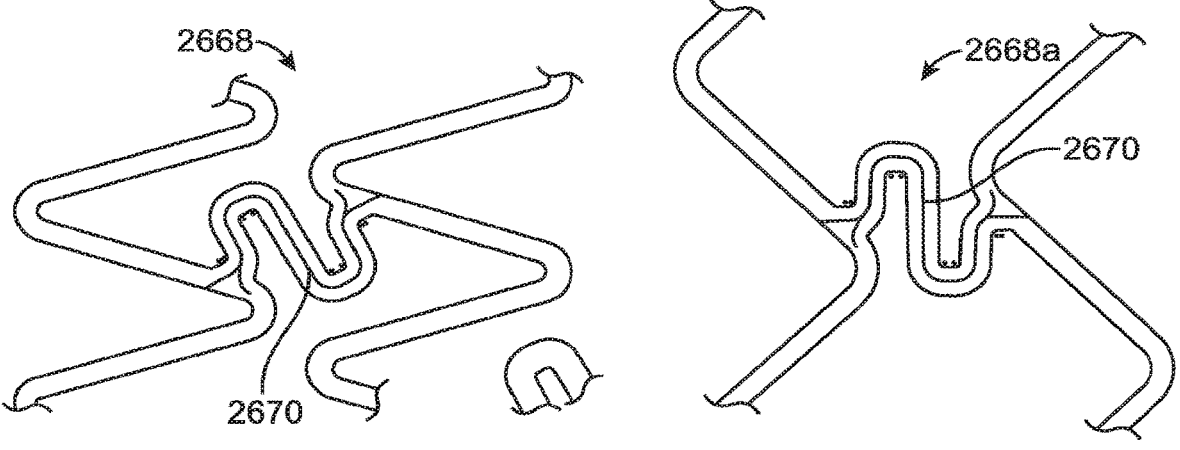
FIG. 38B                    FIG. 38C

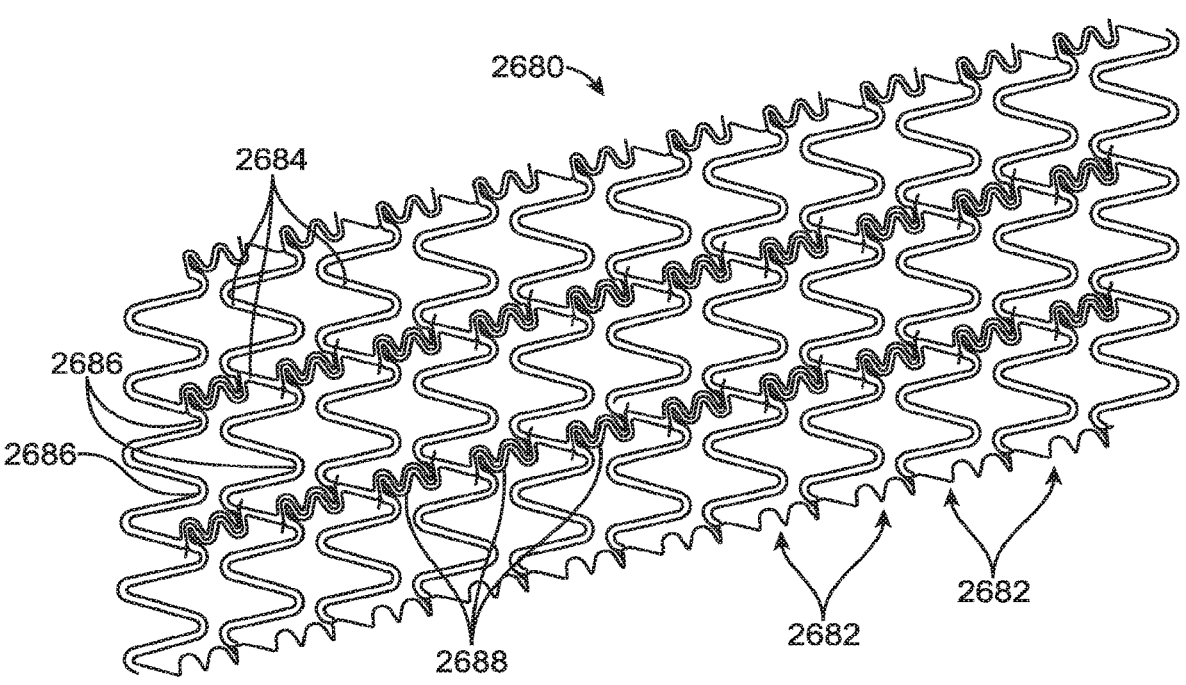
FIG. 39A
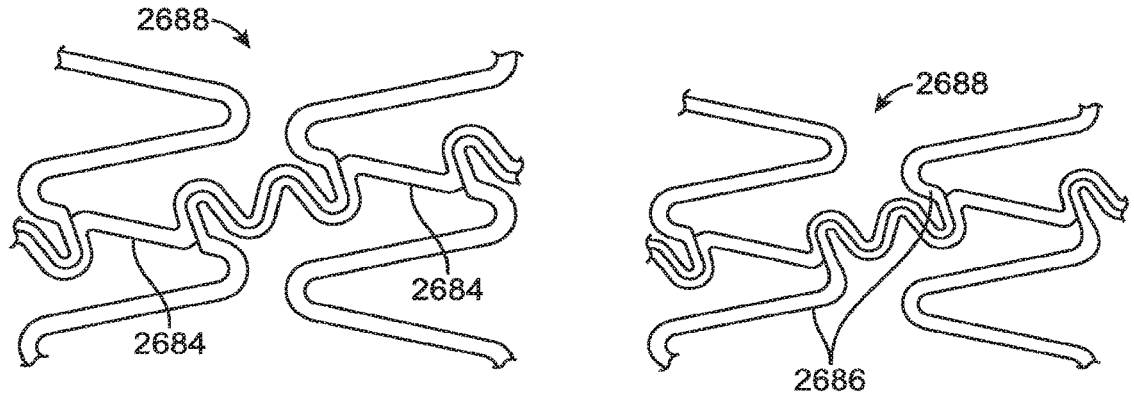
FIG. 39B                    FIG. 39C

2700

2702    2702

2702

2704

2706    2706

2740

UNCAGING STENT

CROSS REFERENCE TO RELATED APPLICATIONS

This application is a continuation of U.S. patent application Ser. No. 16/786,736, filed Feb. 10, 2020, which is a continuation of PCT Application PCT/US18/46561, filed Aug. 13, 2018, which claims the benefit of provisional patent application nos. 62/622,741, filed Jan. 26, 2018; 62/577,624, filed Oct. 26, 2017; 62/558,273, filed Sep. 13, 2017; and 62/544,682, filed Aug. 11, 2017, the full disclosures of which are incorporated herein by reference.

PCT Application No. PCT/US18/46561, filed Aug. 13, 2018, is a continuation-in-part of U.S. patent application Ser. No. 16/039,194, filed on Jul. 18, 2018, which is a continuation of U.S. patent application Ser. No. 15/921,508, filed Mar. 14, 2018, which is a continuation of U.S. patent application Ser. No. 15/605,601, now U.S. Pat. No. 9,943, 426, filed May 25, 2017, which is a continuation of PCT Application No. PCT/US2017/032748, filed May 15, 2017, which claims the benefit of provisional patent application nos. 62/480,121, filed Mar. 31, 2017; 62/430,843, filed Dec. 6, 2016; 62/424,994, filed Nov. 21, 2016; 62/414,593, filed on Oct. 28, 2016; 62/374,689, filed on Aug. 12, 2016; and 62/337,255, the full disclosures of which are incorporated herein by reference.

U.S. patent application Ser. No. 16/786,736, filed Feb. 10, 2020, claims the benefit of U.S. Provisional Nos. 62/812,577 filed Mar. 1, 2019; 62/849,402, filed May 17, 2019; and 62/850,413, filed May 20, 2019, the entire content of which is incorporated herein by reference.

BACKGROUND OF THE INVENTION

1. Field of the Invention

Balloon angioplasty was introduced to open vessels, particularly blood vessels which have narrowed as a result of plaque progression or a heart attack. In successful cases, the blood vessel remained open and/or exhibited positive remodeling over time and/or exhibited vasodilation ability mimicking to a degree the natural vessel ability. In other cases, however, the blood vessel would re-occlude within few days or within months due to various causes such as recoil of the vessel, thrombus formation, or other type of plaque morphology progression.

Metallic stents were developed to provide a structure, often referred to as a scaffold, with sufficient radial strength (crush resistance) to address recoil and hold the vessel open over time. Stents were formed from wire(s), coils, braids, a sheet, and/or tubular bodies. Balloon expandable stents formed from patterned non-degradable metallic tubes, wires, or sheet, are now most commonly used as they display desirable structural characteristics such as limited inward recoil, high strength (crush resistance or crush force), and limited axial shortening upon expansion, when compared to some earlier coiled or braided stents.

Despite their success and widespread adoption, metallic stents such as stainless steel alloys, Platinum iridium alloys, and cobalt chrome alloy stents, suffer from certain shortcomings, such as they jail the lumen or vessel, they do not further expand (after inward recoil) after implantation under physiologic conditions, preventing the lumen or vessel from further expanding which in turn inhibits positive remodeling, and/or such stent inhibits vasodilation or vasomotion of the treated vessel stent segment which is important to healing of the vessel or the normal functioning of the vessel. This phenomenon is commonly referred to as "jailing" or "caging" the vessel. High radial strength is important to support a body lumen upon implantation and/or to maintaining it open upon implantation of the stent and/or high strength is important in preventing the lumen from getting smaller after implantation. In some cases where shape memory self expandable alloys stents are used such stents typically do not exhibit high radial strength (high crush force resistance) like the metallic stents due to the material properties (and as a result the lumen in some cases become smaller after implantation of such stents due to excessive inward recoil due to lumen inward force on the stent and/or due to the lower radial strength of these stents, making such stent less likely to further expand after implantation in a lumen or diseased lumen segment, and/or such stents are less likely to exhibit vaso-dilatation or vaso-motion of the stented segment. In some cases shape memory stents penetrate the lumen wall moving towards the adventitia causing irritation, inflammation of the vessel or lumen, sometimes resulting in unwanted negative clinical events and/or re-occlusion of the body lumen or vessel. Also, the stent is typically maintained in the crimped configuration using a constraint upon delivery into the vessel or lumen which makes the profile of the stent system large and less deliverable. Stents of this type are usually pre-programed to expand to a certain diameter/configuration which makes sizing limited to such pre-programmed diameter/configuration and less likely to expand or maintain an expanded diameter beyond such pre-programed diameter, which makes stent sizing more difficult, and/or such stents do not expand further beyond such pre-program diameter/configuration after deployment, to name a few.

To address some of these shortcomings, biodegradable stents or scaffolds made from metallic or polymeric materials were developed. By allowing the stent to degrade or resorb, the jailing or caging effect would diminish or decrease over time and the scaffold would finally disappear over time. Present biodegradable stents, however, and in particular polymeric biodegradable stents and corrodible metallic stents, have their own shortcomings, including stent fractures, and/or limited ability to over-expand the stent above a nominal expanded diameter, and/or have excessive or high initial inward recoil, and/or have additional inward recoil after implantation and after the initial inward recoil. In some cases they may have insufficient strength to accommodate various lesion types after deployment, and/or limited ability to maintain a lumen or vessel open after deployment. Biodegradable stents typically have lower radial strength (crush resistance/strength) than balloon expandable metallic non-degradable stents, typically are bulky thick strut stents in order to address some of the mechanical shortcomings such as suboptimal crush strength, or having thick struts, which can cause negative clinical events, may cause excessive inflammation (due at least in part to the degradation of the material and the quantity of the degradation material), and/or cause excessive hyperplasia such as neo-intimal hyperplasia (due to at least in part to the degradation of the material and the quantity of the degradation material), to name a few problems.

Attempts have also been made to make scaffolds from a combination of polymeric and metallic materials. However, such designs have displayed their own shortcomings. Such combination designs can lack sufficient initial crush resistance to effectively open a lumen, or maintain it open, after implantation of the stent, or such designs do not uncage the stent, or do not uncage the stent along the entire stent segment, or do not uncage the vessel, or do not further expand the stent under physiologic conditions, or do not further expand the stent and/or allow it to contract using or after use of vaso-dilators and/or vaso-constrictors after implantation. Alternatively, some other such designs will not be able to further expand to a larger configuration (after inward recoil if any) after implantation. Still other designs have so many separate metallic or other non-degradable pieces that they risk releasing the small pieces into the blood stream potentially causing a clinical event. One or more needs as described above in the the following exemplary issues remain unmet by present non-degradable stents: having a stent with low inward recoil, and/or having a stent with low initial inward recoil after expansion while the diameter of the stent is substantially maintained after implantation and after the initial inward recoil, and/or having a non-degradable stent configured to be able to further expand (after inward recoil if any) after deployment under physiologic condition, and/or having a stent able to expand or further expand (after inward recoil if any) after deployment without a pre-programed temperature trigger setting or without a pre-programed expanded diameter/configuration setting, and/or having a stent able to expand or further expand (after inward recoil if any) without a programed temperature, and/or having a stent able to further expand (after inward recoil if any) after deployment under physiologic condition without penetrating or without substantially penetrating the vessel or lumen wall into the advantitia, and/or having a stent that does not cause excessive inflammation, and/or having a stent that does not penetrate the lumen or vessel wall after implantation into the advantitia, and/or having a stents that expands further following any inward recoil, after deployment (implantation) further expanding the lumen or vessel diameter, and/or having a stent maintained or substantially maintained in the crimped configuration upon delivery into the vessel or lumen without a constraint and which further expands after any inward recoil to a larger configuration after deployment, and/or having a stent that can be deployed to a wide range of diameters and still uncages the vessel or lumen after deployment, and/or having a stent that can be deployed to a wide range of diameters and still further expand after any inward recoil to a larger configuration after implantation, and/or having a stent able to further expand after any inward recoil beyond the pre-programed expanded diameter/configuration after implantation, and/or having a stent that exhibit vaso-motion, vaso-dilation, or vaso-constriction, after implantation, and/or having a stent that has sufficient strength after deployment to support a body lumen, has low inward recoil, and where the stent exhibits radial strain of 1% or larger than 1% after deployment, and/or having a non-degradable stent having an initial compliance upon expansion from a crimped configuration to an expanded configuration, wherein the initial compliance increases after implantation, and/or having a non-degradable stent having an initial radial strength (crush resistance) upon expansion from a crimped configuration to an expanded configuration, wherein the initial radial strength decreases after implantation, and/or having a balloon expandable non-degradable stent capable of expanding from a crimped configuration to an expanded configuration, where the expanded configuration comprises diameters ranging from 2.0 mm to 4.0 mm, and wherein the stent exhibits initial inward recoil after an initial expansion, and said stent after initial recoil has an initial diameter, said stent maintains said initial diameter (or configuration) after said initial inward recoil, and wherein the stent responds to a vaso-dilataor after implantation sufficient to expand the stented segment to a second diameter wherein the second diameter (or configuration) is larger than the initial diameter.

A particular concern in vascular and other body lumens after implementation of the stent or other prosthesis is the loss of vessel or lumen remodeling or enlargement, or the loss of vessel or compliance or contractility, referred to above as "caging" or "jailing" of the blood vessel or body lumen. Vessel compliance is necessary for the vessel or body lumen under physiologic conditions such as responding to changes in the internal pressure, external pressure, muscle contraction, muscle relaxation, chemical change, and the like. Such changes can result from many sources, such as the presence of natural, or artificial substances, which can relax or contract the body lumen and/or muscles such as smooth muscle cells, for example within the walls of the body lumen. The implantation of a stent in a blood vessel or body lumen will necessarily contribute to a reduction in the overall or "composite" compliance of the body lumen and the stent. Each of the body lumen's natural compliance and the stent's additional compliance will contribute to a total or overall "composite" compliance which will necessarily be less than that of the body lumen had the stent not been implanted. Thus, it is desirable for a stent implanted in body lumen, particularly implanted in a blood vessel, to minimize the reduction of body lumen compliance which naturally occurs as a result of the implantation of the stent. While a reduction of the compliance may be acceptable for a period of time immediately following implantation, particularly during that period (such as upon implantation or the initial period after implantation) when high radial strength is desired to maintain patency of the vessel (or body lumen) and prevent further inward recoil after implantation. Such strength is less necessary or not necessary after the initial period when healing of the vessel has occurred and eventually the strength of the stent becomes unnecessary or less important. During such healing phase or after such healing phase, it is highly desirable that the compliance of the vessel returned to levels at, or approaching, or closer to the natural compliance of the lumen in the absence of the implanted stent. Thus, it is an object of the present invention to provide stents, stent scaffolds, and other luminal prostheses which, after implantation, display a compliance which increases over time, in response to the vascular or other luminal environment, so that the total or composite compliance of the stents scaffold and the body lumen increase to levels which are closer or approach that of the body lumen in the absence of the stent scaffold.

Loss of compliance is also a problem for valves, rings, and other appliances implanted in heart valve annuluses. While valve scaffolds may not always need a high radial strength, particularly after an initial period of implantation, it is beneficial that they be sufficiently compliant to be able to conform to the annulus as the annulus deforms during the normal systolic-asystolic cycle, or it deforms to conform to the deformed annulus due to disease progression thus maintaining the integrity of the valve function, or it dilates to conform to the annulus dilation due to physiologic conditions or progression of disease, while maintaining the integrity of valve function.

What is needed are implants, stents, stent scaffolds, vascular prostheses, ecto-prosthesis, and/or other luminal prostheses that addresses at least some of these shortcomings as well as others described herein.

2. Listing of Background Art

Relevant background patents and applications include: U.S. Pat. Nos. 7,011,678; 5,922,020; US2003/0153971; U.S.

Pat. No. 9,056,157; US2005/0222671; U.S. Pat. Nos. 9,265,866; 7,169,173; 8,435,281; US2003/0195609; U.S. Pat. Nos. 7,402,168; 7,829,273; 5,695,516; 6,540,777; 8,652,192; 8,128,679; 8,070,794; 6,599,314; 8,961,585; 7,455,687; 7,645,409; 8,202,313; EP2229919; U.S. Pat. Nos. 6,251,134; 6,409,754; 5,766,237; 5,957,975; 5,306,286; 5,961,545; 8,052,743; 9,180,005; 9,192,471; US2008/177373; and US2005/283229.

SUMMARY OF THE INVENTION

The present invention provides numerous examples and embodiments of stents, in particular vascular and luminal stents and prostheses which display strength, modified (or controlled) strength, and/or modified (or controlled) compliance characteristics after expansion and/or implantation. In one particular example, metal, metal alloy, and other non-degradable stents may be modified in numerous ways to control their radial strengths and compliances initially at the time of expansion in the body lumen as well as subsequently during the days, months, and years following the initial expansion and/or implantation. In particular, many of the stent and scaffold designs described and claimed in the present application will provide for a variable (or controlled) compliance which has at an initial compliance, which is relatively low, and increases over time after implantation, and a radial strength which has an initial strength, which is relatively high (e.g. having substantial hoop strength or crush resistance) at the time of implantation or initial expansion, and decreases (or may be reduced) over time after implantation. The increase in compliance and decrease in radial strength may occur over a time period of days, weeks, or months after implantation and may be caused by any one or more of a number of structural transformations in a scaffold which forms all or a portion of the prostheses. In some instances, the compliance may change more abruptly, such as when a locked feature on the scaffold unlocks in response to a partial circumferential or complete expansion of the scaffold. In other instances, such locked features may be combined with other features and designs which alter the effective compliance of the scaffold more gradually over time.

In a first aspect, the present invention provides an endoluminal prosthesis having improved opening characteristics when expanded from a crimped configuration to an expanded configuration. The endoluminal prosthesis comprises a scaffold having a plurality of circumferential rings typically formed or patterned from a non-degradable material. The stent pattern comprises one or more of the following: open cell design, closed cell design, helical back bone, peak to peak rings design, peak to valley rings design, offset peak to peak or offset peak to valley rings design, or other. Typically, stent are formed from a tube, bent wire, or from a flat substrate and formed into a tubular structure. There are several embodiments which provide the improved opening characteristics. In one embodiment, the scaffold contains axial links which are divided into two parts axially with the two parts being held together during expansion of the stent through geometry or with a degradable or non-degradable polymer or adhesive and when the stent expands in a physiologic environment, the two parts of the axial links separate or are permitted to move in one or more directions providing improved opening of the scaffold or stent. In another embodiment, the scaffold comprises a series of complete circumferential rings and one or more partial circumferential rings with the partial rings connected to an adjacent whole or partial ring by one or more separable axial links. The separable axial links are held together either by geometry or with a degradable or non-degradable polymer or adhesive and when the stent expands in a physiologic environment, the two parts of the axial links separate or are permitted to move in one or more directions providing improved opening of the scaffold or stent. In another embodiment described more fully below, the scaffold or stent comprises circumferential rings some of which include two aligned struts, typically with each of the aligned struts connected to an adjacent circumferential ring through a link or connector.

In an example, the stent prosthesis is deployed to the expanded configuration under physiologic conditions wherein the physiologic conditions comprise one or more of temperature of about 37° C., water bath at a temperature of about 37° C., mammalian body lumen, mammalian body vessel, mammalian artery, pressure gradient ranging from 40 mmHg to 200 mmHg, pressure gradient of 100 mmHg, systolic and/or diastolic pressure, arterial, lumen, or vessel torsion, compression, elongation, and/or bending, vessel movement, pulsating artery or mock artery, mock body vessel, or combination thereof.

In the case of separable axial links, the scaffold is configured to expand from a crimped configuration to an expanded configuration and has attachment points on at least some adjacent circumferential rings, where the attachment points are usually axially aligned in pairs. The attachment points are joined by circumferentially separable axial links. Typically, prior to expansion, the axial links will be locked (constrained from separation) by their geometry, as described in more detail below. As the scaffold is radially expanded, usually by internal balloon expansion but alternatively by self-expansion, the axial links will undergo a deformation which "unlocks" their initially locked configurations so that the axial links may circumferentially separate. Alternatively, as the scaffold is expanded, the axial links may undergo a deformation which is not sufficient to "unlock" their locked configuration, but after expansion in a physiologic environment, the axial links will undergo a deformation sufficient to "unlock" their locked configuration. Alternatively, as the scaffold is expanded, the axial links may undergo a deformation which is not sufficient to "unlock" their locked configuration, but after expansion in a physiologic environment, the axial links separate. In a preferred example, a separable axial link has a geometry that locks in said axial link from separating during expansion of the stent from a crimped configuration to an expanded configuration, and is configured to separate after expansion in physiologic environment. Some of the physiologic conditions that contribute to further deformation following implantation and unlocking include the contortion and compression of the stent in the blood vessel or lumen.

In another preferred example, a stent prosthesis comprises structural elements comprising one or more circumferentially separable rings, and wherein said rings have a geometry configured to deform and/or move, rotate or twist during expansion from a crimped configuration to an expanded configuration to prevent the rings from separating. In a preferred example, the separable rings separate through separable axial links joined to said rings. In some cases, the separable axial link segments have a geometry configured to mechanically fit or lock together and are configured to rotate about a radial, circumferential, and/or axial axis during expansion to offset, counter-balance or counteract the forces trying to separate the segments of the axial links. This rotation offsetting or counteracting the expansion forces prevents said rings from separating during expansion. This geometry can be seen in a number of the examples and figures where the axial links comprise a series of bends or interlocking segments. In some cases, the separable rings geometry after expansion in a physiologic environment is configured to further deform prior to separating. In another example, the separable rings geometry after expansion in a physiologic environment is configured to separate by forming one or more discontinuities. In another example, the separable rings geometry after expansion in a physiologic environment is configured to separate by forming one or more discontinuities after degradation of a polymer or adhesive. In another example, the separable rings geometry after expansion in a physiologic environment is configured to separate without further deformation. In another example, the separable rings have a geometry configured to further deform about one or more of the following axes prior to separation comprising a radial, axial, or circumferential axes. In another example, the separable rings have a geometry configured to deform offsetting the expansion forces of the stent and preventing the rings from separating during expansion.

In another embodiment, the stent comprises circumferential rings comprising struts joined by crowns with at least some of the circumferential rings comprising two separable struts aligned and configured to separate after expansion in a physiologic environment. Each of the two separable struts may be linked to an adjacent circumferential ring so that after expansion under physiologic conditions, the struts separate opening the rings circumferentially but with each of the separated struts connected to an adjacent ring. In some embodiments, each circumferential ring of the stent contains one or more sections with two aligned struts, each strut joined to an adjacent circumferential ring through a link or connector. In one example, the aligned struts and their connectors to adjacent circumferential rings may be positioned in a line along the circumferential rings running at an angle to the longitudinal axis of the stent. See FIGS. 54A and B. In some instances, there may be two lines of aligned struts angled along the stent or three lines of aligned struts, each comprising two struts. During expansion of the stent, the aligned struts are held together through geometry or with an adhesive or polymer as described herein but after expansion in a physiologic environment, the struts separate and the scaffold opens, forming one or more sections of the stent, which typically would not have terminal ends. In some instances, there might possibly be a few terminal ends. In some examples, the aligned struts are joined to adjacent circumferential rings through links or connectors to other aligned struts, but in some examples the aligned struts may be connected to an adjacent rings at any location on the ring, typically with aligned sections on the adjacent ring. Or in some examples, rather than aligned struts, sections of overlapping regions (two segments with mirroring geometry may include any section of the rings-struts, crowns or links, in various combinations.

In another example, the separation region comprises two crowns, each from circumferentially adjacent rings. In another example, the separation region comprises one strut and one crown, each from a circumferentially adjacent ring. In yet another example, at least one separation region comprising a strut or a crown from a circumferential ring is connected to second segment on an axially adjacent circumferential ring, wherein the second segment comprises a strut or a crown. In yet another example, the two segments may be considered as separation regions and one separation region on one ring is connected to said second separation region on an axially adjacent ring via a link. In one example, the separation region axial length is substantially the same as one or more of the following: a strut or a crown on circumferentially adjacent rings is 0.1 times to 2 times the strut or a crown axial length on one of the circumferentially adjacent rings.

In a preferred example of any of the examples in this application, it is desirable to have a stent comprising one or more circumferentially rings separate without having terminal ends or without having more than few terminal ends, or without having more than 4 terminal ends, or having terminal ends of no more than 4. Examples of no terminal ends and two terminal ends are shown in FIGS. 35-54. This helps in vessel healing, minimizes vessel irritation, prevents small portions of structural elements from dislodging into the blood stream, and improves manufacturing.

Optionally, in addition to the physical locking, the circumferentially separable axial links may be additionally constrained, held together, kept in close contact, or immobilized by coating, encapsulation, gluing, or the like with a biodegradable material which will continue to inhibit circumferential separation of the axial links until the biodegradable material degrades in the physiologic environment unlocking the axial links. Some or all of the separable axial links or may be coated. In other instances, however, the circumferentially separable axial links may be free from such coatings, encapsulation, adhesives, or other further constraint and will be held together only by the mechanical locking afforded by the geometry of the aligned segments or portions, as described in more detail below The stent may be balloon expanded from a crimped configuration or it may be constrained in the crimped configuration before implantation and allowed to self-expand to the expanded configuration after removal of the constraint or restraint. In yet another example, the stent is balloon expandable to said expanded configuration after an initial self-expansion of the stent in a body lumen.

At least some of the axial links of the scaffolds of the present invention will comprise a first segment and a second segment. The first and second segments will typically separate along an axially extending dividing line which will usually comprise a break, cut, gap, or other discontinuity in the structure of the axial link. By "axially extending," it is meant that the dividing line and the link itself will extend from a first attachment point on a first circumferential ring toward a second attachment point on an adjacent second circumferential ring, where the attachment points are axially separated. That is, at least a component or a vector of the distance between the attachment points will extend axially, and the dividing line will extend to span that axial distance. As described in more detail below, however, the direction of the dividing line at any point along the axial link may be in any orientation, e.g. axial, circumferential, or at any orientation therebetween. Thus, in some embodiments the dividing line will typically follow a non-liner, meandering path which may include curves, bends, linear portions, and combinations thereof. Usually, however, the axial links will not extend significantly outside of the cylindrical envelope of the scaffold prior to circumferential expansion. In particular, sections and regions of the axial links will not overlap in a radial direction while the scaffold is in its crimped configuration.

The first and second segments of the circumferentially separable axial links may be circumferentially interlocked to inhibit circumferential separation thereof while the stent is in its crimped configuration. The interlocking may take any one of a variety of forms, and typically the first and second segments will be curved or bent into a pattern where portions of at least one segment interfere with or otherwise inhibit circumferential passage of or circumferential separation of portions of the other segment when a circumferential separation force is applied to the axial link. As the scaffold is expanded, however, the geometry of the segments will deform. As the stent is expanded, several things may contribute to keeping the segments together during expansion. During expansion, the segments may deform and/or the geometry of the two interlocking segments may cause, permit or provide for rotation of the segments in various directions, circumferentially, axially or radially, to offset, counterbalance or counteract the forces of expansion and prevent expansion until after expansion in physiologic conditions. The deformation may cause the segments of the axial link to catch on each other or hinder separation, and prevent separation but subsequently under physiologic conditions, additional deformation may occur, such that any interfering or blocking portions will shift to allow circumferential separation. The two segments of the axial link may be in contact with each other in the bends or curves so the two segments nest together, mirror each other, or fit together with the two segments forming the same, corresponding, approximate, or similar curves or bends creating a snug fit, a mechanical locking, steric hindrance to impede, resist, delay or inhibit separation of the segments. There may be one or more of the nested or aligned curves or shapes of the two segments along the length of the axial link. The segments may be in close contact along some, most, approximately all, about 50%, about 70%, about 80%, about 85%, greater than 50%, greater than 70%, greater than 75%, greater than 80% or greater than 85% of the length of the separable axial link or aligned segments of the partial ring junction.

The circumferential rings are configured to circumferentially separate, at least at the attachment points. In particular, as the scaffold is circumferentially expanded, both the segments of the axial links and the circumferential rings will separate at the attachment points after the segments have become unlocked. After such separation, opposite ends of each link segment will remain attached to their adjacent circumferential ring so that the rings remain axially linked but have been circumferentially opened. In one example, adjacent circumferential rings are joined axially through axial links wherein each axial link comprises a separation region dividing said axial link axially into two separatable axial links, and after expansion of the stent or scaffold in a physiologic environment the axial link separates into two links, each connecting said two adjacent rings.

The circumferentially separable axial links may extend between virtually any points on the adjacent circumferential rings. That is, the attachment points of the axial links on the circumferential rings may be at any location on the rings. For example, the circumferentially separable axial links joining rings comprising or consisting of struts and crowns may extend between pairs of struts on adjacent rings, between pairs of crowns on adjacent rings, or between a crown on a first ring and a strut on a second ring. Thus, the attachment points may be located at any point in any one or more of the struts and crowns in a circumferential ring. The axial link may be connected to one or more of the following on each adjacent ring: an area of an expansion region of a ring, a crown region of a ring, a strut region of a ring, a low stress area of a ring, a high stress area of a ring. The scaffold may comprise any number of circumferential rings along its axial length. In one example, if there is an even number of circumferential rings in the scaffold, when the separable axial links disengage after expansion of the scaffold in a physiologic environment, the scaffold separates into several units, two, three or four, with unseparated axial links joining the circumferential rings within each unit. In a preferred example, the separation region's axial length is equal to at least the axial length of one ring, that is the distance between rings in an axial direction. In a preferred example, the separation regions axial length ranges from 0.75 times to 2 times the axial length of one ring, or distance from one ring to an adjacent ring. In one example, if there are an uneven number of circumferential rings in the scaffold, when the separable axial links disengage after expansion of the scaffold in a physiologic environment, the scaffold opens, the separable axial links separate, and the scaffold may comprise a unitary connected piece. The scaffold may have the rings in a helical pattern. The scaffold may have some, the majority of, nearly all or all circumferential rings joined to adjacent circumferential rings by separable axial links.

The circumferentially separable axial links may also be arranged in a variety of patterns on the scaffold. In some instances, at least some or all of the axial links will be arranged along one, two, three, or more axial lines along the length of the scaffold. In other instances, at least some or all of the axial links may be arranged along at least one, two, three, or more helical lines along the scaffold.

The geometries of the circumferentially separable links and the dividing lines between the segments may vary widely, so long as the two segments are initially interlocked or bound when the scaffold is crimped and are capable of unlocking as the scaffold is circumferentially expanded. Often, the dividing line will be nonlinear, typically having one or more regions of curvature, and sometimes being entirely curved. In many instances, the axial link and dividing line will include both curved and linear regions, and in other instances the curved sections will have regions of different curvature. Often, the curved sections will include regions of reversing curvature. Employing axial links with curves and bends is advantageous in that flexibility of the stent in the crimped and expanded configurations is enhanced.

In specific embodiments and examples, the two segments of a separable axial link of the scaffold each has first and second ends where the dividing line extends from the first attachment point in a first axial direction toward the second end and makes at least a first turn to travel in a second axial direction back toward the first end. Such a reversal in direction causes an "overhang" or "undercut" in the pattern of the dividing line which inhibits or prevents the two segments from passing each other in a circumferential direction as a circumferential opening force is applied to the scaffold. As the scaffold deforms, however, those sections which are initially opposed in a manner that prevents their bypass will reorient so that they may circumferentially pass each other and allow the axial link to unlock, separate and circumferentially open. Typically, the first turn will traverse an angle of at least about 100°, preferably at least about 120°, more preferably at least about 135°, and even more preferably at least about 180° or more, and will provide a sufficient interference so that the segments cannot pass each other to allow the axial link to open until the scaffold has been significantly opened, typically by at least 25% of the initial diameter, frequently by 200% of the initial diameter, and usually by at least 400% of the initial diameter.

In many embodiments, the dividing line and axial link will make a third turn to travel again in the first axial direction and in still many more instances will make a fourth turn to travel back in the second axial direction.

In other specific instances, the axial link and axially extending dividing line may have an S-shape, may have a W-shape, may have a serpentine shape, and combinations thereof.

In other specific examples, at least some of the circumferentially separable axial links may comprise nested wedges having a male portion and a female portion which engages in interference fit prior to expansion of the scaffold.

The separation regions between segments in separable axial links may comprise any combination of struts and/or crowns and may comprises a geometry that may become deformed, twisted, rotated, compressed, or elongated during expansion, to hold together the segments and subsequently form one or more discontinuities in said circumferential rings after expansion under physiologic conditions (at 37 degrees C.), or upon expansion of the stent from a crimped configuration to an expanded configuration in physiologic conditions. In one example, the separation region comprises a geometry that is deformed, twisted, rotated, compressed, or elongated, about a circumferential axis, longitudinal axis, and/or radial axis, prior to or in order to form one or more discontinuities in said circumferential rings. In another example, the said separation region comprises a geometry is configured to deform, twist, rotate, compress, elongate, prior to or in order to form one or more discontinuities in said circumferential rings after expansion of the stent in a physiologic environment. In one example, the segments may be twisted around each other in the area of contact or close association to hold the segments together during expansion and configured to release, unlock or come apart after expansion under physiologic conditions.

As discussed hereinafter, the scaffolds of the present invention may comprise separation regions in addition to the circumferentially separable axial links. The separation regions may comprise numerous biodegradable or non-degradable polymeric materials and other adhesives, glues, sleeves, and the like which are intended to initially immobilize the separation regions after deployment in a physiologic environment. Such biodegradable polymeric and other materials described below may also find use in temporally immobilizing the circumferentially separable axial links described more particularly herein. Such segments immobilized with such non-degradable or biodegradable material can also be considered separation regions within the scope of this and related applications. The polymer or adhesive may be placed or located on the stent on the abluminal surface, or luminal surface or both of the stent; or on one or more surfaces of the stent; or in the separation region; or in the separation region and on the top and/or the bottom (abluminal or luminal) surface(s) of the separation region. On top of the polymer placed on the stent, there may be a further layer of polymeric material which may be placed or located on the stent on the abluminal surface, or luminal surface or both of the stent; or on one or more surfaces of the stent; or in the separation region; or in the separation region and on the top and/or the bottom (abluminal or luminal) surface(s) of the separation region. The separable axial links may have a gap between the two segments so that the circumferential path of the ring is discontinuous but the coating of a degradable polymer over or in the gap holds the gap together during expansion and provides a continuous circumferential path around the stent. Upon expansion in a physiologic environment, the polymer or adhesive degrades and the gap is exposed providing a discontinuity in the circumferential path and an opening of the ring. The segments of the partial ring junction may have a gap between them which is held together by interlocking shapes of the segments or with a degradable or non-degradable material in the form of a coating, sleeve over the segments, or inclusion of material in the gap. Upon expansion of the stent in a physiologic environment, the segments unlock, separate and open or move more freely, depending upon the way in which the segments are held together. The opened stent expands substantially uniformly and has sufficient strength to support a body lumen. A non-degradable material, polymer or adhesive holds said separation region together during expansion and allows the separation region after expansion in physiologic environment to move in one or more directions comprising radial, circumferential, or axial directions. In one example, the non-degradable polymeric material stretches allowing said movement. In another example, the non-degradable material softens allowing said movement. In one example, the stent has minimal outward force in the expanded configuration. In another example, the stent has lower outward force in the expanded configuration compare to a same stent having continuous circumferential path (no separation region). In yet another example, the stent is more conformable in the axial and/or circumferential directions of the stent. In yet another example, the stent in the expanded configuration has sufficient strength to support a body vessel but does not have sufficient outward force to cause further vessel injury post implantation. In yet another example, the stent in the expanded configuration does not cause adventitial injury to the vessel.

In a preferred example, a stent is formed from a non-degradable material comprising one or more circumferential rings forming a continuous circumferential path around the stent, wherein at least one or more separation regions bisect said circumferential path forming one or more discontinuities in said circumferential path. In a preferred example, the separation regions are pre-formed during or after patterning of the stent. In another preferred example, the separation regions are held together by a material or geometry during expansion of the stent from a crimped configuration to an expanded configuration and wherein the separation region form said one or more discontinuities after expansion in physiologic conditions. In a preferred example, the material holding the separation regions together connects the bisected circumferential path making it continuous prior to forming the one or more discontinuities after expansion in a physiologic environment. In another example, the geometry of the separation region holds the circumferential rings intact allowing uniform expansion of said rings from crimped configuration to an expanded configuration then said geometry disengage forming one or more discontinuities in said circumferential rings. In another example, the separation regions comprise one or more of a degradable polymer: coating or a sleeve, adhesive, one or more bisected structural elements. In another example, the bisected one or more structural elements comprise one or more of the following: a key and lock configuration, a ball and socket configuration, a male and female configuration, or other types of configurations that form a discontinuity after expansion of the stent in physiologic environment. In some instances, it is desired to have a separation region configured to form one or more discontinuities after expansion of the stent in one or more directions to minimize neointimal hyperplasia formation, to reduce torsion stresses of the stent, to maintain or increase lumen configuration, or to reduce elongation or compression stresses of the stent. For example, the separation region forms a discontinuity after expansion of the stent in a physiologic environment only in a radial direction. In another example, the separation region forms a discontinuity after expansion of the stent in a physiologic environment only in a radial and/or axial to the stent length direction. In another example, the separation region forms a discontinuity after expansion of the stent in a physiologic environment only in a radial and/or circumferential direction. In another example, the separation region forms a discontinuity after expansion of the stent in a physiologic environment only in an axial to the stent length direction. In another example, the separation region forms a discontinuity after expansion of the stent in a physiologic environment only in a circumferential direction. In another example, the separation region can form a discontinuity after expansion of the stent in a physiologic environment in axial, radial, or circumferential directions.

In another example, the stent prosthesis may be formed from a non-degradable polymeric or metallic material (including metallic or metallic alloys), or the stent may be formed from degradable polymeric or metallic (including metallic or metallic alloy material).

In another example, the stent prosthesis may be formed from a non-degradable shape memory alloy with one or more circumferential rings, at least some of said circumferential rings having at least one separation region bisecting, cutting or dividing said circumferential ring forming a discontinuous circumferential path around the stent, with said separation region held together during expansion of the stent from a crimped configuration to an expanded configuration and wherein said stent expands substantially uniformly and has sufficient strength to support a body lumen. The held together separation region may be held together through geometry or with degradable or non-degradable polymers or adhesives, any of which may or may not render the discontinuous circumferential path continuous and following expansion in a physiologic environment, it may again become discontinuous with the formation of discontinuities. For example, with geometry or mechanical interlocking, the separation region may have a gap or the sections may be in contact and separate in physiologic conditions. Or, if a degradable material holds the separation region together, the ring becomes continuous until discontinuities form subsequently. With a non-degradable material holding the separation region together, the ring becomes continuous but the material may degrade, stretch or soften to allow movement in circumferential, axial or radial directions. In one example, the stent has minimal outward force in the expanded configuration. In another example, the stent with discontinuities has lower outward force in the expanded configuration compared to a same stent having continuous circumferential path (no separation region). In yet another example, the stent is more conformable in the axial and/or circumferential directions of the stent. In yet another example, the stent in the expanded configuration has sufficient strength to support a body vessel but does not have sufficient outward force to cause further vessel injury post implantation. In yet another example, the stent in the expanded configuration does not cause adventitial injury to the vessel. In an optional example, the separation region maybe held together prior to expansion of the stent by a degradable polymer or adhesive and wherein said adhesive or degradable polymer degrades in a physiologic environment forming one or more discontinuities in the circumferential path of the circumferential ring after expansion of the stent. In another example, the stent is constrained in the crimped configuration and allowed to self-expand to the expanded configuration by removing the constraint. In yet another example, the stent is balloon expandable to said expanded configuration after an initial self-expansion of the stent in a body lumen. In yet another example, at least some rings have from 1 to 4 separation regions bisecting each of said rings.

In a preferred example, a stent comprising one or more circumferential rings wherein said rings comprise structural elements comprising struts and crowns, and wherein said rings comprise one or more separation regions, wherein said separation regions are located in one or more of the following: a strut, a crown, a strut region, a crown region, adjacent to a strut on a single ring, adjacent to a crown on a single ring, substantially parallel to a strut on a single ring, substantially parallel to a crown on a single ring, in place of a strut in said rings, or in place of a crown in said rings. In a preferred example, the separation region comprises two adjacent struts in a single ring, two adjacent struts on two circumferentially adjacent rings or partial rings, two adjacent crowns in a single ring, two adjacent crowns on two circumferentially adjacent rings or partial rings, wherein the two adjacent struts or two adjacent crowns are held together during expansion of the stent and separate after expansion of the stent under physiologic conditions.

It is sometimes desirable to have the stent structure axially connected after formation of discontinuities in circumferential rings. This provides for improved support to a body lumen (or vessel) and prevents neointimal protrusion between rings. This can be achieved by having axially joined circumferential rings separate after implantation. In one example, the stent comprises one or more circumferential rings (turns) wherein each ring is joined to an axially adjacent ring, and wherein at least some rings have one or more separation regions making the circumferential path of each of said rings discontinuous, said discontinuous path is held together by a polymer or adhesive and forms one or more discontinuities after expansion of the stent in a physiologic environment. In another example, the axially joined rings are joined via one or more axial links, wherein at least one or more said axial links are configured to separate after expansion in a physiologic environment. In another example, the axially joined rings are joined via one or more axial links, wherein at least one or more said axial links are configured to separate after expansion in a physiologic environment and after formation of neointimal hyperplasia to substantially lock in the stent in place axially after implantation. In another example, the axially joined rings are joined via one or more axial links, wherein at least one or more said axial links are configured to separate after expansion in a physiologic environment and after formation of neointimal hyperplasia sufficient to cover the strut thickness of the stent to substantially lock in the stent in place after implantation. In another example, the axially joined rings are joined via one or more axial links, wherein at least one or more said axial links are configured to separate after expansion in a physiologic environment and after formation of neointimal hyperplasia sufficient to cover at least 0.25 times the strut thickness of the stent to substantially lock in the stent in place after implantation. In another example, the axially joined rings are joined via one or more axial links, wherein at least one or more said axial links are configured to separate after expansion in a physiologic environment and after formation of neointimal hyperplasia sufficient to cover 0.1 times to 2 times the strut thickness of the stent to substantially lock in the stent in place axially after implantation. In another example, the one or more axial links are configured to separate before, about the same time, or after formation of discontinuities on an adjacent ring. It is also desirable to have the stent being held substantially in place after formation of discontinuities to provide better structural support to body lumen (vessel) and minimize or inhibit neointimal protrusion through gaps in the stent structure. In one example the stent prosthesis comprises one or more circumferential rings being expandable from a crimped configuration to an expanded configuration wherein said rings have one or more separation regions within said each ring, one or more separation regions between said each adjacent ring, or one or more separation regions between circumferentially adjacent partial rings, and wherein at least some of said separation regions (or substantially most separation regions) are configured to form discontinuities after expansion of the stent and after formation of 0.1 times to 2 times the thickness of an adjacent strut, crown, or other adjacent stent structural element, to substantially hold in place the stent in a circumferential and/or axial direction.

Many or all of the stent or other scaffold designs described herein will be able to accommodate or adapt to most or all forms of annulus and/or vessel geometries, motion, anatomical changes, and distortion over time after deployment. For example, the stents and scaffolds having separation regions and/or hinge junctions as described herein will possess sufficient tensile stress, fracture resistance, and ability to accommodate geometric distortion, such as angulation (bending of the vessel), torsional stress (twisting of the vessel about the vessel axis), longitudinal compression and extension, and the like. Such stresses are experienced, for example, by stents and other scaffolds implanted in annulus, arteries and veins located in the heart, or aorta, or peripheral anatomy such as below the knees, or in the superficial femoral artery, and the like. The stents and scaffolds of the present invention are typically able to dynamically conform and respond to both the pulsation of such blood vessels (radial opening and closing) as well as to torsional deformations about the axes of such blood vessels, and longitudinal compression.

In some examples, the endoluminal prosthesis formed from non-degradable material and having circumferential rings comprising struts joined by crowns with separation regions configured to form discontinuities after expansion of the prosthesis under physiologic conditions has stresses induced by longitudinal compression or extension of the expanded prosthesis prior to the separation regions forming discontinuities. In some cases, the maximum stresses induced by longitudinal compression or extension of the expanded prosthesis prior to separation regions forming discontinuities decreases after formation of discontinuities by at least 10%, 15%, 25%, 50%, 75%, 85%, or 90%. In some cases, the maximum stresses induced by longitudinal compression or extension of the expanded prosthesis prior to separation regions forming discontinuities decreases after formation of discontinuities by 15%-95%, preferably by 50% to 95%, more preferably by 70%-95%.

In some cases, the maximum stresses as measured by linear elastic finite element analysis induced by 5-7% longitudinal compression or extension of the expanded prosthesis prior to separation regions forming discontinuities ranges from 400e3 to 800e3 PSI, and after formation of discontinuities ranges from 1e3-300e3 PSI. Sometimes the maximum stresses as measured by linear elastic finite element analysis induced by 5-7% longitudinal compression or extension of the expanded prosthesis prior to separation regions forming discontinuities ranges from 300e3 to 1000e3 PSI, and after formation of discontinuities ranges from 1e3-250e3 PSI.

In some examples, the maximum stresses induced by torsion applied to the expanded prosthesis prior to separation regions forming discontinuities decreases after formation of discontinuities by at least 10%, 15%, 25%, 50%, 75%, 85%, or 90%. Alternatively, the maximum stresses induced by torsion applied to the expanded prosthesis prior to separation regions forming discontinuities decreases after formation of discontinuities by 15%-95%, preferably by 50% to 95%, more preferably by 70%-95%. In some examples, the maximum stresses as measured by linear elastic finite element analysis induced by torsional displacement of 3.5°/cm of prosthesis length applied to the expanded prosthesis prior to separation regions forming discontinuities ranges from 80e3 to 150e3 PSI, and after formation of discontinuities ranges from 1e3-65e3 PSI. Alternatively, the maximum stresses as measured by linear elastic finite element analysis induced by torsional displacement of 3.5°/cm of prosthesis length applied to the expanded prosthesis prior to separation regions forming discontinuities ranges from 65e3 to 150e3 PSI, and after formation of discontinuities ranges from 1e3-50e3 PSI.

Sometimes, the force required to bend the prosthesis by a specified amount in a 3-point bend configuration prior to separation regions forming discontinuities decreases after formation of discontinuities by at least 10%, 15%, 25%, 50%, 75%, 85%, or 90%. Alternatively, the force required to bend the prosthesis by a specified amount in a 3-point bend configuration prior to separation regions forming discontinuities decreases after formation of discontinuities by 15%-95%, preferably by 50% to 95%, more preferably by 70%-95%. In some cases, the force required to bend the center of the prosthesis by approximately 1 mm in a 3-point bend configuration with supports approximately 11 mm apart prior to separation regions forming discontinuities ranges from 1 to 4N, and after formation of discontinuities ranges from 0.1 to 0.8N. Alternatively, the force required to bend the center of the prosthesis by approximately 1 mm in a 3-point bend configuration with supports approximately 11 mm apart prior to separation regions forming discontinuities ranges from 0.7 to 4N, and after formation of discontinuities ranges from 0.01 to 0.5N.

In some examples, the maximum stresses induced by bending the expanded prosthesis to a target radius prior to separation regions forming discontinuities decreases after formation of discontinuities by at least 10%, 15%, 25%, 50%, 75%, 85%, or 90%. Alternatively, the maximum stresses induced by bending the expanded prosthesis to a target radius prior to separation regions forming discontinuities decreases after formation of discontinuities by 15%-95%, preferably by 50% to 95%, more preferably by 70%-95%. Sometimes, the maximum stresses as measured by linear elastic finite element analysis bending the expanded prosthesis to a target radius of 70 mm prior to separation regions forming discontinuities ranges from 100e3 to 800e3 PSI, and after formation of discontinuities ranges from 10e3-90e3 PSI for a 6 mm expanded stent diameter.

Sometimes, the change in angulation of a curved vessel with an expanded physiologic implant placed within prior to separation regions forming discontinuities decreases after formation of discontinuities by at least 10%, 15%, 25%, 50%, 75%, 85%, or 90%. Alternatively, the change in angulation of a curved vessel with an expanded physiologic implant placed within prior to separation regions forming discontinuities decreases after formation of discontinuities by 15%-95%, preferably by 50% to 95%, more preferably by 70%-95%. In some instances, the change in angulation of a curved vessel with an expanded physiologic implant placed within prior to separation regions forming discontinuities ranges from 30 to 70 degrees, and after formation of discontinuities ranges from 10 to 25 degrees. In some examples, the maximum stresses induced by bending the expanded prosthesis by a given angle prior to separation regions forming discontinuities decreases after formation of discontinuities by at least 10%, 15%, 25%, 50%, 75%, 85%, or 90%. Or, the maximum stresses induced by bending the expanded prosthesis by a given angle prior to separation regions forming discontinuities decreases after formation of discontinuities by 15%-95%, preferably by 50% to 95%, more preferably by 70%-95%.

In some examples, the maximum stresses as measured by linear elastic finite element analysis bending the expanded prosthesis to 3.0 mm diameter by a given angle of approximately 7 degrees prior to separation regions forming discontinuities ranges from 100e3 to 800e3 PSI, and after formation of discontinuities ranges from 10e3-90e3 PSI.

The stent or scaffold may have a drug included which will be released in a physiologic environment following implantation. The drug may be coated on one or more surfaces of the stent; on the abluminal surface or the luminal surface or both; included in one or more polymeric materials coated on any surface of the stent; included in a top coat on any surface; or in a matrix with a polymer on the stent or scaffold. Drugs which may be utilized include a variety of drugs listed in this application and include, for example, M-tor inhibitors, including the drugs such as rapamycin, Everolimus, analogues, or derivatives and Taxol, analogues, or derivatives.

Methods for measuring and quantitatively expressing the strength (radial strength) and the compliance and of vascular and other luminal stents and scaffolds are well known and described in the patent and medical literature.

Compliance, as the term is used in many of the examples or embodiments, is a non-dimensional measurement which expresses a percentage change in diameter (or configuration) of a luminal structure, or a segment of a luminal structure, in response to physiologic conditions such as a change in internal pressure within or adjacent to the luminal structure, usually such change in pressure is 100 mmHg. In some other instances, compliance measurement can be expressed as mm/atmosphere, mm/psi, %/atm, %/psi, or the like. The term compliance and radial compliance are used interchangeably.

Body lumens, stents, scaffolds, prostheses, and other tubular structures will each have their own compliance. Body lumens having implanted stents, scaffolds, prosthesis, and other tubular structures will also have a compliance which is a composite of the individual compliances of the lumen and the implant, where the composite is typically lower than the lumen and many cases lower than the implant alone. In many cases or examples, it is the "composite" compliance that will be measured to define the compliance characteristics of the stent; however, it can also be in some cases the stent alone measured compliance, scaffolds, prosthesis, and other tubular structures in many of the examples being claimed herein. In many instances or examples throughout this application, the term "radial strain" is used to mean compliance and is used interchangeably with the term "compliance" (or the composite compliance) as the term compliance or composite compliance is described in this or other paragraphs. Usually, when radial strain is measured at 100 mmHg change in pressure, it refers to the compliance of the implant (or composite compliance), but compliance can also refer to % change in diameter of the implant or composite at a given change in pressure different than 100 mmHg.

In particular, the radial compliance of a stent, scaffold, or other luminal prosthesis will be measured as a composite compliance in vitro in a mock vessel in accordance with well-known principles and techniques, such as those described in ASTM F2477-07R13 which measures compliance at a pressure change of 100 mmHg, but the test can also provide the method required for testing compliance at a given change in pressure other than 100 mmHg, such as at about 176 mm Hg, or other pressure. Also, stent compliance can be tested by having a stent implanted in a vessel, such as a coronary artery vessel, of a porcine animal and the compliance is measured in the stented segment of the vessel.

In a first aspect or example of the present invention, a prosthesis, in particular an endoluminal prosthesis comprises a scaffold having a plurality of circumferential rings formed or patterned from a non-degradable material, typically a metal or metal alloy, where the scaffold is configured to expand from a crimped configuration to an expanded configuration. At least some of the circumferential rings will have at least one separation region, where the separation region(s) are configured to form at least one discontinuity in the circumferential ring after the scaffold has been expanded in a physiologic environment. In a preferred example, after such expansion and exposure to the physiologic environment, typically a vascular or other body lumen environment, at least two of the circumferential rings remain axially joined after all discontinuities are formed, typically being axially adjacent rings. Frequently, all circumferential rings of such endoluminal prostheses will remain axially joined after the discontinuities are formed. For example, the circumferential rings may be joined by axial links, which are typically short structural elements joining a region on one circumferential ring to a region on an adjacent another circumferential ring. In other examples, however, regions on successive adjacent circumferential rings may be directly joined, for example being welded or otherwise joined crown-to-crown, strut-to-strut, or the like, as will be described in more detail hereinafter in this application. In specific examples, adjacent crowns on adjacent rings may be joined by welding, wrapping, binding with wires or other filaments, adhesives, or the like. While separation regions will often be formed within a strut, crown, or other structural element, in some instances a separation region may encompass or comprise an entire structural element. In some examples, a lock and key or other type of separation region may be elongated to form an entire, or almost the entire length of a strut between a pair of abutting crowns. In other examples, the male and female components of a lock and key separation region may be curved to form a crown between a pair of abutting or adjoining struts. The separation region may be located anywhere in the structural element. It may be at approximately the center of the structural element or located at or near one or the other end of the structural element.

The stent prosthesis has at least one separation region, which forms a discontinuity after expansion in a physiologic environment with the separation region placement is in the circumferential ring so that the discontinuity forms in the circumferential ring. In some instances, it provides a break, gap, complete separation or bisection of the ring into separate sections so that the ring no longer has a continuous circumferential path around the scaffold. In some examples, each circumferential ring has a separation region located to form a discontinuity upon expansion in a physiologic environment providing a gap, break or separation in each circumferential ring so that each ring opens or no longer has a continuous circumferential path around the scaffold.

Bisection typically separates a continuous portion or section of a structural element or a circumferential ring or an axial link into two or more separates portions not necessarily of equal lengths. For example, a separation region in a crown or a strut in a circumferential ring will bisect said crown or strut into two or more portions. In some instances, the separation region bisects said crown or strut in the middle of said crown or strut. In other instances, the separation region bisects said crown or strut not in the middle of said crown or strut.

In a preferred example, the phrase "separation region" is a location or region within the scaffold which is configured to form at least one discontinuity in the scaffold after the scaffold has been expanded in a physiologic environment. The discontinuity comprises an opening, break, gap, bisection, or the like, formed between two adjacent portions or segments of a component of the scaffold which in some cases were previously joined so that the portions or segments are no longer directly connected to each other in the region of the portions or segments. The two adjacent portions or segments of the component may have been previously joined before expansion of the stent in any of the ways described elsewhere herein or may have been formed as a continuous structure.

In at least most instances, the discontinuities will not form in the separation regions until after the scaffold has been expanded in the physiologic environment, typically forming over a time period ranging from one week after expansion of the stent to 12 months after expansion of the stent, often from one month after expansion to 9 months after expansion, usually from 2 months after expansion to 7 months after expansion. In particular, in the case of balloon-expandable stents and other prostheses, the separation regions are expected to remain intact as the scaffold is being expanded by the balloon and discontinuities will fully form (i.e. release previously joined regions of a scaffold) only after the scaffold has been deployed in the blood vessel or other physiologic environment for the noted time periods. Although discontinuities normally do not form until after expansion in a physiologic environment, in some cases, one or more rings, typically one or more end rings, may have one or more discontinuities form prior to expansion of the stent (deployment of the stent) under physiologic conditions.

Such endoluminal prostheses according to the present invention, for example, will have circumferential rings with a circumferential structure having an initial radial compliance, typically a composite compliance as discussed above, prior to formation of any discontinuities. After formation of the discontinuities, however, at least some of the circumferential rings will have a radial compliance which is increased relative to the initial radial compliance of the at least some rings prior to formation of the discontinuities. For example, the initial radial compliance of at least some of the circumferential rings of a scaffold (or the composite compliance of the scaffold segment) in accordance with the principles of the present invention may be 0.1% to 1%, typically from 0.1% to 0.5%, while the radial compliance after formation of the discontinuities will typically be from 1.2% to 10%, often being from 1.2% to 5%, or 1.5%-3%.

In one example of measuring the composite compliance of a scaffold one uses a mock vessel system as follows. The scaffold being tested, the mock vessel, the water used to pressurize the mock vessel, and all other test equipment are held at room temperature. All diameter measurements are made with a calibrated non-contact system capable of measuring a diameter to within ±0.01 mm without contacting the scaffold. Suitable measurement instruments include microscopic video measuring system, laser microscopes, and optical comparator. Pressure measurements of water used to pressurize the mock vessel are made with a gauge that can accurately measure fluid gauge pressure to within ±0.05 PSI. Pressure measurements are made at the time the diameter measurements are taken. The length of all connecting tubes used in the setup are under 10 inches and to eliminate any restrictions in the tubes and connectors are eliminated to assure that any dynamic changes in pressure throughout the mock vessel are accurately reflected by the pressure gauge. Diameter measurements should be performed with 30 minutes from initial pressurization of the mock vessel.

The mock vessel is an elastomeric silicone tube with a uniform cross sections and uniform material properties throughout its length. For stents smaller than 2.5 mm diameter, the mock vessel wall thickness is 0.25±0.03 mm. For stents of 2.5 mm diameter and larger, the mock vessel wall thickness is 0.5 mm±0.03 mm. The test pressure within the mock vessel will be 3.4±1 PSI (or approximately 176 mmHg), and the system will be sufficiently leak proof to maintain this pressure for the duration of the test. The stent-mock vessel system is fixtured to prevent changes in length and of the mock vessel resulting from longitudinal forces) that could affect the resting length of the mock vessel and the diameter of the mock vessel. The stent-mock vessel system is further fixtured to prevent changes in diameter from forces other than internal pressurization.

Balloon expandable, non-degradable scaffolds are deployed in air to an ID after inward recoil from the expanded configuration which equal to or 0.1 mm less than the outer diameter of the mock vessel without pressurization. The scaffold is expanded using a balloon or other delivery system suitable for use with the scaffold being tested. The inner diameter (ID) is verified using the non-contact measuring system. Self-expanding scaffolds are deployed in air to their free diameter, and the ID verified using the non-contact measuring system. A mock artery is selected to have an outer diameter equal to or 0.1 mm larger than the inner diameter of the deployed stent.

The expanded test scaffold is slid over the outside of the mock vessel, stretching the mock vessel tubing as necessary to temporarily reduce the tube diameter to allow the stent to be passed over it. After releasing tension on the mock vessel, actual contact between the ID of the scaffold and the outer diameter (OD) of the mock vessel along the entire contact length is verified.

The interior of the mock vessel tube is connected to an Indeflator (an inflation/deflation device used to inflate and deflate angioplasty balloon during angioplasty) capable of providing at least 3.4 psi and having a gauge capable of measuring the pressure in the tube to within 0.05 psi at such pressures.

The OD of the stent and the OD of a reference section of mock vessel away from the stented segment are both measured using the non-contact system at a distance from the stent equal to twice the diameter of the mock vessel, and a similar distance from any fixtures holding the mock vessel. Three OD measurements are made and averaged to obtain a baseline mock vessel OD value. Three OD measurements are made about the mid-length of the scaffold and averaged to obtain a baseline scaffold OD value. The interior of the mock vessel is pressurized with water to 3.4 PSI (176 mmHg), and the OD's of the scaffold and mock vessel measured at the same locations used to establish baseline using the non-contact system while the pressure reading is maintained at 3.4 PSI. The composite compliance is determined dividing the OD value measured when the mock vessel is pressurized by the baseline OD value, subtracting one, and multiplying by 100 to determine the composite compliance as a percentage.

For example, if the applied pressure in the mock vessel causes the OD of the test scaffold to increase in diameter from 3.50 mm OD to 3.73 mm OD, the composite compliance is $((3.73/3.50)-1)\times100=6.6\%$. As a second example, if the applied pressure in the mock vessel causes the OD of the test scaffold to increase in diameter from 3.50 mm OD to 3.52 OD, the composite compliance is $((3.52/3.50-1)-1)\times100=0.6\%$.

The composite compliance of the scaffold can be measured before and after opening of the separation regions to form discontinuities. To obtain the composite compliance before formation of discontinuities, the scaffold is measure as described above while all separation regions remain intact. To obtain the composite compliance after formation of discontinuities, the scaffold is treated to open all discontinuities while the scaffold remains on the mock vessel. The separation regions may be opened by techniques specific to the nature of the particular separation region. For separation regions immobilized by polymeric sleeves, glues, or solvents, the scaffold is exposed to solvents, enzymes, or other chemicals to form discontinuities, without damaging the mock vessel. Alternatively, and for non-polymeric separation regions, the separations regions may be physically separated using mechanical means, laser cutter, ultrasound, or other energy-based cutters form discontinuities. For locking designs or separation regions that open in response to fatigue, the mock artery can be cyclically pressurized at a 5-8 Hz rate until discontinuities form. See Example 5 and FIG. 35. If the scaffold falls apart while the separation regions are being opened, the composite compliance will be considered to be equal to mock vessel compliance without the scaffold.

The scaffolds have an initial crush strength which decreases following expansion in a physiologic environment and formation of the discontinuities. The scaffold has an initial compliance following implantation and the compliance increases following the formation of the discontinuities without decreasing the expanded configuration after recoil.

Radial strength (crush resistance) is measured with parallel flat plates (reference ISO25539-2) which are fixated onto an Instron tensile test machine with a 5N load cell to allow force and displacement measurement. The bottom plate is flat and remains stationary during testing. The upper plate is mounted onto the load cell to record force measurement as a function of displacement. The plates are visually verified to be parallel to each other at the mating surfaces. Both the bottom and upper plates are rectangular in shape with the surfaces completely covering the test stent in length and diameter. Both plates are configured to stay submerged in a bath of body temperature water, maintained by a circulation heater at body temperature of $37\pm2^{\circ}$ C. The circulation pump is turned off during the force measurement to prevent currents from altering the results. The top plate is formed from delrin and the bottom plate is formed from brass.

A test scaffold is deployed at its nominal inner diameter using a standard indeflator or other delivery system. The deployed test stent is removed from the delivery system and the diameter of the test stent is verified by a non-contact measuring system. The test stent is then slid onto a 0.035" diameter mandrel approximately 50 mm in length before placing between the parallel plates submerged in water at 37° C. mimicking physiological conditions. The mandrel will prevent the test stent from rolling at the initial contact with the parallel plates. The upper plate is then slowly jogged down using the displacement controller from the Instron tensile test machine until it is approximately 1 mm above the stent, and the force gauge is zeroed. It is then lowered until it barely touches the test stent, and a force of 0.01 N is detected. The stent is then allowed to stabilize in the bath for 60 seconds. The test cycle is started and the crush resistance force is then measured by decreasing distance between the parallel plates up to 50% of the test stent diameter. A force-distance curve is generated during the test. The rate of decreasing distance (crosshead speed) is 1.5 mm/min. The load force at 10% of stent deformation (compression) is determined in Newtons. For example, for a 3.0 mm labeled stent expanded to nominal diameter (3.0 mm), report the force required to compress it by 0.3 mm (10% compression). The load force in Newtons (N) is then divided by the expanded stent length in mm to normalize the strength in N to the stent length and thus the radial strength of the stent is expressed as N/mm of stent length.

The expanded stent baseline radial strength is measured (in N/mm of stent length), and again after formation of discontinuities (if any), as described in the crush resistance method. For a stent of the present invention, the radial strength decreases after formation of discontinuities compared to baseline radial strength before formation of discontinuities, preferably decreases compared to the baseline radial strength, by a range from 10% to 100% of the baseline radial strength.

The above protocols for measuring composite compliance and radial strength are particularly effective for measuring those values in scaffolds having a nominal diameter from 2 mm to 4 mm and having decicated or conventional deployment systems. For stents, valves, prostheses, and any other scaffold having other size and deployment systems, including non-standard sizes and non-standard deployment systems, the scaffold should be deployed according to the manufacturer's published instructions for use, and the test apparatus adjusted or modified to have the same fit with the deployed scaffold, as described above. In the case of a mock vessel for the measurement of composite compliance, the outer diameter of the mock vessel should be equal to or up to 0.1 mm larger than the inner diameter of the deployed scaffold. In the case of flat plate separation distance for measurement of crush resistance, the scaffold OD should be measured with an accuracy of $\pm0.01$ mm via non-contact methods, and 10% deflection calculated from this measurement. All other parts of the test methods should be followed as much as possible.

In preferred examples, the scaffolds of such endoluminal prostheses may separate into segments after the discontinuities have formed in the circumferential rings. The separation may be along axial, circumferential, helical, irregular, or other lines. For example, two, three or more segments may separate along axial, helical, or irregular lines, allowing the segments to radially expand and contract which increases the composite compliance of the scaffolds when implanted in a body lumen. Often, all or substantially all of the segments will remain axially joined along their entire lengths (or along the entire stent length) so that, while the discontinuities provide for an enhanced (or increased) radial compliance, the structural elements of the scaffolds remain axially joined to continue provide support (or scaffolding) to the lumen (or vessel) wall, and/or so that the elements are at a reduced risk of being dislodged or otherwise released after implantation in the vasculature or body lumen. Other examples of segments include closed cell segments, and the like. In such a preferred example, the scaffold (endoluminal prosthesis) forms a tubular body in the crimped configuration and/or the expanded configuration, and wherein the scaffold maybe formed from a wire, a substantially continuous tube, a sheet, molding, or by printing.

In a closed cell design, such separation region is typically located such that the circumferential path is no longer continuous. In this case, the discontinuity may be located in a circumferential connector between closed cells on the ring or in both sides of the closed cell on the ring such that the ring is opened and the circumferential path is completely bisected or separated.

In other embodiments or/and examples, the scaffold will not separate into segments. That is, while at least one and usually a plurality of discontinuities will form in the scaffold, all circumferential rings, struts, crowns, links, and other structural elements (or components) of the scaffold will remain physically connected so that no portion (or element) of the scaffold is fully disconnected from the remainder of any other portion of the stent. Such physical linkage of all portions of a scaffold even after discontinuities are formed can be an advantage as the risk of any portion of the scaffold being released into the vasculature or other body lumen is reduced.

In one particular example, discontinuities in adjacent circumferential rings may separate along axial lines so that the stent divides into two or more axially aligned segments, each of which extend from a first (usually terminal) end of the scaffold to a second (usually terminal) end of the scaffold. Such axially aligned segments of the individual circumferential rings separate circumferentially along axial (usually straight), helical, or irregular separation lines but remain axially joined or intact (by on or more axial links for example) after all discontinuities are formed. Such intact axial, helical or irregular segments will be elongated, typically having a length corresponding to the full length of the scaffold in its expanded configuration.

While such elongated axial, helical or irregular segments will usually be fully separated along their entire lengths, in other cases one or two circumferential connections may remain after all discontinuities have be formed in the scaffold. In particular, the elongated segments may remain joined at either or both terminal end of the scaffold in order to reduce "dog-boning" or for other purposes.

In some examples, the circumferential rings of the scaffolds of the present invention may have continuous perimeters or peripheries, usually circular perimeters, in which case the adjacent continuous rings are typically joined by axial links or by direct connection, e.g. by welding, fusing, tying, gluing, or otherwise adhering crowns on adjacent circumferential rings together for example. In other instances, at least some of the circumferential rings may have discontinuous perimeters where the end regions are joined to form a helical scaffold. In specific examples and embodiments, the axial links will be composed of a non-degradable metal, metal alloy, or other non-gradable material. Most commonly, such axial links will be patterned from the same tubular component (or material) used to form the scaffolds. Thus, many scaffolds will be formed as integral or monolithic structures from the same metal, metal alloy, or other material forming the stent.

Exemplary endoluminal prostheses of the present invention will often comprise scaffolds having repeating structural elements, such as circumferential rings, closed cells, or the like. Some or all of the circumferential rings, for example, may comprise similar or identical structures, e.g. a plurality of struts joined by crowns in similar or identical patterns (but can also have varying one or more of structure, pattern, and structural elements (thickness, width, shape), etc). The separation regions may be located in the struts, the crowns, or both. Often, at least one separation region will be located in a strut, and at least one to five struts within a ring will have separation regions. Alternatively or additionally, at least one separation region may be located in a crown and from one to five crowns within a ring may have separation regions. Often, however, most or all crowns will be free from separation regions as crowns or crown regions are subjected to high stresses as a scaffold is radially expanded by balloon inflation or otherwise from a crimped configuration to an expanded configuration. Such high stresses can result in premature formation of discontinuities in the scaffold, and loss of structural integrity of the scaffold. The struts are thus a preferred location for the formation of separation regions. Separation regions may also be formed in axial links or other regions of direct axial connection between adjacent circumferential rings. Separation regions in axial connectors between adjacent rings typically will not contribute to the radial compliance of the rings or the stented segment, or typically will not affect the radial strength of the rings or the scaffold, after the formation of discontinuities and are thus optional, and in many cases the axial links and other axial connector regions will be free from discontinuities, and remain intact. Thus, in many examples of the present invention, the scaffold will comprise or consist of a plurality of axially linked circumferential rings wherein the rings comprising or consisting of struts connected by crowns where the separation regions are formed in only the struts and not in the crowns (or crown region) or the axial links or other axial connector regions. Placing the separation regions in the circumferential rings, for example in struts and/or crowns, have the advantage of providing the ability to alter the circumferential properties of the stent at various time points after implantation. The circumferential arrangement of the rings makes the ring structures critical for various stent properties such as radial strength (flat plate), composite compliance of the stented segment, further expansion to a larger diameter after implantation, responding to vaso-dilatation, to name a few. For example, placing the separation regions in the circumferential ring structure provides the stent with altered, improved properties after the discontinuities form following implantation. The needs for luminal stent are inherently time dependent and different at different points in time. Over short period of time after implantation, the stent is required to have high radial strength to support the vessel open, then over the next period, after the tissue remodels and healing starts to occur or is completed, the requirement for high stent strength to maintain the vessel open is no longer necessary, on the contrary, having high strength may impair the physiological function of the vessel. While current non-degradable (non-corrodible) stents such as stainless steel alloy stents, cobalt chrome alloy stents, and Platinum iridium alloy stents, address the immediate initial high radial strength need of a vessel, they typically do not respond to the changing vessel requirements over time after implantation, wherein the vessel no longer requires high radial strength to maintain the vessel open, and by having such high radial strength maintained over time may irritate the vessel and cause further progression of disease or poor healing. A stent, preferably formed from non-degradable material (the stent can also be formed from degradable material), having separation regions within the stent rings which form discontinuities in the circumferential rings after implantation provide the stent with altered, improved properties after the discontinuities form following implantation. Such stents of the present invention are configured to provide high initial radial strength after expansion, where such high initial radial strength then decreases over time after implantation, helping to address the physiological needs of the vessel while maintaining the vessel open. Similarly, current non-degradable stents have low composite compliance of the stented segment "caging the vessel" typically for the life of the stent inhibiting the vessel natural vaso-motion ability, inhibiting the vessel's ability to respond to a vaso-dilator, or inhibiting the stented segment from expanding further to a larger diameter after implantation. The stent of the present invention having discontinuities formed within the circumferential rings following implantation may be configured to have higher (or increased) composite compliance after expansion allowing the stented segment of the vessel to respond to the natural variations in blood pressure (vasomotion), allowing the stent (or the stented segment) to further expand after the initial expansion (and after inward recoil if any), and maintaining the vessel's ability to respond to a vaso-dilator. The stent of the present invention may be configured to have increased composite compliance in the stented segment shortly after expansion or after a longer period of time after implantation.

There are advantages of placing the separation regions in the struts include they usually are lower stress regions of the ring and thus subject to less plastic deformation than the crowns. The location and size of the struts may also offer additional options for more types of separation regions because they are typically larger and have less torque than some other area of a stent, such as the crowns or other curved region of the ring. The struts typically can accommodate more changes within it (such as having separation regions) without impairing the function integrity of the stent, such as being able to expand the stent from a crimped configuration to an expanded configuration. The orientation of the strut changes (opening) as the stent is expanded, allowing for separation regions designs configured to take advantage of the strut angle prior to deployment that is configured to keep the separation region held together upon expansion of the stent, and opening the struts to an angle in the expanded stent configuration that allows for the desired movement direction of the separated strut element such as radial, circumferential, and/or axial movement.

There may be advantages to the placement of the separation regions in the crowns. As a ring expands or contracts, the crowns are typically subject to high bending moments (torques), causing high stress and plastic deformation. Joining elements that are resistant to high moments (torques) can be advantageously used in the crown regions. The motion of deployment in the crown region causes a rotation between adjacent struts. Joining elements that function to free this rotation, for example through a ball and socket like joint or other joints as depicted throughout the application, could lower the ring stiffness while maintaining cohesion between separable regions of the ring so that they maintain a "tubular" overall shape, matching the lumen even after separation. Having separation regions within the crown (in the crown) can have a higher composite compliance as maybe desired in some application. In addition, having separation regions in crowns may allow for use of other material that were not suitable for stent applications due to their limited mechanical properties such as elongation or brittleness, where a separation region in the crown may allow for expansion of the ring without breakage.

In said exemplary endoluminal prostheses, the struts may be joined by crowns to define an angle between them, typically referred as an "included angle." The included angle while the scaffold is in the crimped configuration will typically be small or sometimes even negative. The included angle will increase as the scaffold expands from the crimped configuration to an expanded stent configuration. Typically, the included angle in the crimped configuration of at least some struts joined by crowns ranges from −25° to +25°, more usually ranges from −15° to +55°. The included angle in the expanded configuration typically ranges from 35° to 180°, more usually ranging from 45° to 150°. When present in struts, the separation region(s) can be located anywhere along a length of a strut, typically being located in or about a middle of the struts, typically bisecting the struts. Similarly, when present in crowns, the separation region(s) can be formed at a point on the crown, typically being located about a middle of the crown, e.g. a location which bisects the crown which is typically a semicircle. In a preferred example, the separation region in the at least one strut is a pre-formed break (or gap) bisecting the at least one strut into two separate elements. Examples of the separation regions in the at least one strut include butt joint design, key and lock design, comb design, and/or other, wherein the bisected strut element adjacent to the separation region may have various geometry, shape, dimensions, pattern, configured to have a uniform stent expansion, and/or maintain the structural integrity of the stent upon expansion. The at least one bisected strut (separation region) is usually held together by one or more material as described throughout this application.

In preferred examples, at least some of the separation regions are located on or in "low stress regions" of at least some circumferential rings, i.e. those regions which experience less stress as the scaffold is expanded, either by a balloon or by self-expansion, such as strut regions. As the scaffold expands from a crimped configuration to an expanded configuration, the low stress regions, such as the struts, will experience less stress than high stress regions, such as the crowns, which deform as the result of concentrated stress as the scaffold radially expands. In a particular example, at least some circumferential rings each having one or more separation regions have an initial strength upon expansion of the stent in a physiologic environment, where the initial strength of at least some circumferential rings decreases after formation of discontinuities. In a preferred example, the one or more separation regions are preferably located in struts, where the struts undergo reduced (or minimal) stress as the scaffold is expanded from a crimped configuration to an expanded configuration, thus enhancing the structural integrity of the scaffolds during expansion by inhibiting all, or substantially all, formation of discontinuities during expansion.

The separation regions in the scaffolds of the endoluminal prostheses may take a variety of forms. For example, the separation regions may comprise a pre-formed break or gap in the crown region and/or in the strut region), thereby bisecting the crown and/or strut structural element into two separate sections of said crown and/or said strut) which is joined by, covered by, or embedded in a material which will degrade in the physiologic environment, typically a degradable polymer but sometimes a degradable metal or metal alloy, with many specific examples described in detail below. The degradable material comprising on or more material, in turn, can be provided in a variety of forms and geometries, including sleeves, coatings, solders, adhesives, laminations, and the like, which can be applied to at least one surface of the separation region, applied to at least one surface of the stent, applied to all separation regions surfaces, and/or applied to all stent surfaces. In some examples, at least one surface, most, or all of a separation region surface or a scaffold surface can be coated or laminated with a degradable material. In a preferred example, the material fills all the space between opposed surfaces of a separation region, and the stent abluminal, and luminal surfaces, and acts as an adhesive, glue, or attachment element, holding the surfaces together to maintain the stent structural integrity upon expansion of the stent. In other instances, the degradable material can be located on or in only the separation region and optionally a short distance on either side thereof, e.g. 2 mm, 1 mm, 0.5 mm, or the like. In yet another example, a non-degradable material comprising one or more non-degradable material can additionally be applied to at least one separation region surface and/or additionally applied to at least one stent surface, and/or additionally applied to all separation region surfaces and/or additionally applied to all stent surfaces. The non-degradable material can be applied before the degradable material, or applied after the degradable material. In a preferred example, the degradable and/or the non-degradable material placed on the non-degradable stent are polymeric material. In another example, the polymeric material (degradable and/or non-degradable) contains at least one drug, which may be coated on at least one surface of the stent, preferably to cover at least the abluminal surface of the stent.

In some examples, the separation region comprises a non-degradable material which relaxes, expands, becomes more flexible, or softened to create a discontinuity in the circumferential ring such that the ring continues to be joined but exhibits increased ability to move in various directions at the discontinuity. This separation region may be formed by incorporating the flexible non-degradable material or polymer into the separation regions (gaps, breaks or interruptions) of the scaffold. In some examples a degradable or non-degradable material or polymer is coated on the scaffold, covering all of the scaffold or the separation regions. In the case of a degradable material, it degrades after expansion of the scaffold in physiologic conditions, in some cases releasing a drug which was incorporated into the coating and/or degrading at the separation regions to allow the formation of the discontinuities. When the coating is a non-degradable material, such as a polymer, the coating may cover the whole scaffold or some regions of the scaffold. The non-degradable material may be chosen to cover the separation region, which may be a gap or break in the scaffold, such that the non-degradable material softens after expansion of the scaffold in physiologic conditions and permits increased flexibility and movement at the discontinuity.

In a particular example, the degradable material can be applied by spray coating, dip coating, sleeve encapsulating, printing, soldering, gluing with an adhesive, or the like. The degradable material can be polymeric, metallic, or any other degradable material, as described in greater detail elsewhere herein. Typically, the degradable material has sufficient strength to hold the separation region together to immobilize adjacent structural elements in a separation region while the scaffold of the stent or other prosthesis is expanding from a crimped configuration to an expanded configuration in a physiologic environment. The degradable material usually degrades after expansion of the stent from a crimped configuration to the expanded configuration. The degradable material may have a thickness that is substantially the same as that of adjacent regions of the non-degradable structural elements, i.e. the degradable material will fill the gap or other space between the adjacent structural elements but will not extend over these adjacent regions. In other examples, however, the degradable material may have a thickness adjacent to said separation region, ranging from 5 μm to 30 μm thicker than the non-degradable structural elements thickness adjacent to said separation region, and may extend over said adjacent regions, may extend over, or cover, at least one surface of the stent, or may covers all stent surfaces. The degradable material thickness can be substantially the same for all separation regions or can have different thicknesses, for example, to control timing of the formation of discontinuities.

In preferred examples, the degradable material covers the non-degradable structural elements of the stent substantially uniformly, i.e. having substantially the same thickness over substantially all abluminal surfaces of the structural elements and having the same thickness for substantially all luminal surfaces of the structural elements, but the degradable material can also have different thicknesses for different surfaces of the scaffold structural elements. Typically, a coating or other cover over abluminal and/or luminal surface regions of the scaffold structural elements ranges from 3 μm to 50 μm, more usually ranges from 5 μm to 30 μm. The degradable material may cover and/or fill the separation region(s) only, may cover and/or fill the separation region and surface(s) of adjacent structural element(s), may cover and/or fill the separation region as well as the surfaces of adjacent structural element(s) and adjacent ring(s), or may cover the entire stent and fill all separation regions.

Some or all separation regions can be configured to form discontinuities at about the same time, or at different time periods, as described elsewhere herein. In preferred examples, the degradable material degrades after a period ranging from 1 month to two years after implantation, preferably ranging from 2 months to one year after implantation, more preferably ranging from 3 months to 9 months after implantation.

In another preferred example, a non-degradable scaffold having separation regions held together by at least one degradable material will have an initial stent mean volume (or mean area) after expansion and after initial inward recoil after expansion if any, and wherein said mean area (or mean volume) is from 0.75% to 0.90% of the initial stent mean volume (or mean area), substantially the same (maintained) initial mean stent volume (or mean stent area), or increased mean stent area (or mean stent volume), after degradation of said degradable material after implantation of the stent, and/or within a period ranging from 1 month to 9 months after implantation, in a physiologic environment.

In another example, a non-degradable scaffold (or a stent), or other prosthesis comprises a plurality of circumferential rings having one or more separation regions along the path of each of said circumferential rings. The scaffold has an initial strength, sufficient to maintain a mean stent area (or mean stent volume) after expansion and after initial inward recoil (if any), and the scaffold after formation of discontinuities exhibits a decrease in said initial strength while substantially maintaining or increasing the stent mean area (or mean volume), in a physiologic environment. Such non-degradable scaffolds typically will have degradable material which can be stretchable (elastic), usually sufficiently stretchable (elastic) to hold structural elements adjacent to separation regions together upon expansion of the scaffold, and/or sufficiently stretchable (elastic) to allow the scaffold, or a scaffold segment, to accommodate, or respond to, vaso-motion or vaso-dilatation after deployment, or after deployment and before degradation of the degradable material, or after degradation of the degradable material. The stent or other prosthesis in such examples may accommodate (or exhibit) an increase in diameter (or a change in diameter) in one or more scaffold segments (or in the stented segment) when a vaso-dilator is used, or when a change in pressure of about 180 mmHg is applied. Such change in diameter ranges from 0.05 mm to 0.5 mm, more typically 0.7 mm to 0.4 mm, after expansion under physiologic conditions. In another example, the elastic material adjacent (including in, on, around) at least one or more separation regions is non-degradable material, such as a polymeric material, such as polyurethane material. In a preferred example, the non-degradable material(s) have sufficient strength to contain the separation region together upon initial deployment of the stent from a crimped configuration to an expanded configuration, said elastic non-degradable material allowing the one or more rings or stented segment to further expand and/or contract, after initial expansion of the stent, and/or after formation of discontinuities, under physiologic conditions.

In yet another example, the separation regions may comprise an elastic material disposed in, on, and/or adjacent to a gap, space, or other break formed in a structural element of the ring, usually a strut, and/or a crown. The elastic material typically remains intact after expansion of the scaffold in the physiologic environment, and the elastic material may act as an "expansion joint" allowing expansion and in some cases contraction of the ring in order to increase radial compliance under physiologic conditions. In some examples, such expansion joints will be immobilized by a bio absorbable material in the form of a coating, a sleeve, an adhesive, or any other form as described elsewhere herein connecting or bonding or holding together adjacent separated regions of the scaffold while the scaffold is being deployed. In other examples, the one or more expansion joints will not be immobilized and the elastic material will provide sufficient strength to remain intact during balloon or other expansion while still providing a desired radial compliance or strength after expansion. The elastic material in separation regions may be utilized alone, or in combination with other separation regions immobilized during balloon or other expansion by means such as degradable material.

In still other exemplary embodiments, the separation regions may comprise "key-and-lock" junctions which are immobilized during expansion but configured to separate after the initial expansion in the physiologic environment. In some instances, the key-and-lock junctions may have combed interface surfaces that allow separation in circumferential and/or radial directions but which inhibit separation in an axial direction. In other instances, the key-and-lock junction will have a smooth or straight interface surfaces that allows separation in circumferential, radial and/or axial directions. In other cases, the key-and-lock junction will have non straight interface surface regions such as "saw", "v", "u", inverted "v", inverted "u", or other surface region interface, where such non straight surface region interface can have or more surface region interfaces and where the one or more surface region interfaces can have the same or different shapes, sizes, thickness, lengths, widths. Such key-and-lock junctions are typically immobilized during expansion but configured to separate after the initial expansion in the physiologic environment, for example being covered by, embedded in, or joined by a degradable material such as a biodegradable polymer.

In still other examples, the separation regions of the present invention may comprise a butt joint joined by, covered by, or embedded in the material which degrades in the physiologic environment.

The scaffolds of the endoluminal prostheses of the present invention will comprise a non-degradable material, typically a metal or a metal alloy material. The discontinuities forming in the metal scaffolds allow the scaffolds to further expand after recoil from an initial expansion. The discontinuities will typically further allow the scaffold to further expand to an expansion diameter larger than an initial expansion diameter.

In some embodiments and examples, the circumferential rings may be substantially perpendicular to a longitudinal axis of the scaffold in the expanded and/or crimped configurations. In other embodiments and examples, the circumferential rings may be inclined at an angle relative to the longitudinal axis of the scaffold in one or both the expanded and crimped configurations. In still further examples and embodiments, successive circumferential rings will be joined end-to-end in a continuous helical pattern where each ring defines a single turn of the helix.

In another aspect or example, the present invention provides a variably compliant stent (or a controllable compliance stent, or an increasing compliance stent), scaffold, or other luminal or valve prosthesis comprising a non-degradable metal or metal alloy scaffold, such as cobalt chrome alloys, platinum iridium alloys, and stainless steel alloys, expandable from a crimped configuration to an expanded larger configuration. The scaffold has sufficient strength to support a vascular lumen after expansion, preferably for at least a time period after expansion (or implantation) sufficient for the vessel to heal, and/or for at least a time period after expansion when the risk of further, or additional, vascular lumen inward recoil (after any initial inward recoil of the stent following initial expansion) risk diminishes or is reduced, and/or for at least a time period ranging from 30 days to 6 months after implantation, and/or for at least a time period ranging from 60 days to 6 months after implantation. The stent in some examples has an initial strength after expansion (or immediately after expansion or within 24 hours after implantation (expansion) or within 6 months after implantation (expansion), or within 3 months after implantation or within two months after implantation), said initial strength being sufficient to support a body lumen and where the stent is expanded in air or under physiologic conditions (such as water at 37° C.), then under physiological conditions, the initial strength decreases to a second strength, lower than the initial strength, preferably decreasing within a period ranging from 3 days to 6 months, preferably said initial strength decreases to a second lower strength in a period ranging from 30 days to 6 months. The decrease in strength to said second strength occurs without mass loss, or without degradation of the non-degradable metal or non-degradable metal alloy. The second lower strength in some examples ranges from 10% to 100% of the initial strength, or ranges from 10% to 90% of the initial strength, or ranges from 20% to 80% of the initial strength, or ranges from 30% to 60% of the initial strength. The stent in some other examples has an initial strength after expansion (or immediately after expansion or within 1 hour after implantation (expansion) or within 2 hours after implantation, said initial strength being sufficient to support a body lumen and where the stent is expanded in air or under physiologic conditions, then the initial strength under physiological conditions increases to a first strength, larger than the initial strength typically by 5% to 50%, preferably larger than the initial strength by 10% to 30%, said first strength occurring after initial strength (or after initial strength measurement after implantation (expansion), or after one hour after implantation, or after two hours after implantation, or between one hour after implantation and one month after implantation), wherein said initial strength increases under physiological conditions to a first larger strength then said first strength decreases to a second strength, lower than the initial strength under the same or similar physiological conditions, said first strength preferably decreasing to below initial strength (second strength) within a period ranging from 15 days to 9 months, preferably said first strength decreases to the second lower strength (lower than initial strength) in a period ranging from 30 days to 6 months (or within a period ranging from 60 days to 6 months). The decrease in strength to said second strength being (or occurs) without degradation of the non-degradable metal or metal alloy (without mass loss). The second lower strength in some examples ranges from 10% to 100% of the initial strength, or ranges from 20% to 85% of the initial strength, or ranges from 30% to 65% of the initial strength. Immediately after deployment (or expansion), the scaffold has a composite compliance when measured in the mock vessel (or a thin tube) of no greater than 1%, typically no greater than 0.7%, and often no greater than about 0.5%, typically being in a range from 0.1% to 1%, usually from 0.2% to 0.5%. After expansion under physiologic conditions (including simulated physiologic conditions) or after exposure to vascular conditions, the composite compliance or the stent compliance when measured in a mock vessel will increase to at least 1.2%, often to at least 1.5%, and sometimes to at least 2% or greater. In other examples of the variably compliant stent prosthesis, the composite compliance of the stent when measured in a mock vessel may increase by a factor of at least two, often at least three, and sometimes at least four, five, ten, or more, when compared to an initial composite compliance when measured in the mock vessel.

Such variably compliant stent prostheses may have a variety of specific design features which provide the variable compliance. As described in greater detail below, for example, the stent prostheses comprising non-degradable metal or metal allow scaffolds having separation regions which separate or form discontinuities, after exposure to vascular conditions for a threshold time. For example, some of the separation regions may be initially prevented from separating by a bioabsorbable material which degrades over time when exposed to vascular conditions. More specifically, the bioabsorbable material may be in the form of a coating, a sleeve, an adhesive, or any other form suitable for initially connecting or bonding or holding together adjacent separated regions of the scaffold (or of the scaffold separated struts, or of the scaffold separated crowns, or of the scaffold separated structural elements) together. The bioabsorbable material may degrade over a time period ranging from 30 days to 3 years, often from 3 months to 2 years, and more often from 3 months to 1 year when exposed to the vascular conditions. For purposes of determining whether the stent meets these conditions, the stent may be exposed in vitro to vascular conditions (physiological conditions), as defined elsewhere herein' which are intended to mimic those conditions experienced when implanted in a human blood vessel or lumen. It can also be tested after in vivo vascular conditions. It can also be tested using in vitro test under physiologic conditions as described in the application. In some other examples, one or more rings containing one or more separation regions contain non-degradable material, preferably elastic material, preferably non-degradable polymeric material. The non-degradable material can have sufficient strength to hold such separation region together upon expansion of the stent, or together with another material (such as a degradable material, or other non-degradable material). The elastic non-degradable material can provide for a desired radial compliance immediately after expansion, or within 24 hours after expansion) such as responding to use of nitroglycerin or another vaso-dilator by expanding one or more stent segments (or rings, or the stented segment)

containing the elastic material. The elastic non-degradable material in this example controls desired compliance, control further expansion after initial expansion and inward recoil, controls desired radial strength, and/or other mechanical properties of the stent, immediately after the initial expansion, and/or within 30 minutes after the initial expansion (or implantation), and/or within 24 hours after initial expansion (implantation). The stent can additionally comprise one or more rings (the same or different rings containing the separation regions containing the non-degradable elastic material) containing one or more separation regions, wherein the one or more additional separation regions contain degradable material (such as degradable polymeric material). The one or more separation regions containing the non-degradable material typically inhibits forming discontinuities after expansion in physiologic environment but allow for the ring containing said separation region (or the stent segment) to have a desired compliance, or allows for further expansion after initial recoil after initial expansion, or allows for responding of the stented segment (or the one or more rings) to a vaso-dilator, due to the stretching or elasticity of the non-degradable material. In yet another example, all or substantially all separation regions on one or more rings (or all separation region contained on the stent) contain non-degradable material, wherein the non-degradable material inhibits formation of discontinuities, but allows the stent (or the one or more rings) to have a desired compliance and/or radial strength, and or responding to a vaso-dilator, due to the stretching of the material, elasticity, and/or other material property.

In other specific examples and embodiments, the non-degradable metal or metal alloy scaffold may comprise regions reinforced with a reinforcement material which degrades after exposure to vascular conditions for the threshold time period described above or elsewhere. The reinforcement material may comprise a bioabsorbable material which degrades over said time period. For example, the reinforcement material may fill voids in a crown and/or a strut of the non-degradable metal or metal allow scaffold. Still further alternatively, the reinforcement material may cover or coat at least a region of a surface of the non-degradable metal or metal alloy scaffold.

In addition to displaying the variable compliance, as described above and/or elsewhere, the variably compliant stents of the present invention will display sufficient radial strength after expansion and implantation to hold the vascular lumen open and to inhibit or prevent vascular recoil after initial recoil after initial expansion, for some minimum threshold of time, usually at least 30 days, more usually at least 60 days, and often at least 90 days or longer. Typically, for example for a coronary artery stent, the stent strength, measured using the flat plate compression of 10% test for example, (or the initial stent strength of the expanded stent) will be in the range from 0.030 Newton per millimeter of stent length to 0.14 Newton per millimeter of stent length, particularly being from 0.04 Newton per millimeter of stent length to 0.1 Newton per millimeter of stent length, and often being from 0.05 Newton per mm of stent length to 0.1 Newton per millimeter of stent length, preferably when such stent strength is measured, using the flat plate 10% compression, after the stent is expanded to nominal stent expanded diameter. Usually, although not necessarily, the radial strength of the stent (scaffold) will decrease (in some other example, the initial radial strength of the expanded stent increases to a first strength larger than initial strength before decreasing to a second strength smaller than the initial expanded stent strength) after expansion and exposure to vascular conditions as the composite compliance increases from an initial composite compliance (in some other example, the initial composite compliance decreases before increasing). The decrease in radial strength occurs concurrently (or correspondingly, or at a similar time, or at the same time, or approximately about the same time) with the increase in radial compliance. In most cases, the radial compliance and the radial strength of the expanded stent will vary inversely to each other. Often, the radial strength of the stent scaffolds will decrease in a range from 20% to 100% of the initial radial strength which typically is measured immediately after expansion or shortly after expansion (such as within an hour, after expansion) and exposure to vascular conditions, sometimes decreasing in the range from 20% to 80%, or in some cases, the initial radial strength of the expanded stent increases before decreasing to substantially the initial strength or to a lower strength than the initial strength while the compliance increases from an initial compliance after implantation in physiological conditions, or in some other cases the initial radial strength of the expanded stent is substantially maintained while the compliance increases after expansion in physiological conditions from an initial compliance.

In a particular example or embodiment of the variably compliant stent, the non-degradable metal or metal alloy scaffold has a nominal expanded diameter (the diameter to which the stent or other scaffold is intended to be expanded by a balloon), and the strength and composite compliance are both measured after the stent has been expanded to a diameter which is from 80% to 120% of the nominal expanded diameter. More commonly, the strength and composite compliance will be measured when the stent has been expanded to 100% of the nominal extended diameter.

In other examples, the stent has sufficient strength after deployment to an expanded configuration to support a body lumen, has inward recoil from 1% and 10% after deployment, and where the stent exhibits compliance of 1% or larger than 1% after deployment, and/or having a stent that has sufficient strength after deployment to support a body lumen, and has an inward recoil from 1% to 10% after deployment to the expanded configuration, and then where the stent exhibits outward recoil ranging from 3% to 20% after deployment and after said inward recoil, under physiologic conditions, or under the use of vaso-dilators.

In some other examples, the composite compliance magnitude under physiologic conditions (including vaso-dilator use) ranges from 0.05 mm to 0.5 mm, preferably ranges from 0.07 mm to 0.4 mm, more preferably ranges from 0.1 mm to 0.4 mm. The magnitude of such diameter changes are measured in one or more of the stented segment, or the mean of the stented segment, or preferably in a region about the middle of the stented segment.

In other examples, the stent outward recoil magnitude under physiologic conditions ranges from 0.05 mm to 0.5 mm, preferably ranges from 0.07 mm to 0.4 mm, more preferably ranges from 0.1 mm to 0.4 mm.

In another aspect or example, the present invention provides polymeric prostheses with reinforcement elements and methods for their use and fabrication. An endoluminal prosthesis comprises a circumferential scaffold patterned from a biodegradable polymer and having expansion regions which deform as the circumferential scaffold expands from a small diameter configuration to a larger diameter configuration. In one example, the endoluminal prostheses of the present invention may comprise coronary stent prosthesis. In another example, the endoluminal prostheses of the present invention may comprise a vascular stent prosthesis. In yet another example the stent prosthesis is a non-vascular stent prosthesis. Reinforcement elements are coupled to at least some regions of the circumferential scaffold to stiffen the circumferential scaffold after the scaffold has been expanded to the larger diameter configuration. The reinforcement elements will preferably be deformable and can be degradable (which also includes corrodible and erodible) or non-degradable (which also included non-corrodible and non-erodible). In particular, the reinforcement elements may be malleable or elastic, may comprise metals and metal alloys, may comprise polymers, or may be formed in whole or in part from other materials having mechanical properties that can reinforce the expansion regions and/or other structures of the stent prosthesis as described below or in this application.

The circumferential scaffolds in one example will typically comprise stent scaffolds of the type patterned from a tube or cylinder formed in whole or in part from a biodegradable polymer. The tube or cylinder can be formed by extrusion, dipping, spraying, molding, or printing. The tube or cylinder of the biodegradable polymer will be patterned using any one of many techniques well known in the art of forming stents from polymers, such as laser cutting, photo-lithography, three-dimensional printing, stereolithography (SLA), and the like. The expansion regions will typically comprise joints, hinges, crowns, curves, bends, and/or deformable feature or structures or structural elements which may be joined to adjacent struts, beams, or other less-deformable or non-deformable features or structures or structural elements so that expansion region may open to increase an angle between the adjacent less deformable or non-deformable regions or structural elements, the struts for example, as the diameter of the circumferential scaffold is expanded (or is increased). Stents can also be formed from a wire (solid or hollow) or a fiber, and patterned or braided.

The reinforcement elements, for example, may be provided in order to improve the stiffness, crush strength, crush resistance strength, radial strength, hoop strength, or the like, of the circumferential scaffold upon or after the scaffold has been expanded to the larger diameter configuration from a crimped configuration. In particular, the one or more reinforcement elements may be coupled to one or more expansion regions and/or other region such as struts and/or links on the circumferential scaffold in order to enhance such strength, particularly as measured by a "plate" or "flat plate" test for example as commonly known in the art where the circumferential scaffold is placed between parallel, space-apart plates and a force needed to reduce the expanded scaffold diameter by a pre-determined amount (or % such as 10% compression force (N) or N/mm to normalize to stent length) is measured. Other type of tests to measure radial strength can also be utilized (and measured in psi for example) as commonly known in the art.

Most commonly in another example, the reinforcement elements will be coupled to at least some of the joints, hinges, crowns, bends, or other expansion regions so that such expansion regions, after expansion or opening, are better able to resist closing forces (or crushing resistance force) than they would be without the addition of the reinforcement elements. It will be appreciated that the expansion regions undergo deformation as the circumferential scaffold is expanded and that the presence of the reinforcement elements will open with the expansion regions so that, once opened, the reinforcement elements will assist the scaffold to resist closure forces exerted by the blood vessel or other body lumen or body lumen lesions into which the scaffold has been implanted. In addition to the deformable expansion regions the circumferential scaffold will typically also include non-deformable or less deformable regions which usually retain or substantially retain their shape as the circumferential scaffold is expanded. The reinforcement elements may also be coupled to at least some of these non-deformable or less-deformable regions. In many examples or most embodiments, the expansion regions will be curved joints, crowns, hinges, bends, or the like, as described above, while the non-deformable regions will typically be struts, straight struts, or other usually linear elements of the scaffold, but sometimes may have non-linear or other shapes such as wave, S-, M-, V-, wavy liner, or wavy nonlinear, and U-shapes. Typically, expansion of the circumferential scaffolds of the endoluminal prostheses will be effected by inflatable balloons or other conventional apparatus, but in other cases the circumferential scaffold could be fabricated from an elastic polymer or other material and can be self-expanding where expansion is achieved by release of the circumferential scaffold from constraint.

In one example, the reinforcement elements increase the stiffness or strength of the reinforced region, the reinforced rings or expansion regions, and/or the stent.

In another example the reinforcement elements increase the strength of at least one region of the stent by a range from 15% to 100%, preferably increase the strength by a range from 25% to 150%, more preferably increases the strength by a range from 25% to 200%.

In another example the reinforcement elements increase the strength of the stent by a range from 0.015 N/mm of stent length to 0.035 N/mm of stent length, preferably increases the strength of the stent by a range from 0.015 N/mm to 0.05 N/mm of stent length, more preferably increase the strength of the stent by a range from 0.015 N/mm to 0.09 N/mm of stent length, when measure using flat plate test 10% compression. For example, the strength (using flat plate test method for example) of 0.015 N/mm for a 3.0 mm stent by 28 mm stent length equates to 0.015 N/mm times 28 mm (stent length) which equals to 0.42N strength.

In another example the stent having reinforcement elements has a strength ranging from 0.03 N/mm to 0.06 N/mm of stent length, preferably has strength ranging from 0.025 N/mm to 0.07 N/mm of stent length, more preferably has a strength ranging from 0.025 N/mm to 0.09 N/mm of stent length, when measuring strength using flat plate test 10% compression. For example, a 0.03 N/mm stent length strength (using flat plate test for example) for a 3.5 mm diameter stent by 18 mm stent length equates to 0.03 N/mm times 18 mm of stent length which equals 0.54N.

In another example, the reinforcement elements decrease initial inward recoil (or recoil after expansion or recoil after deployment) or decrease subsequent inward recoil (recoil after implantation, or recoil after procedure completion, or recoil within 30 days from implantation, or recoil within 6 months from implantation, or recoil after implantation initial recoil and 6 months' time period, or recoil after implantation initial recoil and 1 day, or recoil after implantation recoil and 30 days).

In another example, the reinforcement elements decrease the inward recoil of the stent to a range from 1% to 10%, preferable to a range from 1% to 7%, more preferably to a range from 1% to 5%, after implantation. In another example, the reinforcement elements decrease the subsequent inward recoil of the stent to a range from zero to 5%, preferably to a range from zero to 3%, more preferably to a range from zero to 2%, at the various time points discussed.

In another example, the stent having reinforcement elements has an inward recoil ranging from 1% to 10%, preferable ranging from 1% to 7%, more preferably ranging from 1% to 5%, after expansion or deployment. In another example, the stent having reinforcement elements has subsequent inward recoil ranging from zero to 5%, preferably ranging from zero to 3%, more preferably to a range from zero to 2%, most preferably said stents have substantially zero inward subsequent recoil (or said stent substantially maintain the initial recoil after implantation), at the various time points discussed.

In another example, at least some reinforcement elements are coupled to at least some expansion regions on at least some rings of the stent, wherein the stent expands from a crimped configuration to an expanded larger configuration, and wherein the reinforcement elements provide sufficient strength in the expanded stent configuration to support a body lumen.

The reinforcement elements in one example may be coupled to the circumferential scaffold in a large variety of patterns. The reinforcement elements may be attached to some or all of the expansion regions while not necessarily being attached to any of the non-deformable or less deformable regions. In particular, the reinforcement elements may be attached to one, two, three, or more of the expansion regions of the scaffold or scaffold ring. In some examples or embodiments, the reinforcement elements are attached to all of the expansion regions of the scaffold or scaffold ring, and in other preferred examples or embodiments, the reinforcement elements are attached to all but one of the expansion regions of the scaffold or scaffold ring. In other examples or embodiments, the reinforcement elements may be attached to both expansion regions as well as to some or all of the non-deformable or less-deformable regions. In other examples or embodiments, the reinforcement elements may be attached to at least some expansion regions extending at least partially into the non-deformable or less-deformable regions. In other examples or embodiments, the reinforcement elements may be attached to at least some expansion regions extending to at least a mid-point of the non-deformable or less-deformable regions length. In other examples or embodiments, the reinforcement elements may be attached to at least some expansion regions extending substantially the entire length of the non-deformable or less-deformable regions. The reinforcement elements may be embedded (fully or partially) into the material of the circumferential scaffold, for example being embedded into at least some of the expansion regions (or embedded into any of the surface regions of the expansion regions such as abluminal surface region, luminal surface region, and/or side surface regions). Alternatively, the reinforcement elements in another example may be attached or otherwise disposed on the scaffold so that they lie at least partly on an exterior of least some of the expansion or non-deformable regions.

The reinforcement elements can be coupled to the stent prosthesis (including or comprising embedded, attached, or disposed on) after patterning the stent, where the coupling of the reinforcement elements to the patterned stent regions is performed by a variety of ways such as press fitting the reinforcement element onto the stent or stent region, creating or pre-forming a groove or a space or a slot by a variety of means such as laser or mechanical or chemical means and then press fitting the reinforcement elements onto the stent or stent region, dissolving the polymer material partially or softening the material to press fit or insert, to contain the reinforcement element, and/or adhesively attaching the reinforcement elements to the patterned structure surface or region (such as polymeric structure) to name few methods. Alternatively, the reinforcement elements can be coupled to the stent before patterning such as coupled to the tube (such as a polymeric tube) from which the stent is patterned, and wherein the tube and reinforcement elements are patterned together (or separately) to form a patterned stent using the methods discussed above and/or throughout the application and the patterning means discussed in the application such as laser patterning. The reinforcement elements can also be formed with the tube (such as polymeric tube) that forms the stent using dipping, spraying, or molding for example, or the reinforcement element is one or more wires (solid or hollow) that is patterned or woven into a stent, or the reinforcement elements can be a wire (solid or hollow) encapsulated by a material (such as the main polymer material) and is woven or patterned into a stent. The reinforcement elements are coupled as pieces, solid wire, tube, or patterned structure. The reinforcement elements are coupled to the stent structure (such as the polymeric stent material) while having discontinuities or separation regions before coupling to the stent prosthesis as described in this application to uncage the lumen and/or allow scaffold or lumen enlargement, or the discontinuities or separation regions are formed onto the reinforcement elements (through a variety of means such as laser cutting, dissolving, cutting, etc.,) after coupling to the stent, wire, or tube, and then the discontinuities or separation regions are reconnected or held together by means such as adhesives, main polymer, different polymer, sleeve, or other means that holds the stent structural element together upon expansion from a crimped configuration to an expanded larger configuration.

Typically, stents including the circumferential scaffolds will comprise a plurality of adjacent rings where the expansion regions comprise curved, bent, hinged, jointed, crowns, or other regions of the rings which straighten or open as the scaffold is radially expanded. Most typically, such rings will be sinusoidal, serpentine rings, zig-zag rings, diamond (Palmaz-type) rings, or any other type of radially expandable stent ring known in the vascular stent art, including open cell design, closed cell design, or combination, or other known to one skilled in the art. Usually, individual rings will be oriented in planes which are oriented perpendicularly to a central axis, or perpendicular to a longitudinal axis, of the circumferential scaffold in the crimped or expanded configuration. In other embodiments or examples, however, the planes of the rings or expansion regions or circumferential structural elements can be inclined at an angle relative to the scaffold longitudinal axis (e.g. from 1° to 85°, or from 1° to 45°, or from 10° to 75°, or from 25° to 75°, or usually from 5° to 15°), and in some cases, the "rings" or expansion regions or circumferential structural elements may be formed in a helical structure, or joined in a continuous helical arrangement. The individual rings, or adjacent turns of a helical stent structure, may be axially joined together by axial links between hinges, crowns, beams, struts and/or other components of the rings or turns. In other example, the scaffold can be formed from a wire (solid or hollow in at least some regions) and patterned into a stent, where adjacent rings are connected in one or more locations (or regions). In one example stents comprising rings having an orientation ranging from being perpendicular to the longitudinal axis of the stent, to having an angle to such longitudinal axis of the stent ranging from 1° to 85°, to having a helical configuration ring pattern, wherein at least some rings have at least one separation region. In some other example, a stent, such as a valve containing stent, can comprise one or more circumferential rings (or one or more circumferential structural elements). In such example, the stent comprises one or more separation regions, hinges, or other structures as described in this application. In a particular preferred example, the stent comprises one or more circumferential rings, wherein the one or more rings comprise a plurality of struts joined by crowns. Usually, every two struts are joined by a crown, or every crown joins two struts, on a ring. At least some, preferably all rings are joined to adjacent rings by at least one axial link, or by joining one or more crown regions (using solder, adhesive, or fusing of the material) of adjacent rings.

The reinforcement elements in one example may be disposed in segments about the rings, or alternatively may be disposed to extend around substantially an entire circumferential length of at least some of the rings. The reinforcement element(s), however, will be configured to have or form at least one break, discontinuity, or separation region, in their circumferential direction or length so that the reinforcement elements can circumferentially separate or/and uncage, or incrementally expand after deployment as the blood vessel or other body lumen remodels during the healing process. In this way, the reinforcement elements will be able to provide a desired initial strength and resistance to collapse during deployment and/or an initial period after deployment, but will not constrain or inhibit the scaffold from uncaging and/or expanding, and/or the blood vessel/lumen from expanding after the biodegradable polymer (such as the main polymer) of the circumferential scaffold has softened, and/or the polymer's molecular weight has decreased, and/or the polymer has degraded, and/or the polymer has at least partly eroded (including degraded or corroded) leaving the reinforcement elements (which have not eroded or not fully eroded) free to further expand in response to vessel remodeling or other physiologic conditions.

The circumferential scaffolds of the present invention may include some or all conventional features found in the patterns of conventional stents. For example, the stent patterns may include axial links which hold adjacent rings together to form closed-cells of a type well known in the stent arts. In such cases, the reinforcement elements for example may be coupled to at least some of the axial links, in which cases a plurality of individual reinforcement elements may together form box structures which are coupled to substantially parallel rings as well as substantially parallel axial links. In one example the reinforcement element is coupled to at least one axial link has at least one break.

The reinforcement elements in one example can be individual pieces having the shape or geometry, or substantially having the shape or geometry, or having smaller shape or geometry, or having larger shape or geometry, or having different shapes or geometry, from the structural element to be coupled to such as crowns, struts, and/or links. Examples of shapes include square, round, rectangle, triangle, semicircle, and other shapes. In these examples the pieces are discontinuous or discrete pieces (either in contact or not with other adjacent reinforcement elements). The pieces can have deburred end regions, rounded end regions, ball end region, or other types or geometries to prevent inflammation after the polymeric material has degraded and or resorbed. In a preferred example, substantially all of the expansion regions of at least some rings have reinforcement elements pieces coupled to said expansion regions wherein the reinforcement elements pieces span substantially the entire expansion regions segment or at least part of the expansion regions segment. In another example, substantially all of the expansion regions of at least some rings have reinforcement elements pieces coupled to said expansion regions wherein the reinforcement elements pieces span the entire expansion regions segment and extend at least partially into the non-deformable or substantially non deformable (such as struts) segments. In a preferred example, the reinforcement elements, the reinforcement elements pieces' shape and/or geometry generally substantially mimic or contour to the shape and/or geometry of the structural elements to be coupled to. The reinforcement elements pieces in one example can be larger size in at least one dimension, smaller size in at least one dimension, or the same size in at least one dimension to the structural element the pieces are coupled to. Reinforcement elements pieces coupled to at least some structural elements of a biodegradable material allow the stent to further expand, and/or allows the stent to uncage, and/or allows the vessel to exhibit vaso-motion or vaso-dilation, after implantation (or after expansion or after deployment) under physiologic conditions (and/or through the introduction of therapeutic agents such as nitro) while stiffening or strengthening the stent upon expansion of the stent to support a body lumen.

In another example, the reinforcement elements can be one or more reinforcement elements segments coupled to at least some rings and/or other structural elements such as a link. For example, a reinforcement element segment is coupled to (or spans) one crown and one strut on a ring, and/or coupled to (or spans) one crown and one strut on a ring, and one link, and/or coupled to (or spans) multiple crowns and struts on a ring, and multiple links. In another example, the reinforcement elements segments form a pattern on the stent, said pattern is usually symmetrical pattern (but can also be non-symmetrical pattern), said pattern can be a variety of shapes including closed patterns and open pattern. When the reinforcement element segment span the entire structural elements of a ring crowns and/or struts, said reinforcement element segment would have at least one break or discontinuity in said crowns and/or struts (said break or discontinuity is formed before or after coupling to said structural element) to allow the stent to further expand after degradation of the polymeric material, or to allow the stent to uncage, or to allow the vessel to have vaso-motion, or to allow the vessel to have vaso-dilation, after expansion (or after deployment), under physiologic conditions (and/or through the introduction of therapeutic agents such as nitro), said reinforcement elements segment stiffens or strengthens the stent, by having sufficient strength to support a body lumen after deployment.

In another example, the reinforcement elements can be one or more reinforcement elements segments coupled to at least some rings (or circumferential structural elements), or coupled to substantially all rings (or circumferential elements). When the reinforcement elements, or reinforcement element segment spans the entire ring length (or circumferential structural element) without breaks, discontinuities, or separation region, or spans more than one ring entire lengths without breaks, discontinuities, or separation regions, or when the reinforcement elements span substantially the entire stent without breaks, discontinuities, or separation regions, said reinforcement element(s), or reinforcement element segment(s) would have at least one or more regions along the circumferential path for each ring (crowns or struts for example), and/or one or more crown regions along the circumferential path of each ring, and/or one or more strut regions along the circumferential path of each ring, wherein the one or more said region contain a reinforcement element (or one or more reinforcement elements) having a cross sectional area ranging from 200 micron squared to 4000 micron squared, preferably a cross sectional area ranging from 400 micron squared to 3000 microns squared, more preferably a cross sectional area ranging from 700 micron squared to 2500 micron squared, wherein the one or more said regions allow the said one or more rings, and/or the stent, to further expand after degradation of the polymeric material (or metallic degradable material), and/or allow the stent to uncage, and/or allow the vessel to have vaso-motion, and/or allow the vessel to have vaso-dilation, and/or allow the stent to have radial strain ranging between 1% and 5% at 3.0 mm expanded diameter, after stent expansion (or after deployment), under physiologic conditions (and/or through the introduction of therapeutic agents such as nitro), said reinforcement elements segment stiffens or strengthens the stent, by having sufficient strength to support a body lumen after deployment. In another example, the said region having said cross sectional area above spans substantially the entire length of at least some rings, or substantially spans the entire stent. In another example, the said region having said cross sectional area spans at least some rings, or spans substantially all rings, but does not span at least some axial links. In another example, the said regions having said cross sectional area, wherein the reinforcement element width ranges from 10% to 50% of the width of the structural element at said region, preferable ranges from 20% to 40%, more preferably ranges from 25% to 35%. In another example, the said regions having said cross sectional area, wherein the reinforcement element thickness ranges from 10% to 70% of the thickness of the structural element at said region, preferable ranges from 20% to 50%, more preferably ranges from 30% to 40%. In another example, the one or more regions having said cross section area wherein the ratio of thickness to width of the structural elements 1.5:1 to 3:1, and wherein the ratio of the structural element at said one or more regions thickness to width ranges from 0.7:1.4, preferably ranges from 0.8:1. In a preferred example of this example, the reinforcement element is non-degradable metal or metal alloy, and the stent frame material (which the reinforcement element is coupled to) is a polymeric degradable material. In another preferred example of this example, the reinforcement element is a non-degradable metal or metal alloy and the stent frame material is a degradable metal or metal alloy. The stent in this example containing reinforcement elements and having a degradable frame material has sufficient strength to support a body lumen when expanded from a crimped configuration to an expanded configuration, and wherein the stent radial compliance increases after expansion while the strength of said stent decreases after expansion. In another example, the stent radial strain increases after degradation of the degradable polymeric material and wherein the initial strength after expansion decreases after degradation of the polymeric material. In another example of this example, the reinforcement elements combined with the degradable frame stent material, have sufficient strength to support a body lumen, wherein the reinforcement elements alone does not have sufficient strength to support a body lumen. In another example of this example, the reinforcement elements combined with the degradable frame stent material, have sufficient strength to support a body lumen, wherein the reinforcement elements alone, or the stent frame material alone, do not have sufficient strength to support a body lumen.

In another example, the stent having reinforcement elements, bridging elements, separation regions, breaks, and other features described in this application exhibit increase in radial strain (or compliance) after expansion and decrease in radial strength after said expansion. In another example, said increase of radial strain (or compliance) and decrease in strength, begins (or occurs) from a period ranging from one week after expansion of the stent to 9 months after expansion of the stent, preferable begins one month after expansion to 6 months after expansion, more preferably begins 2 months after expansion to 6 months after expansion.

Most commonly, the reinforcement elements will comprise a non-degradable, usually being a metal (including metal alloy), more usually being a malleable metal which can be opened and deformed together with the circumferential scaffold but which has a higher strength to resist closure after the scaffold has been partially or fully expanded. In other examples, however, the reinforcement elements may be a polymer which has a higher stiffness than the main polymer (or the degradable patterned polymer or the polymer the reinforcement elements are coupled to at least in part) of the circumferential scaffold. Polymeric reinforcement elements may be formed from the same or different polymers than those which form the circumferential scaffold. When the reinforcement elements are formed from the same polymer, the reinforcement element polymer will typically have a higher molecular weight and/or higher crystallinity, or will otherwise be a stiffer polymer than that of the main body polymer (or the degradable patterned polymer or the polymer the reinforcement elements are coupled to at least in part) of the circumferential scaffold, the reinforcement polymer in this example can be degradable or non-degradable. In yet another example, the reinforcement elements can also comprise a degradable metal (which includes metal alloys) such as magnesium and/or magnesium alloys.

In yet another example, a stent prosthesis comprising a biodegradable polymeric material where the polymeric degradable material degrades in 1 months to 5 years, preferably degrades in 2 months to 3 years, more preferably degrades in 3 months to 2 years, wherein reinforcement elements are coupled to at least some expansion regions of at least some rings of said stent. The reinforcement elements can be non-degradable or degradable material, metal or metal alloys, polymers (degradable or non-degradable), or other material, that stiffens (or strengthens) said expansion regions (or stent) in the stent expanded configuration. Typically, the polymeric material degrades faster than the reinforcement elements, but can also (the polymeric material) be configured to degrade at the same time (or rate) as the reinforcement elements, or slower than the reinforcement elements. In another example the reinforcement elements do not degrade or corrode.

In yet another example, a stent prosthesis comprising a biodegradable metallic material such as magnesium alloy where the metallic degradable material degrades in 1 months to 5 years, preferably degrades in 2 months to 3 years, more preferably degrades in 3 months to 2 years, wherein reinforcement elements are coupled to at least some expansion regions of at least some rings of said stent in accordance of any of the examples of this application. The reinforcement elements can be non-degradable or degradable material, metal or metal alloys, polymers (degradable or non-degradable), or other material, that stiffens (or strengthens) said expansion regions (or stent) in the stent expanded configuration. Typically, the metallic material degrades faster than the reinforcement elements, but can also (the metallic material) be configured to degrade at the same time (or rate) as the reinforcement elements, or slower than the reinforcement elements. In another example the reinforcement elements do not degrade or corrode.

In still other examples, the reinforcement elements may be formed from an elastic metal or polymer (including spring and/or shape memory like NiTi). For example, for reinforcement elements which are curved or bent to conform (or contour) to a joint or hinge or an expansion region on the polymeric or metallic circumferential scaffold, the reinforcement element will typically be in a closed or constrained configuration when coupled to the corresponding hinge or joint on the circumferential scaffold in the crimped configuration. In this way, the typically metal reinforcement element will act to help open and/or keep open the circumferential scaffold as it is balloon expanded or self-expanded to its larger diameter configuration. Moreover, even after implantation in the blood vessel or other body lumen, the elastic, shape memory, and/or spring-like reinforcement elements will typically still be at least partially constrained by a polymer (such as the main polymer) or metal so that they will continue to bias the circumferential scaffold to open at least in the region where they are coupled to while simultaneously enhancing the strength and crush-resistance of the deployed prosthesis such as endoluminal prostheses themselves and/or through other reinforcement elements with high stiffness disposed on the same, adjacent, or other expansion regions or structural elements of said circumferential scaffold. Optionally, the scaffold may have additional metal, polymer, or other non-elastic (malleable) reinforcement elements coupled to same or other expansion regions, e.g. hinges or joints, on the circumferential scaffolds. For example, as one or more polymers comprising the scaffold or rings (such as main polymer) thereof start to soften, and/or degrade, and/or start to decrease in a molecular weight, and/or as the blood vessel or other body lumen heals and remodels over time, the elastic reinforcement elements will be able to continue to provide an opening bias to enhance enlargement of the scaffold. The magnitude of the opening bias is controlled by the elastic (including spring, shape memory) material properties and/or processing, and/or controlled by the degradation of the polymeric material (such as main polymer) containing the reinforcement elements. The terms stent and scaffold are used interchangeably in this application. In another example, the typically metallic shape memory or spring reinforcement element having two ends can be coupled to adjacent struts (non-deformable or substantially non-deformable structural elements) wherein the reinforcement element is configured as an expansion region connecting the two adjacent struts (along the length of the struts), where the reinforcement element expansion region is in the crimped configuration when the stent is in the crimped configuration, and wherein the reinforcement element expansion region expands as the stent expands to the deployed configuration. The reinforcement elements continue to push open (increasing the angle between said adjacent struts) after deployment of the stent (after the stent inward recoils from the deployed configuration). The reinforcement elements further expand the stent after deployment. The reinforcement elements are attached or coupled to the structural elements as described throughout this application. In one example, the reinforcement elements further expand the stent prosthesis by a mean range from 0.05 mm to 1 mm, from 0.1 mm to 0.5 mm, preferably from 0.1 mm to 0.3 mm, or corresponding mean cross sectional areas, after stent deployment and after stent recoil. In another example, the reinforcement elements increase the stent mean diameter or mean cross sectional area by a range from 2% to 15%, preferably 3% to 10%, of the stent mean expanded diameter or mean cross sectional area, after stent deployment and stent inward recoil). In another example, stent prosthesis comprises a non-degradable shape memory alloy comprising NiTi or other type material, the stent has one or more separation region (and/or one or more hinges), and wherein the stent expands from a crimped configuration to an initial expanded configuration and wherein the one or more separation region (or hinges) form discontinuities (or allow the stent to have radial displacement), allowing the stent to respond to a vaso-dilator, or contours to a changing lumen (or annulus) configuration.

In a preferred example the degradable polymeric stent comprising degradable main polymer (the polymer forming substantially the polymeric scaffold structure, or the polymer forming substantially a continuous scaffold structure, or the polymer forming substantially a scaffold structure without separation regions, or the polymer forming the scaffold structure except for at least some separation regions or discontinuities). The degradable polymeric stent can comprise more than one polymer in addition to the main polymer (adjacent, blended, mixed, etc.). Reinforcement elements are preferably non-degradable metal and metal alloys, having higher crush resistance (strength) compared to the main polymer or other additional polymers, such reinforcement elements are coupled to at least some regions of the scaffold structural elements such as crowns and/or struts, wherein the reinforcement elements have separation regions or discontinuities allowing the stent to uncage and/or expand in a physiological environment. The reinforcement elements can also be polymers (degradable or non-degradable) or corrodible metal and metal alloy.

In a preferred example, the reinforcement elements can have a variety of shapes and geometries including rod (or solid) or hollow wire, circular, semi-circle, triangle, rectangle, square, oval or other shapes and geometries. In a preferred example, the cross sectional area of at least some structural elements (such as crowns and/or struts) containing or coupled to the reinforcement elements, have the reinforcement elements representing 5% to 90% of the cross section area of said structural element, preferably represent 10% to 75% of the cross section area, more preferably represent 15% to 75% of the cross section area of said structural element. The structural element can be fully embedded in the structural element, partially embedded, or attached to one or more surface regions of the structural element, as described in this application.

In another example or aspect of this invention, a stent comprises a biodegradable polymeric material (or biodegradable metallic material) patterned into a structure comprising structural elements where at least one crown region (preferably at least some crown regions, more preferably at least half of the crown on the at least some rings), and/or at least one strut region (preferably at least some strut regions, more preferably at least ¼ of the struts regions on the at least some rings), are not formed (or are partially formed), on at least some rings, and said regions are formed or replaced with reinforcement elements, preferably non-degradable reinforcement elements preferably metallic such as CoCr alloys, Stainless steel alloys, or other metal or metal alloys, or can also be non-degradable polymeric reinforcement elements. The polymeric stent is formed (or formed with the region which is then removed) in one example without the at least one crown region and/or without the at least one strut region, on at least some rings, and where the metallic reinforcement elements having substantially the same size (or preferably smaller size) compared to adjacent polymeric crown regions and/or strut regions, and the reinforcement elements are shaped (or bent or curved) into a crown region shape and/or a strut region shape, and the reinforcement elements crown region two ends are attached to the strut end regions of the not-formed crown. The two ends of the reinforcement elements can be attached to the two strut ends of the polymeric stent as a butt joint and adhesively bonding the two materials together at the junction, and/or containing both reinforcement element and polymeric material junction region with a sleeve, and/or forming a slot in each of the polymeric stent two strut end regions (during laser patterning or after) and inserting or press fitting the reinforcement element crown region ends into the formed slots, optionally adhesively bonding an overlap region (for example 0.05 mm to 1 mm overlap region) of the two materials and/or containing the overlap region with a sleeve (where the sleeve can extend beyond the overlap region), and/or creating or having a slot formed in the reinforcement element end regions where the polymeric ends press fit into, to hold the reinforcement elements and the polymeric material junction together, or to hold the butt joint together, during expansion from a crimped configuration to expanded larger configuration. Similarly, reinforcement elements can connect to not-formed polymeric strut ends (or partially formed struts) as discussed above. The reinforcement elements stiffen the expansion region and/or the non-deformable or substantially non deformable regions in the expanded stent configuration. The stent is expandable from a crimped configuration to an expanded larger configuration and have sufficient strength to support a body lumen. In one example, the stent polymeric biodegradable material degrades from 3 months to 3 years, while the non-degradable reinforcement elements remain in the vessel wall. The stent after deployment, uncages the vessel, exhibits vaso-motion, exhibits vaso-dilation, exhibits vaso-constriction, and/or further expands to a larger configuration, and/or has radial strain ranging from 1% to 10%, preferably ranging between 1% to 7%, more preferably ranging from 1.5% to 7%, under physiologic conditions. The stent in one example comprises degradable polymeric material comprising structural elements comprising crowns and struts where at least some of the crowns and/or struts have been not formed, detached, or removed after forming (such as mechanically such as cutting them or chemically such as using solvents or other material to removing them), and replaced with non-degradable metallic reinforcement elements. The stent is formed from polymeric tube or formed from filaments that are patterned into a stent, or other methods known to one skilled in the art. The reinforcement elements can be formed from a tube or a wire and shaped or patterned into the shape of the structural element it would be replacing such as crown. In one example the reinforcement elements are formed from a patterned tube and then components of said patterned tube are removed (mechanically for example) and inserted (or attached) into the location of the not formed polymeric structural element (to replace it in one example). In another example a wire reinforcement element is shaped into the structural element to be replaced and attached. Other methods of forming the structural elements can include a variety of ways such as forming a pattern flat sheet, injection molding, or other. The shapes and sizes of the reinforcement elements can vary and is discussed throughout the application in more detail.

In another example, a biodegradable metallic stent such as magnesium alloy stent is patterned into a structure comprising structural elements where at least one crown region (preferably at least some crown regions, more preferably at least half of the crown on the at least some rings), and/or at least one strut region (preferably at least some strut regions, more preferably at least ¼ of the struts regions on the at least some rings), are not formed (or are partially formed), on at least some rings, and said regions are formed or replaced with reinforcement elements, preferably non-degradable reinforcement elements preferably metallic such as CoCr alloys, Stainless steel alloys, or other metal or metal alloys, or can also be non-degradable polymeric reinforcement elements. The metallic stent is formed (or formed with and then removed) in one example without the at least one crown region and/or without the at least one strut region, on at least some rings, and where the metallic reinforcement elements having substantially the same size (or preferably smaller size) compared to adjacent metallic stent crown regions and/or strut regions, and the reinforcement elements are shaped (or bent or curved) into a crown region shape and/or a strut region shape, and the reinforcement elements crown region two ends are attached to the strut end regions of the not-formed crown. The two ends of the reinforcement elements can be attached to the two strut ends of the metallic stent as a butt joint and adhesively bonding the two materials together at the junction, and/or containing both reinforcement element and metallic stent junction region with a sleeve, and/or forming a slot in each of the metallic stent two strut end regions (during laser patterning or after) and inserting or press fitting the reinforcement element crown region ends into the formed slots, optionally adhesively bonding an overlap region (for example 0.05 mm to 1 mm overlap region) of the two materials and/or containing the overlap region with a sleeve (where the sleeve can extend beyond the overlap region), and/or creating or having a slot formed in the reinforcement element end regions where the metallic stent structural element ends press fit into, and/or laser welding (or fusing) the two material, to hold the reinforcement elements and the metallic stent junction together, or to hold the butt joint together, during expansion from a crimped configuration to expanded larger configuration. Similarly, reinforcement elements can connect to not-formed metallic stent strut ends (or partially formed struts) as discussed above. The reinforcement elements stiffen the expansion region and/or the non-deformable or substantially non deformable regions in the expanded stent configuration. The stent is expandable from a crimped configuration to an expanded larger configuration and have sufficient strength to support a body lumen. In one example, the stent metallic biodegradable material degrades or substantially degrades in a period of time ranging from 3 months to 3 years, while the non-degradable reinforcement elements remain in the vessel wall. The stent after deployment, uncages the vessel, exhibits vaso-motion, exhibits vaso-dilation, exhibits vaso-constriction, and/or further expands to a larger configuration, and/or has radial strain ranging from 1% to 10%, preferably ranging from 1% to 7%, more preferably ranging from 1.5% to 7%, under physiologic conditions. The stent in one example comprises degradable metallic material comprising structural elements comprising crowns and struts where at least some of the crowns and/or struts have been not formed, detached, or removed after forming (such as mechanically such as cutting them or chemically such as using solvents or other material to removing them), and replaced with non-degradable metallic reinforcement elements. The stent is formed from a metallic tube or formed from filaments (or wires) that are patterned into a stent, or other methods known to one skilled in the art. The reinforcement elements can be formed from a tube or a wire and shaped or patterned into the shape of the structural element it would be replacing such as crown. In one example the reinforcement elements are formed from a patterned tube and then components of said patterned tube are removed (mechanically for example) and inserted (or attached) into the location of the not formed metallic stent structural element (to replace it in one example). In another example a wire reinforcement element is shaped into the structural element to be replaced and attached. Other methods of forming the structural elements can include a variety of ways such as forming a pattern flat sheet, injection molding, or other. The shapes and sizes of the reinforcement elements can vary and is discussed throughout the application in more detail.

In another aspect or preferred example, it is desirable to a have as stent comprised from a non-degradable high strength material, such as metallic material, in order to have sufficient strength upon deployment of the stent in a body lumen (in some cases a degradable material such as degradable metallic material having high crush resistance can also be used for this example, such materials tend to degrade slowly caging the vessel for a long time). However, such stents cage the vessel or segment adjacent to the stent and prevent one or more of the following from occurring potentially reducing the utility, safety, and/or effectiveness of the stent: uncaging the vessel or stented segment, exhibiting vaso-dilation within or spanning the stented segment, exhibiting vaso-constriction within or spanning the stented segment, exhibiting further enlargement of the stent, exhibiting radial strain over the stented segment in the range from 1.5% to 5%, after deployment. In order to solve or address on or more of the previous needs, the non-degradable metallic stent, such as L605 CoCr alloy stent, is configured by patterning into a structure comprising structural elements where at least one crown region (preferably at least some crown regions, more preferably less than half of the crowns on the at least some rings), and/or at least one strut region (preferably at least some strut regions, more preferably at least ¼ of the struts regions on the at least some rings), are not formed (or are partially formed, or are formed and then removed), on at least some rings, and said regions are formed or replaced with degradable bridging elements, such as degradable polymeric material (for example PLLA based polymers) or such as degradable metallic material (for example magnesium alloy). The non-degradable metallic stent is formed (or formed with and then removed) in one example without the at least one crown region and/or without the at least one strut region, on at least some rings, and where the degradable bridging elements having substantially the same size (or preferably smaller size, but can also be larger size) compared to adjacent metallic stent crown regions and/or strut regions, and the degradable bridging elements are shaped (or bent or curved) into a crown region shape and/or a strut region shape and/or the shape of the stent structural elements they are replacing, and the degradable bridging elements crown region two ends are attached to the strut end regions of the not-formed crown. The two ends of the degradable bridging elements can be attached to the two strut ends of the metallic stent as a butt joint and adhesively bonding the two materials together at the junction, and/or containing both degradable bridging element and metallic stent junction region with a sleeve, and/or forming a slot in each of the metallic stent two strut end regions (during laser patterning or after) and inserting or press fitting or fusing or melting the degradable bridging element crown region ends into the formed slots, optionally adhesively bonding an overlap region (for example 0.05 mm to 1 mm overlap region) of the two materials and/or containing the overlap region with a sleeve (where the sleeve can extend beyond the overlap region), and/or creating or having a slot formed in the larger size degradable bridging element end regions where the metallic stent structural element ends press fit into, and/or laser welding (or fusing) the two material, to hold the degradable bridging elements and the metallic stent junction together, or to hold the butt joint together, upon expansion of the stent, or during expansion of the stent from a crimped configuration to expanded larger configuration. Similarly, degradable bridging elements can connect to not-formed metallic stent strut ends (or partially formed struts) as discussed above. The degradable bridging elements are less stiff, or substantially less stiff, and therefore weakens the expansion region, and/or the non-deformable or substantially non deformable regions in the expanded stent configuration. However, the degradable bridging elements provide for one or more of the following benefits: provide continuity of the circumferential structural element (such as rings) at least upon expansion (or for a period of time after expansion) which helps the stent to uniformly expands (or improve expansion uniformity), provide for drug release in said region to inhibit neo-intimal hyperplasia, provide for partial or full expansion of the stent circumferential ring in the said expansion region, provide for lesion coverage and minimize plaque pro-lapse, provide for temporary scaffolding and then uncaging of the stent and/or vessel as the degradable bridging elements degrade or corrode in a period ranging from 1 months to 4 years, preferably ranging from 3 months to 4 years, provide support to the vessel wall. The stent is expandable from a crimped configuration to an expanded larger configuration and have sufficient strength to support a body lumen, The non-degradable stent structural elements remain in the vessel wall substantially intact in one example (or substantially held together, or substantially in place, in one example). The stent after deployment, uncages the vessel, exhibits vaso-motion, exhibits vaso-dilation, exhibits vaso-constriction, and/or further expands to a larger configuration, and/or has radial strain ranging from 1% to 10%, preferably ranging between 1% to 7%, more preferably ranging from 1.5% to 7%, under physiologic conditions (and/or through introduction of therapeutic agents such as nitro). The stent in one example comprises non-degradable metallic material comprising structural elements comprising crowns and struts where at least some of the crowns and/or struts have not been formed, or have been detached, or have been removed after forming (such as mechanically removed such as cutting them or chemically removing them such as using solvents or other material to removing them or to melt them), and are replaced (or formed) with degradable bridging elements in said regions. The stent is formed from metallic tube, metallic sheet, or formed from filaments (or wires) that are patterned into a stent, or formed using other methods known to one skilled in the art. The degradable bridging elements can be formed from a tube or a filament/wire and shaped or patterned into the shape of the structural element it would be replacing such as crown for example. In one example the reinforcement elements are formed from a patterned tube and then components of said patterned tube are removed (mechanically for example) and inserted (or attached or press fitted) into the location (or region) of the not formed metallic stent structural element. In another example a filament degradable bridging element is shaped into the structural element shape replace and attached the ends as described. Other methods of forming the degradable bridging elements can include a variety of ways such as forming a pattern from a flat sheet and using components from the sheet to replace the not formed structural element, injection molding of said degradable bridging elements, or other. The shapes and sizes of the degradable bridging elements can vary (smaller, same, or larger, than the replaced structural element) as discussed throughout the application in more detail.

In one example, the bridging elements are degradable. In another example the bridging elements are non-degradable but provides for one or more of the objectives of this invention. The bridging elements can also be a suture (or wire) tying both ends of the structural element that is not formed, or that is modified or removed partially or completely. The suture can tie both ends of the structural element through a hole adjacent to each end of the structural element where the suture (or wire) is threaded through the holes and tied forming a continuity of the not formed structural element (said suture or wire bridging two crowns or two struts for example).

In another example, the bridging elements can be formed from shape memory material or spring material (which can also be reinforcement elements in other examples), where the bridging elements help bias open at least some crowns to expand further after implantation.

In another example, the non-degradable metallic stent (such as Cobalt Chrome alloy L605 or MP35 for example) comprises a wire (round or substantially round, or oblong, or other shapes), where the wire is patterned into a stent. The stent comprises structural elements comprising a plurality of rings, each ring comprises crowns and struts. At least one strut and/or at least one crown, on at least some rings, are removed. The ends of the stent where the strut and/or crowns were removed are treated to create a hollow space in the wire. A degradable bridging element is inserted in the hollow space at each of the ends of the wire stent to bridge the gap of the removed strut and/or crown. Optionally an adhesive, or degradable sleeve are applied to the junctions or overlap further reinforcing the junction segment so that the junction is held together as the stent expands from a crimped configuration to an expanded larger configuration. In another example, the degradable bridging elements are treated to create a hollow space, where the stent wire structural element is inserted or press fitted into. Optionally an adhesive or sleeve are applied to further hold the junction together.

In another example, the stent prosthesis is formed as a tube where the tube comprises a non-degradable material layer (such as cobalt chrome alloy layer) that is either sandwiched between, on top of, or on the bottom of a magnesium alloy layer. The tubing is patterned into a stent. At least some regions on at least some rings (or at least some crown regions, and/or strut regions, on at least some rings) have the non-degradable material (such as the cobalt chrome alloy layer) substantially removed by laser, chemical means, or mechanical means, to provide the stent to uncage after expansion under physiological conditions. The stent prosthesis in another example can be formed as a sheet where the degradable layer is on top or bottom of the non-degradable material, the stent is patterned and processed as described above. The sheet is rolled and attached (or fused) forming a patterned stent.

In another example, the stent prosthesis is formed as a wire where the wire comprises a non-degradable material layer (such as cobalt chrome alloy layer) on top, or on the bottom of a degradable polymeric or metallic material layer (such as magnesium alloy layer or PLLA based polymer). The wire is patterned into a stent. At least some regions on at least some rings (or at least some crown regions, and/or strut regions, on at least some rings) have the non-degradable material (such as the cobalt chrome alloy layer) substantially removed (forming degradable bridging elements connecting the two ends of the non-degradable structural element, by laser, chemical means, or mechanical means, to provide the stent to uncage after expansion under physiological conditions, preferably uncaging as the degradable material degrades.

In another example, the stent prosthesis is formed as a tube where the tubing comprises a non-degradable material layer (such as cobalt chrome alloy layer) that is on top or inside of a degradable polymeric material layer (such as PLLA based polymer layer). The tubing is patterned into a stent. At least some regions on at least some rings (or at least some crown regions, and/or strut regions, on at least some rings) have the non-degradable material layer (such as the cobalt chrome alloy layer) substantially removed by laser, chemical means, or mechanical means, to provide the stent to uncage after expansion under physiological conditions. The stent prosthesis in another example can be formed as a sheet where the degradable layer is on top or bottom of the non-degradable material, the stent is patterned and processed as described above. The sheet is rolled and attached (or fused) forming a patterned stent.

In one example of any of the examples in this application, the stent is tested, or deployed (expanded) under one or more of the following conditions: in air, in water bath, in water bath at 37° C., under physiologic conditions, in a pulsating (or contracting) environment, under administration of one or more agents that causes vaso-dilation or vaso-constriction of the stented segment, in a tube, in a vessel, in a body lumen, under a pressure difference (gradient) ranging from 100 mmHg to 200 mmHg, under pressure difference (or magnitude) of 100 mmHg, under pressure difference (or magnitude) of about 176 mmHg, or under conditions to test compliance or strength as described in this application, or any other condition described in this application. In some cases, all of the conditions described in this paragraph are referred to as physiologic conditions.

In one example, physiologic conditions comprises one or more of: in ambient air, in water bath, in water bath at about 37° C., at about 37° C. environment, in a radial strain tester (compliance tester), in a fatigue tester, in a pulsating environment, in a pressure or pressure differential environment, in a pulsating environment approximately simulating body lumen or body organ environment, administration of therapeutic agents such as vaso-dilators, or vaso-constrictors, in a contracting and/or expanding environment, in a body lumen, in a body vessel, in a body annulus, or other.

In a preferred example, the stent prosthesis further comprises at least one coating on at least one surface of the stent prosthesis. The coating in one example contains at least one drug, preferably an m-tor inhibitor. In another example the stent prosthesis comprises at least one drug. In another example, the stent prosthesis comprises at least two drugs, an m-tor inhibitor, and a vaso-dilator. In yet another example, the at least one coating degrades at a rate slower than the degradable (polymeric or metallic) material rate of degradation. In another example, the at least one coating degrades at a rate faster than the degradable material rate. In yet another example, at least one coating covering at least one surface of the non-degradable stent. In yet another example, at least one degradable coating covers at least one surface of the non-degradable stent. In yet another example, at least one degradable coating covers at least one surface of the non-degradable stent, and at least one non-degradable coating covers at least one surface of the non-degradable stent.

In one example, the stent prosthesis exhibits, provide, or is configured to do one or more of the following: uncaging the stent, uncaging the stented segment of the lumen or vessel, uncaging at least some circumferential structural elements of the stent, uncaging at least some rings of the stent, uncaging the vessel or vessel wall, exhibiting vaso-motion, exhibiting vaso-dilation, exhibits vaso-constriction, further expansion of the stent to a larger configuration after implantation, and/or the stent has composite radial strain (or compliance) ranging from 1% to 10%, preferably ranging between 1% to 7%, more preferably ranging from 1.5% to 7%, under physiologic conditions (and/or through introduction of therapeutic agents such as nitro). The stent prosthesis in this example exhibits or provides the one or more properties described above (uncaging etc.) in one or more of the following stent states: as formed, as patterned, after treatment or processing after forming (or patterning) of the stent, as the stent is deployed, upon deployment of the stent, upon expansion of the stent, and/or after deployment or expansion of the stent, in a body lumen for example. The stent prosthesis in this example exhibits or provides the one or more properties described above (uncaging, etc.) in (or over) one or more of the following: at least some circumferential structural elements, at least some rings, substantially all circumferential structural elements, substantially all rings, at least some regions, spanning substantially the entire stent or the entire stent segment, the stent region, and/or the stent segment.

In one example of any of the examples, the bridging elements can also bridge at least one link (or link region), in addition to bridging one or more structural elements (such as struts and/or crowns) on at least some rings.

In another aspect of this invention, or another example, a non-degradable (such as metal (including alloy) but can also be polymeric) stent prosthesis comprises structural elements, said structural elements in one example comprise a plurality of rings, each ring comprises struts and crowns, and each ring is connected to an adjacent ring in at least one location (or region). At least one strut (or part of a strut, or a strut region ranging) and/or at least one crown (or part of a crown, or a crown region), on at least some rings are not-formed (or removed after forming), forming a gap (or discontinuity) between said remaining crown ends (or remaining crown regions) and/or between remaining strut ends (or remaining strut regions), wherein the gap magnitude ranges from 1 microns to 3 mm, preferably ranges from 2 microns to 2 mm, more preferably ranges from 3 microns to 1 mm, when said gap is measured as a straight line between the remaining struts and/or remaining crowns in the expanded stent configuration (or in the crimped stent configuration). The ends of the remaining struts and/or crowns can be configured to have different, preferably larger dimensions, geometry, and/or surface area than an adjacent struts and/or crown, and can have various shapes such as round, square, semi-circle, rectangle, etc. In one example, at least some rings have at least one gap (or discontinuity) along said rings. In another example, at least some rings have at least three gaps (or discontinuities) along said rings. In yet another example, at least some rings have from 1 to 3 gaps (or discontinuities). The stent prosthesis is expandable from a crimped configuration to an expanded larger configuration and have sufficient strength to support a body lumen. The stent in a preferred example has a substantially uniform expansion. The stent in another preferred example has a maximum circular diameter of 0.7 mm to 1.5 mm in the gap region. The stent in a further preferred example has sufficient coverage to inhibit (or minimize) smooth muscle cell proliferation. The stent prosthesis exhibits, provide, or is configured to do one or more of the following: uncaging the stent, uncaging at least some circumferential structural elements of the stent, uncaging at least some rings of the stent, uncaging the vessel or vessel wall, exhibiting vaso-motion, exhibiting vaso-dilation, exhibits vaso-constriction, further expansion of the stent to a larger configuration after implantation, and/or the stent has radial strain ranging from 1% to 10%, preferably ranging between 1% to 7%, more preferably ranging from 1.5% to 7%, under physiologic conditions (and/or through introduction of therapeutic agents such as nitro). The stent prosthesis in this example exhibits or provides the one or more properties described above (uncaging etc.) in one or more of the following stent states: as formed, as patterned, after treatment or processing after forming (or patterning) of the stent, as the stent is deployed, upon deployment of the stent, upon expansion of the stent, and/or after deployment or expansion of the stent, in a body lumen for example. In a preferred example, the not formed (or removed) strut and/or crown remaining end region is connected to the same or adjacent structural element provided that such connection does not complete the gap (or discontinuity) of said ring and the gap in said ring remains discontinued.

In another example, the stent prosthesis comprises a plurality of rings comprising struts and crowns, where at least one strut and/or crown regions on at least some rings are severed (or cut) during laser patterning for example but can also be done mechanically, or other methods. The severed region is deburred and/or shaped into a geometry to be atraumatic and/or to create a contact, and/or to maintain a contact, and/or to substantially hold the cut region substantially together, to allow expansion of the stent prosthesis from a crimped configuration to an expanded larger configuration and have sufficient strength to support a body lumen. The stent in a preferred example have a substantially uniform pattern in the expanded configuration. The cut end regions can be abutting, overlapping, or have a temporary holding means, in the crimped configuration, to allow deployment into an expanded configuration, or to allow the stent to have a substantially uniform pattern in the expanded stent configuration, and/or to allow for a substantially sufficient coverage to support a body lumen.

During laser cutting, patterning, or other formation of the separation regions and discontinuities in the scaffold, portions of the partially formed scaffold may be temporarily together so that the structure does not prematurely separate after the discontinuities are formed and before the discontinuities are immobilized by gluing, coating, sleeve formation, or the like. For example, after a tubular member is laser cut or otherwise patterned to form circumferential rings including struts and crowns, the ends of the tubular member may be temporarily held by holding fixtures positioned at each end of the scaffold. In particular, one, two, three, or more terminal crowns at each end of the scaffold may be formed to have holding features, such as enlarged ears or similar features that can be grasped by the holding fixtures. In this way, the holding fixtures will hold the partially formed scaffold together as the separation regions are formed, e.g. by first cutting or bisecting a strut and/or crown in one or more of the circumferential rings and then coating the entire scaffold in a biodegradable sleeve to hold the stent together so that it may be removed from the fixtures and subsequently deployed.

In another example, a non-degradable (such as metal (including alloy) but can also be polymeric) stent prosthesis comprises circumferential structural elements, said structural elements comprises in one example a plurality of rings, each ring comprises struts and crowns, and each ring is connected to an adjacent ring in at least one location. At least some rings are configured (patterned and/or treated for example) to have a gap (or discontinuity) in said rings. For example, the stent can be patterned to have wherein the gap magnitude ranges from 1 microns to 3 mm, preferably ranges from 2 microns to 2 mm, more preferably ranges from 3 microns to 1 mm, when said gap is measured as a straight line to complete (or connect or provide continuity) said rings. In a preferred example, the maximum circular inter-strut (or inter-ring or between rings) distance in the region where the gap is ranges from 0.9 mm to 2 mm, preferably ranges from 1 mm to 1.5 mm. In one example, at least some rings have at least one gap (or discontinuity) along said rings. In another example, at least some rings have at least three gaps (or discontinuities) along said rings. In yet another example, at least some rings have from 1 to 3 gaps (or discontinuities). The stent prosthesis is expandable from a crimped configuration to an expanded larger configuration and have sufficient strength to support a body lumen. The stent in a preferred example has a substantially uniform expansion, sufficient vessel coverage to inhibit SMC proliferation. The stent prosthesis exhibits, provide, or is configured to do one or more of the following: uncaging the stent, uncaging at least some circumferential structural elements of the stent, uncaging at least some rings of the stent, uncaging the vessel or vessel wall, exhibiting vasomotion, exhibiting vaso-dilation, exhibits vaso-constriction, further expansion of the stent to a larger configuration after implantation, and/or the stent has radial strain ranging from 1% to 10%, preferably ranging between 1% to 7%, more preferably ranging from 1.5% to 7%, under physiologic conditions (and/or through introduction of therapeutic agents such as nitro). The stent prosthesis in this example exhibits or provides the one or more properties described above (uncaging etc.) in one or more of the following stent states: as formed, as patterned, after treatment or processing after forming (or patterning) of the stent, as the stent is deployed, upon deployment of the stent, upon expansion of the stent, and/or after deployment or expansion of the stent, in a body lumen for example.

In one example, the stent prosthesis where at least some rings have at least one gap (or discontinuity) on each said ring. In one example, the region (or end region) of the structural elements (ring) where the gap is (or where the gap begins or ends) can be free (not connected to any structural element, or any adjacent structural element), or can be connected to other structural elements such as connected to a strut, and/or crown, (or can be connected to other adjacent structural elements such as connected to a strut, and/or crown) at the end region, or adjacent to the end region, or anywhere along the structural element leading to said end region. The connection to said region can be substantially straight connection, and/or a crown connection, and/or other connection having a variety of shapes, dimensions, and/or geometries from said region to other structural elements (or adjacent structural elements). Examples of connection (including connection shapes) include Z, S, M, U, W, Y, L, or other type connection. The dimension of said connection can be different or substantially the same as other adjacent structural elements. The connections can also be larger or smaller in width and/or thickness in other examples. The connections shapes and/or dimensions can be substantially the same or different on at least some rings.

In another example, the stent prosthesis comprises structural elements comprising a plurality of rings, each ring comprises struts and crowns, and each ring is connected to an adjacent ring in at least one region. At least some rings have at least one region between two crown and/or between two struts, configured (patterned or otherwise) to have two struts (or two strut regions) and/or two crown (or two crown regions) where the two strut regions and/or crown regions overlap over some length. The struts and/or crowns are connected at opposite ends, while the other end region forms a discontinuity in said ring. The struts and/or crowns free end region can have various shapes and geometry to restrain or hold together the stent prosthesis upon deployment of the stent. The strut and/or crown regions can also have grooves or other shapes to hold the restrain the sliding struts and/or crowns upon expansion of the stent prosthesis. The stent prosthesis is typically expandable from a crimped configuration to an expanded larger configuration and has sufficient strength to support a body lumen. The stent allows the body lumen to uncage upon deployment. The stent has sufficient structural elements surface region coverage (thickness, width, and/or geometry) in the discontinuity region to support a body lumen.

In one example of any of the examples in this application, a stent prosthesis comprising circumferential structural elements, wherein the structural elements comprise struts and crowns, and wherein the stent is configured (for example patterned and/or treated) to allow the stent to be expandable from a crimped configuration to an expanded larger configuration, and wherein the stent has sufficient strength in the expanded configuration to support a body lumen, said stent prosthesis uncages, and/or has radial strain (or compliance) ranging between 1% and 5%, and/or further expands, as formed, upon expansion, and/or after expansion, in a body lumen (or under physiologic condition and/or under therapeutic condition such as introduction of nitroglycerine). Examples of said stent prosthesis comprise one or more from the examples comprising reinforcement elements, bridging elements, separation regions, struts and/or crowns having gap regions, or other. Said stent prosthesis can be degradable, non-degradable, metallic (including alloys) or polymeric, over a period ranging from 3 months to 5 years under physiologic condition. The stent prosthesis in an example can be formed from a tube and patterned into a stent or formed from one or more wires (or filaments) and patterned into a stent. The stent can also be formed from a flat sheet and rolled to form a stent. The flat sheet can be patterned before rolling it to form a stent or the flat sheet can be rolled to form a tube and then patterned. In one example the circumferential structural elements comprise a plurality of rings each ring comprising crowns and struts having one or more of the configurations described in this application. In another example the structural elements comprise crowns and struts having one or more discontinuities allowing the stent to uncage as formed, and/or further expands, as formed, upon deployment, and/or after deployment.

In another example of any of the example in this application, at least some struts and/or crowns have at least one separation region, discontinuity, or break. In another example, at least some struts and/or crowns have at least two separation regions, discontinuities, or breaks, on said struts and/or crowns. In still further examples, at least some of the struts and/or crowns will be free from separation regions. In still further and often preferred examples, at least some struts will have separation regions while all crowns in a circumferential ring will be free from separation regions. It has been found that locating separation regions in struts which normally do not deform during expansion is preferable to locating separation regions in crowns which deform as the scaffold expands.

In another aspect or in another example, the present invention provides non-degradable or slowly degradable prostheses material having structural elements such as circumferential elements and/or rings with separation regions and/or environmentally responsive separation regions. By "environmentally responsive," it is meant that the separation regions will separate, become void from material such as a degradable polymer material, create a gap, open, break, allow for movement in one or more direction, and/or degrade, in response to physiologic conditions which includes vascular conditions, and/or other luminal conditions, and/or in response to being placed in water at ambient temperature or at 37° C., and/or in response to being placed in a buffered solution, and/or in saline, and/or in response to the physiologic conditions (e.g. the vascular or luminal conditions), and/or the physiologic pressure, to which the scaffold is exposed to such as after implantation in the blood vessel or other body lumen, and/or in response to the scaffold being exposed to pressure ranging from 30 mmHg to 200 mmHg, preferably ranging from 40 mmHg to 120 mmHg, more preferably ranging from 50 mmHg to 80 mmHg, and/or in response to the scaffold being exposed to pulsating pressure ranges from 30 mmHg to 150 mmHg, preferably pulsating pressure ranges from 30 mmHg to 120 mmHg, and more preferably pulsating pressure ranges from 30 mmHg to 90 mmHg, or in response to therapeutic agents such as vaso-dilators or vaso-constrictors introduction.

The stent in a preferred example in any of the examples in this application can uncage, can uncage in at least some circumferential cross sections or regions, uncages over the stent segment, and/or expand to a larger diameter (or configuration) in physiologic conditions (includes physiologic environment) in at least some circumferential cross sections or regions of the stent prosthesis. The larger stent diameter can be larger than the deployed diameter and/or larger than the diameter of the stent after recoil from the deployed expanded configuration. The stent diameter in response to said pressures and/or pulsating pressure (as described in this application) in one example changes and/or increases from expanded and/or deployed diameter (after recoil if any from said expanded and/or deployed diameter) to a larger diameter permanently or temporarily while exposed to the pressure and/or pulsating pressure, the stent diameter changes and/or increases ranges from 0.045 mm to 1 mm, preferably ranges from 0.05 mm to 0.6 mm, and more preferably ranges from 0.06 mm to 0.3 mm, or changes from 0.1 to 0.3 mm. The stent radial strength after deployment, in the same example or other example, ranges from 12 psi to 30 psi, preferably ranges from 13 psi to 25 psi, more preferably ranges from 15 psi to 25 psi. The stent flat plate strength (10% crush) after expanding the scaffold and/or after deployment, in the same example or a different example, ranges from 0.03 N/mm stent length to 0.95 N/mm stent length, preferably ranges from 0.035 N/mm stent length to 0.9 N/mm stent length, more preferably ranges from 0.0.04 N/mm stent length to 0.085 N/mm stent length. The scaffold inward recoil after expansion of the scaffold and/or after deployment in the same example or a different example ranges from 1% to 10%, preferably ranges from 2% to 7%, more preferably ranges from 2% to 5%. The stent inward recoil preferably remains substantially the same after deployment. The stent prosthesis preferably expands further to a larger configuration after introduction of a vaso-dilator in the body. The stent preferably has radial strain (or compliance) in the expanded configuration ranging between 1% and 5%. In the same example or a different example, the non-degradable stent radial strength after deployment decreases by at least 25%, decreases by at least 50%, decreases by at least 75%, decreases by 100% of the scaffold initial radial strength upon deployment. The period of time in the same example or a different example where the strength decreases ranges from 1 day to 2 years, preferably ranges from 1 month to 1 year, more preferably ranges from 2 months to 9 months, more preferably ranges from 3 months to 9 months. In the same example or a different example, the non-degradable stent radial strength after deployment (initial deployment) decreases by a range from 0% to 25% within 30 days from such initial deployment radial strength, and/or decreases by a range from 10% to 50% within 90 days from such initial deployment radial strength, and/or decreases by a range from 25% to 90% within 180 days from such initial deployment radial strength, and/or decreases by a range from 50% to 100% within 270 days from such initial deployment radial strength. The non-degradable stent in this example further comprises at least one degradable polymer, and further comprises at least one drug. In a preferred example the at least one drug is contained in a polymer. In another example or in addition to the previous example, the stent comprises at least one non-degradable polymer. In yet another example or in addition to the previous examples, the stent further comprises radiopaque markers (degradable or non-degradable).

In a preferred example throughout this application after deployment, there is uncaging of the stent, and further expansion of the stent after deployment, lumen enlargement, and other properties of the stent and/or lumen comprising one or more of the whole stent or lumen, at least one part or region of the stent or lumen, at least one circumferential cross section or region of the stent or lumen, or at least some circumferential cross sections or regions of the stent or lumen segments, or the stented segment.

In another example, the present invention provides non-degradable prosthesis material having circumferential elements and/or rings with separation regions. Separation regions are regions that have discontinuity as formed, and/or as patterned (including after patterning), and/or after processing or treatment, and/or before implantation, and/or after implantation, and/or after implantation in physiologic conditions. Discontinuity includes completely and/or substantially one or more of the following: being separate, becoming void from material, having a gap, forming a gap, open, having a break, forming a break, unlocking, un-touching, un-contacting, removal of material between separation regions or adjacent to separation regions, removal of material holding separation regions together, ability of separation region to move in one or more directions, and/or degrade. In this example, the stent has sufficient strength upon deployment to support a body lumen, and wherein the stent after deployment may recoil to a smaller configuration before further expanding to a larger configuration (larger than the recoil configuration and/or larger than the deployed expanded configuration). The stent can expand to the larger configuration in a body lumen and/or under physiologic condition. In another example the stent uncages, or uncages at least in some regions and/or rings, or the stented segment.

In another example, one or more circumferential rings containing one or more separation regions may contain at least one or more non-degradable material (such as a non-degradable polymeric material) wherein said material inhibits forming a gap or other discontinuity. The one or more circumferential rings containing separation regions comprising a non-degradable material are configured to expand to a larger diameter or cross-section after initial expansion (and recoil if any), due to the elasticity and stretching of the non-degradable material under physiological conditions in response to vascular pulsation and/or expansion in response to a vaso-dilator agent. In this way, one or more rings and typically the entire stented segment exhibits a desired compliance after implantation under physiological conditions.

The non-degradable material in such embodiments and examples typically has sufficient elasticity to continuously expand and/or contract under physiologic conditions including systolic pulsation of the blood vessel.

In yet another example, one or more separation regions comprising non-degradable materials may still form a gap or other discontinuity after the initial expansion, preferably after a period ranging from 30 days to one year after the initial expansion. Although non-degradable, the material may deteriorate or fatigue over time and/or under physiologic conditions thus allowing the separation regions to separate, to form gaps or other discontinuities.

In yet another example, the one or more separation regions may be constrained by one or more non-degradable material, such as a polymeric sleeve or a polymeric coating, wherein the one or more of the separation regions after formation of gaps or other discontinuities remain constrained by the non-degradable material even after formation of gaps or other discontinuities. The non-degradable material, formed as a sleeve or coating for example, can also cover one or more rings of the stent, cover one or more stent surfaces, or can cover the entire stent surface. The sleeve or coating constraining the separation regions allow the one or more rings or the stented segment) to have a desired compliance, further expand after initial recoil, and/or respond to an introduction of a vaso-dilator.

In another example, an endoluminal prosthesis according to this and/or one aspect of the invention and/or a preferred example comprises a scaffold having structural elements such as circumferential elements and/or rings patterned from a non-degradable material, such as a non-degradable metal, metal alloy, or hard non-degradable plastic, where the scaffold is configured to expand from a crimped configuration to an expanded configuration and the scaffold has sufficient strength in the expanded configuration to support a body lumen. At least some of the circumferential elements and/or rings will have at least one separation region configured to form discontinuities in the circumferential element and/or ring soon or immediately after deployment (initial deployment), and/or over time, and/or after an initial expansion in a physiologic environment, and/or after exposure to one or more of the other conditions disclosed in this application. Such discontinuities allow the scaffold or at least some circumferential cross sections of the scaffold to further expand to a larger configuration in at least, preferably to further expand after an initial recoil which may occur after deployment, more preferably to further expand beyond the initial expansion, most preferably allowing the scaffold to uncage or uncage in at least some circumferential cross sections or regions of the stent, preferably uncage in the circumferential direction. That is, after the scaffold has been initially deployed by a balloon or in some instances by self-expanding from constraint, the discontinuities allow portions of the scaffold to move apart and the rings to expand, preferably together with luminal expansion, more preferably together with luminal expansion as a result of luminal remodeling. In one example, the ring separation regions may be present in crowns regions, hinge regions, and/or strut regions. The stent preferably responds to vaso-dilation stimuli by enlarging the lumen in the stented segment. The stent preferably has composite radial strain (or compliance) ranging from 1.5% to 7%.

In another example, the discontinuities which form in the circumferential elements and/or rings will typically comprise partial or total breaks, separations, gaps in the structure of the circumferential scaffold which reduce or eliminate the stress areas, stiffness, hoop, circumferential, and/or radial strength of the scaffold (or ring component of the scaffold as described more particularly below and/or in this application) and/or in the separation region. Most commonly, the discontinuities will be total breaks which allow two resulting free ends in the scaffold or ring or circumferential element to move apart from each other in response to remodeling or other expansion of the body lumen and/or the stent. In one example the discontinuities where the two free ends are contained by a material comprising a sleeve or a coating wherein the sleeve or coating material can be non-degradable or degradable such as a polymer, wherein the sleeve or coating stretches when the free ends move apart. In another example the discontinuities are contained by means of the discontinuity geometry (such as certain key and lock designs and other type of geometry) to hold the structural element containing discontinuities together upon deployment from a crimped configuration to an expanded configuration, wherein the discontinuity is formed before patterning, during patterning, or after patterning, and is held together by the design configuration of the separation region forming said discontinuities as described above and/or in the entire application. The discontinuity in this case allows for crimping and/or deployment of the stent while maintaining the free ends of the structural elements containing said discontinuities to be held together and providing for sufficient strength after deployment of the stent to support a body lumen. The discontinuities in this case can allow movement of the free ends of the structural element in one or more directions after deployment, preferably in the radial direction only after deployment, more preferably substantially only in the radial direction, most preferably said movement primarily in the radial direction, or said movement is in a radial and/or circumferential direction. In one example, At least some of the rings or other portions of the scaffold will have at least one such discontinuity, but more typically each ring will have at least one discontinuity and some or all of the rings may have two or more discontinuities. Individual scaffold rings may have the same number or different numbers of discontinuities, and not all scaffold rings need have discontinuities. For example, rings at or near an end of the scaffold may be free from discontinuities, e.g. to limit the wishbone effect. In a further example at least some rings will have a number of discontinuities ranging from 1 to the same number of crowns, preferably a number of discontinuities ranging from 1 to ¾ of the number of crowns on said ring, and/or will have a number of discontinuities ranging from 1 to same number of the struts on said rings, preferably a number of discontinuities ranging from 1 to ¾ of the number of struts on said ring, and/or will have a number of discontinuities ranging from 1 to ½ of the number of crowns on said ring, and/or will have a number of discontinuities ranging from 1 to ½ of the number of struts on said ring, and/or will have a number of discontinuities ranging from 1 to ¼ of the number of crowns on said ring, and/or will have a number of discontinuities ranging from 1 to ¼ of the number of struts on said ring, and/or will have a number of discontinuities ranging from 1 to 10 on said ring, preferably a number of discontinuities ranging from 1 to 5 on said ring, more preferably a number of discontinuities ranging from 1 to 4 on said ring, and/or a number ranging from 1 to 3 on said ring, and/or a number ranging from 1 to 2 on said ring.

In one example, the physiologic environment causes such discontinuities to form (in other examples the discontinuities are formed independent of the physiologic environment) may be characterized by any physical condition associated with the body lumen into which the prosthesis is to be implanted. For example, the physiological environment or condition may comprise any one or more of the following: a physiologic temperature, e.g. 37° C., as maintained in the body lumen, or in a water bath heated to about 37° C., and/or a physiologic pressure, and/or, pressure and/or pulsating pressure, and/or introduction of a drug agent such as vasodilator or vaso-constrictor, as described in this application. Additionally, the physiologic environment may comprise blood or other aqueous media into which the scaffold has been implanted, particularly oxygenated blood that may enhance corrosion of certain feature. Often, the physiologic environments will comprise pulsation of a blood vessel, particularly an artery, which can subject the implanted scaffold to mechanical stress which in turn can fatigue and break particular features formed in the scaffold structure. The discontinuities, whether resulting from degradation, corrosion, dissolution, or mechanical stress, will in one example typically form from thirty days to six months, but can also form from few days to 1 year after initial expansion of the circumferential scaffold and exposure of the expanded scaffold to the environment of the body lumen. In other embodiments, discontinuities form in a water bath at ambient temperature.

In one example, the separation regions may comprise any one of a variety of structures in or modifications of the scaffold, for example including notches, variations in the grain structure, pre-formed breaks which are rejoined by degradable polymers, adhesives, sleeves, rivets, or the like.

In one particular example of the separation regions comprises a key and key hole, and/or a key and lock, and/or ball and socket, and/or hook junction which is immobilized and/or held together as formed, and/or after forming, and/or before deployment, and/or before expansion, and/or during deployment, and/or during expansion, and configured to separate and/or form a discontinuity, after deployment, and/or after additional expansion in the physiologic environment. For example, the key and key hole, and/or key and lock, and/or ball and socket, and/or hook junctions may be initially held together by means, such as by a material such as a polymer, cement, adhesive, solder, and/or the like, which degrades in the physiologic environment, where the key and key hole, and/or key and lock, and/or ball and socket, and/or hook are configured to separate or form a gap once the means holding the junctions comes apart or degrades, or once the key and key hole, and/or key and lock, and/or hook junction is free from the material such as polymer, cement, adhesives, solder, e.g., in response to normal pulsations of the blood vessel or other body lumen, or other physiologic conditions described throughout this application. In one example, the key and key hole, and/or key and lock, and/or ball and socket, and/or hook junctions may be substantially held together by the geometry of the junction which restricts or substantially restrict movement of the junction in one or more directions sufficiently to allow for stent deployment and for the stent to have a strength sufficient to support a body lumen after deployment (initial deployment). In a preferred example such junction remains substantially held together upon deployment (expansion from crimped configuration to an expanded larger configuration) and wherein the stent has sufficient strength in the expanded configuration to support a body lumen. In this preferred example, the junction means to hold it together is the geometry of the junction such as the type of key and key hole, and/or key and lock, and/or ball and socket, and/or hook, and/or other type of junction. The separation region junction can also be a butt junction connecting and/or joining two ends of a stent structural element and/or a ring, said ends having various shapes and/or cross sectional shapes (including substantial shapes type) such as round, and/or ball, and or square, and/or rectangle, and/or a nerve synapse type junction, and/or other type shapes, and/or substantially such shape. In one example the deployment means such as balloon catheter provides for holding the discontinuities together upon deployment of the stent and wherein the stent is allowed to have controlled movement after deployment in one or more directions, preferably in the radial direction, after deployment, and wherein the stent has sufficient strength after deployment from a crimped configuration to an expanded larger configuration.

The separation regions in another example may also comprise a simple butt joint or overlapping sections of stent structural elements where the structural elements are solid wire (having various shapes such as substantially round, rectangle, and/or square, and/or nerve synapse, and/or other shapes), and/or hollow wire/tube structural elements (hollow at least in regions adjacent to the separation regions) having opposed free ends which are temporarily joined by means, such as an adhesive and/or connector and/or polymer and/or solder and/or sleeve which degrades and/or separate and/or discontinue in the physiologic environment. Such means can hold the free ends together by placing them between the free ends, adjacent to the free ends, covering the free ends, inside the hollow section of the free ends, and/or combination of all the above, of said structural elements.

In still other instances or examples, the separation regions may comprise notches or thinned sections formed in the circumferential rings and/or circumferential structural elements, where these notches or thinned sections will preferentially erode or fatigue in the physiologic environment, forming partial or complete separations which allow expansion of the circumferential rings thereafter. In still other embodiments or examples, the separation regions may comprise modifications to the material of the circumferential ring itself. For example, in metallic rings, the separation regions may have modified grain boundaries which are selected to preferentially break and/or erode (including corrode) in the physiologic environment when compared to the remaining regions of the circumferential ring. Other examples are joints may be formed beginning with an intact circumferential ring, forming one of more breaks in the ring, and thereafter rejoining the breaks with means such as sleeve, adhesives, solder, connectors, coating, and/or the like, which are configured to degrade or erode or fatigue or break or separate in the physiologic environment. For example, solder, adhesives and/or polymer may be applied to the butt and/or or overlapping and/or hollow ends of the resulting joint. Alternatively, connectors may comprise sleeves, rings, coils, or other circumscribing structure which holds the joint together until such structures degrade and/or separate in the physiologic environment. In a preferred example a sleeve or coating comprising a polymer such as parylene can be applied which allows the separate free ends of the joint and/or junction to be contained within such sleeve or coating.

In another example the stent comprising a non-degradable metal or metal alloy, said stent comprising a structure comprising a plurality of rings where the rings comprising struts joined by crowns where at least some of the rings have at least one crown and no more than ¾ of the number of crowns (preferably at least one and no more than ½ the number of crowns) are formed and/or patterned to have said crowns cross sectional area being smaller and/or smallest than the cross sectional area of an adjacent crown and/or the largest crown cross sectional area within said ring. Cross sectional area can be measured at approximately the peak of the crown and/or at any other point/section on the crown. The cross sectional area of the smaller (including smallest) crowns ranges from 25% to 90% smaller than an adjacent crown cross sectional area and/or the largest crown cross sectional area within said ring, (preferably 50% to 75% smaller). The cross sectional area of the smaller (including smallest) crowns ranges from 400 micron squared to 3000 micron squared, preferably ranges from 400 micron squared to 2500 micron squared, and more preferably ranges from 400 micron squared to 1500 micron squared, such smaller cross sectional area crowns allowing said crowns to open up further after expansion. The smaller (including smallest) crowns can optionally have a sleeve, and/or coating, and/or solder comprised from polymer and/or adhesive and/or other material to hold the crown (and/or struts joined by said crown) in a crimped or substantially crimped configuration upon deployment of the stent, and where the sleeve and/or coating and/or solder degrade and/or dissolve and/or loosen after deployment (expansion) allowing the stent to further expand as the smaller cross sectional crowns are allowed to open and/or expand under physiologic conditions. The stent has sufficient strength upon deployment to support a body lumen. In another example the stent has sufficient strength to support a body lumen upon deployment where the stent strength decreases after the sleeve, and/or coating, and/or adhesive, and/or solder, dissolves and/or degrades under physiologic conditions after deployment. The cross sectional area of at least ¼ to ¾ of the crowns, preferably at least ½ to ¾ of the crowns, more preferably at least ¾ of the crowns, ranges from 3500 micron squared to 25000 micron squared, preferably ranges from 4000 micron squared to 10,000 micron squared, and more preferably ranges from 4500 micron squares to 8000 microns squared. The cross sectional area measurements in the above example are of same type (or same) non-degradable material (metal or metal alloy material) of the stent or structural element such as the crown and does not include other materials such as polymers, metals, coatings, etc. that are on or within the crown, when comparing smaller cross sectional area crowns to larger cross sectional area crowns. Alternatively, smaller cross sectional area crowns can be accomplished by incorporating a different material from the non-degradable metal or metal alloy in the crown region, or having less dense or weaker material, and/or having one or more of a groove, a hole, a dent, a crescent shape, a crown shaped, and/or a channel, in, on, and/or through the crown region. The groove, the hole, the dent, the crescent shape, the crown shaped, and/or the channel in, on, and/or through the crown region can be filled and/or coated with at least one material comprising a polymer, metal or metal alloy (preferably different from metal or metal alloy forming the stent), adhesive, and/or solder, and/or other suitable material. In this example the smaller cross sectional area is accomplished by having a softer or weaker or less dense material or gap in the crown region which effectively reduces the cross sectional area of the non-degradable metal or metal alloy in the crown (even though the total cross sectional area of said crown maybe similar to other crown cross sectional areas) compared to cross sectional area of same type metal or metal alloy in adjacent crown (or larger cross sectional area of same type metal or metal alloy). The material preferably is different from the crown material. The material can remain in the crown region, dissolve, and/or degrade/ erode after deployment to allow the stent to uncage and/or further expand under physiologic conditions. The stent upon deployment has sufficient strength to support a body lumen and where the stent strength does not decrease after deployment, or decreases after deployment, preferably decreases within 30 days after deployment, more preferably decreases within 3 months after deployment, and/or within one year after deployment. The material has lower stiffness than the crown material (preferably 2-10 times lower stiffness), softer, stretchable, and/or lighter than the crown material. The said crowns can have in one example a sleeve and/or a coating and/or adhesive containing said crown region and/or struts joined by said crowns. In another example, the stent exhibit increase in radial strain after expansion, and/or decrease in radial strength after said expansion. In another example, said increase of radial strain and/or decrease in strength, begins one week after expansion of the stent to 9 months after expansion of the stent, preferable begins one month after expansion to 6 months after expansion, more preferably begins 2 months after expansion to 6 months after expansion. In another example at least some struts have thinned cross sectional areas as described in this paragraph, In another example, the stent formed from non-degradable metal or metal alloy is patterned to have one or more regions on at least some rings or other structure "hollowed out" to create void regions or "voids" within the crown, strut, or other structural component of the stent scaffold where the metal has been removed, e.g. by patterning, cutting (such as laser cutting), abrading, or the like. Optionally, the voids may be entirely or partially filled with a degradable or non-degradable filling material which contributes to the strength of the scaffold for at least a time after implantation so that the scaffold has sufficient initial strength to support a body lumen. The filling material may be more or less stiff than the metal or metal alloy material of the stent, or in some cases may have an equivalent stiffness. The void may be completely filled, partially filled, or in some cases over-filled so that the filler material extends beyond the boundary of the stent scaffold prior to void formation.

Such filled-voids on crown regions for example will deform upon expansion of the stent and allow the compliance and strength of the stent to vary over time. In many examples, the filled-voids on the crowns will enhance strength of the scaffold at the time of expansion and implantation, but will also reduce compliance. By using a filler material that degrades, softens, or otherwise loses strength when exposed to a vascular or other physiologic environment, however, the compliance of the scaffold will increase which in turn increases the composite or composite compliance of the stent and blood vessel or other body lumen. While the strength may concurrently decrease, such reduction in strength is usually acceptable after the vessel or other body lumen has been opened and the luminal wall at least partially healed. In this way, at least some rings of the stent to uncage, to further expand, and/or to exhibit vaso-reactivity. The thickness of the metal or metal alloy surrounding the hollowed-out or void region in the crown regions (side surface region, luminal surface region, or abluminal surface region) ranges from 10 microns to 50 microns, preferable ranging from 20 microns to 40 microns. The hollowed out crown region can have a variety of ways to be hollowed out such as: two side surface regions of the crown region remain intact and the region between the two side surface regions is hollowed out, one side region and a luminal surface region remain intact while the other side region and abluminal surface region is hollowed out, two side surface regions and a luminal surface region remain intact while the abluminal surface region gets hollowed out, all surface region (abluminal, luminal, 2 sides) remain intact but the inner core of the crown region is hollowed out, and/or one side region, the abluminal surface region, and luminal surface region remain intact while the core gets hollowed out from the other side surface region, or other; such that the crown region allows uncaging of the stent after expansion. The combined total cross section area of the non-degradable metal or metal alloy for the said one or more crown regions at at least one section of the crown region ranges from 200 micron squared to 4000 micron squared, preferably ranges from 400 to 3000 micron squared, and more preferably ranges from 500 to 2500 micron squared. In another example, the hollowed-out region is filled with another material (degradable or non-degradable), wherein the material after expansion allows the crown region, the ring, and/or the stent to uncage, and/or to have increase in radial strain, and/or to have increase in radial strain and decrease in radial strength. In another example, at least some of the struts along at least some rings are hollowed out as described in this section.

Voids may also be formed in the struts, and other components of a scaffold ring or other scaffold structure. For example, channels, slots, and the like can be formed over some or all of a length of at least some rings, including struts, crowns, and any other structural components. As with other voids described previously, the channels, slots, and the like may be partially or fully filled with a second degradable polymeric or metallic material, referred to herein as a "reinforcement material," to provide sufficient combined material strength to enhance the radial strength of the stent immediately following expansion, wherein the reinforcement material typically degrades after expansion and implantation to enhance compliance while typically also reducing stent strength. The base non-degradable material of the struts, and other components of a scaffold ring or other scaffold structure will typically have a cross-sectional area in a range from $1000 \, \mu m^2$ to $4000 \, \mu m^2$, preferably from $1500 \, \mu m^2$ to $3500 \, \mu m^2$, where the degradable reinforcement material covering all or portions of the non-degradable material adds an additional $40 \, \mu m$ to $120 \, \mu m$ to a thickness and/or a width of the scaffold base material component, and wherein the combined base and covering reinforcement materials have sufficient strength to support a body lumen (and prevent recoil in vascular lumens) upon expansion, and wherein the compliance increases and strength in at least some rings decreases following expansion and implantation to uncage the stent. Channel depths are typically from 40% to 90% of the non-degradable material thickness, preferably from 50% to 85%, and more preferably from 60% to 80%, and the widths of the channels and slots are typically from 40% to 90% of the non-degradable material width, preferably 50% to 85%, more preferably 60%-80%. Channel and slot widths and thickness can vary along the length of the channels and slots on at least some rings. Channels may be disposed on abluminal surface regions, luminal surface regions, and/or both abluminal and luminal surface regions. Slots will typically penetrate from an abluminal surface to a luminal surface.

One or more thinned regions may alternatively or also be formed be along some or all of the rings or other circumferential elements of a non-degradable scaffold in order to increase scaffold compliance and promote uncaging of the scaffold after implantation. Such thinned out regions may be present in crown regions, strut regions, or on other components of a ring or other structure that affects circumferential compliance. By "thinned out," it is meant that a crown, strut, or other scaffold component has baseline cross-sectional dimensions over a majority of a length of that component, and that the baseline cross-sectional dimensions are reduced in a region is referred to as being "thinned out." Thinned-out regions can be located in adjacent crowns, in alternating crowns, in every third crown, or in other patterns or configurations to achieve sufficient strength to support a body lumen upon deployment and to increase compliance after expansion. Such thinned out regions can have a smaller thickness and/or width and/or cross section relative to the baseline dimensions sufficient to promote uncaging after implantation. Without any further modification, the thinned out regions will usually provide both lower scaffold strength and an increased compliance in at least the thinned out region of the component. Optionally, the thinned out regions can be reinforced with a coating, lamination, or other coupling of a reinforcement material to provide strength upon expansion while usually degrading after expansion to increase compliance. Such bio-degradable reinforcement materials can be similar to the filler materials described elsewhere herein, typically being degradable polymers but also being degradable metals. Suitable reinforcement materials will degrade over a time period after implantation in or expose to a vascular environment ranging from 30 days to 3 years, preferably from 3 months to 2 years, more preferably from 3 months to 1 year. The base non-degradable material (base stent), usually metal or metal alloy comprises one or more rings (or circumferential structural elements), usually a plurality of rings, each ring comprises struts and crowns along the length of said ring, and wherein the base stent in some examples does not have sufficient strength to support a body lumen (or to maintain a body lumen) in the absence of a reinforcement material coupled to the base stent, said reinforcement material having sufficient weight and thickness (such as a polymer coating) to increase the strength of the base strength to being sufficient to support a body lumen (or maintain a body lumen open).

For example, thinned-out cross-sectional regions along a length of a circumferential ring may be coated, laminated, or otherwise covered with sufficient reinforcement material to reinforce the stent scaffold upon expansion where the stent strength decreases and compliance increases as the material degrades after expansion and exposure to a vascular or other luminal environment. The scaffold may be formed from a non-degradable base material component having a cross-sectional area in a range from 1000 $\mu m^2$ to 4000 $\mu m^2$, preferably from 1500 $\mu m^2$ to 3500 $\mu m^2$, wherein the degradable reinforcement material covering the non-degradable material adds additional 40 $\mu m$ to 120 $\mu m$ to a thickness and/or a width of the scaffold base material forming an underlying component, and wherein the combined base and covering materials have sufficient strength to support a body lumen upon expansion, and wherein the compliance increases and strength in at least some rings decreases following expansion and implantation to uncage the stent.

In another example in any of the examples in this application, the stent prosthesis exhibits one or more of the following: uncages after expansion (which also includes one or more of the following): increase in radial strain (or compliance), increase in radial strain (or compliance) and decrease in radial strength, exhibit vaso-reactivity or vas-dilatation of the stented segment, further expand to a second larger configuration, being able to expand and/or contract after deployment, change in the shape configuration from the deployed shape configuration, change in the displacement of the stent in at least one dimension, have a displacement after expansion in at least one direction larger.

Suitable stent material including polymeric, metallic (metel and metal alloys), adhesives, coatings, solder, sleeves, sealants, fixation materials, cement, energy fixation, include but are not limited to the following: adhesives and fixation materials include but are not limited to adhesives, sealants, and potting compounds such as cyanoacrylate such as poly-alkyl-2-cyanoacrylate, methyl-2-cyanoacrylate, ethyl-2-acrylate; n-butyl cyanoacrylate, 2-octyl cyanoacrylate, or others; epoxy; epoxamine; UV-curable from Loctite, Dymax, Master Bond, or other; acrylic; silicone; hot melt; polyurethane; gorilla glue; lysine based adhesive such as TissueGlu, Sylys Surgical Sealant, or others; fibrin glue; beeswax. Other fixation materials may also be used, such as solder or fusible alloy material such as tin or its alloy such as Sn97Cu3, Sn50Zn49Cu1, Sn95.5Cu4Ag0.5, Sn90Zn7Cu3, Sn98Ag2, Sn96.5Ag3Cu0.5, Sn91Zn9, Sn85Zn15, Sn70Zn30, Sn89Zn8Bi3, Sn83.6Zn7.6In8.8, Sn86.9In10Ag3.1, Sn95Ag3.5Zn1Cu0.5, Sn86.5Zn5.5In4.5Bi3.5, Sn95Sb5, Sn96.2Ag2.5Cu0.8Sb0.6, Sn90Au10, or others; Indium or its alloy such as In97Ag3, In90Ag10, In50Sn50, In52Sn48, or others; zinc or its alloy such as Zn95Al5, Zn60Sn40, Zn95Sn5, or others; bismuth or its alloy such as B57Sn42Ag1, Bi58Sn52, or others; gold or its alloy such as Au80Sn20, Au98Si2, Au87.5Ge12.5, Au82In18, Other means for fixation includes laser bonding or welding or fusing, or other means of energy fixation (including bonding or joining), or solvent based, polymer dispersion or neat adhesives, sealants, and potting compounds such as cyano-acrylate such as polyalkyl-2-cyanoacrylate, methyl-2-cya-noacrylate, ethyl-2-acrylate; n-butyl cyanoacrylate, 2-octyl cyanoacrylate, or others; epoxy; epoxamine; UV-curable from Loctite, Dymax, Master Bond, Henkel, or other; acrylic; silicone; hot melt; polyurethane; gorilla glue; poly-ester; polylactide and their copolymers and blends; polyt-rimethylene carbonate and their copolymers or blends; poly-vinyl alcohol; polyvinyl acetate; ethylene-vinyl acetate (a hot-melt glue); phenol formaldehyde resin; polyamide; polyester resins; polyethylene (a hot-melt glue); polypro-pylene; polystyrene; Polycarbonate; polychloroprene; natu-ral rubber; silicone rubber; lysine based adhesive such as TissueGlu, Sylys Surgical Sealant, or others; fibrin glue; beeswax; bioadhesives such as casein, mussel adhesive proteins, and collagen, combination thereof, or the like, solder or fusible alloy material such as tin or its alloy such as Sn97Cu3, Sn50Zn49Cu1, Sn95.5Cu4Ag0.5, Sn90Zn7Cu3, Sn98Ag2, Sn96.5Ag3Cu0.5, Sn91Zn9, Sn85Zn15, Sn70Zn30, Sn89Zn8Bi3, Sn83.6Zn7.6In8.8, Sn86.9In10Ag3.1, Sn95Ag3.5Zn1Cu0.5, Sn86.5Zn5.5In4.5Bi3.5, Sn95Sb5, Sn96.2Ag2.5Cu0.8Sb0.6, Sn90Au10, or others; Indium or its alloy such as In97Ag3, In90Ag10, In50Sn50, In52Sn48, or others; zinc or its alloy such as Zn95Al5, Zn60Sn40, Zn95Sn5, or others; bismuth or its alloy such as B57Sn42Ag1, Bi58Sn52, or others; gold or its alloy such as Au80Sn20, Au98Si2, Au87.5Ge12.5, Au82In18, combination thereof, or the like. Suitable stent materials non-degrad-able in the vascular or other physiologic environment include but are not limited to metals and metal alloys, such as stainless steel, such as 304V, 304L, and 316LV stainless steel; steel alloys such as mild steel; cobalt-based-alloys such as cobalt chrome; L605, Elgiloy®, Phynox®; plati-num-based alloys such as platinum chromium, platinum iridium, and platinum rhodium; tin-based alloys; rhodium; rhodium based-alloys; palladium; palladium base-alloys; aluminum-based alloys; titanium or their alloy; rhenium based-alloys such 50:50 rhenium molybdenum; molybde-num based-alloys; tantalum; gold and gold alloys; silver and silver alloys; shape memory metal or alloys; chromium-based alloys; nickel-titanium alloys such as linear-elastic and/or super-elastic nitinol; nickel alloys such as nickel-chromium-molybdenum alloys (e.g., INCONEL 625, Hastelloy C-22, Hatelloy C276, Monel 400, Nickelvac 400, and the like); nickel-cobalt-chromium-molybdenum alloys such as MP35-N; nickel-molybdenum alloys; platinum enriched stainless steel; combinations thereof; or the like, and other malleable metals of a type commonly employed in stent and prosthesis manufacture. In other examples, the non-degradable material may comprise a non-degradable polymer, such as polyaryletherketone; polyetheretherketone; polyimide; polyethylenes such as UHMW, HDPE, LDPE, or others; polypropylene; polyester; polyethylene terephthalate; polycarbonate; polysulfone; polyphenylsulfone; polyethersulpone, Ultem; polyetherimide; polyurethane; polyamide; nylon such as nylon 12, nylon 6, nylon 6-6, or others; polyvinylchloride; PTFE; FEP; ETFE; PFA; PVDF; polyvinylchloride; acrylobutadiene styrene; Delrin; polymethylmethacrylate; polystyrene; polyacrylamide, polyphenylsufide; PEBAX; or other materials. In still other examples, the non-degradable material may comprise an elastic metal, such as a shape or heat memory alloy, shape memory polymer, or superelastic materials, typically a nickel-titanium alloy; a spring stainless steel; Ni50-Mn28-Ga22; copper-aluminium-nickel; alloys of zinc, copper, gold and iron; iron-based-alloys such as Fe—Mn—Si; copper-based-alloys such as Cu—Zn—Al and Cu—Al—Ni; poly(ε-caprolactone)dimethacrylate; PVDF/PMMA; PVDF/PVA; PLA/PVAc; or other, or the like. Examples of degradable material such as degradable polymeric material comprise one or more of: lactides, caprolactones, trimethylene carbonate, glycolides, poly(L-lactide), poly-DL-Lactide, polylactide-co-glycolide (e.g., poly(L-lactide-co-glycolide), copolymer of poly(L-lactide-co-epsilon-caprolactone (e.g., weight ratio of from around 50 to around 95% L-lactide to about 50 to about 5% caprolactone; poly(L-lactide-co-trimethylene carbonate), polytrimethylene carbonate, poly-caprolactone, poly (glycolide-trimethylene carbonate), poly(lactide-glycolide-trimethylene carbonate) or the like; polyhydroxybutyrate such as poly(3-hydroxybutyrate) and poly(4-hydroxybutyrate); polyhydroxyvalerate; polyhydroxybutyrate/polyhydroxyvalerate copolymers (PHV/PHB); polyhydroxyalkanoate; poly orthoesters; poly anhydride; polyiminocarbonate; tyrosine-derived polycarbonate; tyrosine-derived polyacrylate; iodinated and/or brominated tyrosine-derived polycarbonate; iodinated and/or brominated tyrosine-derived polyacrylates polyesteramide; polycarbonate copolymer, lactone based polymers such as poly(propylene fumarate-co-ethylene glycol) copolymer (aka fumarate anhydride); polyanhydride esters; polyorthesters; silk-elastin polymer; polyphosphazene; aliphatic polyurethane; polyhydroxy acid; polyether ester; polyester; polydepsidpetide; poly(alkylene oxalates); polyaspartimic acid; polyglutarunic acid polymer; poly-p-dioxanone; poly-beta-dioxanone; asymmetrically 3,6-substituted poly-1,4-dioxane-2,5-diones; polyalkyl-2-cyanoacrylates; polydepsipeptides (glycine-DL-lactide copolymer); polydihydropyranes; polyalkyl-2-cyanoacrylates; poly-beta-maleic acid (PMLA); polyalkanotes; poly-beta-alkanoic acids, polymers, blends, and/or co-polymers, or combination thereof.

In another example, suitable materials including suitable stent material including polymeric and metallic (degradable or non-degradable), adhesives, coatings, solder, sleeves, sealants, sealants, potting compounds, fixation materials, cement, energy fixation, elastomers and other type material, include but are not limited to: adhesives such as cyanoacrylate such as polyalkyl-2-cyanoacrylate, methyl-2-cyanoacrylate, ethyl-2-acrylate; n-butyl cyanoacrylate, 2-octyl cyanoacrylate, or others; gorilla glue; lysine based adhesive such as TissueGlu, Sylys Surgical Sealant, or others; fibrin glue; beeswax. Non-degradable adhesives, sealants, and potting compounds such as epoxy; epoxamine; UV-curable from Loctite, Dymax, Master Bond, or other; acrylic; silicone; hot melt; polyurethane; Degradable sleeve materials, stent material, and coatings such as polyester; polylactide and their copolymers and blends; copolymers of lactide, caprolactone, trimethylene carbonate, glycolide; poly(L-lactide), poly-DL-Lactide, polylactide-co-glycolide (e.g., poly(L-lactide-co-glycolide); copolymer of poly(L-lactide-co-epsilon-caprolactone (e.g., weight ratio of from around 50 to around 95% L-lactide to about 50 to about 5% caprolactone; poly(L-lactide-co-trimethylene carbonate; polytrimethylene carbonate; poly-caprolactone; poly(glycolide-trimethylene carbonate); poly(lactide-glycolide-trimethylene carbonate) or the like; polyhydroxybutyrate such as poly(3-hydroxybutyrate) and poly(4-hydroxybutyrate); polyhydroxyvalerate; polyhydroxybutyrate/polyhydroxyvalerate copolymers (PHV/PHB); polyhydroxyalkanoate; poly orthoesters; poly anhydride; polyiminocarbonate; tyrosine-derived polycarbonate; tyrosine-derived polyacrylate; iodinated and/or brominated tyrosine-derived polycarbonate; iodinated and/or brominated tyrosine-derived polyacrylates polyesteramide; polycarbonate copolymer, lactone based polymers such as poly(propylene fumarate-co-ethylene glycol) copolymer (aka fumarate anhydride); polyanhydride esters; polyorthesters; silk-elastin polymer; polyphosphazene; aliphatic polyurethane; polyhydroxy acid; polyether ester; polyester; polydepsidpetide; poly(alkylene oxalates); polyaspartimic acid; polyglutarunic acid polymer; poly-p-dioxanone; polybeta-dioxanone; asymmetrically 3,6-substituted poly-1,4-dioxane-2,5-diones; polyalkyl-2-cyanoacrylates; polydepsipeptides (glycine-DL-lactide copolymer); polydihydropyranes; polyalkyl-2-cyanoacrylates; poly-beta-maleic acid (PMLA); polyalkanotes; poly-beta-alkanoic acids; protein such as elastin, fibrin, collagen, glycoproteins, gelatin, or pectin; poly-serine; polycaprolactam; cyclodextrins; polysaccharides such as chitosan, and hyaluronan; alginate; polyketals; fatty acid-based polyanhydrides, amino acid-based polyanhydrides; poly(ester anhydride); polymer blends; and/or co-polymers; or combination thereof; or the like. Corrodible solder or fusible alloy such as Sn97Cu3, Sn50Zn49Cu1, Sn95.5Cu4Ag0.5, Sn90Zn7Cu3, Sn98Ag2, Sn96.5Ag3Cu0.5, Sn91Zn9, Sn85Zn15, Sn70Zn30, Sn89Zn8Bi3, Sn83.6Zn7.6In8.8, Sn86.9In10Ag3.1, Sn95Ag3.5Zn1Cu0.5, Sn86.5Zn5.5In4.5Bi3.5, Sn95Sb5, Sn96.2Ag2.5Cu0.8Sb0.6, Sn90Au10, or others; Indium or its alloy such as In97Ag3, In90Ag10, In50Sn50, In52Sn48, or others; zinc or its alloy such as Zn95Al5, Zn60Sn40, Zn95Sn5, or others; bismuth or its alloy such as Bi57Sn42Ag1, Bi58Sn52, or others. Non-corrodible solder or fusible alloy such as gold or its alloy such as Au80Sn20, Au98Si2, Au87.5Ge12.5, Au82In18. Degradable and non-degradable polymers include: polyester; polylactide and their copolymers and blends; copolymers of lactide, caprolactone, trimethylene carbonate, glycolide; poly(L-lactide), poly-DL-Lactide, polylactide-co-glycolide (e.g., poly(L-lactide-co-glycolide); copolymer of poly(L-lactide-co-epsilon-caprolactone (e.g., weight ratio of from around 50 to around 95% L-lactide to about 50 to about 5% caprolactone; poly (L-lactide-co-trimethylene carbonate; polytrimethylene carbonate; poly-caprolactone; poly(glycolide-trimethylene carbonate); poly(lactide-glycolide-trimethylene carbonate) or the like; polyhydroxybutyrate such as poly(3-hydroxybutyrate) and poly(4-hydroxybutyrate); polyhydroxyvalerate; polyhydroxybutyrate/polyhydroxyvalerate copolymers (PHV/PHB); polyhydroxyalkanoate; poly orthoesters; poly anhydride; polyiminocarbonate; tyrosine-derived polycarbonate; tyrosine-derived polyacrylate; iodinated and/or brominated tyrosine-derived polycarbonate; iodinated and/or brominated tyrosine-derived polyacrylates polyesteramide; polycarbonate copolymer, lactone based polymers such as poly(propylene fumarate-co-ethylene glycol) copolymer (aka fumarate anhydride); polyanhydride esters; polyorthesters; silk-elastin polymer; polyphosphazene; aliphatic polyurethane; polyhydroxy acid; polyether ester; polyester; polydepsidpetide; poly(alkylene oxalates); polyaspartimic acid; polyglutarunic acid polymer; poly-p-dioxanone; poly-beta-dioxanone; asymmetrically 3,6-substituted poly-1,4-dioxane-2,5-diones; polyalkyl-2-cyanoacrylates; polydepsi-peptides (glycine-DL-lactide copolymer); polydihydropyranes; polyalkyl-2-cyanoacrylates; poly-beta-maleic acid (PMLA); polyalkanotes; poly-beta-alkanoic acids; protein such as elastin, fibrin, collagen, glycoproteins, gelatin, or pectin; poly-serine; polycaprolactam; cyclodextrins; polysaccharides such as chitosan, and hyaluronan; alginate; polyketals; fatty acid-based polyanhydrides, amino acid-based polyanhydrides; poly(ester anhydride); polymer blends; and/or co-polymers; or combination thereof; or the like, polyvinyl alcohol; polyvinyl acetate; ethylene-vinyl acetate (a hot-melt glue); phenol formaldehyde resin; polyamide such as nylon 12, nylon 6, nylon 6-6, or others; polyester resins; polyethylene (a hot-melt glue), UHMW, HDPE, LDPE, or others; polychloroprene; polyaryletherketone; polyetheretherketone; polypropylene; polystyrene; polyester; polyethylene terephthalate; polycarbonate; polysulfone; polyphenylsulfone; polyethersulpone, Ultem; polyetherimide; polyurethane; polyvinylchloride; PTFE; FEP; ETFE; PFA; PVDF; polyvinylchloride; acrylobutadiene styrene; polyacetal such as Delrin; polymethylmethacrylate; polystyrene; polyacrylamide, polyphenylsufide; PEBAX; and/or co-polymers, and/or combination thereof. Elastic non-absorbable polymeric or elastomers such as silicone rubber; C-flex; poly(n-butylmethacrylate); poly(n-butylmethacrylate) blended with poly(methamethacrylate), Poly(hexyl methacrylate), and polyvinylpyrrolidone; Kraton; poly(styrene-ethylene/butylene-styrene) (SEBS); poly(styrene-ethylene/propylene-styrene) (SEPS), poly(acrylic acid-b-styrene-b-isobutylene-b-styrene-b-acrylic acid; poly(styrene-b-isobutylene-b-styrene); polybutadiene; PVDF-HFP poly(vinylidene fluoride-hexafluorpropylene); polyvinylpyrrolidone; poly(ethylene-co-vinyl acetate); phosphorylcholine; PEBAX; polyurethane elastomers; Tecoflex; Biomer; Pellethane; corethane; silicone rubber; rubbers; elastomers; blends; copolymers; combination thereof; or the like. Non-corrodible elastic metal or metal alloys such as shape or heat memory alloy, shape memory polymer, or superelastic materials, typically a nickel-titanium alloy; a spring stainless steel; Ni50-Mn28-Ga22; copper-aluminium-nickel; alloys of zinc, copper, gold and iron; iron-based alloy such as Fe—Mn—Si; copper-based alloy such as Cu—Zn—Al and Cu—Al—Ni; or the like. Metals or metal alloys that have high initial strength and weaken over time include Ti6Al4V, Ti5Al2.5Sn, or Ti-10V-Fe-3Al; stainless steel such as SAF2507; zinc alloys such as Zn5al, Zn10Al, Zn18Al, Zn30Al, platinum metal and its alloys; tin alloys such as Sn3.9Ag0.6Cu, Sn-3.8Ag-0.7Cu, SnPb, or SnPbAt; aluminum alloys such as Al1.7Fe, Al0.7Cu, A1.5MgScZr, Al6Mg0.2Sc0.15Zr, 3004, 8090, 7075, 6061, or 5056; zirconium alloy such as Zr55Al10Ni5Cu30; magnesium alloy such as AZ31B or MG11li5Al1Zn0.034Sc (LAZ1151); iron alloy such as Fe29.7Mn8.7Al1C, 30HGSA alloy steel, 4140, C45 steel, Fe36Ni, or low carbon steel; Nickel Alloys such as Ni21Cr17Mo or Haynes 230. Non-corrodible (non-degradable) metals or metal alloys such as conventional titanium alloys such as Ti6Al4V, Ti5Al2.5Sn, or Ti-10V-Fe-3Al; stainless steel such as SAF2507; platinum metal and its alloys; aluminum alloys such as Al1.7Fe, Al0.7Cu, A1.5MgScZr, Al6Mg0.2Sc0.15Zr, 3004, 8090, 7075, 6061, or 5056; zirconium alloy such as Zr55Al10Ni5Cu30; 304V, 304L, and 316LV stainless steel; steel alloy such as mild steel; cobalt based alloy such as cobalt chrome; L605, Elgiloy, Phynox; platinum based alloy such as platinum chromium, platinum iridium, and platinum rhodium; tin based alloys; rhodium; rhodium based alloy; palladium; palladium base alloy; aluminum based alloy; titanium or their alloy; rhenium based alloy such 50:50 rhenium molybdenum; molybdenum based alloy; tantalum; gold or their alloy; silver or their alloy (degradable); shape memory metal or alloy; chromium based alloy; nickel-titanium alloy such as linear-elastic and/or super-elastic nitinol; nickel alloy such as nickel-chromium-molybdenum alloys (e.g., INCONEL 625, Hastelloy C-22, Hatelloy C276, Monel 400, Nickelvac 400, and the like); nickel-cobalt-chromium-molybdenum alloy such as MP35-N; Nickel Alloys such as Ni21Cr17Mo or Haynes 230; or other; nickel-molybdenum alloy; platinum enriched stainless steel; combination thereof; or the like. Corrodible metals or metal alloys (degradable) include nickel, cobalt, tungsten; tungsten alloys of rhenium, cobalt, iron, zirconium, zinc, titanium; magnesium, magnesium alloys, magnesium alloy AZ31, magnesium alloy with less than 20% zinc or aluminum by weight, without or with one or more impurities of less than 3% iron, silicone, manganese, cobalt, nickel, yttrium, scandium or other rare earth metal, AZ31B or MG11li5Al1Zn0.034Sc (LAZ1151); zinc or its alloy such as zinc alloys such as Zn5al, Zn10Al, Zn18Al, Zn30Al; bismuth or its alloy; indium or its alloy, tin or its alloy such as tin-lead, Sn3.9Ag0.6Cu, Sn-3.8Ag-0.7Cu, SnPb, or SnPbAt; silver or its alloy such as silver-tin alloy; cobalt-iron alloy; iron or its alloys such as 80-55-06 grade cast ductile iron, other cast ductile irons, AISI 1010 steel, AISI 1015 steel, AISI 1430 steel, AISI 8620 steel, AISI 5140 steel, Fe29.7Mn8.7Al1C, 30HGSA alloy steel, 4140, C45 steel, Fe36Ni, low carbon steel or other steels; melt fusible alloys (such as 40% bismuth-60% tin, 58% bismuth-42% tin, bismuth-tin-indium alloys; alloys comprising one or more of bismuth, indium, cobalt, tungsten, bismuth, silver, copper, iron, zinc, magnesium, zirconium, molybdenum, indium, tin; or other material; or the like.

In another example or aspect, the present invention provides non-degradable prostheses having rings with energy-responsive separation regions. Such endoluminal prostheses comprise a scaffold having circumferential rings patterned from a non-degradable material, where the scaffold is configured to expand from a crimped configuration to an expanded configuration. At least some of the circumferential rings will have separation regions configured to form one or more discontinuities in said circumferential rings in response to energy applied to the separation regions after deployment, and/or after implantation of said prosthesis in a body lumen. Such discontinuities allow the scaffold to uncage and/or further expand, e.g. beyond an initial expansion diameter after recoil if any, typically achieved by balloon expansion, self-expansion, or the like.

The energy which promotes or causes the discontinuity may be energy associated with the site of implantation or may be energy from an external source directed at the site of implantation. For example, the separation regions may be configured to fatigue in response to, introduction of a drug agent, and/or pulsation of a blood vessel or other body lumen in which the endoluminal prosthesis has been implanted. Alternatively, the separation regions may be configured to respond to external energy which results in heat and/or mechanical motion, e.g., vibration, of the separation region. In particular, such motion-responsive separation regions may comprise notches, thinned regions, junction, butt joints, key and lock designs, or other localized regions or foci which in one example preferentially fatigue and breaking response to the applied energy and/or preformed separation regions which discontinue in response to the applied energy. For example, the separation regions may comprise "living hinges" which cycle open and close in response to the pulsation or application of external energy and separate or eventually fatigue and break. In still other examples, the separation regions may comprise modified grain boundaries in metal rings, where the grain bodies are particularly susceptible to vibration-induced fatigue.

In other embodiments or examples, the separation regions may comprise pre-formed breaks or pre-formed separations regions in the circumferential rings, where those breaks or discontinuities are reconnected with connectors configured to open in response to applied or endogenous energy (or in response to physiologic condition). Typical forms of externally applied energy include ultrasound, drug agents, heat, magnetism, radio frequency energy, high intensity focused ultrasound (HIFU), and the like.

In other examples and/or embodiments, the separation regions may comprise a key and lock junction formed in the circumferential rings and/or circumferential structural elements, where the key and lock junctions are initially immobilized before or during expansion or upon expansion but configured to open in response to applied energy, or physiologic condition, either external or endogenous. In still other examples or embodiments, the separation regions may comprise a rivet or other fastener joining breaks in the circumferential elements, where the fasteners are configured to open in response to applied energy, either external or endogenous, or in response to physiologic conditions.

In another example and/or fourth aspect, the present invention provides non-degradable or slowly degradable prostheses having rings with constrained hinges and methods for their use and fabrication. An endoluminal prosthesis comprises a scaffold as having a circumferential ring pattern from a non-degradable material. The scaffold is configured to deploy from a crimped configuration to an expanded configuration, and the circumferential rings have hinges which open as the scaffold is being deployed and/or after deployment. At least some of the hinges on at least some of the rings are constricted from expansion during deployment and are configured to open in response to a physiologic environment or application of external energy after deployment. Particular physiologic environments and external energies which can release the hinges from constriction have been well described above or throughout this application.

In one example, by initially constraining at least some of the hinges of the circumferential rings, the scaffold will be initially expanded to a diameter which is appropriate for the body lumen being treated and will possess sufficient strength to maintain patency of that body lumen while still in its configuration with the constrained hinge(s). After deployment and/or over time, however, the initially constrained hinges will be released from constraint, which lowers the effective circumferential rigidity of the scaffold. That is, with the addition of more hinges or other expansion regions, the force required to incrementally open the scaffold, preferably beyond its initially expanded configuration, will be lowered. In this way, the endoluminal prosthesis will have a reduced energy to cage or jail the treated body lumen, thereby allowing the scaffold to enlarge and/or lumen to enlarge.

In another example or aspect, the present invention provides a non-degradable prosthesis having rings with joint or active joints and methods for their fabrication and use. An endoluminal prosthesis comprises a scaffold having circumferential rings patterned from a non-degradable material. This scaffold is configured to deploy from a crimped configuration to an expanded configuration, and the circumferential rings include struts connected by joints which open as the scaffold is being deployed, typically by balloon expansion. At least some of the joints will be pivoted to allow the scaffold in its expanded configuration to uncage and/or further expand. The pivots or "active joints" may in some cases be asymmetric. That is, the joints will allow radial expansion of the circumferential rings, but will limit radial contraction of the rings.

In different embodiments or examples, the shapes of the reinforcing elements or bridging element can be substantially round (solid round wire or hollow round wire), rectangular, square, egg-shaped, or other shapes and geometries. The size of the reinforcing elements in some examples may be substantially the same size/geometry as the hinges, expansion regions, and/or struts to which the reinforcing elements are coupled, while in other examples the size/geometry of the reinforcing elements may be smaller or larger than the expansion regions. In one example, the ends of the reinforcing elements are atraumatic, and/or smooth, and/or have bulbous shapes or rounded shapes, and/or have larger cross sectional area to reduce trauma to the vessel. In one example a surface finish of the reinforcing elements is similar to that of a polished vascular metallic stents. In another example, the surface finish is textured.

In one example of degradable material, the polymeric body of the circumferential scaffold is configured to substantially degrade under physiologic conditions within a period from 1 month to 3 years, preferably from 3 months to 2 years, more preferably from 6 months to 1 year, after deployment of the endoluninal prosthesis. In another example, the reinforcement elements are encapsulated at least in part by a material, such as a thin polymer material. Examples include Parylene and C-Flex material.

In another example, the separation regions of a non-degradable scaffold are configured to separate in a period of up to 3 years after deployment, typically ranging from 1 day to 3 years, 1 month to 3 years, preferably from 3 months to 2 years, more preferably from 6 months to 1 year. In one example the separation region separate about the same time period, in another example the separation regions separate at different time periods.

In another example the endoluninal prosthesis further comprises at least one coating, preferably a degradable coating, on at least one surface of the stent prosthesis (scaffold prosthesis). In another example the stent prosthesis further comprises at least one drug on at least one surface of the stent prosthesis. In another example the stent prosthesis further comprises at least one coating containing at least one drug, on at least one surface of the stent prosthesis. In a preferred example, the polymeric material or adhesive joining or containing or holding together the separation regions are stretchable type polymers or adhesive materials (degradable or non-degradable) to allow no movement to some movement of the separation regions without prematurely forming the discontinuities (before deployment, or after deployment). This also allows for consistent performance of the scaffold and improved storage conditions and shelf life of the stent and separation regions to allow for extended shelf life under various typical environmental conditions of heat, humidity, and time. The material can withstand temperature ranging from 5° Celsius to 50° Celsius, preferably from 10° Celsius to 40° Celsius, and from 1 months to 3 years shelf life, preferably from 1 month to two years, or from one month to 18 months. At relative humidity from 10% to 95%, preferably from 20% to 70% relative humidity. Examples of material are described in this application.

In one example the endoluminal prosthesis further comprises radiopaque markers. In a more specific example the radiopaque markers comprise non-degradable radiopaque marker. In a preferred example the non-radiopaque radio markers comprises a metal or metal alloy.

In one example the reinforcing elements and/or the separation regions and/or the environmentally responsive separation regions are formed from non-degradable materials such as non-degradable metals and/or polymers or other material. The reinforcing elements and/or the separation regions and/or environmentally responsive separation regions may alternatively be formed in whole or in part from a degradable (corrodible) material, such as a degradable metal (such as magnesium and magnesium alloys), or a degradable polymer (such as a lactide polymer, co-polymer, and blends thereof); or a combination thereof. In one example the reinforcing elements and/or separation regions and/or environmentally responsive separation regions are formed from a corrodible material which corrode after implantation to uncage the stent or other endoluminal prosthesis, preferably uncaging the stent prosthesis without formation of unwanted by products such as hydroxyapatite materials adjacent to the separation region.

In one example, the endoluminal prosthesis is a stent prosthesis comprising a substantially tubular structure, the tubular structure is patterned, the stent prosthesis comprises separation regions, and the stent prosthesis is crimped to a smaller diameter, and being deployed from the crimped configuration to a larger expanded configuration, where the stent in the expanded larger configuration has sufficient strength to support a body lumen and/or does not fracture and/or has low recoil. The stent after deployment in this example is configured to do one or more of the following: the stent and/or circumferential structural elements and/or rings are configured to separate, expand, form discontinuities, and/or come apart at least in one section and/or region or more after deployment and/or after implantation, and/or the stent undergoes modification comprises unlocking, degradation, or containment by a sleeve or material that does not prevent the separation region from uncaging, of the separation region or material adjacent to the separation region after deployment or implantation causing at least one part of the stent structures and/or to separate, expand, and/or come apart, and/or the stent expands further after deployment, and/or the stent expands further after deployment and after modification, and/or the stent expands further after deployment radially, and/or the stent expands circumferentially after deployment, and/or the stent expands further after deployment and after assisted modification from a source (chemical, energy), and/or the stent is configured to push the lumen to expand for a period after deployment or implantation, and/or the stent is configured to allow the lumen or vessel to expand/enlarge, or a combination thereof. The stent comprises a non-degradable material, or comprising two non-degradable materials, or comprising a degradable material, or comprising two degradable materials, or comprising two degradable materials and one non-degradable material, or comprising non-degradable material and a corrodible material, or comprising a degradable material and a corrodible material, or comprising a degradable material, and a corrodible material, and a non-degradable material. The stent may further comprise at least one coating on at least one surface of the stent prosthesis, said coating is degradable and/or non-degradable coating. The materials above exclude marker material(s) that can be degradable or non-degradable. The stent may further comprise at least one drug on at least one surface of the stent. The stent can also comprise at least one coating on at least one surface of the stent prosthesis.

In one example, the stent prosthesis comprises a structure, preferably substantially tubular structure, more preferably substantially tubular patterned structure having separation regions. The stent prosthesis is typically expandable from a crimped configuration to a deployed expanded larger configuration. The stent structure comprises at least one main or principle material on at least one section of the stent, preferably the frame material is degradable material such as a polymer material, and the stent structure further comprises at least one piece of a second material, preferably a stronger material than the frame material, more preferably a metal material, more preferably a non-degradable metal material, interfacing with or coupled to at least said section of the frame material, preferably said section is a crown section of the stent structure. The stent is deployed to a larger expanded configuration. The stent in the expanded deployed configuration has sufficient strength to support a body lumen, and/or expand without fracture, and/or expand with low recoil. The stent undergoes modification after deployment where the modification comprises degradation of at least part of the frame material, and/or degradation of at least part of the second material, and/or corrosion of at least first material, and/or corrosion of at least part of the second material, or combination thereof. The stent after modification comprises one or more discontinuity in at least one ring, and/or at least one discontinuity in at least one crown, and/or at least one discontinuity in at least one strut, and/or a combination thereof. In another example the stent after modification has at least one discontinuity in at least part of the frame material, and/or at least one discontinuity in at least part of the second material, and/or at least one discontinuity in adjacent parts of the frame and second material. In another example, the stent after modification further expands to a larger configuration from the configuration before modification, and/or further expands to a larger configuration from the deployed configuration, and/or further expands to a larger configuration from a "recoil after deployment" configuration, and/or further expands to a larger configuration for any of the previous causes in at least one ring of the stent prosthesis, and/or further expands to a larger configuration in at least one ring other stent prosthesis wherein the ring is located about the mid portion of the stent length. In another example, the at least one discontinuity of at least one ring of said stent after modification allows the stent to further expand at said at least one ring under physiologic pressure. In another example, the stent prosthesis comes apart after deployment and/or modification in at least one ring, crown, and/or strut. In one example the stent prosthesis after deployment and/or after modification and/or after coming apart has a structure, and/or has a tubular structure, and/or has a tubular patterned structure, and/or has a substantially maintained tubular structure, and/or has at least part of a structure, and/or has a at least one window, and/or substantially has no structure, and/or comprises at least one crown structure, and/or comprises at least one strut, and/or comprises at least one link, and/or has a strength, and/or a combination thereof.

In a particular example, the stent comprises a substantially tubular patterned structure comprising a plurality of rings, (serpentine, diamond, zig-zag, and/or other open cell or closed cell structure), wherein the ring comprises crowns and struts, wherein at least some rings are connected to adjacent rings by at least one link, or in some cases some adjacent rings are connected together in at least one location.

In an example a scaffold or ring material comprises metal and/or metal alloy. The metal and/or metal alloy may be non-degradable or degradable/corrodible. The metal herein excludes markers and marker material which can be metal or metal alloy and can be degradable or non-degradable. The corrodible metal or metal alloy corrodes in a period ranging from 1 month to 10 years, preferably in a period ranging from 3 months to 5 years, and more preferably in a period ranging from 3 months to 3 years.

In an example the second material (or reinforcement elements) has at least two ends, wherein the ends are deburred, shaped into a ball, a shape like a "nerve synapse," and/or smoothed, to prevent injuring the lumen or vessel, and/or causing inflammation after the stent come apart, and/or after modification. In another example the stent is configured to not break apart other than in the separating region and/or the section configured to break apart by reducing stress areas and/or fatigue areas, on the stent after modification, and/or after separation of the separation region forming discontinuities and/or breaking apart of the stent.

In an example the main or frame material comprises a polymeric material. The polymeric material may be degradable or non-degradable. In one example the polymeric material degrades in a period ranging from 1 month to 10 years, preferably ranging from 3 months to 5 years, more preferably degrades in a period ranging from 3 months to 3 years.

In an example the main or frame material is non-degradable, and/or degradable at a faster rate than the second material (reinforcement elements), and/or degradable at a substantially the same rate as the second material, and/or degradable at a slower rate than the second material.

In an example, the stent in any of the examples and/or embodiments in this application is formed from one or more of the following: a tube, a continuous wire or filament, a wire, a hollow wire hollow either hollow entirely or in certain regions such as less stress regions and/or substantially straight regions, or a braid, or mold, or by printing, or by extrusion, or by spraying, or by dipping, or by stamping, or a combination thereof. The stent has separation regions formed before patterning, during patterning, or after patterning, or after treatment to form such separation regions and/or discontinuities. Means to hold said discontinuities are describes throughout this application.

In an example, a second reinforcing material coupled to or interfacing with a structural scaffold material is embedded entirely inside the frame, or at least one surface or surface region is embedded inside at least one surface or surface region of the frame, or at least two surfaces embedded inside at least one surface of the frame, or at least three surfaces embedded inside at least one surface of the frame, or at least one surface of the second material attached (and/or joined, and/or abut, and/or glued, and/or force fit) to at least one surface of the frame material. The at least one surface of the frame material may be an abluminal surface, may be the luminal surface, or may be a side surface of the frame material. The second material may be sandwiched within the frame material. In one example the second material has a discontinuity, where the second material discontinuity is held together or joined together by said frame material, and/or glue, and/or a coating.

In an example, the second reinforcing material may in the form of one or more pieces comprising one or more of a wire, ribbon, strut, crown, link, and/or filament. A cross-section of the piece(s) may have any one of a variety of shapes comprising round or substantially round, rectangle or substantially rectangle, square or substantially square, oblong or substantially oblong, egg shaped or triangle, or other shapes. The length, number, and location of the pieces vary and maybe at least one or more on at least one or more stent rings, ranging from the length of a stent strut or smaller, the length of a stent crown or smaller, the length of a stent link or smaller, and/or the length of a stent ring or smaller. Preferably, the pieces of the second material are on/in/around at least one stent crown in at least one stent ring, and/or on/in/around at least two stent crowns in at least one stent ring, and/or on/in/around substantially all stent crowns or part of a stent crown in at least one stent ring of the stent, and/or on/in/around all except one of a stent crown on at least one stent ring, and/or on at least one ring, on/or on at least one ring about the middle of the stent length, and/or on at least one window of the stent patterned structure, and/or on at least one strut or part of a strut, and/or on at least one link or part of a link, and/or other variety or combination thereof. In one example a patterned stent structure comprises plurality of windows each window comprises reinforcing material comprising at least two crown, and at least four struts. In another example the window comprises at least four crowns, and at least four struts, and at least one or at least two links. In another examples links maybe straight, and/or or have shapes such as S-shaped link, V-shaped link, M-shaped link, and/or other link shapes. In an example, at least one structural element (comprising crown, strut) in each window has a separation region configured to expand and/or have a discontinuity and/or separate. In another example, the structural element comprises a plurality of circumferential rings comprising one or more windows, wherein each window has at least one separation region configured to expand and/or have a discontinuity and/or separate.

In a preferred example it is desired to have a stent structure having separation regions, wherein the stent after deployment forms discontinuities in said separation regions (or such discontinuities are formed before deployment and held together by means of design geometry or deployment means such as balloon catheter), or other type of embodiments of this application, wherein the stent structure is substantially maintained after said separation regions come apart (or separate), and/or move in one or more direction. The benefit of having a stent structure, preferably along the length of the stent length or part of the stent length, helps prevent vulnerable material underneath the stent such as vulnerable plaque from rupturing into the blood vessel and causing harm. The stent structure is sufficient to prevent (or hold) a vulnerable material (such as vulnerable plaque) in a body lumen. In another example, the stent structure after deployment and/or after coming apart and/or after forming discontinuities is substantially sufficient to support a body lumen. In another example, the stent structure after deployment and/or after coming apart and/or after forming discontinuities is substantially sufficient to support a body tissue.

In one example the at least some structural elements of the stent uncage and/or come apart and/or have separation regions comprises one or more of un-fix, un-hold, un-done, un-latched, un-attach, detached, disconnected, break up, break apart, push, push apart, separate, pull apart, create a gap, create a space, disintegrate, corrode, degrade, fragment, fracture, shatter, splinter, decompose, unlock, break down, deteriorate, degenerate, decay, discontinue, become free, and/or combination thereof, of said stent or said stent structural element, as formed, after treatment (including modification), and/or after deployment, under physiologic conditions. Stent structural elements in one example comprises one or more of rings, crowns, struts, and/or links. Stent structural elements in another example comprises one or more of rings, said rings comprise crowns, and/or struts.

In an example, the stent prosthesis is deployed to the expanded larger configuration under physiologic conditions and/or simulating conditions comprising in air, and/or in air at ambient temperature, and/or in air at 37° C. temperature, and/or in water, and/or in water at ambient temperature, and/or in water at 37° C., and/or in a body lumen, and/or at body temperature, and/or in a tube, under pressure, under pulsating pressure, and/or combination thereof.

In an example, the stent prosthesis is deployed to the expanded larger configuration and undergoes modification in air, and/or in air at ambient temperature, and/or in air at 37° C. temperature, and/or in water, and/or in water at ambient temperature, and/or in water at 37° C., and/or in a body lumen, and/or at body temperature, and/or in at least one solvent, and/or in at least one solvent or corrosion inducing agent at ambient temperature, and/or in solvent or corrosion inducing agent at 37° C., and/or in a tube, and/or pressurizing the stent at 1.5 psi to 5 psi, under pressure, under pulsating pressure, and/or accelerated fatigue, and/or accelerated any of the conditions, and/or combination thereof.

In another example or aspect of this invention, a non-degradable stent prosthesis comprises a structure, wherein the structure comprising a wire, hollow wire (hollow at least in some regions where it is hollow as formed and/or after treatment (modification)) where the wire and/or hollow wire are patterned into a stent, preferably a substantially tubular stent structure, more preferably a substantially tubular patterned stent structure wherein the stent is patterned from a tube. The stent prosthesis is expandable from a crimped configuration to a deployed larger or expanded configuration. The stent structure comprises a strong material, such as a non-degradable polymeric or metal (including metal alloy) such as metal stainless steel or cobalt chrome. The material is configured to have a at least one section and/or region in at least one ring where the material will come apart (environmentally responsive separation region, or separation regions) after deployment, and/or after modification; and/or the material is configured to have at least one discontinuity in at least one ring, and/or at least one discontinuity in at least one strut, and/or at least one discontinuity in at least one crown, and/or combination thereof. The discontinuity in the material is held together and does not substantially affect the crimping and/or deployment of the stent to the larger expanded configuration, and/or the stent prosthesis has sufficient strength in the deployed configuration to support a body lumen; and/or the material is configured to have at least one discontinuity in at least one ring, and/or at least one discontinuity in at least one strut, and/or at least one discontinuity in at least one crown, and/or combination thereof. The discontinuity in the material is held together and does not substantially affect the crimping and/or deployment of the stent to the larger expanded configuration, and/or the stent prosthesis has sufficient strength in the deployed configuration to support a body lumen. The material being held together comprises holding, latching, attaching, connecting, pushing together, pulling together, removing a gap, removing a space, and/or locking, together the material discontinuity adjacent parts. The means to hold the material discontinuity parts together comprises a sleeve, an adhesive, a press fit, a lock, a coating such as polymer or metallic coating, a gel, solder, and/or designs such as key and lock design. The stent in the expanded deployed configuration has sufficient strength to support a body lumen, and/or expand without fracture, and/or expand with low recoil. The stent in one example undergoes modification after deployment where the modification comprises uncaging, un-fixing, un-holding, un-done, un-latching un-attaching, detaching, disconnecting, breaking up, breaking apart, pushing, pushing apart, separating, pulling apart, creating a gap, creating a space, disintegrating, corroding, degrading, fragmenting, fracturing, shattering, splintering, decomposing, unlock, break down, deteriorate, degenerate, decay, and/or discontinue, of at least part of the material and/or the means holding the material discontinuity parts together. The stent after modification comprises one or more come apart material sections and/or discontinuity in at least one ring, and/or at least one or more come apart material sections and/or discontinuity in at least one crown, and/or at least one or more come apart material sections and/or discontinuity in at least one strut, and/or a combination thereof. In another example, the stent after modification allows the lumen or vessel to further enlarge from after implantation, and/or allows the stent to further expands to a larger configuration from the configuration before modification, and/or further expands to a larger configuration from the deployed configuration, and/or further expands to a larger configuration from a "recoil after deployment" configuration, and/or uncage, and/or further expands to a larger configuration for any of the previous causes in at least one ring of the stent prosthesis, and/or further expands to a larger configuration in at least one ring of the stent prosthesis wherein the ring is located about the mid portion of the stent length. In another example, the at least one or more come apart material sections (separation regions) and/or discontinuity of at least one ring of said stent after modification allows the stent to uncage and/or further expand at said at least one ring under physiologic pressure. In another example, the stent prosthesis comes apart after deployment and/or modification in at least one ring, crown, and/or strut. In one example the stent prosthesis after deployment and/or after modification and/or after coming apart and/or after the material discontinue has a structure, and/or has a tubular structure, and/or has a tubular patterned structure, and/or has a substantially maintained tubular structure, and/or has at least part of a structure, and/or has a at least one window, and/or substantially has no structure, and/or comprises at least one crown structure, and/or comprises at least one strut, and/or comprises at least one link, and/or has a strength, and/or a combination thereof.

In one example the means to hold the material together and/or to hold the material separation regions and/or discontinuity together, and/or to prevent the stent from coming apart before deployment, comprise adhesive, metal, polymer, coating, solder, press fit, welding, weaving or braiding a material, and/or other. In one example said means decomposes, degrades, corrodes, come unlocked, and/or unfit in a period ranging from 1 months to 5 years, preferably from 3 months to 3 years, more preferably from 3 months to one year. In one example the stent material degrades after said means degrades and/or corrodes and/or unlocks, etc.

In another preferred example a stent prosthesis comprising a structure, where in the structure separation regions and/or discontinuity is located in areas not affecting radial expansion, and/or or circumferential expansion, preferably in lower stress areas such as struts, or strut regions.

In another example a stent prosthesis is configured to have a patterned structure where the structure has separation regions discontinuity such as a key and lock, an abut, two plates, press fit, ratchets, rivets, inserts, magnets, or other, on at least one strut, and/or on at least one crown, such that the stent after deployment, and/or after deployment and after modification, allows the lumen or vessel to further enlarge, and/or uncage, and/or separate.

In another example a stent prosthesis is configured to have a patterned structure where the structure comprises a plurality of rings wherein the rings in one example is serpentine rings, wherein the rings comprises crowns and struts, wherein at least one crown and two struts are held in the crimped configuration by a coating and/or a sleeve, wherein the stent after deployment and modification comprising degradation of said sleeve and/or coating allows the stent to uncage and/or further expand to a larger configuration, and/or allow the lumen or vessel to enlarge.

In another example a stent prosthesis is configured to have a patterned structure where the structure comprises a plurality of rings wherein the rings in one example is serpentine rings, wherein the rings comprises crowns and struts, wherein at least one crown and/or at least one strut, on at least one ring are configured to have separation regions and/or come apart at at least in one section or region after deployment and under physiologic condition such as after fatiguing of said section or region. Said stent structure after coming apart allows the stent to uncage, and/or further expand to a larger configuration, and/or allow the lumen or vessel to enlarge.

In another example a stent prosthesis is configured to have a patterned structure where the structure comprises a plurality of rings wherein the rings in one example is serpentine rings, wherein the rings comprises crowns and struts, wherein at least one crown and/or at least one strut, on at least one ring are configured to come apart at at least one section or region after deployment and under physiologic conditions such as after fatiguing of said section or region. Said stent structures after coming apart allows the stent to uncage, and/or further expand to a larger configuration, and/or allow the lumen or vessel to enlarge.

In another example, a stent as in any of the examples above is configured to further expand after implantation using an external energy source wherein the energy source comprises magnetic field, infrared heat, inducing heat, ultrasound, and the like.

In another example in any of the examples above wherein the stent material comprising the stent structure is a shape memory material wherein the stent can uncage, and/or further expand after deployment using a shape memory material such as nickel-titanium alloy (NiTi available under the tradename Nitinol®), and where in the shape memory material expands the stent further after deployment to a larger configuration, wherein the stent undergoes modification such as having separation regions wherein the stent comes apart or forms discontinuities in at least one section or region of the stent, and/or comes apart in at least one ring, wherein the stent structure(s) after coming apart slows the further stent expansion, and/or stops the stent further expansion, and/or stops causing injury or inflammation to the vessel wall.

In another example in any of the examples above wherein the stent material comprises a material that additionally softens after modification or after expansion under physiologic condition, such as Platinum alloys, wherein the softening of said material reduces the stresses after deployment on the vessel wall and potentially brings the compliance of the vessel and stent closer from before softening of the material.

In a preferred example, the pieces, and/or structure of stent, and/or structure or part of a structure after modification and after the stent comes apart is configured to have a shape and/or structure to avoid dislodging such pieces or structure elements into the blood stream. Examples include 2-D, and/or 3-D structures, stent windows, structures comprising part of stent windows, structures comprising at least one crown shape, structure comprising at least one crown and at least one link shapes, structure comprising at least one crown, at least two struts, and at least one link shapes, a structure comprising at least one crown and at least two struts shapes.

In another example, the stent prosthesis is capable of being deployed from the crimped configuration to the larger expanded configuration under one or more of the deployment condition in a previous example.

In another example the stent can be deployed at a rate of 1-2 atm per seconds, the stent is capable of being deployed beyond the labeled (nominal/intended deployed) diameter without fracture.

In preferred example of corrodible material such as magnesium, the stent is configured to have sections or regions wherein the material does not degrade (corrode), and wherein said section or region would not degrade, providing stent sections or regions that do not cage the lumen or vessel providing for a lumen or vessel capable of enlarging as a result of not having by product from the magnesium stent in said sections that would result in caging the stent due to the hydroxyapatite by product caging the vessel.

In one example the stent comprising the separation regions or sections coming apart, and/or degrading, and/or corroding, and/or the stent section discontinue, and/or unlock, after deployment in a period from 1 day to 3 years, 1 month after deployment to 3 years, preferably from a period ranging from 3 months to one year.

In another example, the number sections or regions per at least one ring or in at least some rings that come apart, and/or unlock, and/or degrade, and/or corrode for at least one ring ranges from 1 to 4, preferably ranges from 1 to 3, more preferably ranges from 1 to 2, wherein the stent has a structure after coming apart, and/or wherein the stent has no structure after coming apart, and/or wherein the stent in the absence of tissue has an unsupported structure, or collapses, and/or wherein stent in the absence of tissue recoils, and/or wherein the stent in the absence of tissue recoils, or shrinks.

In another example, the number of sections per at least one ring that come apart, and/or unlock, and/or degrade, and/or corrode for at least one ring ranges from 1 to 4, preferably ranges from 1 to 3, more preferably ranges from 1 to 2, wherein the stent has a structure after coming apart, said structure has sufficient strength to support a body lumen, or has no strength, and/or wherein the stent has no structure after coming apart, and/or wherein the stent in the absence of tissue has unsupported structure, or collapses, and/or wherein stent in the absence of tissue recoils, and/or wherein the stent in the absence of tissue shrinks.

In another example, the number of sections per at least one ring that come apart, and/or unlock, and/or degrade, and/or corrode for at least one ring ranges from 1 to 4, preferably ranges from 1 to 3, more preferably ranges from 1 to 2, wherein the stent has a structure after coming apart, said structure has sufficient strength to support a body lumen, or has no strength, and/or wherein the stent has no structure after coming apart, and/or wherein the stent in the absence of tissue has unsupported structure, collapses, and/or wherein stent in the absence of tissue recoils, and/or wherein the stent in the absence of tissue shrinks.

In any one of the previous examples, the lumen or vessel is uncaged, and/or allowed to further enlarge or expand when the stent prosthesis comprising reinforcing elements and/or comprising non-degradable material for stent strength, and/or when the remaining stent prosthesis non-degradable material weight is lighter than the weight of the stent prosthesis comprising non-degradable and degradable material. In a preferred example, the stent prosthesis weight after degradation (or removal) of degradable material (if any) ranging from 0.1 mg/mm to 1.5 mg/mm, preferably ranging from 0.1 mg/mm to 1.2 mg/mm, and more preferably ranging from 0.2 mg/mm to 0.9 mg/mm, and most preferably ranging from 0.2 mg/mm to 0.6 mg/mm. These weights exclude the weight of non-degradable radiopaque markers.

In another example, the conformability of the stent prosthesis (3-point bend test) after formation of discontinuities, or after degradation of degradable material (if any) forming discontinuities is desirable to be as conformable as possible to avoid potential irritation and inflammation to the vessel wall after implantation. For example, the conformability of the stent prosthesis after formation of discontinuities, or after removal (or degradation of degradable material) is preferably ranging from 0 N/mm to 0.05 N/mm, preferably ranging from 0 N/mm to 0.03 N/mm, more preferably ranging from 0 N/mm to 0.1 N/mm. In another example the conformability of the stent after formation of discontinuities in the deployed configuration is improved (compared to before formation or compared to upon deployment of the stent) by at least 10%, or improved by at least 25%, or improved by at least 50%, or improved by at least 75%. In another example the conformability after formation of discontinuities is improved (compared to before formation or compared to upon deployment of the stent) by a range from 10% to 100%, preferably from 20% to 75%. In another example the radial strain of the stent after formation of discontinuities or after deployment ranges from 2% to 5% in a simulated bench test (as describe but not limited to example 5). In another example, the radial strain (or compliance) for the stent after formation of discontinuities and/or after deployment is larger than stent not having discontinuities by a factor ranging from 2 times to 10 times, preferably ranging from 2 times to 5 times (as described but not limited to example 5).

In another example the stent or other endoluminal prosthesis is in an uncaged configuration prior to being deployed from a crimped configuration, wherein the stent or other endoluminal prosthesis has strength in the deployed configuration to support a body lumen. In another example, the stent or other endoluminal is in an uncaged configuration in a circumferential direction prior to implantation or deployment.

In another example, the stent or other endoluminal prosthesis is configured to uncage after deployment or after implantation, in a physiologic environment, preferably configured to uncage in a circumferential fashion or direction by having at least one or more gaps (discontinuities) along the path of at least some, preferably every ring in the circumferential direction. Optionally, the stent can also unzip along the longitudinal axes of the stent in one or more paths (or lines) through the formed discontinuities in a variety of patterns separating the stent into one or more segments. In one example, the stent does not unzip along the longitudinal axis, or unzips at least part of the longitudinal axis of the stent.

In another example, uncaging of the stent or other endoluminal prosthesis comprises one or more of separation of the stent in at least one region or section in at least one ring, at least one discontinuity, at least one break, at least one gap, ability of the stent to further expand after deployment, ability of the lumen or vessel to positively remodel in the presence of the stent or re-enforcement elements or in the presence of the stent, ability of the stent or other endoluminal prosthesis to further expand after deployment without having stent breaks, separation, or discontinuities, ability of the lumen or vessel to positively remodel in the presence of the stent or other endoluminal prosthesis without having discontinuities, breaks, or separations.

In one example, the endoluminal prostheses of the present invention will typically comprise scaffolds with circumferential structures such as rings which comprise a plurality of struts joined by crowns, commonly referred to as zig-zag stents, serpentine stents, closed cell designs, and the like. In accordance with a further aspect of the present invention, at least some of the struts in at least some of the zig-zag or serpentine rings will include at least one separation region configured to form a discontinuity and/or uncage in the circumferential ring after expansion of the stent and/or strut in a physiologic environment. In these examples, the crowns of the rings and connected links which joins adjacent rings are preferably free from separation regions. This allows for a controlled expansion of the individual rings as well as of the stent as a whole in response to luminal remodeling.

In another example, endoluminal prostheses having separation regions in individual struts of their circumferential rings will form discontinuities which allow the scaffold to uncage, and/or expand beyond an initial expansion after deployment in a target blood vessel or other body lumen. The physiologic environment in which the prostheses are expanded will typically be physiologic conditions such as that of a body lumen, such as a vascular environment which may be mimicked by a water bath at 37° C. In the vascular environment, the discontinuities which form in the rings will allow the scaffold to circumferentially uncage, and/or open as the blood vessel and/or lumen positively remodels after placement of the stent or other prosthesis. The discontinuities will typically form in a period from 30 days to 6 months after the initial expansion of the circumferential scaffold within the physiologic environment but can have such discontinuities form 1 day after deployment to 3 years after deployment. In one example the discontinuities are formed and/or occur before implantation wherein such discontinuities still allow for crimping, and/or allow for stent deployment from a crimped configuration to an expanded configuration and have sufficient strength to support a body lumen. In such case the stent or stent structures regions uncages, and/or allows for further expansion in at least said region of discontinuity of the stent structure.

In another example, the separation regions within the struts of the circumferential rings may comprise "key and lock" or similar type junctions in the struts and/or other structural elements, which junctions are held together and/or immobilized during expansion but configured to open or release after the initial expansion in the physiologic environment. In one specific type of key and lock junction, the key and lock will open to allow the joined segments of the strut to separate from each other in a radial direction only after the separation region is free to separate (i.e. is mobilized). In other specific example, the key and lock type junctions are configured to allow the joined segments of the strut to separate from each other in both radial direction and axial direction after they are mobilized. The key and lock junctions type may be held together and/or immobilized by a polymer, coating, a sleeve material, cement, and/or adhesive which is applied to abutting surfaces of the junctions where the coating, cement, sleeve, or adhesive is selected to degrade in the physiologic environment over time.

The lock and key separation regions comprise connections, junctions, or other structures including a female portion comprising two spaced-apart arms forming a slot there between and a male portion adapted to fit in the slot. The two arm portions will typically have opposed inner walls which define a width of the slot, and the width will typically be constant along at least a majority of the length of the slot, usually over 60%, more usually over 75%, and often over 100%, so that the walls are parallel over most or all of the length and surfaces forming a slot with parallel walls. The male portion will have oppositely disposed outer walls with surfaces facing the inner surfaces of the slot. The outer walls of the male portion will typically have a geometry or shape congruent with the inner walls of the slot (e.g. the walls of the male portion will be parallel if the walls of the slot are parallel and the walls of the male potion will be tapered if the walls of the slot are tapered), but there will usually be a gap, spacing, or other opening between the outer wall surfaces of the male portion and the inner surfaces of the slot, where the gap will typically be filled with a biodegradable polymer or other adhesive as described elsewhere herein. The male portion of such lock and key separation regions typically remain contained within the slot of corresponding female portion during expansion of said scaffold and, in some cases, even following expansion. This can be seen e.g. in FIGS. 16G-2, 16G-7B, and 16G-8B.

Consideration should also be given to the geometry of the sides of the lock forming the slot or groove. The sides may be substantially the same width, or wider or narrower than the structural elements containing the junction, to minimize or inhibit bending or deformation of the slot or groove upon expansion of the stent from a crimped configuration to an expanded configuration or after expansion of the stent in physiologic environment. In another preferred example, the geometry of the sides of the lock forming the slot or groove may have widths which may be substantially equal or different and which may be equal to or greater than ¼ of the width, equal to or greater than ½ of the width, equal to or greater than ¾ of the width, substantially the same width, wider, 1.25 times or more wider, 1.5 times or more wider, or 2 times or more wider, than the structural element width said lock slot or groove is contained in, to minimize or to inhibit bending or deformation of the slot or groove upon expansion of the stent from a crimped configuration to an expanded configuration or after expansion of the stent in physiologic environment. In another preferred example, the geometry of the sides of the lock forming the lock comprising female portion and male portion may have combined widths which may be equal to or greater than ¼ of the width, equal to or greater than ½ of the width, equal to or greater than ¾ of the width, substantially the same width, wider, 1.25 times or more wider, 1.5 times or more wider, or 2 times or more wider, than at least one or either of the structural element widths said lock comprising female and male portions contained in, to minimize or to inhibit bending or deformation of the slot or groove upon expansion of the stent from a crimped configuration to an expanded configuration or after expansion of the stent in physiologic environment. In another preferred example, the geometry of the sides of the lock forming the lock comprising female portion and male portion may each have widths which may be equal to or greater than ¼ of the width, equal to or greater than ½ of the width, equal to or greater than ¾ of the width, substantially the same width, wider, 1.25 times or more wider, 1.5 times or more wider, or 2 times or more wider, than at least one or either of the structural element widths said lock comprising female and male portions contained in, to minimize or to inhibit bending or deformation of the slot or groove upon expansion of the stent from a crimped configuration to an expanded configuration or after expansion of the stent in physiologic environment. In another preferred example, the geometry of the sides of the lock forming the male portion may have a width which may be equal to or greater than ¼ of the width, equal to or greater than ½ of the width, equal to or greater than ¾ of the width, substantially the same width, wider, 1.25 times or more wider, 1.5 times or more wider, or 2 times or more wider, than the structural element width said lock male portion is contained in, to minimize or to inhibit bending or deformation of the slot or groove upon expansion of the stent from a crimped configuration to an expanded configuration or after expansion of the stent in physiologic environment. In a preferred example, the thickness of one or more the female portion arms and male portion may have the same thickness or different thickness to each other or to the thickness of the structural element said female portion or male portion are contained in. In a preferred example, inhibition of bending or deformation comprises one or more of: substantially maintaining geometry of said lock after expansion compared to before expansion of the stent, substantially maintaining the shape of lock after expansion compared to before expansion of the stent, substantially maintaining the configuration of the lock after expansion compared to before expansion of the stent, or having substantially the same bending or deformation to at least one of the structural elements said lock is contained in. On the other hand, thinner width may be desired to minimize surface area, or to result in some bending to release the tongue from the groove upon a defined applied stress. The geometry of the tongue or the features forming the groove may be tapered, wavy, or have other shapes typically fitting within one another and usually having a gap in-between.

In such examples, the width and/or thickness may be measured as average width or median width, along the length of the tongue or groove. In a preferred example, the lock and key connection comprises a female portion comprising two spaced apart arms and a male adapted to fit between the arms of the female portion. In a preferred example, the lock and key connection comprises a female portion comprising two or more spaced apart arms and a male portion comprising one or more arms adapted to fit between the arms of the female portion. In a preferred example, the female arms and the male portion can have a variety of complementary shapes or geometries comprising straight, wavy, one sided wavy, saw-tooth, one sided saw-tooth, circular, half circular (or arc), or other, or a combination thereof. The features and geometry of the interface between the male portion and female portion including one or more of surface area, length, width, thickness, surface roughness and/or the female and male arms shapes, inhibit the complete separation of the male and female portions during expansion of the stent from a crimped configuration to an expanded configuration, or maintains the male and female arms interface during expansion of the stent from a crimped configuration to an expanded configuration, or maintains the male arms to be contained within the female arms during expansion of the stent from a crimped configuration to an expanded configuration, wherein in any of the examples the separation region is configured to separate after expansion (or in the expanded configuration) under physiologic environment.

In a preferred example, the one or more male arms and two or more female arms can have various orientations and/or geometries comprising in line, straight, wavy, or at an angle (or offset), or at a 45 degrees angle or at a 90 degrees angle, to the structural element containing the key and lock separation region. In a preferred example, the female and male portions can be in the same plane (in plane) with one another, and/or in the same plane with one another and in the same plane as adjacent structural elements. In a preferred example, the male and female arms can have one or more of the following: the same thickness, same width, same thickness and width, same length, different lengths, the male portion shorter than female arms, female arms shorter than male portion. The lock and key junction may be wider than the strut or structural element containing it with a configuration similar to a sword in a sheath, as shown in numerous Figures, including FIGS. 24B-31. In a preferred example, the male and female arms can be one or more of the following: same thickness, same width, same thickness and width, same length, different lengths, male arm shorter than, male arm longer than, female arms shorter than, female arm longer than, the structural element adjacent to said male or female arms.

In another example, the female portion may comprise three arms and the male portion may comprise one arm fitting within said three arms. In another example, the female portion comprises three arms joined at an interface and wherein the male arm fits within the three female arms.

In another example, the separation region may comprise two female portions each including two or more arms or slots wherein each arm is spaced apart from an adjacent arm, and wherein one or more male portions fit within the spaces between the arms or slots of the female portions, said male and female portions being connected to a strut, crown or axial link.

In another example, at least one separation region comprises a key and lock configuration wherein the key and lock configuration is oriented along the path of the structural element said separation region is connected to, or is oriented at an angle to the path of the structural element said separation region is connected to. In a preferred example, the angle between the separation region and structural element ranges from 5 degrees to 90 degrees, preferable ranges from about 25 degrees to 90 degrees, more preferably the angle ranges from 25 degrees to 75 degrees.

The separation region is often a lock and key junction with male and female interlocking or mating portions but the separation region may have other forms. Some interlocking regions, such as combs, are possible and might not be considered as male and female portions. Additionally, interfaces between opposing sides of the separation region may have waviness, tapering sections or other shapes which mate or fit together to create a bond which inhibits separation during expansion. Generally, to inhibit separation, the opposing portions of the strut flanking the separation region have an increase in surface area created by texture, undulations, interlocking portions or some shape or geometries which forms an increased interface. The separation region is then filled with a material, typically a biodegradable polymer and/or adhesive.

In another example, at least one separation region is located in a strut; or the separation region is located in a crown; or the separation region is located between two adjacent crowns on a circumferential ring; or the separation region is located between two adjacent crowns on circumferential rings where the separation region has at least two ends and each of the at least two ends is connected to one of said crowns; or the separation region is located between two adjacent crowns on circumferential rings where the separation region has at least two ends and each of the at least two ends is connected to one of said crowns providing a connection or continuity between said two crowns; or the separation region is located between two adjacent struts on a circumferential ring; or the separation region is located between two adjacent struts on a circumferential ring; or the separation region is located between two adjacent struts on a circumferential ring where the separation region has at least two ends and each of the at least two ends is connected to one of said struts; or the separation region is located between two adjacent struts on a circumferential ring where the separation region has at least two ends and each of the at least two ends is connected to one of said struts providing a connection or continuity between said two adjacent struts.

A crown is typically the region where struts meet or come together and may be a curving area of varying lengths, or may be just the juncture of the struts. Also, the separation regions may have various lengths and may constitute a portion, most of, nearly all or approximately all of the length of the strut, crown or axial link. In the case where the separation region occupies most or all of a structural element, the region occupied by the separation region or separation interface may still constitute or be designated as a crown, strut or axial link.

In another example, at least one separation region comprises a female portion, which female portion comprises two or more arms spaced apart, and wherein the two or more arms have one or more of the following: the same or substantially the same length, width, thickness, or shape. In another example, at least one separation region comprises a female portion wherein the female portion comprises two or more arms spaced apart, and the two or more arms have one or more of the following: different lengths, thickness, width, or shape. In yet another example, the said separation region further comprises one or more male portions fitting between the two or more arms of said female portion, wherein the male portion comprises one or more tongues having one or more of the following: same or substantially the same length, thickness, or width as the one or more of the female arms, different length, thickness, or width as one or more of the female arms and/or each other. In a preferred example, the male portion has substantially the same length as at least one of the female arms. In another example, the male portion is shorter than at least one of the female arms. In yet another example, the male portion comprising one or more tongues has substantially the same thickness as the female two or more arms' thickness. In yet another example, the male portion comprising at least one tongue has a width less than the width of at least one of the female portion arms. In yet another example, the male portion comprising at least one tongue has a width greater than the width of at least one of the female portion arms. In one example the male portion has a width less than the opening of the female arms into which it fits. In another example the male portion has a width approximately the same as the opening between the female arms. In some examples the key and lock junction or connection is wider than the structural element containing it; in some examples key and lock junction or connection is not as wide as the structural element containing it, and in some examples, key and lock junction or connection is the same width as the structural element containing it. The width and thickness of the tongue and the strut or crown containing it are preferably the same (1:1). The width of the tongue may be thinner to minimize the overall width of the separation region or the width of the tongue may be wider to strengthen the separation region.

In another example, the male portion length ranges from 0.1 mm to 2 mm, preferably ranges from 0.2 mm to 1 mm, 0.3 mm to 1.5 mm, 0.4 mm to 1.0 mm, 0.4 mm to 0.9 mm, and more preferably ranges from 0.2 mm to 1 mm. In another example, the female portion arms lengths ranges from 0.1 mm to 2.2 mm, preferably ranges from 0.2 mm to 1.1 mm, 0.3 mm to 1.5 mm, 0.4 mm to 1.0 mm, 0.4 mm to 0.9 mm, and more preferably ranges from 0.2 mm to 1.1 mm. In a preferred example, the length of the separation region in a strut or crown comprises at least 30%-100% of the length of the strut or crown containing it or struts or crown said separation region is connected to; preferably, the length of the separation region comprises at least 40%-100% of the length of the strut or crown containing it or the structural element said separation region is connected to; preferably the length of the separation region comprises at least 50%-90% of the length of the strut or crown containing it or the structural element said separation region is connected to; more preferably, the length of the separation region comprises at least 55%-80% of the length of the strut or crown containing it or the structural element said separation region is connected to. A longer tongue, or male portion, is more deeply seated within the slot of the female portion of the connection and is less likely to flex, bend, or rotate out of the slot during expansion from a crimped configuration to an expanded configuration. In some examples, the separation region is located in an axial link between two adjacent circumferential rings or located radially between portions of circumferential rings. Separation regions located in connectors may comprise 40% to 100% of the length of the connector, 50% to 90% of the length or 55% to 85% of the length of the connector. Additionally, the length of the connector compared to the length of adjacent struts may be 40% to 150%, 50% to 125%, 75% to 110%, or 80% to 100%.

In a preferred example, the separation region comprises a female portion and a male portion fitting within the female portion. In yet another example, the male portion and/or female portion has a length which ranges from 2-10 times the width of said male portion and/or female portion, or has a length which ranges from 2-10 times the width of the structural elements (typically struts or crowns) said male and/or female portions are connected to or contained in. In yet another example, the male portion and/or female portion has a length which ranges from 3.5-10 times the width of said male portion and/or female portion, or has a length which ranges from 3.5-10 times the width of the structural elements (or struts or crowns) said male and/or female portions are connected to or contained in. In yet another example, the male portion and/or female portion has a length which ranges from 5-10 times the width of said male portion and/or female portion, or has a length which ranges from 5-10 times the width of the structural elements said male and/or female portions are connected to or contained in.

In another example, the separation region comprises a female portion and a male portion wherein the male portion fits within the arms of the female portion and the male portion has sufficient length and/or surface area and/or bond length and/or shape to inhibit complete separation from said female portion and wherein the male portion remains at least partially contained within the female portion when the stent is being expanded from a crimped configuration to an expanded configuration in physiologic environment.

In another example, the separation region comprises a key and lock comprising one or more female portions comprising two or more arms and at least one male portion wherein the male portion fits within the female portion, and wherein at least one of the arms of the female portions further has one or more of the following: one or more bumps protruding from at least one surface region of the at least one arm and fitting within one or more grooves, notches, dents, detents or impressions, configured in the male portion to inhibit separation of the male portion when the stent is being expanded from a crimped configuration to an expanded configuration. Alternatively, the male portion can have one or more bumps configured to fit within one or more grooves, notches, dents, detents or impressions, on one or more arms of the female portion to inhibit separation of the male portion from the female portion during expansion of the stent from a crimped configuration to an expanded configuration. In other examples, other geometry or shapes such as a saw tooth and mating saw tooth configuration on one or more surface regions of the male and corresponding female portions can be appreciated. Other examples, include protrusions and grooves of various shapes, sizes, and length along the male portion length and/or female portion length, wherein such protrusion and grooves substantially fit together before expansion to inhibit complete separation of the male portion from the female portion during expansion of the stent. In another example, the male and female portions may be smooth, textured, rough, or abraded to provide more friction or surface area to inhibit separation during expansion. The surfaces of the lock and key may typically be visually smooth due to electropolishing but may be textured on some, or all, surfaces to increase the bond strength between the lock and key. The surface roughness of the material ranges from 0.01 microns 400 microns preferably ranges from 0.015 microns to 100 microns, more preferably from 0.02 microns to 10 microns.

The separation regions or separation interfaces may occur in various regions of the scaffold, such as, the struts, crowns, rings or axial links between two adjacent circumferential rings. Although sometimes described or depicted as bisecting these structural elements, the separation region or separation interface may be located anywhere along the length of the structural element. That is, the structural element may be divided, separated or severed into approximately equal portions by the pre-formed gap or break because the gap or break is located at about the middle of the structural element or the gap or break may produce unequal portions of the structural element because the gap or break is located closer to one end or the other of the structural element containing it. In this context, bisecting does not necessarily mean an even division.

In another example of a separation region comprising an interface between two mating, interlocking and/or opposed portions, the separation region is straight, or not straight; or is aligned with the axis of the stent in the crimped configuration; or aligned at an angle to the length or axis of the stent in the crimped configuration; or have an interface changing in one or more directions along the length of the interface of the separation region portions, wherein the one or more directions comprise first axial, first circumferential, axial in the opposite direction to first axial, circumferential in opposite direction to the first circumferential, or combinations thereof, before expansion of the stent from a crimped configuration to an expanded configuration. In a preferred example, the separation region has an interface along its length comprising changes in direction axial and circumferential to the stent length in the crimped stent configuration, prior to expanding the stent from the crimped configuration to the expanded configuration. In a preferred example, the separation region has an interface along its length having more than one direction comprising axial and/or circumferential, before expanding the stent from the crimped configuration to the expanded configuration. These axial separation interfaces have non-linear congruent shapes which nest together prior to separation. The axial interfaces may have curved, somewhat squared off, or squared off surfaces which nest together prior to separation; the curved surfaces may extend from a first crown in a first generally circumferential direction, turn to extend in an opposite generally circumferential direction, and turn again to extend in the first circumferential direction before they attach to a second crown or region where struts meet. In one embodiment, the curved surfaces may extend from a first crown in a first generally circumferential direction, turn to extend in an opposite generally circumferential direction, and turn again to extend in the first circumferential direction and then this curved or squared off surface interface may turn at least one more time to extend in the opposite circumferential direction before they attach to the second crown. In one embodiment, the curved surfaces may extend from a first crown in an first generally circumferential direction, turn to extend in a opposite generally circumferential direction, and turn again to extend in the first circumferential direction and then this curved or squared off surface interface may turn at least one more time to extend in the opposite circumferential defection, and turn at least one additional time in the first circumferential direction before they attach to the second crown. For example, the interfaces may take the shape of interlocking S's, W's, M's or U's, with rounded or somewhat squared off turns and the shapes may be symmetrical and even or they may be asymmetrical with one side being longer than another in the turns or contours of the linkage. These interfaces extend through the axial link and into the adjacent crown so that upon separation after expansion, the scaffolds separate circumferentially at the axial links and through the crowns but because the interfaces extend into the adjacent crowns, the rings remain axially linked even after all separation occurs or discontinuities have formed. In some examples all of the crowns joined by axial links are configured to circumferentially separate into two opposed portions along the axial separation interfaces which extend through the crowns and axial links. The length of the interface and the changes in direction or contouring contribute to improved bonding interfaces which maintain the interface during expansion. The length of the axial link along the length of the axis may be 0.10 mm to 1.4 mm, preferably 0.2 mm to 1.1 mm, more preferably 0.2 mm to 0.7 mm. The length along the length of the axis link may be 10% to 150% compared to the length of the adjacent struts, more preferably 20% to 70% compared to the length of the adjacent struts. These interfaces typically would have the application of a biodegradable polymer or adhesive as described elsewhere in the disclosure. The changes in direction or contouring of the linkage offers advantages of stability during expansion, increased integrity of the separation region during expansion by changing the forces applied from tension to shear, increased flexibility in the crimped state, and increased vessel conformability in the expanded state.

The axial separation interfaces may be nested wedges with an interference fit prior to expansion of the scaffold (FIGS. 42A and 42B). The axial separation interfaces may be arranged in a directionally reversing pattern, with in one example, the axial separation interfaces arranged in a circumferential direction (FIGS. 35A-35C). In another example, the axial separation interfaces are aligned at an angle oblique to the circumferential direction. (FIGS. 38A, 39A, 40, and 41).

In addition to filling the gap, spacing, or other opening, the biodegradable polymer or other adhesive will often coat, cover, or otherwise be distributed over abluminal, luminal, or other surfaces of struts, crowns, or other adjacent structural elements of the scaffold. In many instances, the biodegradable polymer or other adhesive will often coat, cover, or be distributed over an entire abluminal or luminal surfaces of the scaffold. In some embodiments, at least 50%, usually at least 75%, often at least 90%, and frequently the entire the abluminal and/or luminal surfaces will be coated, laminated, or otherwise covered with the biodegradable polymer or other adhesive. In contrast to localizing the biodegradable polymer or other adhesive at the site of the separation region, it has been found that coating a majority or all of the abluminal or luminal surfaces of the scaffold enhances immobilization of the separation region and adjacent structural elements as the prosthesis is being expanded from a crimped configuration to an expanded configuration in a physiologic environment. Providing a coating which covers the separation regions and struts, crown and/or circumferential rings adjacent or in close proximity to the separation regions may provide better and more uniform expansion of the prosthesis. Immobilizing the regions with the polymer and/or adhesive keeps the structural elements in their original spatial relationship to each other, provides uniform expansion and reduces or eliminates flexing, bending, twisting and/or deformation of the structural elements. This coating may be in addition to a coating of just the separation regions but preferably, the coating of larger swaths of the prosthesis including the separation regions and adjacent and nearby structural elements is the first coating of the prosthesis with no additional coating of the separation region underneath the more extensive coating. This simplifies the manufacture of the prosthesis by allowing one coating, with or without a drug, over large surfaces of the stent and provides advantages of more uniform expansion. Thus, the prosthesis may have a coating of 50%, 60%, 70%, 80%, or 90% on some or all of the abluminal surface as the first and/or only coating securing the separation regions before expansion.

In one example, a stent prosthesis comprises one or more circumferential rings with said one or more rings having one or more separation regions. The separation regions have an in-plane interface and are in-plane to the structural elements containing said separation region. The separation regions may be covered by polymeric material wherein the polymeric material covers the separation regions and structural element containing the separation region. The polymer may also coat adjacent structural elements so the separation region and said structural elements remain aligned as before expansion and in substantially the same plane upon expansion from a crimped configuration to expanded configuration in physiologic environment.

The separation region and adjacent structural elements are coated by spray coating or dip coating. For example the stent is rotated around a longitudinal axis and spray coated once or multiple times until the desired coating thickness is achieved. Typically, the desired coating thickness ranges from 2 microns to 50 microns, preferably ranges from 3 microns to 25 microns, and more preferably ranges from 3 microns to 15 microns.

The coating covers at least some structural elements adjacent to said separation region such as a struts and/or crowns, preferably covers at least one surface of said some adjacent structural elements such as struts and/or crowns on the abluminal or luminal surface, and more preferably covers two or more surfaces of said some adjacent structural elements such as abluminal, luminal, and side surfaces. In another example, the coating covers at least one surface of structural elements such as struts and/or crowns that do not contain separation regions, preferably covers an abluminal surface of said structural elements not containing separation regions. In another example, the coating covers at least two surfaces of structural elements such as struts and/or crowns that do not contain separation regions, preferably covers an abluminal surface of said structural elements and at least one of the side surfaces of said structural elements not containing separation regions.

In another example, in addition to coating the separation regions, the coating additionally covers all surfaces of structural elements such as struts and/or crowns that do not contain separation regions. In another example, a coating covers at least one circumferential ring surface wherein the ring contains at least one separation region. Preferably the coating coats an abluminal surface of the ring, or a luminal surface of the ring. In another example, a coating covers at least one stent surface wherein the stent contains a plurality of separation regions contained in one or more circumferential rings of the stent. In a preferred example, the coating coats an abluminal surface of the ring, or a luminal surface of the ring. In yet another example, the coating coats all or substantially all stent surfaces wherein the stent contains one or more separation regions located or contained within one or more circumferential rings of the stent. In yet another example, a coating covers at least one surface, or at least two surfaces, or substantially all or all surfaces, of the separation region and an adjacent crown and strut and adjacent axial link. In yet another example, a coating covers at least one surface, or at least two surfaces, or substantially all or all surfaces, of the separation region and an adjacent crown and strut and adjacent axial link or strut and/or crown containing the separation region. In yet another example, a coating covers at least one surface, or at least two surfaces, or substantially all or all surfaces, of the separation region and an adjacent crown and/or strut and adjacent axial link or strut and/or crown containing the separation region. In a preferred example, the coating comprises a polymeric material and/or adhesive. In another preferred example, the coating coats at least one surface of a circumferential ring structural elements comprising one or more struts, crowns, and separation regions, wherein the coating of the at least one surface is substantially uniform. In a preferred example the at least one surface is an abluminal or luminal surface. In another example, at least one surface of a plurality of circumferential rings has a substantially uniform coating. The coating in a preferred example is configured to hold at least one separation region together along with adjacent structural elements to allow the circumferential ring or the stent to substantially uniformly expand from a crimped configuration to an expanded configuration, wherein the structural elements comprise one or more of struts, crowns, and/or axial links, adjacent to the separation region. The coating in this preferred example provides a continuous circumferential path around the circumferential ring or the stent and is configured to hold the separation region interface contained within said ring together along with adjacent structural elements to allow the stent to substantially uniformly expand from a crimped configuration to an expanded configuration. The coating in a preferred example coats, fills in, or substantially fills in the circumferential rings' preformed breaks and/or preformed gaps within said circumferential rings, wherein said coating provides the circumferential continuity of said rings before expansion of the stent from a crimped configuration to an expanded configuration. In a preferred example, one or more surfaces may be coated adjacent to said separation region to hold the separation region and adjacent structural elements together upon expansion of the stent from a crimped configuration to an expanded configuration. The coating of at least one surface of the separation region and at least one or more adjacent structural elements or ring containing the said separation region is substantially uniform, preferably ranging from 2 microns to 50 microns. In another example, the coating covers the separation region and one or more structural elements comprising struts, crowns, and/or axial links, wherein the coating covers the separation region and preformed break and/or preformed gap of the separation region. In one preferred example, the coating covers at least one surface, at least two surfaces, or all surfaces, of the separation region and adjacent structural elements or ring containing said separation region, or the stent.

In a preferred example, at least one separation region is configured to mimic deformation of the structural elements connected to the separation region, substantiality mimic deformation of the structural elements connected to the separation region, or the separation regions do not deform or do not substantially deform.

In a preferred example, the separation regions are configured to prevent complete axial separation and/or to prevent complete circumferential separation prior to expansion of the stent from a crimped to an expanded configuration. In a preferred example, at least one separation region comprises a plurality of shapes or geometries to inhibit one or more of axial, circumferential, or radial separation during expansion of the stent from a crimped to an expanded configuration. Examples of the geometries or structures comprise, a large surface area sufficient to inhibit separation in one or more directions; a long interface of the opposing sides of the junction sufficient to inhibit separation in one or more directions; an interface changing direction along the interface length sufficient to inhibit separation in one or more of axial, circumferential, or radial directions: a long length sufficient to inhibit separation in one or more directions; or one or more bumps or other shapes fitting within one or more grooves or corresponding mating shapes to inhibit separation in one or more directions. In another example of the above, one or more of the geometries or shapes are configured to prevent separation in axial, circumferential, and radial direction.

In another example, a stent prosthesis comprises at least one separation region which is configured not to separate in a radial, axial, or circumferential direction when the stent is being expanded from a crimped configuration to an expanded configuration, and wherein the separation region is configured to have a key and lock connection comprising a female and male portions and wherein the male portion fits within the female portion, said key and lock being coated with a polymeric material and/or adhesive such that the coating extends to structural elements adjacent to said separation region to hold the stent together and provide substantially uniform expansion of the stent from a crimped configuration to an expanded configuration.

While the separation regions of the present invention will usually be immobilized by the biodegradable polymer or other adhesive during scaffold expansion, the biodegradable polymers or other adhesives will usually display some elasticity which permits some movement before separation of the separation region. Thus, there may be some movement of the separation region during expansion stemming from the elastic material holding the separation region in place, but the separation regions will still remain intact and hold the adjacent structural regions of the scaffold in alignment. In particular, the coating in some embodiments will be able to substantially restrict movement of the separation region in an axial direction upon expansion of the scaffold from a crimped configuration to an expanded configuration. In other instances, the elasticity of the material will permit some stretching so the ends of the structural elements move apart somewhat but never completely separate or form a discontinuous region. This movement allows the prosthesis to expand with the heartbeat and with dilation of the vessel but without any change in the strength or recoil of the prosthesis.

The male portions and slots of the female portions of the lock and key connections will typically have a length in the range from 0.15 mm to 2 mm, with shorter male and slot portions having lengths usually from 0.3 mm to 0.70 mm, and with longer male and slot portions having lengths from 0.3 mm to 2 mm, usually from 0.4 mm to 2 mm. In some examples having relatively long male portions and slots, the male portion is usually about 3.5 to 5 times longer than the width of the structural elements containing said connection. In other examples, the male portion of said connection is approximately 40% to 90% of the length of the structural element, typically a strut, containing said connection. The struts of the prosthesis are typically measured along their length between the curving portions of the crowns. Struts generally range from about 0.25 mm to 3.0 mm, 0.5 mm to 2 mm, 0.75 mm to 1.5 mm, 0.8 mm to 1.3 mm, or 0.9 mm to 1.1 mm. The struts are more preferably 0.75 mm to 1.5 mm and often are about 1 mm in length. The male and female potions will usually be formed by patterning tubular substrates, typically by laser cutting or photoetching, and will have thicknesses similar or identical to those of adjacent struts, crowns, or other structural elements, typically in the range from 5 microns to 150 microns, preferably thickness ranging from 5 microns to 120 microns, often from 5 to 50 microns. The male and female portions will thus usually not overlap either before or after expansion of the scaffold.

The tongue will typically have a width in the range from 0.025 mm to 1 mm, usually from 0.05 mm to 0.25 mm, and thickness in the range from 0.025 mm to 0.200 mm, usually from 0.03 mm to 0.100 mm. The corresponding slot of the lock can have similar dimensions. A bond area is formed by the surfaces forming the lock and key. The total area of the sidewalls is formed by the sidewalls of the lock and the key; the sidewall of the key is typically in the range of 0.01 mm$^2$ to 0.56 mm$^2$, and the sidewalls of the mating lock or slot is similar, and the total area is typically in the range of 0.02 mm$^2$ to 1.12 mm$^2$, preferably in the range of 0.1 mm$^2$ to 0.3 mm$^2$. It should also be appreciated that the mating inner and outer diameter surfaces can contribute to the bond strength in the separation region if the adhesive is not confined to the void formed by the sidewalls, and for a lock and key configuration the total outer and inner surface area of the lock and key range from 0.02 mm$^2$ to 5.4 mm$^2$, preferably 0.1 mm$^2$ to 0.5 mm$^2$. These inner and outer areas comprise the surface of the lock and key region on the outer diameter and the inner diameter of the stent combined.

The length of the lock (or tongue) relative to the strut can vary, and may preferably be in the range of 40-60%. The width of the lock relative to the strut can also vary, and may be in the range of 75-125%, preferably 90-110% of the width of the strut.

The surface of the opposing sides of the lock and key may be smooth, slightly rough, wavy, jagged or have combs which interlock. These various surfaces aid in creating friction, surface area and adhesion to allow some movement but prevent complete separation of the junctions.

In many embodiments and examples, the male and female portions of the lock and key separation regions are formed and present in the same plane as the structural element(s) in which they reside. That is, both the male and female portions will have substantially the same thickness as each other and as adjacent structural elements with the luminal and abluminal surfaces being "coplanar." To be clear, the surfaces will usually be curved and not actually planar, but the curvatures of the structural elements and the male and female portions of the lock and key separation regions disposed therein will be identical. Such continuity of the shape will typically be a result of forming the structural elements and the separation regions by patterning the scaffold from a single tubular substrate.

Separation regions having longer male portions and female slots beneficially provide opposing surface areas which are sufficiently large to provide an increased adhesion or friction between opposing walls on the male portions and the slots which can prevent or inhibit premature separation of the separation region upon expansion of said scaffold. That is, the biodegradable polymer or other adhesive which fills the gap, spacing, or other opening between the outer wall surfaces of the male portion and the inner surfaces of the arms will adhere to larger surface areas, increasing the stability and strength of the bond during expansion and prior to degradation of the polymer or adhesive in the physiologic environment. Additionally, the larger surface area of the junction or connection, even without a coating or inclusion of polymer and/or adhesive in the gap, provides increased friction and resistance to complete separation.

In another example, the separation regions have or define a gap between the two opposite ends of the structural elements adjacent to the separation, and/or between the two adjacent ends of the structural element adjacent to the separation region (for example the two ends of the non-degradable metal alloy containing or defining or comprising a separation region). The gap width ranges from zero to 50 microns, preferably ranges from zero to 30 microns, more preferably ranges from 1 to 20 microns, more preferably ranges between 5 and 20 microns, most preferably ranges from 5 microns to 15 microns. The gap can be filled with a coating such as a degradable polymer coating. The coating can extend beyond the separation region to further hold in place the separation regions upon deployment of the stent from a crimped configuration to an expanded larger configuration.

While the separation regions may be formed anywhere in the scaffold, one or more separation regions will usually be formed within a circumferential path formed by at least some of the circumferential rings. The phrase "circumferential path," as used herein, means the path of structural elements, e.g. struts and crowns, which form the ring. In many examples and embodiments, the separation regions are formed within the structural elements and the separation regions form part of the circumferential path prior to opening of the separation region which will form a break in the path. That is, prior to the formation of discontinuities in a circumferential ring after expansion in a physiologic environment, the circumferential path is defined by both structural elements which are usually formed from a non-degradable material as well as the separation regions which comprise a biodegradable polymer, adhesive, or the like.

Separation region interfaces which extend through axial links and adjacent crowns may be aligned perpendicularly to the axis of the scaffold or may be aligned at an angle. In some examples, the separation interface may be aligned at an angle to the circumference when in a crimped configuration but designed to move to about a 0 degree angle to the circumference when in an expanded state. The angle may range from –60 degrees to 60 degrees. See FIGS. 38A-38C.

The separation regions may be formed on the S-links as shown above. In this example, the S-link is split down the centerline or about the centerline of the link and forms a bond surface 1.53 mm in length with a surface area of 0.124 mm$^2$ on the sidewalls, and 0.19 mm$^2$ each on the top (outer surface) and bottom (inner surface). The bonded S-link is 0.005"-0.006", and becomes 0.0025"-0.003" in width upon separation. The bond line itself has a length and thickness, and is for example 0.5 to 7 mm in length, preferably 0.9-5.5 mm in length, more preferably 1.4 to 3.7 mm in length, and 60-90 microns in thickness, or 0.03 to 0.7 mm$^2$ in surface area on each side of the bond.

The S-link can be extended, or lengthened, for example, to 1.69 mm in length with a surface area of 0.127 mm$^2$. Or, the S-link can be shaped with multiple undulations, forming a double-S, increasing the bond length to 1.8 mm and 0.135 mm$^2$. The bond line itself has a length and thickness, and is for example 0.5 to 7 mm in length, preferably 0.9-5.5 mm in length, more preferably 1.4 to 3.7 mm in length, and 60-90 microns in thickness, or 0.03 to 0.7 mm$^2$ in surface area on each side of the bond.

The S-link can be angled as shown above, for example at 29 degrees, such that upon expansion of the stent the S-link is circumferentially aligned. But it can also range from 15 degrees to 45 degrees, or it can be configured to upon expansion of the stent to be circumferentially aligned.

A further aspect of the above example is that the path formed by the crowns, struts, and links is continuous, forming a looped path. Upon separation of the separation regions, the stent remains one continuous piece. Depending on the adhesive used, the separation region may disengage immediately upon deployment, or after some period of time in vivo. The separation region is formed from a single layer of the base stent. It is not formed from layering the stent upon itself.

FIGS. 35A-35C illustrate an example of a scaffold (stent) having circumferential rings which are axially joined by separation regions formed as bisected links that are offset from the apex of the crowns. FIG. 35A is an unexpanded pattern where the separation regions are intact. FIG. 35B is a partially expanded view after some of the separation regions have disengaged, eventually forming three separate and distinct "loops" or patterns. The separation regions divide the axial links and the crowns of the two adjacent circumferential rings separating the links and crowns upon the formation of the discontinuities but with the two adjacent circumferential rings remaining attached through the divided axial links. In this example, the separation region is formed by an association, interlocking or junction of adjacent opposed portions of the axial links and crowns which meet at the axial link. The axial link is formed with two opposed halves or portions from adjacent circumferential rings. The junction is depicted as approximately equal portions from each side of the interface but may be formed of unequal segments.

The above examples also have the ability to move in multiple degrees of freedom (or in one or more directions) once the separation region disengages (or forms a discontinuity). For example, in some embodiments the two parts of the separation region may move in the radial direction and circumferential direction after disengagement. In some embodiments, the two parts of the separation region may move in a helical direction or move parallel to the longitudinal axis of the stent, depending on the geometry. It is not necessary for the separation region to move in the same direction in which it was assembled. The geometry and orientation of the separation region can also be designed to reduce stresses that the part would otherwise be subjected to during torsion and compression of the stent, thus increasing the fatigue factor of safety, improving fracture resistance, and minimizing stresses and strains after expansion. FIG. 40 illustrates a design where the S-links are oriented to allow torsional movement while potentially minimizing contact between the two sides of the bisected S-link.

In the above examples, all of the links between rings have separation regions, and all of the links are substantially the same in geometry, but in other examples the geometry of the links may be different. There may be 2 to 4 links between rings, preferably 2 to 3. The advantage of such a design is consistency along the length of the stent, which may result in better conformability to the artery. Furthermore, by having more separation regions per ring (for example, two or three per ring as shown in the above figures), the arterial compliance will be more close to the artery. The shape of the links in an S-shape as shown in the examples also results in less foreshortening upon expansion as the S-shapes may lengthen, resulting in foreshortening of 0-10%, preferably ranges from 0 to 7%, more preferably from 0 to 4%. In other example, the stent having S-Shape or other shapes described in this application will have lengthening of the stent after expansion. In some cases the lengthening ranges from 1% to 10%, preferably ranges from 1% to 7%, and more preferably ranges from 1% to 5%.

In yet another example of any of the separation region configurations, the stent is configured to be axially joined and/or have axial links configured to have shortening ranges from 0%-10% upon expansion of the stent from a crimped configuration to an expanded configuration, and wherein the shortening magnitude of the stent is substantially maintained after expansion of the stent in physiologic environment, or wherein the stent after expansion in a physiologic environment lengthens by a magnitude ranging from 1% to 10%. Furthermore, upon disengagement (or formation of discontinuities) of the separation regions shown, the flexible S-shaped separation regions may further accommodate arterial changes in the axial direction, as they would be less rigid.

In a preferred example, at least one separation regions bisecting at least one link and at least one of: two crowns (two hinge regions) on adjacent rings wherein the link connects said crowns, one crown on one ring and a strut on an adjacent ring wherein the link connects said crown and strut, two struts on adjacent ring wherein said link connects said struts, or a crown and adjacent strut on one ring and a crown and adjacent strut on an adjacent ring wherein the link connects said crown and strut on one ring to said crown and strut on an adjacent ring, may be deformable but remain intact after deformation and/or remains intact after deformation and after formation of discontinuities, before expansion of the stent, when the stent is being expanded from a crimped configuration to an expanded configuration, or after expansion of the stent, in physiologic environment. Typically, the separation region comprises a biodegradable material and/or adhesive holding the bisected separation region together and/or forming a continuous circumferential path around at least one or more rings or around the stent and is configured to form at least one discontinuity, preferably at least two discontinuities comprising one discontinuity for two adjacent rings, after expansion of the stent in physiologic environment. In some cases, the separation region partially separates when the stent is being expandable from a crimped configuration to an expanded configuration but maintains axial and circumferential structural integrity of the stent. In a preferred example, the at least one link containing at least one separation region after formation of said at least one discontinuity remains connected to said bisected structural elements comprising struts and/or crowns on two adjacent rings. Typically, the at least one link is connected to each of the two bisected rings in two locations. Typically, the at least one link after formation of all discontinuities remains axially connecting two or more circumferentially separated rings. In another example, the at least one link after formation of discontinuities may also be configured to separate axially in one or more locations. It may be desirable to have the separation region deformable to increase flexibility and deliverability of the stent, during deliverability and/or during expansion of the stent. Other advantages are minimizing length changes of the stent upon expansion or after expansion, or minimizing foreshortening of the stent.

In another preferred example, at least one separation regions bisecting at least one link and at least one of: two crowns (hinge regions) on adjacent rings wherein the link connects said crowns, one crown on one ring and a strut on an adjacent ring wherein the link connects said crown and strut, two struts on adjacent ring wherein said link connects said struts, or a crown and adjacent strut on one ring and a crown and adjacent strut on an adjacent ring wherein the link connects said crown and strut on one ring to said crown and strut on an adjacent ring, and wherein the link is patterned from a non-degradable material and remains intact after formation of discontinuities. In another example, the said at least one link after formation of discontinuities maintains axial connection between two adjacent rings but separates said two adjacent rings circumferentially. In another example, the said at least one link is formed from a non-degradable material and remains intact after formation of discontinuities maintaining axial connection between two adjacent rings but separates said two adjacent rings circumferentially.

In another preferred example, a stent prosthesis comprises structural elements comprises two or circumferential more rings and at least one axial link connecting said two rings, and wherein said at least two adjacent rings have a gap between said two rings in at least a portion of the circumferential path of said two rings separating said adjacent rings, and wherein the at least one link connects said two adjacent rings in at least part of said gap, and wherein at least one separation regions bisecting at least the one said link and at least one of: two crowns on adjacent rings wherein the link connects said crowns, one crown on one ring and a strut on an adjacent ring wherein the link connects said crown and strut, two struts on adjacent ring wherein said link connects said struts, or a crown and adjacent strut on one ring and a crown and adjacent strut on an adjacent ring wherein the link connects said crown and strut on one ring to said crown and strut on an adjacent ring, wherein the separation region bisects said two adjacent rings and axial link connecting said rings along the gap between said two rings.

The separation region in many of the examples is formed by laser cutting, resulting in a gap formed by the laser kerf and subsequent electropolishing between the two parts forming the separation region. The gap is then filled with the bonding agent. Having a gap is helpful in bonding the separation region portions together, whereas typically two metallic portions in intimate contact with each other tend to have less bond strength or integrity. The gap allows for various bond line thicknesses, which can be configured for characteristics such as durability and strength, or to minimize the volume of material. The material used to fill the gap can be configured for integrity of the stent upon expansion, strength of the bond region, manufacturability, or other reasons, such as consistency of performance. Factors include polymer type, concentration of the polymer solution and solvent type (and resulting viscosity) as well as application method and surface roughness can improve bond strength. For example, a PLLA-based polymer may be used to bond the separation region. The polymer solution is prepared to a concentration of preferably 0.1-20 mg/mL, more preferably 0.5-5 mg/mL, most preferably 1-3 mg/mL. The polymer may be applied using an ultrasonic spray nozzle (such as a Sono-tek Medicoat set to ultrasonic setting 1.2 W, pump rate 70 μL/min, air shroud 3 psi), or dip coated.

Alternatively, the bond line may be filled with a polymer solution using a manual syringe dispenser or automated fluid dispensing method.

The length and geometry of the separation region is designed such that the amount of material required is also optimized, both within the bond line as discussed above, and also around the separation region. For example, the coating thickness on the inside and outside surfaces of the stent required to hold the separation region together may only be 2 to 50 microns, more preferably 2 to 15 microns. The bond line itself has a length and thickness, and is for example 0.5 mm to 7 mm in length, preferably 0.9 mm to 5.5 mm in length, more preferably 1.4 mm to 3.7 mm in length and 60-90 microns in thickness or 0.03 mm² to 0.7 mm² in surface area on each side of the bond.

It can be appreciated that the stent shown in FIGS. 37A-37B form a single loop or ring after all separation regions form discontinuities, which offers potential advantages. One advantage may be decreased likelihood of a portion of the stent becoming dislodged. Manufacturability may also be improved, as there are fewer small pieces required to assemble the part.

In another example of suitable adhesives, stent material, sleeve material, coatings, and cements, include but not limited to polylactide; poly(L-lactide); poly(D-lactide); poly-DL-Lactide, polyglycolide; polylactide-co-glycolide (e.g., poly(L-lactide-co-glycolide) with 85% L-lactide to 15% glycolide); copolymer of poly(L-lactide-co-epsilon-caprolactone (e.g., weight ratio of from 50 to around 95% L-lactide to about 50 to about 5% caprolactone; poly(L-lactide-co-trimethylene carbonate); polytrimethylene carbonate; poly(glycolide-trimethylene carbonate); poly(lactide-glycolide-trimethylene carbonate) or the like; polyhydroxybutyrate such as poly(3-hydroxybutyrate) and poly(4-hydroxybutyrate); polyhydroxyvalerate; polyhydroxybutyrate/polyhydroxyvalerate copolymers (PHV/PHB); polyhydroxyalkanoate; poly orthoesters; poly anhydride; polyiminocarbonate; tyrosine-derived polycarbonate; tyrosine-derived polyacrylate; iodinated and/or brominated tyrosine-derived polycarbonate; iodinated and/or brominated tyrosine-derived polyacrylates polyesteramide; polycarbonate copolymer, lactone based polymers such as poly (propylene fumarate-co-ethylene glycol) copolymer (aka fumarate anhydride); polyanhydride esters; polyorthesters; silk-elastin polymer; polyphosphazene; aliphatic polyurethane; polyhydroxy acid; polyether ester; polyester; polydepsidpetide; poly(alkylene oxalates); polyaspartimic acid; polyglutarunic acid polymer; poly-p-dioxanone; poly-beta-dioxanone; asymmetrically 3,6-substituted poly-1,4-dioxane-2,5-diones; polyalkyl-2-cyanoacrylates; polydepsi-peptides (glycine-DL-lactide copolymer); polydihydropyranes; polyalkyl-2-cyanoacrylates; poly-beta-maleic acid (PMLA); polyalkanotes; poly-beta-alkanoic acids; protein such as elastin, fibrin, collagen, glycoproteins, gelatin, or pectin; poly-serine; polycaprolactam; cyclodextrins; polysaccharides such as chitosan, and hyaluronan; alginate; polyketals; fatty acid-based polyanhydrides, amino acid-based polyanhydrides; poly(ester anhydride); or the like; and combinations thereof.

In other examples, the key and lock junctions type are held together and/or immobilized by an overlying sleeve or similar external structure which envelopes the junction and which prevents the junction from completely and/or partially releasing and/or opening while the sleeve remains intact and/or substantially intact and/or non-degraded but which degrades in the physiologic environment over time in order to open and release the junctions.

In still other examples, the separation regions located within the struts of the circumferential rings may comprise butt joints, notches or thinned regions within the struts, modified grain boundaries within the struts, and the like, which preferentially erode or fatigue within the struts, or any of the other specific separation regions described elsewhere herein.

In further specific examples of the endoluminal prostheses of the present invention, a scaffold comprises circumferential rings patterned from a metal or other non-degradable material, where the scaffold is configured to expand from a crimped configuration to an expanded configuration. In these embodiments, at least some of the circumferential rings comprise a plurality of struts joined by crowns and at least some of the struts have at least one separation region which is pre-formed as a break in the structure of the strut, e.g. formed by laser or otherwise cutting across the strut as or after it has been patterned, which is immobilized by a sleeve or an adhesive which will degrade in physiologic environment over time.

While the separation region examples may be any of those described previously herein, a preferred separation region examples comprises a key and lock junction where the struts are held together and/or substantially held together or immobilized during expansion and configured to open after an initial expansion within the physiologic environment. The key and lock junction types in this example may be configured to allow the joined segments of the strut to separate from each other in a radial direction only after the joints are free. Alternatively, the key and lock junctions may be configured to allow the joined segments of the strut to separate from each other in both a radial direction and an axial direction after the junctions are free, i.e. opened or released from constraint. In both cases, the key and lock junctions may be initially immobilized by a cement or adhesive or a sleeve or a coating which holds the budding surfaces of the strut segments together or close together and which degrades in physiologic environment. Alternatively, the strut segments joined by the key and lock junctions may be immobilized by an overlying sleeve which degrades in the physiologic environment. Such junctions are immobilized, substantially immobilized, held together, substantially and/or held together; to restrict or substantially restrict movement, in one or more directions (preferably substantially restrict movement in an axial direction) upon deployment from a crimped configuration to an expanded configuration. Immobilization of such junction are accomplished using a material such as polymer, sleeve, or adhesive, or by the configuration of junction design.

In a preferred example, the stent (scaffold) prosthesis in this invention is formed from a substantially tubular body (said tubular body in a preferred example is substantially free from holes and/or discontinuities). The stent comprises structural elements capable of radial expansion from a crimped configuration to an expanded deployed larger configuration. The structural elements in a preferred example comprises a plurality of circumferential rings, said rings comprising struts joined (connected) by crowns. At least some of said rings are connected to adjacent rings. The stent in preferred examples can be crimped onto a balloon delivery system or a delivery system (optionally constrained in the crimped configuration by a sleeve). The stent in a preferred example is balloon deployable and/or self-expanding stent. The stent prosthesis can also be formed from a wire or a fiber (round or substantially round, square or substantially square, rectangle or substantially rectangle, and/or other shapes, wherein the wire or fiber is patterned into a stent capable of radial expansion from a crimped configuration to a deployed larger configuration. The stent can also be formed from a hollow or partially hollow wire (having hollow regions within the wire or fiber) or fiber wherein the hollow or partially hollow wire or fiber is patterned into a stent capable of radial expansion from a crimped configuration to a deployed larger configuration. The stent pattern in preferred examples can be serpentine rings, zig zag rings, diamond, interwoven and/or mesh pattern, closed cell design, open cell design, and/or combination thereof. Preferably, the stent shape in the deployed configuration is substantially tubular (cylindrical), tapered stent, hour glass stent, and/or other shapes. The rings, crowns, struts, dimensions (length, thickness, angle of curvature, width) are configured in to allow the stent to deploy (expand) and have the various shapes above.

One skilled in the art would appreciate the applicability of the embodiments and/or examples throughout this application to prosthesis across various mammalian body applications where a stent prosthesis is implanted, such as endoluminal prosthesis, outer-luminal prosthesis, annulus prosthesis such as valves comprising circular or other shapes, and/or other type of lumen, duct, annulus, cavities, sinus, etc. within a mammalian body.

In one example the stent prosthesis comprises a valve such as an aortic and/or mitral valve and/or tricuspid valve, wherein the stent prosthesis comprising an expandable stent prosthesis (balloon expandable or self-expanding) wherein the stent circumferential structural elements such as for example struts joined by crowns (and/or including for example a plurality of rings), or other type stents formed from a tube, a wire, a sheet, or a braided stent formed from one or more wires, and the stent is configured into an open cell design pattern, a closed cell design pattern, or combination of open cell and closed cell pattern, or other, and wherein the stent prosthesis comprises shape memory alloy such as NiTi, and/or non-degradable metal or metal alloy such as stainless steel 316L or L605, or other materials described in this application, or other, and wherein at least some struts (but can also be crowns, circumferential links/connector, or combination) in at least one ring or at least one segment of the stent (a proximal segment, a mid-segment, and/or distal segment, and/or regions within a segment) have at least one or more of: junctions, bridging elements, joints, discontinuities, and/or separation regions as described throughout this application, which are configured to uncage, and/or configured to have a displacement (or movement) in one or more directions or movement pattern, and/or configured to have radial strain, and/or configured to have radial contraction and expansion, or configured to have inferior contraction and/or expansion, and/or configured to have superior contraction and/or expansion, after deployment of the stent prosthesis within, in, or around, or above, or adjacent to, an annulus of a body valve, wherein the displacement magnitude (or radial strain magnitude, or contraction magnitude, or further expansion magnitude, or movement magnitude) ranges from 0.05 mm to 10 mm, preferably ranges from 0.1 to 7 mm, preferably ranges from 0.2 mm to 5 mm, more preferably ranges from 0.3 mm to 3 mm, and wherein the displacement or radial strain movement is in at least one or more of the following: radial direction, circumferential direction, longitudinal direction, superior direction, inferior direction, valve leaflets closure direction, annulus (or lumen) contraction and/or expansion direction, or combination thereof, and wherein the stent prosthesis is substantially cylindrical, oblong, annulus shape, saddle shape, circular, or other shape to conform to the anatomy where the stent prosthesis is to be implanted in, wherein the separation regions, junctions, bridging elements, gaps, joints, form discontinuities, and/or allow at least one or more structural elements to have movement (displacement) in one or more direction such as circumferential, radial, and/or longitudinal, or combination thereof (as formed, before implantation, and/or after implantation) wherein the stent prosthesis have sufficient strength to support (including hold, or maintaining) the implantation site (including valve annulus, cavity)) open, and/or have sufficient strength to hold (including maintaining) a structure associated with the implanted stent prosthesis in place (including the valve and/or sheath associated with the stent prosthesis as deployed or after deployment), wherein the stent prosthesis upon deployment (expansion from a crimped configuration to an expanded larger configuration) has sufficient strength to support the valve annulus and/or associated stent valve open and/or in place, and wherein said discontinuities, and/or movement, allow uncaging, displacement, contraction, and/or further expansion, of at least one or at least some regions of at least one or at least some segments of the stent prosthesis or stent prosthesis structural elements, and/or said discontinuities, and/or movement (displacement), allow expansion and/or contraction of at least one or at least some regions of at least one or at least some segments of the stent prosthesis or stent prosthesis structural elements, and/or said discontinuities, and/or movement, allow the stent and/or at least one or at least some regions of the stent to be less rigid (including more compliant (radial strain) in at least one or more directions such as the circumferential direction, the radial direction, the longitudinal direction, or combination thereof).

In a preferred example, the separation regions, junctions, bridging elements, gaps, joints, are placed (including located) in a pattern that allows for the stent (or at least some regions or segments of the stent) to have sufficient strength after deployment, and allows at least some regions or segments of the stent prosthesis (including the circumferential regions of said stent regions) to uncage, to be more compliant (radial strain) under physiologic conditions, to expand and/or contract under physiologic condition, and/or prevent (including minimize, reduce) blood leakage after stent (including valve) implantation. The prevention of the blood leakage can be minimized by having the stent in at least some region be and/or become more compliant (including less rigid) making the stent in at least said regions more conformable to the anatomy the stent is implanted in as the anatomy moves or changes shape under physiological conditions (more dynamically compliant). The prevention of blood leakage can occur upon implantation or after implantation. The separation regions, junctions, bridging elements, gaps, joints, can be placed in at least one ring, or at least some regions of at least one segment of the stent prosthesis such as the proximal segment of the stent, a mid-segment of the stent such as the segment holding the valve, and/or a distal segment of the stent, and/or all three segments of the stent prosthesis. Optionally, a sheath surrounding at least a region or segment of the stent prosthesis can be configured to respond (including contour, expand, adapt) to the corresponding discontinuities, and/or movement of the stent prosthesis adjacent to the sheath region. The sheath can be configured and/or formed from stent like structure having separation regions, junctions, bridging elements, gaps, joints, and/or a sheath capable to adapt to the adjacent stent region in expansion and/or contraction or in other ways. In a preferred embodiment or example the stent prosthesis in at least one ring or in at least some regions (preferably the entire stent) maintain sufficient strength after implantation, in other examples the stent prosthesis strength decreases over time after implantation ranging from 30 days to 3 years, preferably ranging from 3 months to 2 years, more preferably ranging from 6 months to 2 years. In this other example the residual strength is either sufficient strength to perform one or more of the functions described and/or other functions, or the stent prosthesis in at least some regions (or all the stent) will have no residual strength over the said time period ranges.

In one example, a stent prosthesis for valve replacement or repair, wherein the stent is substantially cylindrical or have other shapes conforming to the annulus where the stent is to be implanted in, and wherein the stent is patterned from a tube, a wire, or braided, and wherein the stent is balloon deployable or self-expandable, and wherein the stent is configured to expand from a crimped configuration to an expanded larger configuration, and have sufficient strength in the expanded larger configuration to hold the annulus open (or to support an annulus). The stent prosthesis optionally comprises a valve (such as bicuspid or tricuspid) coupled to said stent prosthesis. The stent prosthesis optionally comprises at least one skirt on at least one surface region such as the abluminal and/or luminal surface region of the stent prosthesis coupled to the stent prosthesis and/or the prosthetic valve. The at least one skirt in one example can also be weaved into the abluminal and/or luminal surface regions. The at least one skirt in another example can be coupled to at least one segment of the stent prosthesis, such as a proximal segment of the stent prosthesis, a distal segment of the stent prosthesis, a mid-segment of the stent prosthesis, and/or the entire stent segments, on the abluminal and/or luminal surface regions. The at least one skirt in one example can have a pouch configured to swell or fill up with blood after the stent prosthesis implantation. In one example, the stent is configured to have at least one segment (or region) of the stent to have at least one or more of separation regions, discontinuities, bridging elements, junctions, joints, gaps, to allow uncaging and/or higher displacement in one or more of the following after expansion of the stent prosthesis: higher strain, higher displacement, higher contractility and/or expandability, better valve closure, less valve leakage, better accommodation of valve closure when the heart is dilated, said displacement in at least one segment and/or stent taking place in one or more of: stent radial direction of the stent, stent circumferential direction, stent longitudinal direction, towards a superior direction of the stent, towards an inferior direction of the stents, and/or other type directions or movements such as a saddle shape direction to accommodate a mitral valve annulus. The at least one or more separation regions, discontinuities, joints, junctions, bridging elements, gaps, etc., are configured (or positioned, or located, or placed) along the desired stent, stent segment, or stent region, to provide for the required movement (or displacement). Examples for placement locations of such uncaging and/or displacement features include: the stent segment (or region) adjacent to the synthetic valve, attached at least in part to the synthetic valve in at least one region, placement in a mid-segment of the stent prosthesis, placement in a distal segment of the stent prosthesis, placement, placement in a proximal segment of the stent prosthesis, placement on at least one side of at least one segment of the stent prosthesis, placement on one half side of at least one segment of the stent prosthesis (while the other half of said segment is free from such uncaging features) in a cylindrical shape stent for example, or combination thereof. The at least one segment having displacement magnitude in at least one direction in one example ranging from 0.1 mm to 10 mm, preferably ranging from 0.2 mm to 7 mm, more preferably ranging from 0.35 mm to 7 mm. The stent prosthesis optionally have supporting features (such as additional struts joined by crowns within the stent prosthesis rings) to further provide strength, support, or other mechanical properties, to the main stent prosthesis structural elements. The supporting features can have uncaging features or be free from uncaging features. The stent prosthesis in this example has sufficient strength in the expanded configuration to support a body annulus (or to maintain a body annulus open, or to hold the stent in a body annulus in place) while providing after expansion one or more of: higher (or larger or increased) radial strain (or compliance), larger (or higher or increased) displacement, higher (or increased) compliance, larger contraction and/or expansion, in at least one stent segment (or region) of the stent prosthesis compared to an adjacent stent segment (or region), or the stented segment, under physiological conditions.

In one example, an implant having length, width, and thickness, is attached (or held in place) adjacent to a body lumen or a body annulus (or within a body lumen or within a body annulus) and wherein the implant is configured to be coupled with (or attached) to an expandable prosthesis, and wherein at least one of the implant and the stent prosthesis are configured to have one or more of separation regions, junctions, joints, hinges, bridging elements, gaps, on at least one segment or region of the implant and/or stent allowing the at least one segment or region of implant and/or stent to have displacement, in one or more directions, that is larger than an adjacent segment (or region) of the said implant or stent prosthesis, under physiological conditions.

In one example, an implant having length, width, and thickness, is attached (or held in place) adjacent to a body lumen or a body annulus (or within a body lumen or within a body annulus) and wherein the implant is configured to be coupled with (or attached) a prosthetic (or natural) valve, and wherein at least one segment or region of the implant is configured to have one or more of separation regions, junctions, joints, hinges, bridging elements, gaps, allowing the at least one segment or region of implant to have displacement, in one or more directions, that is larger than an adjacent segment (or region) of the said implant, and wherein said displacement is configured to allow the valve to operate (or to function or to open and close) under physiological conditions, or allows (or enhance) the valve to conform (or contour) to the annulus or deformed annulus preserving the function of the valve.

In another example, a stent prosthesis formed from a shape memory material, or formed from a spring (or coil) material, and is patterned from one or more wires into a braided pattern, or is patterned from a tube into a closed cell type design or an open cell type design, or is patterned from a wire into a closed cell type design or an open cell type design, or combination thereof, and wherein the stent is self-expandable from a crimped configuration to an expanded larger configuration and have sufficient strength to support a body annulus, and wherein the stent prosthesis is coupled to a valve, said stent having one or more of separation regions, junctions, hinges, discontinuities, in at least one segment: distal, proximal, or adjacent, to the coupled valve, and wherein said segment after expansion and formation of discontinuities (or after uncaging) has lower outward radial force while the stent is in the expanded configuration but smaller than the nominal or maximum expansion diameter force, preferably between 5-15% smaller than the maximum expansion diameter outward force, more preferably between 15% and 75% smaller than the nominal or maximum expansion diameter outward force.

In preferred example, the composite radial strain/compliance (or vessel dilation under pressure or therapeutic drug such as nitroglycerine) in one example of the stent prosthesis having at least one or more separation regions forming discontinuities after expansion ranges from 1% to 10%, or from 1% to 5%, preferably ranges from 1.5% to 4%, and/or has a diameter change ranging from 0.03 mm to 3 mm, preferably ranging from 0.05 mm to 0.15 mm, or more preferably ranging from 0.07 mm to 0.15 mm, or most preferably ranging from 0.1 mm to 0.3 mm, under physiologic conditions or simulated physiologic conditions. The pattern of separation regions can be configured for example to adapt to the anatomy the stent prosthesis is implanted in to accommodate the forces of such anatomy and/or dynamic movement and thereby comprising one or more planes to uncage or allow movement (and/or expand, etc) ranging from circumferential to axial planes and/or in between, and/or radial. One skilled in the art would appreciate the application of these embodiments to balloon expandable stents and/or self-expanding stents, including open cell designs, closed cell design, coil design, or weaving stent patterns, etc. In another example the stent prosthesis uncages, and/or allows movement, and/or further expands, and/or have higher radial strain (compliance), and/or etc., upon deployment or after deployment by incorporating other means described in this application.

In a preferred embodiment or example where in many instances an implant such as s stent prosthesis is implanted to open, hold open, to hold in place, to support, to repair and/or replace a malfunctioning structure such as a valve, or other; the stent in such instances are implanted in a variety of anatomy such as an artery, a vein, a duct, a valve annulus, sinus, cavity, and/or other mammalian body lumen, where such artery, a vein, a duct, a valve annulus, sinus, cavity, and/or other mammalian body lumen, are usually undergoing various physiologic conditions such as pressure, pulsating pressure (systole and diastole), movements (or displacement) in one or more planes/directions, shaping and/or reshaping of said lumen or annulus, expansion and/or contraction, forces from one or more planes/directions, where the implant is desired to have sufficient strength at least upon implantation to open, hold open, support, repair and/or replace a malfunctioning structure; and at the same time, and/or over time after implantation the implant/stent is desired to have the ability to comply with (accommodate, and/or to conform) at least partially to the physiological conditions of movements (displacement), forces, expansion and/or contraction, shaping or re-shaping of the lumen, etc thereby preserving the function of the implant and the integrity of the stent support (or valve contained within the stent). The implant prosthesis described throughout this application allows the artery, vein, duct, cavity, annulus, and/or other body lumen, to at least partially restore (or accommodate or comply with at least partially) some of said movement (displacement), expansion and/or contraction, forces, and/or shaping or re-shaping of lumen; thereby reducing and/or preventing the unwanted effects of an implant and thereby reducing and/or preventing unwanted adverse events such as narrowing and/or re-narrowing of a lumen, restenosis, blood leakage, occlusion, thrombus formation, angina, ischemia, aneurysm, etc., the stent as described throughout this application allows at least one or more regions, and/or at least one segment (and/or the entire stent) to uncage, to allow to move, to expand, to further expand, to further expand from the deployed/expanded configuration, to shape and/or re-shape into a new configuration from the deployed configuration, to expand and/or contract, to have a radial strain (compliance) closer to the natural radial strain (compliance) of the lumen (and/or anatomy where the stent is implanted in), to have a higher radial strain (compliance) than immediately after deployment radial strain/compliance (or before forming discontinuities in some cases), to accommodate at least some of the lumen (annulus, cavity etc.,) physiological conditions (including dynamic movement/displacement, and/or dynamic forces, and/or dynamic expansion and/or contraction, and/or dynamic shaping and/or re-shaping), and/or to lessen the resistance of the implant (stent) to the physiologic conditions of the implant site, and/or to provide sufficient stent structure after deployment (or after formation of the discontinuities) to protect body lumen, protect vessel lumen, support body lumen, and/or support vessel lumen, from potential harmful plaque such as vulnerable plaque. The stent after formation of discontinuities maintains sufficient stent structure which can have radial strength, or no radial strength after formation of discontinuities and/or after deployment.

In a preferred example, the stent prosthesis is formed from and/or comprises a non-degradable material that has high radial strength (for example sufficient to support a body lumen upon deployment of the stent), wherein the material is preferably a metal or metal alloy but can also be a polymer, or other material of high radial strength upon deployment. In a preferred example non-degradable material does not degrade within at least five years from implantation in a body lumen (or under physiologic conditions), preferably does not degrade within at least ten years from implantation in a body lumen (or under physiologic conditions, more preferably does not degrade within at least 20 years from implantation, and/or within at least 50 years from implantation. Examples of non-degradable metal or metal alloys include but not limited to the following: stainless steel alloys such as 304 stainless steel (including 304V and 304L), 316 stainless steel (including 316 L and 316 LV), stainless steel alloys having % Fe by weight ranging from 30% to 80%, Cobalt alloys such as Cobalt Chrome including L605, MP 35, cobalt alloys having % Co by weight ranging from 25% to 60%, Platinum alloys including platinum alloys having % Pt by weight ranging from 25% to 40%, metal alloys having Chrome in the alloy including alloys having % chrome by weight ranging from 15% to 25%, Mo—Re based alloys (including Icon-Nuloy alloy), Tantalum and Tantalum alloys, gold and gold alloys. Tungsten and Tungsten alloy and/or silver and silver alloys, are corrodible (degradable) metals.

The words corrodible and degradable are used interchangeably in this application.

In another example, the expandable stent having separation regions, and/or other configurations as described throughout this application, wherein at least some regions of the stent form discontinuities after deployment, uncage upon or after deployment, expand further, have higher (or increased) radial strain, allow less resistance to the implant site or lumen, and/or have the strength decreases ater implantation, wherein at least said regions of the separation regions (and/or other configurations) maintain substantially their position within the stent prosthesis structural elements after expansion, protrude (or move) outwardly from the stent prosthesis structure, protrude (or move) inwardly from the stent prosthesis structure, move in an adjacent way (or direction) to the stent prosthesis, and/or combination of the above, after deployment of the stent and/or after forming discontinuities.

In another example the stent prosthesis in any of the examples described throughout this application, wherein the stent prosthesis upon deployment has sufficient strength to support a body lumen (and/or hold in place a valve while maintaining a body lumen (such as valve open) and wherein the strength is substantially maintained after deployment (and/or after forming discontinuities). In another example, the strength after deployment decreases in a step function (or the strength decreases as step function after deployment, and/or the strength decreases after forming discontinuities) within 30 days, preferably within 3 months, more preferably within one year). In yet another example, the strength after deployment decreases in a gradual manner, and/or decreases in a linear decay manner, within 30 days, preferably within 3 months, more preferably within one year, after deployment (and/or after forming discontinuities). In yet another example the stent prosthesis strength after deployment (and/ or after forming discontinuities) decreases, said decreased strength sufficient to support a body lumen (and/or hold a structure in place, and/or hold a lumen or annulus open). In yet another example the stent prosthesis strength after deployment (and/or after forming discontinuities) decreases and reaches a plateau, said plateau strength sufficient to support a body lumen (and/or hold a structure in place, and/or hold a lumen or annulus open). In yet another example the stent prosthesis strength after deployment (and/ or after forming discontinuities) decreases but does not reach zero. In yet another example the stent prosthesis strength after deployment (and/or after forming discontinuities decreases to zero within one months, within 3 months, and/or within one year. In a preferred example, the stent having decreased strength compared to initial strength but larger that zero strength, or having zero strength, maintains (or has) a sufficient circumferential structure to support a body lumen.

In another example of any of the examples of this application, preferably wherein the stent prosthesis comprises and/or formed from a non-degradable material such as non-degradable metal or metal alloy, the stent prosthesis upon deployment from crimped configuration to an expanded larger configuration has, low inward recoil, preferably zero inward recoil to low inward recoil, preferably zero inward recoil to 6% inward recoil, more preferably zero inward recoil to 10% inward recoil, when deployed/expanded from the crimped configuration to the expanded configuration/diameter. In another example the stent prosthesis after deployment (after initial recoil (if any)) has substantially zero inward recoil to 3% inward recoil from the expanded configuration (preferably has substantially zero inward recoil), within 30 days after deployment, preferably within 60 days after deployment, more preferably within 3 months after deployment. In another example, the stent prosthesis after deployment from a crimped configuration to an expanded larger configuration (after initial recoil (if any)) and/or after forming discontinuities, further expands (on its own or unaided) to a larger configuration, further expands to a larger configuration larger than the expanded configuration after recoil, and/or further expands to a larger configuration larger than the deployed configuration (before initial recoil). The stent prosthesis in the example further expands within 360 days, preferably within 270 days, more preferably within 6 months, more preferably within 3 months, most preferably within one month, from deployment and/or implantation. In another example the stent prosthesis after deployment and/or after forming discontinuities, will expand and/or contract by a total magnitude of 2%-15% of the deployed diameter/configuration (after initial recoil (if any)), preferably by a total magnitude of 3% to 10% of the deployed diameter/configuration (after initial recoil (if any)), or more preferably by a total magnitude 4% to 15%) of the deployed diameter/configuration, within one month after deployment, preferably within 3 months after deployment, more preferably within 6 months after deployment, most preferably within one year after deployment.

In another example the stent prosthesis having separation regions (and/or other configurations describes throughout this application) as described throughout this application, preferably wherein the stent prosthesis comprises and/or formed from non-degradable material such as non-degradable metal or metal alloy, wherein the stent after deployment forms at least some discontinuities in at least some circumferential structural elements separation regions, and wherein the stent prosthesis after deployment (and/or after forming said discontinuities) substantially maintains the stent prosthesis structure and/or shape. In another example, the stent prosthesis substantially maintains the stent prosthesis circumferential structure and/or shape. In yet another example the stent prosthesis after deployment (and/or after forming said discontinuities) substantially maintains the stent prosthesis deployed configuration. In yet another example the stent prosthesis after deployment (and/or after forming said discontinuity/discontinuities) has no more than one discontinuity per any ring (or per at least some rings), preferably no more than two discontinuities per any ring (or per at least some rings), more preferably no more than three discontinuities per any ring (or per at least some rings), more preferably no more than four discontinuities per any ring (or per at least some rings). The stent prosthesis having separation regions forming discontinuities in one example along the length of the stent prosthesis in a substantially straight, or helical, or other shape, along the stent length, slicing the stent in this example along the longitudinal stent length (while maintaining intact one, some, or all or axial links connecting (joining) adjacent rings) in straight, helical, or other configurations. In another example, the stent prosthesis forming discontinuities slicing the substantially cylindrical stent structure along (or extending) the length of the stent prosthesis (while maintaining intact one, some, or more axial links connecting (joining) adjacent rings) into two structures or segments (such as two circumferential semi circles structures along (or extending) the stent length), In another example the stent prosthesis forming discontinuities slicing the substantially cylindrical stent structure along the length of the stent prosthesis (while maintaining intact one, some, or all axial links joining adjacent rings) into three structure (such as three partial circumferential structures extending along the stent length). In another preferred example, the separation regions and/or discontinuities are located onto strut structural elements, such that no more than one separation region and/or discontinuity per strut (or per some struts), and no separation regions and/or discontinuities on crowns, and/or no separation region and/or discontinuities in regions joining struts to crowns. In another preferred example, the separation regions and/or discontinuities are located at least within a strut region of a ring(s), or substantially in the middles of struts, or along the length of the strut (away from the crown and/or away from the junction joining the strut to the crown), and/or located in regions that are substantially non deformable or less deformable of the ring, and/or located in regions that have less or has reduced stress forces of a ring as the stent expands from a crimped configuration to an expanded deployed configuration, and/or located in regions that are substantially non deformable or less deformable on a ring when the stent expands from the crimped configuration to an expanded configuration, and/or located in regions where the separation regions are substantially maintained together (or substantially held together) upon deployment of the stent, on a ring, from a crimped configuration to an expanded configuration.

In another example, the separation regions have (or defines, or comprises) a gap between the two opposite ends of the structural elements adjacent to the separation, and/or between the two adjacent ends of the structural element adjacent to the separation region (for examples the two ends of the non-degradable metal alloy containing or defining or comprising a separation region). The gap width ranges from zero to 50 microns, preferably ranges from zero to 30 microns, more preferably ranges from zero to 15 microns, more preferably ranges between zero and 10 microns, most preferably ranges from 5 micros to 30 microns. The gap can be filled with a coating such as a degradable polymer coating. The coating can extend beyond the separation region to further hold in place the separation regions upon deployment of the stent from a crimped configuration to an expanded larger configuration.

In a preferred example, the stent prosthesis comprises structural elements, preferably circumferential structural elements comprising plurality of rings, each ring comprises struts joined by crowns, and each ring is connected to an adjacent ring (or non-adjacent ring) through (or by) a link or joined directly without a link. The stent prosthesis is expandable from a crimped configuration to an expanded configuration to support a body lumen and/or to hold a lumen open and/or to hold a structure (connected or attached to the stent) in place. The stent prosthesis can have a sheath surrounding and/or attached to the stent or at least a segment of the stent (preferable in a circumferential direction). The stent can hold in place (and/or attached before deployment or after deployment) a structure such as a valve (synthetic or biologic). The stent can also have means to anchor the stent or regions within the stent to body lumen, tissue, etc. The stent can also have tendons or wires attached to some regions of the stent to anchor the stent or pull it inwardly from at least one region or segment. In another example, the stent comprises one circumferential structural element comprising. In another example the stent prosthesis comprises one ring, said ring comprises struts joined by crowns. In another example, the stent and/or implant comprises a structure capable of expansion from a crimped configuration to an expanded larger configuration.

In another example, the coating thickness, and/or sleeve thickness, covering at least part of the separation regions, and/or crowns, ranges from 3 microns to 100 microns, preferably ranges from 5 microns to 50 microns, more preferably ranges from 10 microns to 50 microns. The coating, sleeve, material can be degradable or non-degradable such as degradable polymer or non-degradable polymer. In case of non-degradable polymer example, such as parylene or C-flex or polyurethane, in one example the polymer contains (holds together) the separation region together within the epolymer, wherein the separation region and/or discontinuity after deployment is allowed to uncage and/or separate (form discontinuities) within the non-degradable polymer (i.e. the non-degradable polymer continues to encapsulate the separation region and/or discontinuity), but allows the stent and/or stent region to uncage, and/or further expand, and/or become more compliant, or have increased compliance after formation of discontinuities.

In a preferred example in any of the examples in this application, the stent prosthesis is capable to expand from a crimped configuration to an expanded larger configuration without coming apart, and/or is capable to expand from a crimped configuration to an expanded larger configuration while maintaining structural integrity, and/or is capable to expand from a crimped configuration to an expanded larger configuration while maintaining the separation regions being held together, and/or is capable to expand from a crimped configuration to an expanded larger configuration while maintaining the discontinuities being held together. The expansion from crimped configuration to an expanded configuration ranges from deployment to nominal stent diameter to 3 mm above nominal stent diameter, preferably ranges from nominal stent diameter to 2 mm diameter above nominal stent diameter, more preferably ranges from nominal stent diameter to 1 mm above nominal stent diameter. Nominal stent diameter includes nominal delivery system balloon diameter, labeled delivery system balloon diameter, nominal delivery system labeled diameter, and/or labeled delivery system diameter.

In one example the measurements of any parameter such as strength compliance, diameter, configuration, recoil, displacement, dimensions, etc., such measurements are specific measurements of one sample, mean of multiple samples, mean of multiple samples from one lot, mean from multiple samples from multiple lots, and/or measurements from different samples (for examples testing strength) where the samples are built to the same or similar specifications. In another example the measurement is the mean of multiple measurements, examples include the mean lumen area representing measurement for lumen area, mean stent diameter representing stent diameter measurement, etc. In another example, standard testing methods or commonly used test methods known to those skilled in the art can be utilized for the various tests such as dimensions, size, radial strength, recoil, expansion, contraction, diameters, radial strain (or compliance), resistance, etc., it is also applicable for example to utilize IVUS, OCT, MSCT, QCA, or other measurements apparatus to measure bench, in-vitro, and/or in-vivo measurements. Measurements can also be on bench, in-vitro, ex-vivo, or in-vivo. Measurements can also be on the stented segment, the segments of the stent ring having separation region(s), a proximal stent segment, a mid stent segment, and/or a distal stent segment.

In one example, a stent prosthesis comprising a non-degradable material (such as polymeric material) which has been patterned into a stent comprising structural elements comprising rings, said rings comprise expansion regions (such as crowns), and struts, wherein at least some reinforcement elements (such as metallic non-degradable) are coupled to at least some expansion regions of the non-degradable stent, and at least some rings have at least one separation region, and wherein the stent prosthesis expands from a crimped configuration to an expanded larger configuration and have sufficient strength to support a body lumen, and wherein the separation region forms discontinuity on said rings after implantation allowing the stent to further expand in a physiologic environment.

In an example, metallic stent prosthesis are formed from a tube, or a wire (solid, or hollow at least in certain region of the wire (preferably hollow in the non-deformable regions of the wire) and patterned into a structure expandable from a crimped configuration to an expanded larger configuration. The stent structure in one example comprises plurality of rings (and at least some rings having one or more separation regions) composed of structural elements of struts and crowns, non-deformable elements (or substantially non deformable elements) such as struts, and deformable elements such as crowns. At least some of the rings are connected to adjacent rings in at least one region by for example a link. The metallic stents can also be formed from a patterned sheet that is then rolled into a tube and joined forming a stent. In yet another example, the stent prosthesis can be formed by 3-D printing.

In another example, a polymeric stent prosthesis is formed from a tube by spraying, extrusion, dipping, molding, or 3-D printing, and patterned into a stent. Alternatively, the stent prosthesis can be formed from one or more fibers or filaments and patterned or woven into a stent.

In a preferred example, the stent prosthesis is configured to uncage upon or after deployment, to exhibit vaso-dilation in a body lumen after deployment, to further expand to a larger configuration after deployment, and/or to have a radial strain ranging between 1% and 10%, preferably to have radial strain ranging between 1% and 7%, over (or on or across or along) substantially the entire stent segment, the stent segment, the stent length, the stent circumferential diameter, and/or the stent. In another example, the stent prosthesis is configured uncage upon or after deployment, to exhibit vaso-dilation in a body lumen after deployment, to further expand to a larger configuration after deployment, and/or to have a radial strain ranging between 1% and 10%, preferably to have radial strain ranging between 1% and 7%, over (or on or across or along) at least one segment of the stent, at least one region of the stent, at least some stent length, at least some stent circumferential diameter, and/or the stent.

In a preferred example, the stent prosthesis for coronary arteries application is configured to have one or more of the following in at least some rings, preferably in substantially all rings: reinforcement elements reinforcing a degradable ring structural elements (frame) of the stent (strut and/or crown), bridging elements bridging non-degradable ring structural elements (frame) of the stent (strut and/or crown), separation regions in a non-degradable ring structural elements (frame) of the stent, gaps in non-degradable ring structural elements (frame) of the stent, and/or discontinuities on overlapping or non-overlapping non-degradable ring structural elements (frame) of the stent (struts and/or crowns). The stents are configured to have 10% flat plate compression initial strength ranging from 0.025 N/mm of stent length (0.45N for a 3.0 mm by 18 mm stent length for example) to 0.07 N/mm stent length or higher (up to 0.3 N/mm stent length) after initial expansion, and the stents is configured to have dimensions range from 60 microns thick to 130 microns thick, while the width dimension ranges from 60 microns wide to 150 microns wide. The inward recoil is configured to range from 1% to 10%, and is substantially maintained after expansion (deployment). The stents are deployed in water at about 37° (or in a body lumen) and tested either in water or in air after expansion (deployment). The stents are configured to uncage upon deployment or after deployment, expand to a larger configuration after the inward recoil, and/or exhibit vaso-dilatation (or allow the stented body lumen to exhibit enlargement (or expansion or further expansion) after introduction of a vasodilator in the body lumen, when the stent is deployed (or expanded) in a body lumen. The stents are expandable from a crimped configuration to an expanded larger configuration without fracture. The stent has sufficient strength to support a body lumen. In a preferred example, the stent has sufficient strength to support a body lumen without additional recoil after initial inward recoil after expansion (deployment), when the stent is expanded in water at about 37 C or in a body lumen.

In a preferred example of any aspect, example, or embodiment of this invention, the stent prosthesis has sufficient strength to support a body lumen ranging from 0.025 N/mm stent length to 0.07 N/mm of stent length, preferably ranging from 0.04 N/mm stent length to 0.3 N/mm of stent length.

In another example, at least some struts and/or crowns, on at least some rings are configured to have one or more of discontinuities, separation regions, bridging elements, and/or reinforcement elements. At least one discontinuity, separation region, bridging element, and/or reinforcement element, are configured or formed on the said each strut, and/or each crown, of the at least some rings, or combination thereof.

In another example, the stent comprising structural elements, said stent patterned in a closed cell type design, a diamond shape rings, mesh type stent design, coil type design, and/or weaved (or braided) type stent design. The stent circumferential structural elements (such as rings) are configured to have one or more of discontinuities, separation regions, bridging elements, and/or reinforcement elements, and/or combination thereof, sufficient to uncage the stent circumferentially after expansion in a body lumen, to exhibit vaso-dilation in a body lumen after deployment, to further expand to a larger configuration after deployment, and/or to have a radial strain ranging between 1% and 10%. The stent upon deployment to the expanded larger configuration has sufficient strength to support a body lumen.

In a preferred example of any aspect, example, or embodiment of this invention, the stent prosthesis has an initial inward recoil after the stent is deployed (expanded) from a crimped configuration to an expanded larger configuration, where the initial inward recoil is substantially maintained, after the stent is expanded in water at 37 C (or after the stent is expanded under physiologic conditions, or after the stent is expanded in a body lumen). The stent initial recoil is measured within 1 minute after deployment (expansion) of the stent, or the stent initial recoil is measured within 5 minutes after deployment (expansion) of the stent. The inward recoiled is substantially maintained after deployment, maintained after deployment for at least 30 minutes, for at least 1 hour, or for at least 1 day. In all cases in this example, the stent inward recoil is measured after deployment and deflation of the deploying balloon or deploying means. The stent prosthesis in a most preferred example further expands after said initial recoil over a period ranging from 1 minute to 1 year or more, preferably over a period ranging from 30 minutes to 1 year or more, wherein the stent further expansion configuration is less than the initial recoil magnitude, preferably larger than the initial recoil magnitude (or diameter or mean diameter), or more preferably wherein the stent further expansion configuration is larger than the deployed (expanded) stent configuration magnitude (or diameter or mean diameter). In a preferred example the stent prosthesis comprises non-degradable metal or metal alloy comprising a plurality of rings.

In another example of any of the examples, the stent prosthesis has at least one, or some links that connect (or join) at least some adjacent rings, wherein the one or some links remain substantially intact (or remain intact) upon, or after expansion (deployment), or after formation of all discontinuities. In another example, all the stent prosthesis links remain intact upon or after expansion (deployment). In another example, at least some rings (or substantially all rings) are connected to adjacent rings in at least one region (or at least by one connection or by at least one link) and where the at least one connection remains substantially intact upon or after deployment or after formation of discontinuities. In another example, at least some rings are connected to adjacent rings in at least two regions (or by at least two connections, or by at least two links) and where the at least two connection remains substantially intact upon or after deployment or after formation of all discontinuities. In yet another example, at least one link, preferably at least some links (or connections), joining at least some rings are configured to have one or more of reinforcement elements. The stent prosthesis in these examples is also configured to have at least some struts and/or crowns on at least some rings having one or more of reinforcement elements. In yet another example, substantially all links (or connections), joining at least some rings are configured to have one or more of reinforcement elements. The stent prosthesis in this example is also configured to have at least some struts and/or crowns on at least some rings having one or more reinforcement elements.

In an example of any of the examples in this application, the stent prosthesis (or at least one segment of the stent prosthesis) is configured to have high crush resistance after deployment (or expansion) from a crimped configuration to an expanded larger configuration, where the stent circumferentially uncages, the stent circumferentially uncages the stented segment, further expands to a larger configuration, responds to a vaso-dilator introduction, and/or has a radial composite strain (or compliance) in the range of 1.5% to 7%, after expansion. The stent prosthesis in a preferred example substantially maintains the initial high crush resistance after expansion. The stent prosthesis in another example exhibits a reduction (decrease) in crush resistance over a period of time ranging from after deployment and 1 year, where the crush resistance decreases ranges from 20% to 80%, over a period of time ranging from one month to one year, said remaining crush resistance is sufficient to support a body lumen. In yet another example the stent prosthesis exhibits a decrease in crush resistance after deployment from a period of time ranging from after deployment and one year, said stent prosthesis after said period of time substantially has no crush resistance.

In a preferred example of any of the examples in this application, the stent prosthesis has a patterned structure after deployment (expansion), where the structure is substantially maintained (or intact, or substantially intact). In another example, the stent prosthesis has an initial patterned structure after deployment (expansion), where the initial patterned structure changes (or becomes different or is modified) after expansion. In another example, the stent prosthesis has a patterned structure comprising structural elements (comprising in a preferred example struts, crown, and links (or connections), wherein the stent after deployment (expansion), maintains (or has) at least one longitudinal structural elements segment along substantially the length of the stent. The longitudinal structural element segment has (or comprise) one or more breaks, separation regions, and/or discontinuities along the longitudinal segment (excluding the link or connection regions which are axial connectors and which remains intact). The longitudinal segment circumference in one example ranges from ¼ the circumference of the stent to ½ the circumference of the stent. The longitudinal segments pattern can be substantially straight along substantially the length of the stent, or can be helical along the stent length, or other longitudinal pattern along the length of the stent. The at least one longitudinal structural elements segment remains substantially intact (preferably remains substantially intact through the one or more links (or connections) along the length of the stent). In another example, the stent prosthesis has a patterned structure comprising structural elements (comprising in a preferred example struts, crown, and links (or connections), wherein the stent after deployment (expansion), maintains (or has) at least one circumferential structural elements segment along substantially the circumference of the stent. The circumferential structural element segment has (or comprise) one or more breaks, separation regions, and/or discontinuities along the circumferential segment (excluding the link or connection which are axial connectors and which remains intact). The number of circumferential segments in one example ranges from 1 to 4. In another example, the stent prosthesis has a patterned structure comprising structural elements (comprising in a preferred example struts, crown, and links (or connections), wherein the stent after deployment (expansion) maintains at least one circumferential segment along the stent circumference and/or at least one longitudinal segment along the stent length, wherein the segment comprises at least one crown and at least two struts, preferably comprises at least one crown and at least two struts and at least one link (or connection) remain intact or connected, more preferably, comprises two or more rings, partial rings (or ring regions). The segment has at least one separation region, break, and/or discontinuity on at least some rings (or partial rings or ring regions).

In another example, a stent comprising a degradable (including corrodible) material, wherein the material degrades in a period ranging from 1 year to 20 years, preferably from 2 years to 15 years, more preferably from 3 years to 10 years, wherein the material is patterned into a stent comprising structural elements, said structural elements comprising a plurality of rings, each ring comprises struts and crowns. At least struts and/or crowns, on at least some rings have one or more of separation regions, discontinuities, breaks, gaps, and/or bridging element, and wherein the stent prosthesis uncages after expansion from a deployed configuration to an expanded larger configuration. The stent in one example uncages upon deployment. The stent in another example uncages from a period ranging from 1 month to one year. The degradable material comprises one or more of a metal or metal alloy, a polymeric material, or other material that degrades from 1 year to 20 years. The stent prosthesis upon expansion has 10% flat plate crush resistance ranging from 0.025 N/mm stent length to 0.085 N/mm of stent length, but can also range from 0.05 N/mm to 0.2 N/mm of stent length.

In another example, a stent prosthesis comprising structural elements, said structural elements comprise a plurality of rings, each ring comprises struts, crowns, and each ring is connected to an adjacent ring by at least one link (or connection), at least some struts and/or crowns on at least some rings have one or more of separation regions, bridging regions, discontinuities, gaps, and/or breaks, or combination thereof. In another example, a stent prosthesis comprising structural elements, said structural elements comprise a plurality of interconnected rings, substantially all rings have one or more of separation regions, bridging regions, reinforcement element, discontinuities, gaps, and/or breaks, or combination thereof. In yet another example, a stent prosthesis comprising structural elements, said structural elements comprise a plurality of interconnected rings, at least half of all rings have one or more of separation regions, bridging regions, reinforcement element, discontinuities, gaps, and/or breaks, or combination thereof.

In another example, a stent prosthesis comprises structural elements, said structural elements comprises a plurality of rings each ring comprises struts and crowns, said stent prosthesis is plastically deformable from a crimped configuration to an expanded larger configuration, where the stent in the expanded larger configuration has composite radial strain (or compliance) ranging between 1% and 5%. The stent in the expanded configuration is crush resistant and have sufficient strength to support a body lumen. The stent in preferred example further expands to a larger configuration after deployment and after an inward recoil (if any). The stent in another preferable example is plastically deformable over a range of diameters ranging from 1 mm to 2 mm diameter range, preferably ranging from 2 mm to 4 mm diameter range, more preferably ranging from 3 mm to 4.5 mm diameters.

In another example, a stent prosthesis as in any of the examples, wherein the stent prosthesis is delivered to a body lumen without a restrain (or sleeve), said stent expands from a crimped configuration to an expanded larger initial configuration, then said stent exhibits inward recoil, before expanding to a second configuration (smaller or larger than initial configuration).

In another example or aspect of this invention, a stent prosthesis comprised of metal and metal alloys material wherein the stent prosthesis is expandable from a crimped configuration to an expanded larger configuration and has sufficient strength to support a body lumen upon (or after) expansion. The stent material is pre-formed, or treated, and/or configured to exhibit one or more of the following after expansion: softening of the material, weakening of the material, becoming less stiff, has reduced crush resistance, has reduced strength, and/or has no strength, has an initial strength sufficient to support a body lumen wherein the strength decreases over time, has an initial strength sufficient to support a body lumen wherein the strength remains substantially the same over time, and/or has an initial compliance upon expansion and wherein the compliance increases after expansion, and/or has an initial compliance immediately after expansion (or within 24 hours after expansion) and wherein the compliance increases after expansion (or within 6 months after expansion), under one or more of the following conditions: physiologic conditions (which also includes one or more of the following): in water at 37 C, cyclic physiologic fatiguing (pulsation), and/or physiologic temperature, in a period ranging from 1 month to 5 years, preferably ranging from 3 months to 3 years, more preferably ranging from 3 months to 2 years, after expansion, pressure differential ranging from 50 mmHg to 200 mmHg. The stent material treatment comprises, heat, quenching, cyclic fatiguing, or other, said treatment taking place at one or more of the following: before forming, during forming, after forming, before stent patterning, or after stent patterning. The stent after expansion exhibits one or more of the following: being further expandable to a larger configuration, expands further in response to vaso-dilator introduction, and/or has a composite radial strain (or compliance) ranging from 1.5% to 5%, in water at 37 C, or under physiologic condition, and/or in a body lumen.

In another example, the stent material comprises, or composed of, one or more of the following metals or alloys such as conventional titanium alloys such as Ti6Al4V, Ti5Al2.5Sn, or Ti-10V-Fe-3Al; stainless steel such as SAF2507; zinc alloys such as Zn5al, Zn10Al, Zn18Al, Zn30Al, platinum metal and its alloys; tin alloys such as Sn3.9Ag0.6Cu, Sn-3.8Ag-0.7Cu, SnPb, or SnPbAt; aluminum alloys such as Al1.7Fe, Al0.7Cu, A1.5MgScZr, Al6Mg0.2Sc0.15Zr, 3004, 8090, 7075, 6061, or 5056; zirconium alloy such as Zr55Al10Ni5Cu30; magnesium alloy such as AZ31B or MG11li5Al1Zn0.034Sc (LAZ1151); iron alloy such as Fe29.7Mn8.7Al1C, 30HGSA alloy steel, 4140, C45 steel, Fe36Ni, or low carbon steel; Nickel Alloys such as Ni21Cr17Mo or Haynes 230; Tungsten or Tungsten alloys, or other. In a preferred example, the material strength after expansion decreases by at least 25%, preferably by at least 50%, more preferably by at least 75%, compared to the strength just after deployment (initial strength), over a period ranging from 1 month to 3 years. The material in a preferred example softens (decreased strength) comprising one or more of the following reasons: body temperature, time, cycling (or fatigue), creep, recrystallization, grain growth, dislocation, precipitation interaction, dislocate interactions or other. The stent material is degradable (including corrodible) or non-degradable. The stent material can be formed as a tube and patterned into a stent, formed as a wire (or formed from a wire) and patterned into a stent, or formed as a patterned sheet (or formed from a patterned sheet) into a stent.

In another example or aspect of this invention, a degradable stent prosthesis comprising degradable polymeric material or degradable metallic or metallic alloy material, wherein the stent is configured to have one or more separation regions, uncage after expansion (or deployment), exhibit radial strain (or compliance) ranging from 1.5% to 5%, further expands to a larger configuration after deployment (including after initial recoil), and/or expand in response to a vaso-dilator. The stent is configured to have one or more of the following: at least some rings (preferably substantially all rings) have one or more of the following: gaps, bridging elements, separation regions, discontinuities. In a preferred example, the separation regions are configured to form discontinuities before (or substantially before) the degradable stent degrades. In another example, the separation regions are configured to form discontinuities before the degradable stent degrades by a period ranging from 1 month to 5 years, preferably by a period ranging from 2 months to 3 years, more preferably by a period ranging from 3 months to 1 year. In yet another example, the separation regions are configured to form discontinuities within a period ranging from after initial expansion to 1 year after initial expansion, preferably within a period ranging from one month after initial expansion to 9 months after initial expansion, more preferably, within a period ranging from one month after initial expansion to six months after initial expansion.

In another example, the degradable stent material comprises metal or metal alloy of Nickel, Cobalt, Tungsten, Iron, Zinc, Magnesium, Magnesium alloy AZ31, Tin, 1010 Steel, Steel, 5140 Steel, 8620 Steel, Iron Nickel Alloy, Cellulose, or other. In one example, the degradable material substantially degrades in a period ranging from 1 year to 20 years, preferably degrades from 1 year to 10 years, more preferably in a period ranging from 1 year and 5 years, or most preferably in a period ranging from 6 months to 3 years. In one example, the degradable stent material comprises (or composed of) polymeric stent material comprises PLLA polymeric material. In yet another example, the degradable stent comprises polymeric material comprising poly-lactide polymeric material. In yet another example, corrodible metal or metal alloy (degradable) that corrodes (degrade) from 1 to 10 years such as tungsten, tungsten alloys, Tungsten alloys of rhenium, cobalt, iron, zirconium, zinc, titanium; alloy of cobalt; magnesium alloy AZ31, tin, 1010 steel, steel, 5140 steel, 8620 steel, iron nickel alloy; or the like. In yet another example of Degradable polymer and copolymers that degrade from 3 to 10 years examples include cellulose; chitin; chitosan; PLLA or its copolymer; or the like.

In still further examples, the stents and other endoluminal prostheses of the present invention may be formed from non-degradable metals or metal alloys and/or other non-degradable materials and will be configured to have breaks, or openings formed (usually pre-formed) in the scaffold circumferential structure (such as one or more rings) to allow uncaging of the stent after implantation in a vascular or other body lumen. The scaffold will typically be defined by a plurality of circumferential rings which are configured to expand from a crimped condition to an expanded configuration, where at least some of the circumferential rings follow a circumferential path about the circumference of the scaffold. There will be at least one break or opening in the circumference of at least some of the rings, and adjacent circumference rings will be axially linked so that substantial portions or segments of the scaffold remain connected and intact (by the axial links) after the scaffold has been expanded to its expanded configuration and the breaks (gaps) or discontinuities have formed in the one or more rings. In some examples, the entire scaffold will remain both axially and circumferentially connected so that no portion of the scaffold may inadvertently disconnect from the remainder of the scaffold after expansion and after the breaks (or discontinuities) have formed. In other examples, the expanded scaffold may separate into two, three, or more axially intact segments. In still other examples, the scaffold may separate into random segments after expansion, where such random segments will have sufficient size and persistence so they will not dislodge or substantially migrate from the implantation location in blood vessel or other body lumen after expansion. An example of that is a plurality of crowns and/or struts remaining connected within one or more rings, and/or along the length of the scaffold.

In a first set of examples, the openings or breaks in the scaffold will (or may) comprise gaps in the circumferential rings. For example, the gaps may be formed in either or both of the struts and the crowns of the circumferential rings. In some examples, the gaps will be closed when the scaffold is in its crimped (unexpanded) configuration and will open when the scaffold is expanded to its expanded configuration. Such examples include breaks in the struts or crowns where the adjacent edges formed by the breaks remain in contact with each. Such "breaks" may be formed as part of the initials fabrication of the scaffold, e.g. patterning of a tube or bending of a wire, or may be formed after the initial fabrication but cutting of severing a previously formed strut or crown. In other examples, the gaps in the circumferential rings may be present even when the scaffold is in its unexpanded (crimped) condition or the separation distance between the opposed ends of the gap and the strut or crown will increase upon expansion of the scaffold. Such initially open gaps may also be formed during or after initial fabrication of the scaffold.

The gaps formed in the circumferential rings may be rotationally staggered or rotationally aligned along a longitudinal or central axis of the scaffold. When the gaps in the circumferential rings are rotationally staggered, the adjacent rings may be joined by axially links which are also formed in a staggered pattern which may be the same or different than that of the rotationally staggered gaps. Similarly, when the gaps are rotationally aligned, the axially links may also be rotationally aligned or rotationally staggered.

In a second set of examples, the openings or breaks in the circumferential rings will (or may) comprise biodegradable segments which form "bridges" between opposed surfaces or portions of the struts or crowns which contain the break or opening. The biodegradable segments may be configured to remain intact while the scaffold is expanded in a vascular environment, forming gaps in the rings only after the bridging segments have degraded in the vascular or other luminal environment. Biodegradable segments may be configured to degrade in the vascular or other luminal environment over a time period in the range from 1 month to 3 years, preferably degrade over a period ranging from 3 months to one year.

As with the gap embodiments described previously, the biodegradable "bridge" segments may be rotationally aligned or rotationally staggered within the scaffold structure. Similarly, the axial links which hold adjacent circumferential rings together may also be rotationally aligned or staggered, and when staggered may be staggering in a pattern which is similar to that of the staggered biodegradable segments.

For both the gap and the bridge examples, the scaffolds may display a composite compliance (radial strain) in the range from 1% to 10%, usually from 1.5% to 5%, when expanded within a vascular environment (or under physiologic conditions) and subjected to systolic/diastolic pressure cycling.

In yet another aspect of the present invention, in the vascular prostheses having a biodegradable bridging segment (element) in their struts and/or crowns may be made (or fabricated) as follows. A scaffold is fabricated having a plurality of rings which define a circumference of the scaffold. The plurality of rings is (or maybe formed) formed from a non-degradable material, typically a metal. A second scaffold having a plurality of rings which define a circumference of the scaffold is also fabricated but from a biodegradable material. Typically, the first and second scaffolds will (or may have) have identical geometries, at least over the regions where the bridging structures are to be located. After the first and second scaffolds are formed, gaps may be cut into at least into the struts and/or crowns of at least some of the rings of the first non-degradable scaffold. Corresponding segments are then cut from the second scaffold, where the segments are selected to fill in the gaps formed in the first scaffold. The segments cut from the second scaffold are (or maybe) secured into the gaps formed in the first scaffold to form a complete scaffold having a non-degradable base structure with a plurality of degradable bridges in selected struts and/or crowns thereof.

In still further examples of the present invention, the scaffold separation regions of the present invention can (or maybe used) be used in helical stents of the type having a helical backbone including a plurality of struts joined by a plurality of crowns. The helical backbone is formed to include a multiplicity of adjacent turns where at least some of the adjacent turns are attached or otherwise coupled to each other by a separation region. For example, the separation regions may be formed between immediately adjacent turns of the helical backbone, with specific examples including between adjacent pairs of crowns, between a crown on one turn and a strut on an adjacent turn, and between a pair of struts on adjacent turns. The helical backbone typically has a serpentine arrangement, a zig-zag arrangement, or follows another "meandering path" of the type commonly utilized in stent fabrication. The stents may be formed from a bent wire or alternatively may be formed by patterning a tube in a conventional manner. The separation regions may comprise any one or more of the separation regions described elsewhere herein, such as degradable regions, mechanically separable regions, fatigue-responsive regions, bridging elements, and the like.

In yet additional examples of the present invention, luminal prostheses may compromise scaffolds having a plurality of circumferential rings formed from a non-degradable material, such as a metal, metal alloy, or a non-degradable polymer, where the scaffold is configured to expand from a crimped configuration to an expanded configuration. At least some of the circumferential rings will be formed from structural elements (such as crowns and/or struts) having divided regions which overlap and lie adjacent to each other when the scaffold is in its crimped configuration. For example, the adjacent regions which overlap and lie adjacent to each other may be straight, typically together forming a "divided" portion of a strut of the scaffold, or may be curved, typically together forming a "dived" portion of a crown of the scaffold. Such straight adjacent regions will typically separate from each other when the scaffold is expanded to its expanded configuration. In contrast, such curved overlapping adjacent regions will typically deform when the scaffold is expanded to its expanded configuration, for example, straightening in response to the bending forces applied by expansion of the stent.

The overlapping adjacent regions may be initially unattached when the scaffold in its crimped configuration. Alternatively, the overlapping regions of the scaffold may be temporarily joined to each other, for example, being held together by an adhesive, by an overlying sleeve, by a coating, and/or by any of the other permanent or temporary immobilization material, methods, and/or structures described herein previously. Such temporary immobilization material (or structures), comprises degradable materials such as degradable polymeric material, will be configured to degrade in a physiologic environment, to fatigue, or to otherwise separate after implantation to enhance the compliance of the scaffold after the prosthesis has been implanted in a body lumen for a desired period of time. Permanent immobilization material comprises non-degradable material such as non-degradable polymeric material, wherein the material is typically elastic, allowing the stent prosthesis to have enhanced compliance after the prosthesis has been implanted in a body lumen for a desired period of time.

In still other examples, the scaffold separation technology (separation regions and other methods to uncage the circumferential structural elements (or to allow for uncaging the stented segment of the lumen) as described in various examples and/or aspects of this application) of the present invention may be applied to a variety of otherwise conventional closed-cell stent patterns. For example, the scaffold may have a plurality of circumferential rings formed from a non-degradable material to expand from a crimped configuration to an expanded configuration. At least some of the circumferential rings will be formed as expandable closed cell structures which are joined circumferentially, and such circumferential rings will have one or more separation regions configured to form discontinuities in the rings after deployment in the luminal environment, uncaging the stented segment of the lumen. In some cases, at least two or more separation regions, in a circumferential ring, configured to form discontinuities, are necessary to uncage a circumferential ring, in other cases, at least three or more separation regions in a circumferential ring are required to uncage a circumferential ring. The one, two, three, or more separation regions may be located in the expandable closed cell structures and/or in circumferential connectors between the closed cell structures.

In specific examples, the closed cells may comprise quadrangles having opposed axial sides and opposed circumferential sides. The scaffolds may further comprise circumferential connectors which join the axial sides of circumferentially adjacent closed cells, where the separation regions may be located in the circumferential connectors and/or in the closed cell structures themselves.

Typically, at least some of the closed cells in axially adjacent circumferential rings will be joined by axial links, where the axial links are typically non-degradable and free from separation regions in order to enhance the integrity of the stent after deployment, and/or in order to enhance the stent uniformity of expansion, and/or in order to maintain the structural integrity of the stent upon expansion, or after expansion.

The discontinuities which form in the scaffold after implantation will typically allow the stent to display a compliance (or radial strain) and range from 1% to 10%, preferably ranging from 1.5% to 5% once subjected to systolic/diastolic pressure cycling (or vaso-dilator) after implantation, usually in a blood vessel of a mammalian.

In alternative closed cell configurations, the scaffolds may comprise closely packed quadrangles formed from a plurality of common crossing members where the separation regions are present in the common crossing members and/or at junctions where the crossing members cross one another. The separation regions may comprise any of the separation regions described herein, often being biodegradable regions in the closed cell scaffolds just described.

In still further examples of the present invention, a stent prosthesis may comprise a patterned circumferential scaffold including non-degradable structural elements. The structural elements may have expansion regions configured to plastically deform as the scaffold is radially expanded from a crimped configuration to a first expanded configuration. The structural elements (such as rings) may be further configured to allow the scaffold to passively (unaided by a mechanical means and/or human intervention) expand to a second, larger configuration after experiencing (or exhibiting) inward recoil from the first expanded configuration after implantation. The scaffold will retain sufficient strength to support a body lumen for at least an initial time period following implantation. The initial time period will typically be at least about 1 day, often being at least 3 months, and typically being in a range from 30 days to 9 months. The expansion regions may be any of the separation regions described previously herein. The second larger configuration may be larger than the first expanded configuration, or can be smaller than the first expanded configuration. In one example, the non-degradable structural elements comprise a plurality of rings wherein each ring is composed of struts and crowns, said non-degradable structural elements are composed of metal or metal alloy that plastically deforms when expanded from a crimped configuration to an expanded configuration. In one example, at least some rings are configured to have one or more separation regions (in one or more struts and/or crowns of the at least some rings), wherein the separation regions are configured to form discontinuities after expansion in physiologic environment.

In still further examples, the stent prosthesis of the present invention may comprise a non-degradable patterned, circumferential scaffold including structural elements. The structural elements (such as rings) may have expansion regions configured to plastically deform as the scaffold is radially expanded from a crimped configuration to a first expanded configuration, and the scaffold may be further configured to have a radial strain (or composite compliance) in a range from 1.1% to 15%, preferably in a range from 1.2% to 10%, more preferably in a range from 1.5% to 7% after the stent is expanded in a body and to retain sufficient strength to support the body lumen. These scaffolds are often further configured to have an inward recoil after deployment in a range from 1.5% to 7%, and may further be configured to have an initial radial strain (or compliance) after deployment of 1% or less before increasing to the radial strain in said range above. In additional examples, the radial strain of the stent prostheses just described may reach a value in the desired range within two months to one year after deployment, and a diameter magnitude of the radial strain (or compliance) may be in a range of 0.07 mm to 0.5 mm, or of 0.1 mm to 0.5 mm. In a preferred example, at least some rings are configured to have one or more separation regions, wherein the separation regions are configured to form discontinuities after expansion of the stent under physiologic conditions. In another preferred example, all rings are configured to have one or more separation regions, wherein the separation regions are configured to form discontinuities after expansion of the stent under physiologic conditions. In yet another example, at least some rings have two or more separation regions, have three or more separation region, have one to four separation regions, or have 2 to 4 separation regions.

In other examples, stent prostheses according to the present invention may comprise a non-degradable, patterned circumferential scaffold including structural elements, where the structural elements have expansion regions configured to plastically deform as the scaffold is radially expanded from a crimped configuration to a first expanded configuration. In some of these examples, the scaffold in the deployed configuration has a sufficient strength to support a body lumen, and the scaffold may be further configured (by incorporating one or more aspects (or examples) of the present invention as described throughout this application, such as separation regions on at least some rings for example) to allow a stented segment of the body lumen to vaso-dilate in the presence of a vaso-dilator in the body lumen. The stented segment of the body lumen may vaso-dilate in the range of 0.05 mm to 0.5 mm and frequently in a range from 0.1 mm to 0.3 mm, or in a range from 0.07 mm to 0.5 mm.

In yet additional examples of the stent prostheses of the present invention, a non-degradable, patterned circumferential scaffold may include structural elements, where the structural elements have expansion regions configured to plastically deform as the scaffold is radially expanded from a crimped configuration to a first expanded configuration. The scaffold in the deployed configuration will have sufficient strength to support a body lumen, and the scaffold will typically also be configured (by incorporating one or more of the various aspects (or examples) described in this application) to contract and/or expand after deployment in the body lumen under physiologic conditions. The expansion and/or contraction may occur passively or alternatively may occur in response to vaso-dilation and/or vaso-constriction of the body lumen. The expansion and/or contraction may also occur under physiologic pulsation. Such expansion and/or contraction often has a magnitude in a range from 0.05 mm to 1 mm, more typically range from 0.1 mm to 0.5 mm relative to a deployed diameter or mean diameter of the body lumen.

In some examples, one or more of the following: at least one ring of the stent prosthesis, at least some rings of the stent prosthesis, all rings of the stent prosthesis, at least some circumferential elements of the stent prosthesis, all circumferential elements of the stent prosthesis, and/or the stent prosthesis, of this invention is configured (by incorporating one or more of the present invention aspects (or examples) as described within this application) to do one or more of the following: Un-caging of the lumen or vessel while having high crush resistance upon or after implantation of the stent, and/or uncaging the stented segment of the lumen or vessel, and/or a stent having sufficient strength to support or hold the vessel or lumen open after implantation and further expands (after inward recoil if any) after implantation, and/or not having pieces of stents such as small components dislodging into the blood stream potentially causing a clinical event, and/or having a stent with low inward recoil after initial expansion, and/or having a stent with low inward recoil after initial expansion that is substantially maintained after implantation, and/or having a stent with low inward recoil after initial expansion that increases by no more than 1%-5% after said initial inward recoil, after implantation, and/or having a stent configured to be able to further expand (after inward recoil if any) after deployment under physiologic condition, and/or having a stent able to expand or further expand (after inward recoil if any) after deployment without a pre-programed temperature trigger setting or without a pre-programed expanded diameter/configuration setting, and/or having a stent able to expand or further expand (after inward recoil if any) without a programed temperature, and/or having a stent able to further expand (after inward recoil if any) after deployment under physiologic condition without penetrating or without substantially penetrating the vessel or lumen wall, and/or having a stent that does not cause excessive inflammation, and/or having a stent that does not penetrate the lumen or vessel wall after implantation, and/or having a stents that expands further (after inward recoil if any) after deployment (implantation) further expanding the lumen or vessel, and/or having a stent maintained or substantially maintained in the crimped configuration upon delivery into the vessel or lumen without a constraint and further expand (after inward recoil if any) to a larger configuration after deployment, and/or having a stent that can be deployed to a wide range of diameters and still uncages the vessel or lumen after deployment, and/or having a stent that can be deployed to a wide range of diameters and still further expand (after inward recoil if any)

to a larger configuration after implantation, and/or having a stent able to further expand (after inward recoil if any) beyond the pre-programed expanded diameter/configuration after implantation, and/or having a stent that exhibit vaso-motion, vaso-dilation, or vaso-constriction, after implantation, and/or having a stent that has sufficient strength after deployment to support a body lumen, has low inward recoil (or said stent undergoes inward recoil) after the initial expansion, and where the stent exhibits radial strain (or compliance) below 1% immediately after expansion (deployment), and a radial strain (or compliance) of 1% or larger than 1% after deployment, and/or having a stent that has sufficient strength after deployment to support a body lumen, said stent undergoes inward recoil after the initial expansion of the stent, and where the stent has an initial radial strain (or compliance) after initial expansion, and wherein the radial strain (or compliance) increases after deployment (or increases over time after deployment), and/or having a stent that has sufficient strength after deployment to support a body lumen, said stent undergoes inward recoil after the initial expansion of the stent, and where the stent has an initial radial strain (or compliance) after expansion (deployment), and wherein the radial strain (or compliance) increases, wherein the increase in compliance ranges from 150% to 3000% the initial compliance, preferably wherein the increase in compliance ranges from 200% to 3000% the initial compliance, and more preferably, wherein the increase in compliance ranges from 300% to 3000% the initial compliance, and/or having a stent that has sufficient initial strength after deployment (initial expansion) to support a body lumen, said stent undergoes inward recoil after the initial expansion of the stent, and where the stent has an initial radial strain (or compliance) after expansion (deployment), and wherein the radial strain (or compliance) increases after initial expansion, preferably wherein the increase in compliance ranges from 150% to 3000% the initial compliance, preferably wherein the increase in compliance ranges from 200% to 3000% the initial compliance, and more preferably, wherein the increase in compliance ranges from 300% to 3000% the initial compliance, and wherein the initial strength decreases after deployment (or decreases after deployment over time, or preferably decreases after deployment from 30 days to 1 year after deployment), and/or any of the above examples, wherein the stent does not undergoes an inward recoil after initial expansion, and/or a stent as in any of the above examples, wherein one or more of the stented segment further expand by a magnitude ranging from 0.07 mm to 0.5 mm under physiologic conditions (including the infusion of vaso-dilator) into the vessel or lumen, and/or any of the examples under physiologic conditions, and/or having a stent that has sufficient initial strength after deployment (initial expansion) to support a body lumen (or annulus), and where the stent has an initial radial strain (or compliance) after expansion (deployment), and wherein the radial strain (or compliance) increases, after expansion, preferably wherein the increase in compliance ranges from 150% to 3000% the initial compliance, preferably wherein the increase in compliance ranges from 200% to 3000% the initial compliance, and more preferably, wherein the increase in compliance ranges from 300% to 3000% the initial compliance, and wherein the stent prosthesis has an initial configuration after an initial expansion of the stent prosthesis, and wherein the stent configuration changes after implantation (or after completion of the procedure), and/or any of the examples under physiologic conditions, and/or having a stent that has sufficient initial strength after deployment (or after an initial expansion) to support a body lumen (or annulus), and wherein the stent prosthesis has an initial diameter (or configuration (after an inward recoil if any), or wherein one or more segments of the stent has an initial configuration) after an initial expansion (and after an inward recoil, if any) of the stent prosthesis, and wherein the stent diameter (or configuration, or one or more segments of the stent circumferential elements (such as rings) changes after implantation (or after completion of the procedure, or changes over time, or changes over a period ranging from 30 days to one year, in one or more of the x-axis, y-axis, or z-axis of the stent, or one or more segments of the stent, and/or having a stent that has sufficient initial strength after deployment (or after an initial expansion) to support a body lumen (or annulus), and wherein the stent prosthesis has an initial diameter after an inward recoil, if any, (or configuration, or wherein one or more segments of the stent has an initial configuration) after an initial expansion of the stent prosthesis and after an inward recoil, if any, and wherein the stent diameter (or configuration, or one or more segments of the stent circumferential elements (such as rings) becomes smaller or larger after implantation (or after completion of the procedure, or changes over time, or changes over a period ranging from 30 days to one year, in one or more of the x-axis, y-axis, or z-axis of the stent, or one or more segments of the stent, to contour to the luminal (or annulus) configuration (or diameter) change.

In a preferred example, the stent prosthesis having (or may have) one or more separation regions on at least some rings, preferably on substantially all rings, wherein the stent is expandable from a crimped configuration to an expanded larger configuration and have sufficient strength in the expanded configuration to support a body lumen, and wherein at least one separation region per at least some rings forms a discontinuity in the circumferential path of said ring uncaging said ring, and wherein the stent after formation of discontinuities maintains a structure pattern with the substantially the same number of discontinuities as the number of separation region, wherein the number of separation regions per ring ranges from 1 to 4.

In a preferred example, the stent prosthesis having (or may have) one or more separation regions on at least some rings, preferably on substantially all rings, wherein the stent is expandable from a crimped configuration to an expanded larger configuration and have sufficient strength in the expanded configuration to support a body lumen, and wherein at least one or more separation regions per at least some rings sufficient to form at least one discontinuity in the circumferential path of said ring uncaging said ring, and wherein the stent after formation of discontinuities maintains a structure pattern with the substantially the same number of discontinuities as the number of separation region, wherein the number of separation regions per ring ranges from 1 to 4.

In one example, the stent in accordance of this invention is configured to uncage upon expansion or after expansion from a crimped configuration to an expanded larger configuration and have sufficient strength to support a body lumen or annulus in the expanded configuration. At least some rings, or at least some stent segments, or at least some stent regions, or substantially all rings, ring segments, or ring regions, or the stent, uncage after expansion. Uncaging comprises one or more of the following: having one or more breaks, discontinuities, separations, in a circumferential path of each of the at least some rings, or of each of the at least some circumferential structural elements, or of the stent circumferential elements, sufficiently to separating the rings, circumferential structural elements, and/or the stent in at least one or more circumferential direction; having the stent or a stent segment being able to expand to a larger configuration after expansion and after formation of discontinuities, having a stent or a stent segment in the expanded configuration exhibiting radial strain (or compliance) ranging from 1% to 10%, preferably ranging from 1.5% to 7%, more preferably from 2% to 5%; having a stent or a stent segment in the expanded configuration (after expansion) exhibiting contraction or expansion, expansion and contraction, expansion and/or contraction ranging from 0.1 mm to 1 mm, preferably ranging from 0.15 mm to 0.7 mm, more preferably ranging from 0.2 mm to 0.5 mm, and/or having a stent in the expanded configuration being responsive to vaso-dilators and/or vaso-constrictors, and/or other therapeutic agents; or other.

In some examples, a non-degradable stent material is preferred for its high strength (or high crush resistance) properties or other mechanical properties. A degradable material such as metallic or metallic alloy can be configured to have high crush resistance and properties substantially similar to non-degradable material or to non-degradable alloy and therefore can also be suitable for these examples or embodiments. In some examples, the biodegradable material can be configured to have sufficient strength in the stent expanded configuration to support a body lumen and degrade in a period ranging from 3 months to 10 years, preferably degrade in a period ranging from 1 year to 5 years. A degradable material can also be polymeric material having sufficient strength in the expanded configuration and degrades over a time period ranging from 3 months to 10 years, preferably degrading in a period ranging from 1 year to 5 years.

In one example, a coronary stent comprising 2.0 mm to 4.0 mm diameter expansion range by one or in some cases multiple stents to accommodate such range, 15 mm to 40 mm stent length range, formed from a wire, a tube, or a sheet rolled up into a tube (patterned before or after rolling into a tube), having strut thickness ranging from 50 microns to 150 microns, preferably thickness ranging from 50 microns to 120 microns.

In a preferred example, a stent configured to uncage after expansion in accordance with one or more aspects of this invention, is desired to have the ability to withstand fatigue for at least 400M cycles, or to have stresses and/or strains on structural elements such as rings, expansion regions (such as crowns), non-deformable regions (such as struts), or axial links connecting adjacent rings, to be sufficiently in a range to withstand 400M cycles of stent fatigue without uncontrolled fracture. In one example, the expansion region of the stent is configured to uncage, can have a wider neck, a key hole type design, or other design, shape, geometry to maintain stresses or to distribute stresses along a longer or larger area, when one or more separation regions on the same ring or adjacent ring form discontinuities. Other examples include larger width or thickness of structural elements, longer structural elements, and/or varying the number, location, shapes, and geometry of separation regions. Another example is manipulating the axial links locations, shape, and number. In another example, having one or more rings with one or more separation regions followed by one or more adjacent rings that do not have separation regions or a different number of separation region on said rings to manage overall stresses on the stent structure and on the rings with separation regions. In a preferred example, the stent of this invention is configured after expansion to have support to the body lumen or annulus without substantial incremental stresses to the body lumen or annulus, while the stent remain axially connected.

In another example of any of the examples in this application, at least one ring having one or more separation regions and/or joints, and/or the stent prosthesis is desired to withstand an approximately 400 million cycles simulating approximately 10 years of heart beats. The stent is configured to have a safety factor of one, preferably greater than one, more preferably greater than 1.2 safety factor on the Goodman line. The Goodman line in one example is generated as follows: In a graph of Alternating stress measured in MPa of the stent material, versus mean stress measured in MPa also of the stent material, the mean and alternating stress for every point in the stent subject to physiological conditions (for example using FEA or physical testing to generate such points simulating physiological conditions) is desired to fall on or below a line connecting the fatigue limit measured in MPa (measured from the stent material sample) on the alternating stress axis, and the ultimate stress on the mean stress axis (that is the Goodman line), giving a factor of safety of one, greater than one, or preferable 1.2 or greater factor of safety. This allows simulating approximately ten year fatigue cycle of the stent prosthesis under physiologic condition without breakage. In another example, the stent prosthesis is configured to have controlled breakage or discontinuities at certain location on one or more circumferential structural element (such as rings), and at approximate time duration within ten years, or beyond.

In one example, a non-degradable stent prosthesis comprising a non-degradable metal alloy such as L605 that is patterned from a tube or a wire, wherein the stent is configured in accordance with one or more aspects or examples of this invention to uncage after expansion in a body lumen or under physiological conditions, said stent has sufficient strength in the expanded configuration to support a body lumen, and wherein the stent strength after expansion decreases. The stent further comprises a degradable coating and a drug agent (incorporated in the coating or separate from the coating) to suppress neointimal proliferation. In one example the stent strength decreases from the deployed strength (after deployment immediately or within 1 hour) by a range from 25% to 75% over a period ranging from 1 month to 1 year after deployment. In another example, the stent strength decreases from the deployed configuration strength by a range from 50% to 90% over a period ranging from 1 month to 1 year after deployment. In yet another example, the stent strength decreases to zero after deployment in a period ranging from 1 month to 2 years.

In one example, a stent prosthesis comprising a non-degradable metal alloy such as L605 that is patterned from a tube or a wire, wherein the stent is configured to uncage after expansion in a body lumen (or under physiological conditions), said stent has sufficient strength in the expanded configuration to support a body lumen, and wherein the stent strength after expansion is substantially maintained. The stent optionally further comprises a degradable coating and/or a drug agent to suppress neointimal proliferation. In one example the stent strength decreases from the deployed strength (after deployment immediately or within 1 hour) by a range from 25% to 75% over a period ranging from 1 month to 1 year after deployment. In another example, the stent strength decreases to a level still sufficient to support a body lumen. In another example, the stent strength decreases to a level insufficient to support a body lumen in the absence of neointimal proliferation maintaining the uncaged stent substantially in place.

In another example, a stent prosthesis comprising a degradable metallic material, such as Tungsten or Tungsten alloy, wherein the stent prosthesis is configured to uncage (by incorporating one or more example or aspects of this invention such as one or more separation regions) after expansion in a body lumen and wherein the stent prosthesis in the expanded configuration has sufficient strength to support a body lumen, and wherein the metallic material degrades in a period ranging from 1 year to 5 years. The stent optionally further comprises a degradable coating and/or a drug agent to suppress neointimal proliferation. In an example where separation region provide discontinuities providing for uncaging of the stent, the discontinuities are usually configured to form before the degradation of the degradable metal or metal alloy.

In another example, the stent prosthesis as in any of the examples or aspects of this application, comprises circumferential structural elements patterned to expand from a crimped configuration to an expanded larger configuration, and wherein the stent in the expanded configuration has sufficient strength to support a body lumen and wherein the stent is configured to circumferentially uncage (forming discontinuities in at least some rings or all rings) after expansion under physiologic conditions. The stent in one example comprises a plurality of rings connected by one or more axial links, wherein at least one or more links are configured to separate at about the same time as the stent uncages circumferentially, or separate after the stent uncages circumferentially, or separate before the stent uncages, or a combination thereof, while at least one link remains intact between two adjacent rings, or while at least one link remains intact between all adjacent rings, or while at least some adjacent rings remain joined in one region.

In another example of any of the examples in this application, the stent prosthesis is configured to have one or more of separation regions, gaps, bridging elements, and/or discontinuities, etc., wherein the structural elements adjacent to said separation regions, gaps, bridging elements, and/or discontinuities, are configured (or allowed) to move in a circumferential direction, and/or configured (or allowed) to move in a longitudinal direction, and/or configured (or allowed) to move in a radial direction, and/or allow movement in a combination of the above.

In another example of any of the examples in this application, the stent prosthesis is configured to have one or more of separation regions, gaps, and/or discontinuities, etc., wherein the structural element opposite ends adjacent to said separation regions, gaps, and/or discontinuities, are configured to do one or more of the following: move freely in relationship to one another, move in a confined direction (or manner), move in an unconfined direction (or manner), move in a constrained fashion (or manner), move in an unconstrained fashion (or manner), wherein such movement is longitudinal, radial, circumferential, or combination thereof.

In another example of any of the examples in this application, the stent prosthesis in the expanded configuration comprising structural elements wherein at least some of the structural elements are configure to allow movement of the at least some circumferential elements in one or more directions (such as circumferential, longitudinal, radial, or combination thereof) wherein said movement uncages at least said structural elements, further expands said at least some structural elements, allow vaso-dilation of the at least some structural elements, allows the at least some structural elements to contract and/or expand, under physiologic conditions. In another example the stent prosthesis comprising structural elements (crowns and/or struts) wherein at least some of the structural elements are configured to have one or more of separation regions, joints, gaps, bridging elements, junctions, wherein the separation regions, gaps, bridging elements, joints, junctions, form discontinuities after expansion of the stent prosthesis, wherein said discontinuities uncages the at least said structural elements, further expands said at least some structural elements, allow vaso-dilation of the at least some structural elements, allows the at least some structural elements to contract and/or expand, under physiologic conditions. In another example the stent prosthesis comprising structural elements (crowns and/or struts) wherein at least some of the structural elements are configured to have one or more of separation regions, joints, junctions, gaps, bridging elements, wherein the one or more of separation regions, gaps, bridging elements, joints, junctions, allow the said structural elements to move, after expansion of the stent prosthesis, in one or more directions (such as radial, circumferential, and/or radial), and wherein said movement uncages the at least said structural elements, further expands said the at least some structural elements, allow vaso-dilation of the at least some structural elements, allows the at least some structural elements to contract and/or expand, under physiologic conditions.

In another example of any of the examples in this application, the stent prosthesis comprising structural elements (crowns and/or struts) wherein at least some of the structural elements are configured to uncage after expansion of the stent prosthesis from a crimped configuration to an expanded larger configuration, and wherein the uncaging of the stent comprises allowing the at least some structural elements to move in one or more directions (comprising one or more directions of circumferential, radial, or combination thereof), and wherein said movement allows the at least some structural elements (or the stent) to further expands, to exhibit vaso-dilation, to contract and/or expand, to have higher radial strain (be more compliant), under physiologic conditions.

In one example the stent prosthesis comprising structural elements formed from a metallic or polymeric material, and wherein the structural elements forms the stent pattern, and wherein the stent pattern comprises open cell type design, closed cell type design, helical stent type design, coil stent type design, braided stent type design, and/or combination thereof, and wherein at least one segment of the stent and/or the stent prosthesis is configured to uncage in accordance with this invention (comprising one or more of separation regions, gaps, reinforcement elements, junctions, joints, discontinuities, etc.,) in at least one segment (preferably the entire stent segment) in the expanded stent configuration, allowing the at least one segment and/or the stent to move in one or more directions comprising a circumferential direction, a radial direction, a longitudinal direction, and/or combination thereof, where such movement allows the at least one segment and/or the stent to have one or more of the following: increased radial compliance (radial strain), contraction and/or expansion from the expanded configuration, further expansion after recoil (if any), exhibiting or responding to a vaso-dilator, under physiologic conditions, wherein the movement is substantially higher after uncaging of the at least one stent segment and/or the stent.

In one example the stent prosthesis comprising structural elements wherein the structural elements comprises a plurality of rings wherein at least some rings comprises struts joined by crowns, and wherein at least some rings are connected to adjacent rings at one or more surface regions, and wherein the at least some rings have one or more separation regions, discontinuities, junctions, gaps, joints, bridging elements, reinforcement elements, and wherein the stent prosthesis being expandable from a crimped configuration to an expanded larger configuration, and wherein the at least some rings and/or the stent uncages after deployment to the expanded configuration, and wherein the at least some rings and/or the stent exhibit one or more of the following after uncaging compared to before uncaging in the expanded stent configuration: increased radial strain (radial compliance), increased vaso-dilatation or vaso-constriction, further expand to a second expanded configuration (after inward recoil if any from the deployed configuration), increased contraction and/or expansion after deployment, under physiological conditions.

In another example, the stent prosthesis as in any of the examples in this application, wherein the stent being expandable from a crimped configuration to an expanded larger configuration (first expanded configuration or initial expansion) and have sufficient strength in the expanded configuration sufficient to support a body lumen, and wherein the stent is configured in accordance with one or more aspects of this invention to uncage after expansion allowing for one or more of the following: increased radial strain, further expand to a second expanded configuration after inward recoil from first expanded configuration, increased radial contraction and/or expansion, increased radial or circumferential displacement, than before uncaging, under physiologic conditions.

In another example, the stent prosthesis as in any of the examples in this application, wherein the stent being expandable from a crimped configuration to an expanded larger configuration (first expanded configuration) and have sufficient strength in the expanded configuration sufficient to support a body lumen, and wherein the stent is configured to have (or to allow) movement of at least some of the stent structural elements and/or the stent in one or more directions (such as circumferential, radial, longitudinal, and/or combination thereof) after expansion allowing for (or resulting in) one or more of the following: higher radial strain, further expansion to a second expanded configuration after inward recoil from first expanded configuration, higher radial contraction and/or expansion, higher radial, or circumferential displacement, than before allowing said movement of the at least some structural elements and/or the stent, under physiologic conditions.

In another example, the stent prosthesis comprising structural elements, wherein said structural elements comprise a stent pattern, and wherein the stent being expandable from a crimped configuration to an expanded larger configuration and have sufficient strength to support a body lumen, and wherein the stent is configured to uncage and to have movement (in one or more directions) in the expanded configuration, larger than the movement in the caged configuration, under physiological conditions. In another example of this example, the stent strength after expansion is substantially maintained until at least some of the stent structural elements are covered with biological tissue (or material, or cells). In another example of this example, the stent strength after expansion is substantially maintained until at least substantially all of the stent structural elements are covered with biological material (or tissue, or cells). In another example of this example, the stent strength after expansion is substantially maintained until at least some of the stent structural elements are covered with biological material (or tissue, or cells), and wherein the stent is configured to uncage in some regions along the stent as described in various aspects or examples in this application, and wherein the biological material substantially holds the uncaged patterned stent in place.

In another example, the stent prosthesis as in any of the examples of this application, wherein the stent is configured to have a movement in one or more directions in at least one segment of the stent prosthesis, wherein the movement comprises displacement in said one or more directions, under physiologic conditions. In another example of this example, the one or more direction comprises circumferential, radial, and/or longitudinal, combination thereof, and/or other directions, or other directions patterns. In another example of this example, the stent prosthesis comprises uncaging of the at least one segment allowing said movement (or displacement), and wherein the movement (or displacement) in one or more direction is larger than said movement (or displacement) before uncaging, under physiologic conditions.

In another example, the stent prosthesis can have a variety of shapes, forms, and structures. For example, structural elements can comprise struts or screw like elements, crowns or knots or bolts type joining struts and/or screw type elements together. The examples of this application apply to the various types of stents, prosthesis, and other implants such as vascular or non vascular stents, stents containing valves, and/or other prosthesis or implants, where one or more of the following is desired: uncaging of the stented segment lumen or part of the stented segment lumen, increased radial compliance from an initial compliance, high initial strength that decreases after implantation (or over time), provide for one or more stent segments (or the stented segment) to further enlarge after implantation, provide for having one or more stent segments (or the stent) having an initial configuration (shape, and/or diameter) substantially contouring to a vessel, lumen, or annulus, upon expansion, to continue to contour (or to continue to substantially contour) to the vessel, lumen, or annulus, after implantation, in response to a change in the vessel, lumen, or annulus configuration, under physiologic conditions, and/or a desired displacement after implantation is required in one or more diameter dimensions of one or more stent segment (or the stent).

In another example, the various examples and aspects of this invention applies to not only expandable prosthesis, but applies to a variety of implants such as non-expandable implants where they are attached or placed in a body lumen (or placed adjacent to a body lumen or annulus, or placed in tissue) and wherein such implants are configured to provide uncaging, and/or provide desired displacement (in diameter for example) after implantation in at least one segment or region of the implant.

In one example, an implant having length, width, and thickness, is attached (or held in place) adjacent to a body lumen or a body annulus and wherein the implant is configured to be coupled with (or attached) to an expandable prosthesis, and wherein at least one of the implant and the stent prosthesis are configured to have one or more of separation regions, junctions, joints, hinges, bridging elements, gaps, on at least one segment or region of the implant and/or stent allowing the at least one segment or region of implant and/or stent to have displacement (change in diameter), in one or more direction or one or more axis (x, y, or z), that is larger than an adjacent segment (or region) of the said implant or stent prosthesis.

In yet another example or aspect of the present invention, a stent prosthesis comprises a scaffold having circumferential rings patterned from a polymeric or metallic material. The scaffold is configured to expand from a crimped configuration to an expanded configuration, and at least some of the circumferential rings have at least one circumferential displacement region which allows the circumferential ring to circumferentially expand and contract in a physiologic luminal environment, such as a blood vessel, and more particularly an arterial blood vessel. For example, the displacement regions may allow the one or more circumferential rings to circumferentially expand and contract in response to a patient's systolic/diastolic rhythm in an arterial lumen.

The displacement regions in one example will allow such circumferential expansion and contraction after implantation of the stent prosthesis in the blood vessel or other body lumen. While the displacement region could be any of the separation regions, open gap, or key-and-lock structures, or others, described previously, they will frequently be regions which are joined or filled by a material (including polymeric material) such as an elastomeric cushion material, such as an elastomeric polymer. In such cases, the elastomeric cushion material will frequently join or connect adjacent regions on the circumferential rings, thus acting as an elastic restraint which permits relative movement of adjacent segments and/or regions to accommodate pulsing of the blood vessel or other body lumen, or other physiologic condition. The amount or degree of relative movement between immediately adjacent stent regions may vary widely, often being in the range from 0.01 mm to 1 mm, often from 0.03 mm to 0.5 mm, and frequently from 0.05 mm to 0.5 mm. The amount or degree of stent circumferential elasticity may also vary widely, often being in the range from 0.05 mm to 0.2 mm, often from 0.07 mm to 0.15 mm, and frequently from 0.07 mm to 0.012 mm.

The scaffolds having circumferential displacement regions in accordance with the principles of the present invention in one example will typically include a plurality of circumferential rings coupled together along an axis. In such instances, at least some of the circumferential rings will often comprise struts joined by crowns, where at least some of the struts or crowns will have circumferential displacement regions that allow the circumferential ring(s) to circumferentially expand and contract in response to the systolic/diastolic rhythm in an arterial lumen, and/or other physiologic conditions. Such regions may comprise discontinuities such as gaps, channels, breaks, junctions, bridging elements, and the like, between adjacent or opposed segments of a strut or crown. In specific examples, the gaps may be defined by opposed segments of a strut and comprise a female coupling element, typically having a pair of opposed constraining walls attached at one end of the strut segment, and a male coupling element disposed on an opposed strut segment. By locating the male strut segment between the pair of opposed constraining walls on the adjacent strut segment, the male element and female element will be free to at least circumferentially move relative to each other to provide the desired circumferential expansion and contraction.

As described previously in other examples, the gaps may be left open or in other instances may be filled with an elastomeric cushion material which dampens the circumferential movement of the male element between the opposed walls of the circumferential rings. Depending on the size of the gap, the male element will be able to move axially, laterally, and/or in elevation relative to the adjacent strut segment. Such ability to move with multiple ° of freedom enhances the elasticity of the stent in response to body lumen pulsation. In other examples, the gap between two opposed segments of a strut may comprise a coupling element having a channel that includes a pair of opposed constraining walls and a bottom surface. A male coupling element opposed on an adjacent strut segment will be located within the channel defined by the opposed constraining walls and bottom surface, allowing the male element to move at least circumferentially between the opposed walls and axially within the channel. As with previous examples or embodiments, the channel may be left open or may be filled with an elastic material or other material (including polymeric).

In yet another example of a circumferential displacement region in accordance with the principles of the present invention, gaps may be defined between opposed segments of the strut and further comprise a coupling element there between. For example, a pin may be positioned to span a gap between a pair of opposed walls of a female coupling element and to further pass through a pivot hole and a male coupling element there between, allowing for movement, and/or for expansion and substantially maintaining said expansion, and/or for expansion and contraction. In still another example or aspect of the present invention, a method for fabricating a stent prosthesis comprises patterning two or more panels or sheets of stent material to include a plurality of partial ring structures. Each partial ring structure will be formed to terminate in two or more attachment ends so that the two or more panel structures, which are typically initially flat, may be formed into a cylindrical assembly with each attachment and on one panel being joined to an adjacent attachment structure on another panel. After properly positioning the adjacent panel structures, the attachment ends will be joined to complete the circumferential stent structure.

The partial ring structures in one example will typically comprise struts joined by crowns and the attachment ends will often be patterned as male and female elements configured to mate with a gap there between, where the gap allows the circumferential scaffold to circumferentially expand and/or contract in the physiologic luminal environment. Optionally, the gaps may be left open but more often will be filled with a material, preferably a polymeric material, more preferably with an elastomeric material to provide an elastic attachment between the attachment ends. The material can be degradable or non-degradable.

Forming the two or more panel structures into a cylindrical assembly in one example typically comprises bending the panels over a mandrel, usually a cylindrical mandrel. After the two or more panels are formed into their desired shapes, the adjacent end structures on each panel may be joined, typically by applying an elastomeric material between or over the adjacent end structures.

In still another example or aspect of the present invention, a stent prosthesis comprises a scaffold having circumferential rings patterned from a polymeric or metallic material (including non-degradable and degradable). The scaffold is configured to expand from a crimped configuration to an expanded configuration, and at least some of the circumferential rings are joined by axial links where at least some of the axial links are joined to an adjacent circumferential ring by a circumferential displacement region. The circumferential displacement region(s) allow the circumferential ring to circumferentially expand and/or contract in a physiologic environment, while maintaining the axial link(s) intact (connecting two adjacent rings) in a preferred example.

In certain examples, at least one displacement region wherein the displacement is in at least one direction, such as circumferential displacement region allows the circumferential ring to circumferentially expand and/or contract in response to a systolic/diastolic rhythm in an arterial lumen, or other physiologic conditions. Usually, the scaffold includes a plurality of circumferential rings coupled together along an axis by axial links. In such instances, at least some of the circumferential rings typically comprise struts joined by crowns, and a strut on the adjacent circumferential ring terminates in the circumferential displacement region which is joined to the axial link.

As with previous examples, the displacement regions wherein the displacement is in at least one direction, such as circumferential displacement regions may comprise discontinuities which allow the circumferential ring(s) to at least circumferentially expand and/or contract in response to a systolic/diastolic rhythm in an arterial lumen, typically comprising gaps between opposed segments of a strut or a crown. More typically, the circumferential displacement regions comprise a male segment and a female coupling element. Where the male segment will typically be at a terminal end of a strut and the female coupling element is on the axial link. Conversely, the female segment may be at a terminal end of a strut and the male coupling element be located on an axial link.

In one example of any of the examples of this application, the implant comprises a stent, a substantially tubular stent in the crimped configuration, a substantially tubular stent in the expanded (deployed) configuration, a tubular stent in the expanded and/or crimped configuration, a cylindrical or substantially cylindrical stent in the crimped and/or expanded configuration, a non-cylindrical stent in the crimped and/or expanded configuration; wherein the stent is expandable from a crimped configuration to an expanded larger configuration and has sufficient strength to support a body lumen (including annulus).

In another example of any of the examples of this application, the implant is a fixation device to anchor to a body lumen, adjacent to a body lumen (including annulus), or anchor to an anatomy; where the fixation device connects to another implant (such as stent, a valve (native or synthetic).

In another example of any of the examples of this application, the implant (prosthesis) is an arterial stent, a stent for valve repair or replacement, a fixation device for valve repair or replacement, and/or a luminal stent.

In another example of any of the examples of this application, the implant comprises a stent wherein the stent is expandable from a crimped configuration to an expanded larger configuration and has sufficient initial strength in the expanded configuration to support a body lumen (or annulus), and has one or more of the following: an initial shape, an initial displacement, an initial radial strain, an initial vaso-motion reactivity; and wherein the stent prosthesis after expansion will have one or more of the following: increased radial strain, increased radial strain and decreased strength from the initial strength, decreased strength below the initial strength, increased displacement in at least one direction wherein the initial displacement in said direction is substantially small, having displacement in at least one direction where the initial displacement is substantially zero in said at least one direction, and/or changes the shape of the stent from the initial shape after expansion. The stent in the above example is configured to have one or more of the following: Uncaging, having variable compliance (radial strain) after expansion, having controlled compliance (radial strain) after expansion that is different from the radial compliance upon expansion, having adaptive to lumen or vessel compliance (radial strain) after expansion, having variable displacement, having controlled displacement different from initial expanded configuration, having adaptive to lumen or vessel displacement after expansion or deployment, having variable movement, having controlled movement, having adaptive to lumen or vessel movement after expansion, and/or allowing vaso-reactivity after expansion. The stent in this example includes stents that are degradable and stents that are non-degradable stents, metal stents, polymer stents, or combination. The implants include but are not limited to stents, tubular structures, non-tubular structures, and other implants having a structure in the expanded and/or crimped configuration. In another example the stent prosthesis has a substantially cylindrical shape upon deployment (expansion) from a crimped configuration to an expanded configuration, wherein the stent shape changes after expansion to one of: non cylindrical, substantially non cylindrical, oblong, oval, or other shape; to accommodate changes in a body lumen (including annulus).

In another example of any of the examples of this application, the stent prosthesis after expansion has an initial shape (or shape configuration) that substantially fits or suited to a body lumen (including annulus shape), and wherein the said shape (or shape configuration) of the stent after expansion changes to accommodate a change in the body lumen (including annulus shape changes) shape (or shape configuration); preventing or minimizing said fit mismatch, or having improved fit compared to an initial fit before said change of lumen shape or configuration after initial expansion of the stent. In another example, the change in shape (or shape configuration) after expansion is a dynamically changing shape (or shape configuration) which responds to the forces exerted by the lumen, while substantially maintaining the expanded configuration of the stent.

In one example of any of the examples of this application, the implant is a fixation device having initial shape, displacement, and fixation strength, and wherein the implant after fixation adjacent to a body lumen or within a body lumen has one or more of the following: larger displacement in at least one direction, changes the shape in at least one dimension, decreases strength in at least part of the implant, or other.

In another example, the stent prosthesis configured to have separation region or joints further expand to a second larger configuration under physiologic environment, wherein the stent would not further expand if not exposed to physiologic conditions. In another example, the stent prosthesis as in any of the examples of this application further expands to a second larger configuration (after initial inward recoil if any) only under physiologic conditions.

In another example, the stent prosthesis exhibit vaso-reactivity after deployment, and prior to formation of discontinuities, and/or exhibit vaso-reactivity over substantially the entire stented segment.

In one example of any of the examples of this application, the stent comprises one or more separation regions (or discontinuities), wherein the separation regions (or discontinuities) comprises one or more joints, wherein the joints allows movement or displacement in at least one direction or dimension after expansion, and wherein the joints do not come apart in physiological conditions.

In one example of any of the examples of this application, the stent comprises one or more separation regions (or discontinuities), wherein the separation regions (or discontinuities) comprises one or more joints, wherein the joints allow movement or displacement in at least one direction or dimension after expansion, and wherein the joints come apart after expansion in physiological conditions.

In one example of any of the examples of this application, wherein the stent comprises a plurality of rings and wherein at least some rings have one or more separation regions (or joints), configured to form discontinuities (or displacement) at substantially the same, or different time periods.

In one example of any of the examples of this application, the implant (including stents) has one or more separation regions wherein the separation regions comprise joints, wherein the joints allow displacement in at least one direction after expansion. Example of joints include but are not limited to: pivot type joint, hinge type joint, ratchet type joints, saddle type joint, ball-and-socket type joint, condyloid type joint, and/or plant type joint. In one example the joint do not come apart. In another example the joints come apart, after expansion. In another example, the implant has an initial displacement upon expansion that is less than the displacement magnitude after expansion.

In one example, the separation region comprises a joint. In another example, the separation region is a joint.

In one example of any of the examples of this application, the implant (including stent) has an initial shape upon expansion, and one or more separation regions wherein the separation regions comprise joints, wherein the joints allow change in said shape after expansion. Example of joints include but are not limited to: pivot type joint, hinge type joint, ratchet type joint, saddle type joint, ball-and-socket type joint, condyloid type joint, and plant type joint. In one example the joint do not come apart. In another example the joints come apart, after expansion.

In one example of any of the examples of this application, the stent prosthesis comprises a plurality of circumferential rings, wherein at least one ring has one or more separation regions (or joints) forming discontinuities (or displacement(s)) after expansion in physiologic conditions.

In another example of any of the examples of this application, the physiologic conditions comprise one or more of: body lumen (including annulus), physiologic pressure, heart beat, muscle contraction, temperature of about 37 C, temperature of about 37 C where the implant is in a water bath at said temperature, a sleeve mimicking a body lumen (or annulus), and/or a test fixture mimicking physiologic conditions.

In one example of any of the examples in this application, the stent prosthesis comprises at least one ring, wherein the ring comprises struts joined by crown, and wherein the rings comprise one or more separation regions, or one or more joints along the circumferential path of said ring, configured to form discontinuities, and/or displacement, and/or change in shape configuration. In one example, the one or more separation regions or joints are located on struts and/or crown regions, allowing at least the ring to uncage, to have displacement, to further expand and/or contract, and/or change shape configuration, after expansion of the stent prosthesis in physiologic environment.

In one example of any of the examples of this application, wherein the stent prosthesis comprise one or more separation regions (or discontinuities) and wherein said separation region or discontinuities after expansion has one or more of the following: displacement in one or more directions, increased displacement in one or more directions, change in shape configuration from initial expanded shape configuration, change in radial strain from initial expanded radial strain, increased radial strain from initial expanded radial strain, decreased strength, decreased strength from initial expanded strength, increased radial strain while decreased strength from initial radial strain and initial strength.

In one example, the stent prosthesis or implant comprises one or more separation regions wherein the separation regions comprise linkages. Linkages allow for displacement (movement) in the same direction (Push Pull Linkages) or in opposite directions (Reverse Motion Linkages). Linkages may be connected in a variety of ways including pins, screws, split pins, polymer fasteners, pop rivets, clevis pins, and/or nut and bolts, etc. The linkages may change the magnitude or direction of the displacement, increase displacement magnitude, reverse displacement direction or magnitude, or combination thereof.

In one example, the stent prosthesis or implant comprises one or more joints wherein the joints are connected in a variety of ways including pins, screws, split pins, polymer fasteners, pop rivets, clevis pins, and/or nut and bolts, etc.

In one example of any of the examples of this application, the prosthesis is an implant comprising one of: stent, implant having a structure, implant having a structure, implant having a structure and a fixation means, or other.

In one example of any of the examples of this application, the stent prosthesis comprising a plurality of adjacent rings, wherein substantially all rings comprise one or more separation regions, discontinuities, or joints, and wherein substantially all rings are capable of one or more of the following: similar radial strain (or compliance) magnitude or change, vaso-motion reactivity of substantially all rings that is substantially similar, uncaging of substantially all rings, further expansion to a larger configuration of substantially all rings, expansion and/or contraction of substantially all rings, displacement in at least one direction (or dimension), change in shape configuration, after expansion from a crimped configuration to an expanded larger configuration under physiological conditions. In another example, the substantially all rings have similar one or more of: radial strain initially and subsequently, further expansion, radial contraction and/or expansion, similar uncaging, similar displacement, similar change in shape configuration, in the expanded configuration under physiological conditions. In another example, some rings have different one or more of: radial strain after expansion, displacement magnitude, shape configuration, contraction and/or expansion, vaso-reactivity, in the expanded configuration under physiologic conditions.

In another example, the stent prosthesis is configured to uncage, wherein uncaging comprises one or more of: having variable compliance (radial strain) after expansion, having controlled compliance (radial strain) after expansion that is different from the radial compliance upon expansion, having adaptive to lumen or vessel compliance (radial strain) after expansion, having variable displacement, having controlled displacement different from initial expanded configuration, having adaptive to lumen or vessel displacement after expansion or deployment, having variable movement, having controlled movement, having adaptive to lumen or vessel movement after expansion, and/or allowing vaso-reactivity after expansion, after said stent expands from a crimped configuration to an expanded configuration under physiologic conditions.

In another example of any of the examples in this application, at least some circumferential structural elements (such as rings) or the implant or stent prosthesis after expansion has a composite radial strain (or compliance) ranging from 1% to 20%, preferably ranging between 1% and 15%, more preferably ranging from 1.5% to 10%, most preferably ranging from 2% to 7%. In another example the radial strain magnitude ranges from 0.07 mm to 3 mm, preferably ranging from 0.1 mm to 2 mm, more preferably ranging from 0.1 mm to 1 mm, and most preferably ranging from 0.1 mm to 0.5 mm. In another example the vaso-reactivity magnitude ranges from 0.07 mm to 3 mm, preferably ranging from 0.1 mm to 2 mm, more preferably ranging from 0.1 mm to 1 mm, and most preferably ranging from 0.1 mm to 0.5 mm.

One skilled in the art would appreciate the various examples and aspects described in this application can be employed to facilitate movement in radial, and/or circumferential, or other direction, or combination thereof.

As with prior examples or embodiments, the male element will typically be free to move circumferentially between opposed walls of the female coupling member to allow circumferential expansion (and/or radial) and/or contraction of the stent prosthesis. The male segment and the female coupling element may be separated by a gap, and the gaps may be left open or conversely may be filled with a material such as an elastomeric cushion material which dampens the circumferential movement of the male element between opposed walls of the circumferential ring.

In a preferred example, a stent prosthesis comprises one or more structural elements configured to expand from a crimped configuration to an expanded configuration, wherein the one or more structural elements have one or more continuous circumferential path around the stent, and wherein the structural elements have one or more separation regions bisecting said structural elements of said continuous circumferential path. In a particular example, the one or more separation regions bisecting the one or more structural elements are formed before expansion of the stent, and wherein the bisected structural elements are held together during expansion of the stent, and wherein the bisected structural elements are configured to separate after expansion of the stent forming one or more discontinuous circumferential paths around the stent. The one or more separation regions in one example are formed during patterning of the stent. The one or more separation regions in another example are formed after patterning of the stent. The one or more structural elements in one example comprise one or more rings (turns). The scaffold comprises one or more structural elements. The one or more structural elements in another example comprise one or more rings (or turns) forming a helical stent. The one or more structural elements in another example comprise a plurality of struts and crowns. The one or more structural elements in another example comprise one or more rings (turns) wherein the one or more rings (turns) comprise a plurality of struts and crowns. The one or more structural elements in yet another example comprise one or more rings wherein the one or more rings are composed of a plurality of struts and crowns. The one or more structural elements in another example comprise two or more rings (turns) wherein adjacent rings are axially joined during patterning or after patterning. The one or more structural elements in another example comprises two or more rings (turns) wherein at least two adjacent rings are joined by one or more links during patterning or after patterning, and wherein at least one link joining said at least two adjacent rings remains intact after separation of all bisected structural elements on said at least two adjacent rings. The one or more structural elements in another example comprises two or more rings (turns) wherein at least two adjacent rings are joined by two or more links during patterning or after patterning, and wherein at least two links joining said at least two adjacent rings remains intact after separation of all bisected structural elements on said at least two adjacent rings. In one particular example, the one or more structural elements in comprise two or more adjacent rings (turns) wherein the two or more adjacent rings are axially joined by fusing, soldering, or linking structural elements on said adjacent rings, wherein at least some adjacent rings remain joined after all bisected structural elements on said at least some rings separate at the formed discontinuities. In one particular example, the one or more separation regions comprise one or more of a junction, a gap, and an interface. In another particular example, the structural elements adjacent to the one or more separation regions form one or more of a junction, a gap, and an interface. In yet another example, the bisected structural elements adjacent to the one or more separation regions are held together prior to expansion of the stent by one or more of polymeric material, adhesive, solder, material different from the stent material, mechanical lock, or other means. In a preferred example, the polymeric material is a degradable material. In one particular example, the stent has at least one ring which is configured to have one or more separation regions bisecting at least one structural element on said ring, wherein the bisected structural element of the at least one ring remains separate prior to expansion of the stent. The stent prosthesis in this example may be formed from a non-degradable material such as metal or metal alloy material, but can also be formed from polymeric material, or other. In another example, the stent prosthesis may be formed from a non-degradable metallic or metallic alloy material, is patterned into a stent capable of expansion from a crimped configuration, and wherein the stent comprises one or more rings (turns) with adjacent rings (turns) are axially joined by fusing, soldering, or forming a link, between said two adjacent rings from the same non-degradable stent material, or a non-degradable solder material.

In a preferred example, the stent prosthesis being expandable from a crimped configuration to an expanded configuration and comprise one or more structural elements forming one or more continuous circumferential paths around the stent. The one or more structural elements comprise one or more circumferential rings (turns), wherein at least one ring have one or more separation regions bisecting said ring into one or more discontinuous circumferential paths around the stent, and wherein the bisected ring is held intact by a material comprising one or more of adhesive, polymer material, and solder, and wherein the bisected ring is configured to separate after expansion of the stent in a body lumen and wherein the bisected ring does not separate after expansion of the stent in air. The stent prosthesis in this example may be formed from a non-degradable material such as metal or metal alloy material.

In a preferred example, a stent prosthesis comprises one or more structural elements configured to expand from a crimped configuration to an expanded configuration, wherein the one or more structural elements have one or more continuous circumferential path around the stent, and wherein the structural elements have one or more separation regions bisecting said structural elements of said continuous circumferential path. In a particular example, the one or more separation regions bisecting the one or more structural elements are formed before expansion of the stent, and wherein at least some of the bisected structural elements are held together before crimping of the stent, and wherein the at least some bisected structural elements are configured to separate after expansion forming one or more discontinuous circumferential paths around the stent. In one particular example, it is advantageous that one or more segments of the stent have improved compliance upon expansion of the stent. In such example, although most discontinuities form after expansion, at least one of the bisected structural elements is configured to separate as formed or after forming and before expansion of the stent to the expanded configuration. Typically, in this case the one or more stent segments comprise one or more rings along the length of the stent such as the proximal end ring and/or the distal end ring, and are configured to have one or more bisected structural elements separate prior to expansion of the stent. The stent prosthesis in this example maybe formed from a non-degradable material such as metal or metal alloy material.

In a preferred example, the stent prosthesis is expandable from a crimped configuration to an expanded configuration and comprise one or more structural elements forming one or more continuous circumferential paths around the stent and wherein the one or more structural elements comprise one or more circumferential rings (turns), wherein at least one ring have one or more separation regions bisecting said ring into one or more discontinuous circumferential paths around the stent, and wherein the bisected ring is held intact and configured to separate after expansion of the stent, and wherein the stent prosthesis in the expanded configuration under physiologic conditions has an initial crush strength and wherein said initial crush strength decreases afterwards, and wherein the stent prosthesis remain axially connected along a portion of the stent length, and wherein at least one crown in the bisected ring does not have any separation regions. The stent prosthesis in this example maybe formed from a non-degradable material such as metal or metal alloy material.

In a preferred example, the stent prosthesis is expandable from a crimped configuration to an expanded configuration and comprise one or more structural elements forming one or more continuous circumferential paths around the stent and wherein the one or more structural elements comprise one or more circumferential rings (turns), wherein at least one ring has one or more separation regions bisecting said ring, and wherein the bisected ring is held intact and configured to separate after expansion of the stent, and wherein the stent prosthesis in the expanded configuration under physiologic conditions has an initial crush strength while the ring is held intact and wherein said initial crush strength decreases after the ring separates, and wherein the stent prosthesis remain axially connected along at least a portion of the stent length, and wherein at least one crown in the bisected ring does not have any separation regions. In a preferred particular example, the stent is balloon expanded and the expanded configuration is the configuration of the stent after inward recoil of the stent after balloon deflation. The stent prosthesis in this example may be formed from a non-degradable material such as metal or metal alloy material.

In a preferred example, the stent is expandable from a crimped configuration to an expanded configuration and comprises one or more structural elements forming one or more continuous circumferential paths around the stent and wherein the one or more structural elements comprise one or more circumferential rings (turns), wherein at least one ring has one or more separation regions bisecting said ring, and wherein the bisected ring is held intact and configured to separate after expansion of the stent into one or more discontinuous circumferential paths around the stent, and wherein the bisected ring is held intact and configured to separate after expansion of the stent, and wherein the stent prosthesis in the expanded configuration under physiologic conditions has an initial compliance and wherein said initial compliance increases after said ring separates, and wherein the stent prosthesis remain axially connected along a portion of the stent length, and wherein at least one crown in the bisected ring does not have any separation regions. The stent prosthesis in this example maybe formed from a non-degradable material such as metal or metal alloy material.

In a preferred example, the stent prosthesis is expandable from a crimped configuration to an expanded configuration and comprise one or more structural elements forming one or more continuous circumferential paths around the stent and wherein the one or more structural elements comprise one or more circumferential rings (turns), wherein at least one ring has one or more separation regions bisecting said ring, and wherein the bisected ring is held intact and configured to separate after expansion of the stent in a body vessel into one or more discontinuous circumferential paths around the stent, and wherein the stent prosthesis in the expanded configuration under physiologic conditions has an initial stented segment compliance and wherein said initial compliance increases to a second stented segment compliance after said ring separates, said second compliance being larger than initial compliance, and wherein the second compliance remains smaller than a compliance of an unstented vessel segment adjacent to the expanded stent under said physiologic conditions. In a preferred example, the initial compliance ranges between 0.1% and 0.5%, the second compliance ranges between 1% and 3%, and the unstented adjacent segment compliance ranges between 3.5% and 5%, under physiologic conditions. The stent prosthesis in a particular preferred example remains axially connected via one or more axial links for at least a portion of the stent length. The stent prosthesis in this example maybe formed from a non-degradable material such as metal or metal alloy material.

In another example, the stent prosthesis is formed in the expanded configuration and comprises one or more structural elements forming a continuous circumferential path around the stent and wherein the one or more structural elements comprise one or more circumferential rings (turns), wherein at least one ring have one or more separation regions bisecting said ring, and wherein the bisected ring is held intact by means comprising one or more of adhesive, polymer material, and solder, and wherein the bisected ring is configured to separate in a body lumen into one or more discontinuous circumferential paths around the stent. The stent prosthesis in this example maybe formed from a non-degradable material such as metal or metal alloy material.

In a preferred example, the stent prosthesis is expandable from a crimped configuration to an expanded configuration and comprise one or more structural elements forming one or more continuous circumferential paths around the stent and wherein the one or more structural elements comprise one or more circumferential rings (turns), wherein at least one ring has one or more discontinuities bisecting said ring into one or more discontinuous circumferential paths around the stent, and wherein the bisected ring is held intact by material comprising one or more non-degradable polymeric material containing said bisected ring region, and wherein the bisected ring is configured to remain contained by said non-degradable polymeric material after expansion of the stent in a physiologic environment. The stent prosthesis in this example maybe formed from a non-degradable material such as metal or metal alloy material.

In a preferred example, a stent prosthesis is expandable from a crimped configuration to an expanded larger configuration, and wherein the stent has one or more circumferential structural elements, and wherein the one or more structural elements form one or more continuous circumferential path around the stent, and wherein said one or more structural elements have one or more separation regions, wherein the one or more separation regions are configured to separate circumferentially the one or more structural elements (or the stent) after expansion of the stent in physiologic environment. In a preferred example, the one or more separation regions comprise one or more of: a break formed during patterning or after patterning of the stent, formed in the one or more structural elements bisecting each of said elements into two or more sections, a junction formed in the one or more structural elements having the shape of a key and lock, butt joint, overlapping structural elements regions, overlapping struts region, overlapping crown regions, or other junction type. The bisected structural elements adjacent to the break or gap are held together by materials comprising polymers, adhesive, or a solder and upon or after expansion in a physiologic environment the separation regions separate to provide the gap, complete break, or separation in the ring breaking the ring so there is no longer a continuous circumferential path.

In another example, a stent prosthesis being expandable from a crimped configuration to an expanded configuration, wherein the stent is patterned from a non-degradable material, and wherein the stent comprises one or more circumferential structural elements forming one or more continuous circumferential path around the stent, wherein the structural elements comprises one or more rings (turns), and wherein at least one ring has one or more separation regions bisecting said ring, and wherein the ring is held intact and configured to separate after expansion of the stent in a physiologic environment. In one example, the stent comprises two or more rings wherein at least some rings comprise a plurality of struts joined by crowns, and wherein at least one crown on one ring is joined to another crown on an adjacent ring, and wherein at least one separation region bisects both said joined crowns on said adjacent rings. In another example, the stent comprises two or more rings wherein at least some rings comprise a plurality of struts joined by crowns, and wherein at least one crown on one ring is joined to another crown on an adjacent ring by a link, and wherein at least one separation region bisects the said link and both said crowns on said adjacent rings. In another example, the stent comprises two or more rings wherein at least some rings comprise a plurality of struts joined by crowns, and wherein at least one crown on one ring is joined to a strut on an adjacent ring, and wherein at least one separation region bisects both said joined crown and strut on said adjacent rings. In another example, the stent comprises two or more rings wherein at least some rings comprise a plurality of struts joined by crowns, and wherein at least one crown on one ring is joined to a strut on an adjacent ring by a link, and wherein at least one separation region bisects the said link and both said crown and strut on said adjacent rings. In another example, the stent comprises two or more rings wherein at least some rings comprise a plurality of struts joined by crowns, and wherein at least one strut on one ring is joined to a another strut on an adjacent ring, and wherein at least one separation region bisects both said joined struts on said adjacent rings. In another example, the stent comprises two or more rings wherein at least some rings comprise a plurality of struts joined by crowns, and wherein at least one strut on one ring is joined to another strut on an adjacent ring by a link, and wherein at least one separation region bisects the said link and both said struts on said adjacent rings.

In one example, the stent prosthesis is patterned from a non-degradable material, wherein patterning comprises one or more of forming one or more structural elements being expandable from a crimped configuration to an expanded configuration, forming one or more structural elements by laser, forming one or more structural elements by chemical etching, winding one or more wires forming a stent being expandable from a crimped configuration to an expanded configuration, winding one or more wires forming a helical stent being expandable from a crimped configuration to an expanded configuration forming a tubular stent, forming one or more structural elements from a flat sheet which is rolled to form a stent wherein the stent is expandable from a crimped configuration to an expanded configuration, forming one or more rings being expandable from a crimped configuration to an expanded configuration, wherein the one or more rings comprise a plurality of struts joined by crowns, forming an open cell stent pattern, forming a closed cell stent pattern, or forming a hybrid open and closed cell pattern.

In one example, the stent prosthesis is formed from a non-degradable material such as cobalt chrome, and patterned into a structure being expandable from a crimped configuration to an expanded configuration, and wherein the structure comprises one or more structural elements forming one or more continuous circumferential path around the stent, and wherein one or more separation regions are formed to bisect the one or more circumferential continuous paths, and wherein at least some of the bisected structural element are held together after forming of the separation regions and before expansion of the stent by means comprising polymeric material, adhesives, and solder, and wherein the said structural elements are configured to separate after expansion of the stent under physiologic condition. The stent in a preferred example further comprises a coating wherein the coating comprise one or more of degradable polymer, and non-degradable polymer, and wherein the coating further comprises at least one drug.

In another example, the stent prosthesis comprises one or more structural elements forming one or more continuous circumferential paths around the stent, wherein the structural elements comprise one or more rings, and wherein at least some of the rings comprise one or more of crowns, struts, circumferential connectors, or other elements on the continuous circumferential path, and wherein at least one or more separation regions are formed on the one or more continuous circumferential paths separating the ring circumferentially, and wherein the stent comprises one or more of open cell pattern, closed cell pattern, open and closed cell patterns, helical backbone stent, bent wire, patterned tube, patterned sheet, or other, and wherein at least some of the bisected circumferential rings are held intact and configured to separate after expansion of the stent in a physiologic environment. In one particular example, at least one ring is left circumferentially separated before expansion of the stent in a physiologic environment.

In another example, the stent prosthesis comprises a tubular body which has been patterned from a non-degradable material, and wherein the stent pattern comprises one or more circumferential rings, and wherein the one or more rings are expandable from a crimped configuration to an expanded configuration, and wherein at least some of the rings are formed with one or more discontinuities circumferentially bisecting the at least some rings into separate sections, and wherein the separated sections are held together prior to expansion of the stent by means comprising adhesive, polymer material, material different from the stent material, and solder, and wherein the sections are configured to separate after degradation (deterioration) of said means in a physiologic environment, and wherein the stent is formed to have adjacent rings axially connected and wherein at least some axial connections on at least some adjacent rings remain intact after expansion of the stent and circumferential separation of the rings sections, and wherein the stent comprises one or more of open cell pattern, closed cell pattern, open and closed cell patterns, helical backbone stent, bent wire, patterned tube, patterned sheet, or other, and wherein at least some of the bisected circumferential rings are held intact and configured to separate after expansion of the stent in a physiologic environment. In one example, at least one bisected ring is left separated prior to expansion of the stent in physiologic environment.

In one example, The stent material is pre-formed, treated, annealed, cycle fatigued, and/or configured to have an initial strength after expansion of the stent and wherein the stent exhibit one or more of the following after expansion of the stent under physiologic conditions: softening of the material, weakening of the material, becoming less stiff, has reduced crush resistance, has reduced strength, and/or has no strength, has an initial strength sufficient to support a body lumen wherein the strength decreases over time, has an initial strength sufficient to support a body lumen wherein the strength remains substantially the same over time, and/or has an initial compliance upon expansion and wherein the compliance increases after expansion, and/or has an initial compliance immediately after expansion (or within 24 hours after expansion) and wherein the compliance increases after expansion (or within 6 months after expansion or within one year after expansion or within 18 months after expansion or within two years after expansion), under one or more of the following conditions: physiologic condition, in water at 37 C, cyclic physiologic fatiguing (pulsation), and/or physiologic temperature, in a period ranging from 1 month to 5 years, preferably ranging from 3 months to 3 years, more preferably ranging from 3 months to 2 years, after expansion and pressure differential ranging from 50 mmHg to 200 mmHg. In one example, the stent comprises a material having an initial Young's Modulus (defined as the ratio between stress and strain in elastic deformation) ranging from ranging from 175 GPa to 350 GPa after expansion of the stent under physiologic conditions, and wherein the Young's Modulus of the stent material deceases to a range from 25 GPa to 150 GPa after expansion of the stent in a period ranging from 2 months to 2 years, preferably a period ranging from 6 months to 1 year. In another example, a stent material has an initial Young's Modulus after expansion of the stent under physiologic conditions and the stent material Young's Modulus decreases thereafter. The stent having an initial Young Modulus may also have one or more separation regions bisecting on or more circumferential rings which form discontinuities upon or after expansion, further increasing the compliance of the stent.

Example of material having an initial Young's Modulus that decreases under physiologic conditions comprise one or more of the following: Ti6Al4V, Ti5Al2.5Sn, or Ti-10V-Fe-3Al; stainless steel such as SAF2507; zinc alloys such as Zn5al, Zn10Al, Zn18Al, Zn30Al, platinum metal and its alloys; tin alloys such as Sn3.9Ag0.6Cu, Sn-3.8Ag-0.7Cu, SnPb, or SnPbAt; aluminum alloys such as Al1.7Fe, Al0.7Cu, A1.5MgScZr, Al6Mg0.2Sc0.15Zr, 3004, 8090, 7075, 6061, or 5056; zirconium alloy such as Zr55Al10Ni5Cu30; magnesium alloy such as AZ31B or MG11li5Al1Zn0.034Sc (LAZ1151); iron alloy such as Fe29.7Mn8.7Al1C, 30HGSA alloy steel, 4140, C45 steel, Fe36Ni, or low carbon steel; Nickel Alloys such as Ni21Cr17Mo or Haynes 230, or other metal and metal alloys.

In another example, a stent prosthesis patterned from non-degradable material comprising circumference structural elements, being expandable from a crimped configuration to an expanded configuration, and wherein the structural elements comprise one or more circumferential rings, and wherein at least some rings comprise a plurality of struts and crowns, and wherein the at least some rings form one or more continuous path around the stent, and wherein the at least some rings have one or more separation regions bisecting said at least some rings separating them circumferentially, and wherein the at least some rings each have at least some crown free from separation regions, and wherein the said at least some rings remain axially connected after formation of all discontinuities, and wherein the patterned stent forms a tubular body in the crimped configuration and maintains a substantially tubular body after expansion in a physiologic environment and formation of discontinuities.

In another example, A stent prosthesis comprising one or more circumferential rings, and wherein the stent has been patterned from a non-degradable material, and wherein the rings comprise a plurality of structural elements, wherein the structural elements comprise a plurality of crowns and struts, and wherein said rings form one or more continuous circumferential paths around the stent, and wherein said rings being expandable from a crimped configuration to an expanded configuration, and wherein said rings have one or more separation regions bisecting one or more circumferential paths around the ring, and wherein the bisected rings structural elements are held together by means and configured to separate after expansion under physiologic conditions forming discontinuous circumferential rings. The stent in a particular example comprise two or more rings, wherein at least two rings are axially joined and remain axially joined after said two rings form discontinuous circumferential paths around the stent, and wherein said at least two rings have at least some crowns free from separation regions after said at least two rings form discontinuous circumferential paths around the stent. In a particular example, the bisected rings provide one or more of: improved durability of the stent, improved conformability of the stent, increased flexibility of the stent, reduce strut fractures, inhibit strut fractures, or other.

In another example, a stent prosthesis comprising one or more circumferential rings, and wherein the stent has been patterned from a non-degradable material, and wherein the rings comprise a plurality of structural elements, wherein the structural elements comprise a plurality of crowns and struts, and wherein said rings form one or more continuous circumferential paths around the stent, and wherein said rings being expandable from a crimped configuration to an expanded configuration, and wherein said rings have one or more separation regions bisecting one or more circumferential paths around the ring, and wherein the bisected rings structural elements are held together by means and configured to separate after expansion under physiologic conditions forming at least one discontinuous circumferential path around the ring. The stent in a particular example comprise two or more rings, wherein at least two rings are axially joined and remain axially joined after said two rings form discontinuous circumferential paths around the stent, and wherein said at least two rings have at least some crowns which are free from separation regions after said at least two rings form discontinuous circumferential paths around the stent. In a particular example, the bisected rings provide one or more of: improved durability of the stent, improved conformability of the stent, increased flexibility of the stent, reduce strut fractures, inhibit strut fractures, or other.

In another example, A stent prosthesis comprising one or more circumferential rings, and wherein the stent has been patterned from a non-degradable material, and wherein the rings comprise a plurality of structural elements, wherein the structural elements comprise a plurality of crowns and struts, and wherein said rings form two or more continuous circumferential paths around the stent, and wherein said rings being expandable from a crimped configuration to an expanded configuration, and wherein said rings have one or more separation regions bisecting two or more circumferential paths around the rings, and wherein the bisected rings structural elements are held together by means and configured to separate after expansion under physiologic conditions forming at least one discontinuous circumferential path around said rings and at least one continuous circumferential path around the same said rings. In a particular example, the bisected rings provide one or more of: improved durability of the stent, improved conformability of the stent, increased flexibility of the stent, reduce strut fractures, inhibit strut fractures, or other.

In another example, A stent prosthesis comprising one or more circumferential rings, and wherein the stent has been patterned from a non-degradable material, and wherein the rings comprise a plurality of structural elements, wherein the structural elements comprise a plurality of crowns and struts, and wherein said rings form continuous circumferential path around the stent, and wherein said rings being expandable from a crimped configuration to an expanded configuration, and wherein said rings have one or more separation regions bisecting said rings, and wherein said separation regions maintain the continuous circumferential path of said rings. In a particular example, the bisected rings provide one or more of: improved durability of the stent, improved conformability of the stent, increased flexibility of the stent, reduce strut fractures, inhibit strut fractures, or other.

When expanded in arteries, conventional stents or other scaffolds cause a difference in vessel compliance (a compliance mismatch) between a stented vessel segment and an adjacent unstented vessel segment. In particular, the difference between the end rings of a conventional stented segment and an adjacent unstented segment is typically greater than 0.2 mm, usually greater than 0.25 mm, or sometimes greater than 0.3 mm; the difference in compliance may be in a range from 0.2 mm to 0.7 mm, or from 0.25 to 0.5 mm, or from 0.30 mm to 0.5 mm. This difference in compliance can in some cases cause the adjacent unstented segment to further expand, dilate or "balloon" (become abnormally more compliant) which causes abnormal stresses (shear and/or tensile) on the end ring stented segment and adjacent unstented segment, potentially causing an aneurysm and/or re-stenosis in that region.

In some embodiments and/or examples, the separation regions of the present invention may be used to reduce the difference in vessel compliance between the end segments of a stent or other scaffold and an adjacent artery wall. In one example, one or more separation regions on one or more end rings may be configured to separate after stent expansion to reduce the compliance mismatch between said end ring of a stented segment and an adjacent unstented segment to less than 0.2 mm, less than 0.15 mm, or less than 0.1 mm; or the difference in compliance may be in a range from 0.05 to 0.15 mm. In another example, a stent prosthesis or other vascular scaffold may have a greater number of separation regions in one or more end rings as compared to a number of separation regions in one or more mid-stent rings, or as compared to one or more rings adjacent to said one or more end rings. In still another example, at least one separation region in one or more end rings may be configured to form one or more discontinuities prior to expanding the stent or other scaffold from a crimped configuration to said expanded configuration. In still another example, at least one separation region in one or more end rings may be configured to form one or more discontinuities upon expanding the stent or other scaffold from a crimped configuration to said expanded configuration. In still another example, at least one separation region in one or more end rings may be configured to form one or more discontinuities within 72 hours after expanding the stent or other scaffold from a crimped configuration to said expanded configuration. In yet another example, a crush strength of said one or more end rings may be smaller than a crush strength of one or more mid-stent rings after formation of discontinuities.

It may be possible to achieve more compliant end rings compared to adjacent rings or compared to adjacent unstented segment to said end rings by providing the end rings with strut lengths longer than strut lengths in the adjacent inner rings. For example, in a stent or other scaffold comprising three or more rings (turns), said stent or other scaffold being expandable from a crimped configuration to an expanded configuration, one or more end rings may have a longitudinal length (length along the stent longitudinal axis, or length of struts joining two crowns) in the crimped stent configuration which is longer than length of an adjacent ring and/or longer than a length of one or more mid-stent rings, where the length may be longer by at least 100%; by at least 200%; by at least 300%, or longer. In other instances, the end ring strut length may be longer than a length of an adjacent ring and/or longer than a length of one or more mid-stent rings by from 100% to 500%; from 200% to 400%; or from 300% to 400%. In still other instances, the end ring strut length may be longer than a length of an adjacent ring and/or longer than a length of one or more mid-stent rings by from 1.5 mm to 5 mm, more preferably from 2 mm to 5 mm, and most preferably from 2.5 mm to 5 mm, and wherein the length of a ring adjacent to one or more end rings or one or more mid-stent rings length ranges from 0.5 mm to 1.3 mm, preferably from 0.7 mm to 1.2 mm, and more preferably from 0.8 mm to 1.2 mm.

In another example, a stent or other scaffold comprising three or more rings (turns) is expandable from a crimped configuration to an expanded configuration, where one or more end rings have one or more crowns and where at least some of said crowns have a width in the widest region and/or apex in the crimped stent or other scaffold configuration which is thinner than a width in the widest region and/or apex of one or more crowns of an adjacent ring, and/or where at least some of said crowns have a width thinner in the widest region and/or apex than a width of one or more crowns of one or more mid-stent rings in the widest region and/or apex of said crowns. For example, the width in the widest region is thinner by at least 50%; by at least 70%; by at least 80%; or the widest width and/or apex may be thinner by from 50% to 90%; from 70% to 85%; or from 75% to 80%. Exemplary widest widths and/or apex of one or more crowns of in one or more end rings range from 10 micrometers to 65 micrometers, preferably from 20 micrometers to 55 micrometers, and more preferably ranges from 25 micrometers to 50 micrometers, wherein the widest width and/or apex of one or more crowns of an adjacent ring, or one or more crowns widest width and/or apex in one or more mid-stent rings ranges from 0.7 micrometers to 150 micrometers, preferably ranges from 80 micrometers to 125 micrometers, and most preferably ranges from 80 micrometers to 110 micrometers.

In still another example, a stent or other scaffold comprising three or more rings (turns) is expandable from a crimped configuration to an expanded configuration and has one or more end rings at least some of which have a thickness which is thinner than a thickness of an adjacent ring and/or one or more mid-stent rings, where the thickness may be thinner by at least 50%; by at least 75%; or by at least 80%. For example, the thickness of at least some crowns of the end ring may be thinner than an adjacent and/or mid-stent ring crowns by from 50% to 90%; by from 70% to 85%; or by from 75% to 80%. Exemplary thicknesses of at least some crowns of the end ring are preferably in a range from 15 micrometers to 60 micrometers, more preferably from 20 micrometers to 55 micrometers, and most preferably from 25 micrometers to 50 micrometers, while exemplary thicknesses of a ring crowns adjacent to one or more end rings or one or more mid-stent rings crowns thickness range from 65 micrometers to 150 micrometers, preferably from 75 micrometers to 120 micrometers, and more preferably from 80 micrometers to 120 micrometers.

In further examples, a stent or other scaffold comprising three or more rings (turns) is expandable from a crimped configuration to an expanded configuration where one or more end rings may have one or more of the following: at least one crown having a thickness less than a thickness of a crown in an adjacent ring or in one or more mid-stent rings; or having at least one strut length in the crimped stent configuration greater than at least one strut length on an adjacent ring or on one or more mid-stent rings; or having at least one crown width in the widest region of the crown being less than at least one crown width in the widest region in an adjacent ring or in one or more mid-stent rings, or having at least one separation region which forms one or more discontinuities after expansion of the stent in physiologic environment. In some examples, a stent or other scaffold may combine all of these features where one or more end rings have a reduced thickness, a reduced width, longer struts, and at least one separation region. In other examples, a stent or other scaffold may combine at least some of these features where one or more end rings have at least some of a reduced thickness, a reduced width, longer struts, and/or at least one separation region. In yet other examples, a stent or other scaffold may combine at least some of struts having a reduced width, longer struts, and/or at least one separation region. Providing one or more of these differences to the end ring(s) or to the struts forming the end ring(s) compared to the adjacent rings or struts of those rings or struts located around the middle of the prosthesis creates an improved compliance of the prosthesis end rings, produces a smoother, less abrupt transition between the unstented and stented regions of the vessel and thus reduces or eliminates the ballooning that can sometimes occur in the adjacent unstented vessel or in the region of the end rings. The features in each of these embodiments or examples may further have a reduced crush strength (or 10% crush strength) in the expanded stent configuration (preferably expanded to nominal and/or labeled stent expansion diameter) that is smaller than a crush strength of an adjacent ring and/or one or more stent mid segment crush strength. In addition, each of these example stents may further be patterned from a non-degradable material, from a degradable material, or from a combination of non-degradable material(s) and degradable material(s).

In yet additional examples, a stent or other scaffold having one or more rings (turns) is expandable from a crimped configuration to an expanded configuration and includes at least one ring (turn) having one or more separation region(s) configured to bisect said ring into two or more circumferentially separate sections after expansion of the scaffold in a physiologic environment. The separated sections of the stent or other scaffold are typically held together during expansion, expansion typically occurs by exerting a radially outward force within a lumen of the stent or other scaffold, e.g. by balloon inflation, until after expansion, in some cases, expansion occurs by constraining a self-expanding stent with a means such as a sleeve and wherein the sleeve is removed allowing the self-expanding stent to expand to the expanded configuration. In one example, the separation region is covered by, encapsulated by, contained by, or otherwise circumscribed by a coating and/or sleeve formed from a non-degradable material, or formed at least partially from a non-degradable polymer, as described elsewhere herein. The one or more separation regions form one or more discontinuities after expansion of the stent or other scaffold in the physiologic environment, and the non-degradable material (such as non-degradable polymer) after formation of discontinuities continues to encapsulate, cover, circum-scribe, or contain said one or more separation regions. Typically, the non-degradable materials are configured to allow formed discontinuities in the separation region to move in one or more directions comprising circumferential, radial, longitudinal, or combination thereof. Provision of an at least partially non-degradable sleeve structure over the discontinuity has a number of advantages, such as protection an arterial, venous or other luminal wall from any free-ends or elements of the discontinuity that might otherwise trau-matize the vessel wall uncovered. While covering the dis-continuity to provide a protective barrier between the dis-continuity and the vessel wall, such coating and/or sleeves or other circumscribing structures typically will not immo-bilize or significantly inhibit relative motion of the free ends of the discontinuity so that the stent or other scaffold will still be able to radially further expand and/or contract with vessel wall pulsation allowing further scaffold expansion during pulsation and/or over time and adaptive remodeling of the vessel wall as described in other examples or embodi-ments of the present invention.

In specific examples, such protective coatings and/or sleeves or other barriers may be formed in whole or in part from a porous polymer or other porous material that allows fluid intrusion into the separation region after the stent or other scaffold is implanted in the vascular or other physi-ologic environment. Such fluid intrusion can initiate forma-tion of the discontinuity, e.g. the blood or other body fluid will be available to initiate dissolution of a degradable polymer that holds the separation region intact during expansion. Alternatively, the protective coating and/or sleeve may be formed as a lattice, cage or other structure having open passages that allow exposure of the separation region to the physiologic conditions in the blood vessel or other body lumen. The coating and/or sleeve or other barrier may comprise a non-degradable or degradable material and be utilized alone to cover the separation region or the non-degradable or degradable materials may be used in combination. These combinations may be in adjoining por-tions of the separation regions, combined together in a region, or the non-degradable material may be utilized over the separation region(s) which comprise degradable mate-rials. For example, the non-degradable material or degrad-able material may fill a gap in the interface between struc-tural elements (such as male and female structural elements) of the separation region. This allows for example, joining (or bonding) the separation region together (filling the gap of the interface of a male and female portions for example) with the non-degradable or degradable material thereby joining (or holding them together) before expansion of the stent to the expanded configuration. These materials typically are configured to prevent the separation regions to form discontinuities prior to expansion of the stent to the expanded configuration. The material typically degrades or deteriorates under physiologic conditions forming disconti-nuities after expansion of the stent and allowing the struc-tural elements of the separation region (for example the male and female portions) to move in one or more directions comprising radial, circumferential, longitudinal or combi-nation thereof. The material may also allow cushioning of the separation region structural elements (such as male and female interface) during crimping of the stent, during expan-sion of the stent, and after expansion of the stent to the expanded configuration. In some cases, the separation region is held together by design configurations to allow crimping and/or expansion of the stent to the expanded configuration prior to uncaging of the separation region. In another example, the degradable and/or non-degradable material can be coated and/or deposited onto the separation region (with or without filling the gap between the interface of structural elements (such as male and female portions). This can hold the separation region together during crimping of the stent to the crimped configuration and/or holding the separation region together during expansion of the stent to the expanded configuration and/or holding the separation region together till after the expansion of the stent to the expanded configuration. The material under physiologic conditions will degrade or deteriorate forming discontinuities in the separation region and allowing the structural elements to move in one or more directions as described above. In some cases, a non-degradable sleeve (or layer) may continue to contain the structural elements of the separation region after formation of discontinuities under physiologic conditions to protect the vessel wall from the movement of the structural elements and prevent potential untoward effect. In some cases, the separation region is configured to allow some movement after expansion of the stent to the expanded configuration wherein the movement increases as the mate-rial degrades and/or deteriorates. In yet another example, some of the separation regions are configured to form discontinuities or provide movement in one or more direc-tions upon expansion of the stent to the expanded configu-ration. The degradable material or non-degradable material in one example is configured to degrade or deteriorate in a period ranging from 30 seconds after expansion of the stent under physiologic conditions to one year or longer, prefer-ably degrade or deteriorate in a period ranging from 1 hour to 9 months after expansion of the stent in a physiologic environment, more preferably degrade or deteriorate in a period ranging from 1 day to 9 months. In another example, the non-degradable material is configured to remain intact (not deteriorate) under physiologic conditions, or remain intact (not deteriorate) under physiologic conditions for a period ranging from 2 years to 5 years after expansion of the stent from a crimped configuration to an expanded configu-ration in a physiologic environment. The material may also be configured to soften under physiologic conditions allow-ing uncaging and/or movement of the separation region or stent prior to degradation or deterioration of the material. The degradable material may fill gaps in the separation region, cover one or more surface region of the separation region such as abluminal, luminal, or side surface regions, and/or cover one or more surface regions on adjacent structural elements to the separation region such as struts and crowns, and/or cover one or more surface regions on the ring containing the separation region, and/or cover one or more surface regions on a plurality of rings, and/or cover one or more surface regions on the stent. The thickness of the coating may be the same or different for different surface regions of the separation regions or surface regions within a separation region or within a stent. The coating filling an interface gap can range from 0.1 micrometer to 500 micrometers, preferably ranges in thickness from 1 micrometer to 50 micrometers, more preferably ranges from 3 micrometers to 25 micrometers. The coating thickness covering one or more surface regions on a separation region ranges from 0.1 microns to 500 microns, preferably ranges from 1 micrometer to 100 micrometer, more preferably ranges from 2 micrometers to 25 micrometers. Typical degradable material and non-degradable material comprise polymeric materials but can also comprise metallic material or ceramic material, or other.

In specific examples, such protective coatings and/or sleeves or other barriers may be formed in whole or in part from a non-degradable material and/or from a porous material, such as a polymer or other non-degradable and/or porous material that at least in part holds the separation regions together until expansion of the stent to the expanded configuration, and then allows the separation regions to form discontinuities and to move in one or more directions as a result of one or more of the following: fluid intrusion into the separation region after the stent or other scaffold is implanted in the vascular or other physiologic environment which degrades a material at least in part holding the separation regions together, fluid intrusion into the separation region after the stent or other scaffold is implanted in the vascular or other physiologic environment which loosens the grip of the non-degradable material on the separation regions allowing said separation regions to form discontinuities and to move in one or more directions, and/or the pulsation of a vessel, pressure, or fluid thrust loosens the grip of the non-degradable material coating and/or sleeve on the separation regions allowing them to form discontinuities and move in one or more directions, while continuing to contain the separation regions after formation of discontinuities.

In one preferred example, at least one separation region in at least some rings are contained by at least one non-degradable material coating and/or sleeve, wherein the non-degradable material grips the separation region holding it together until after expansion of the stent to the expanded configuration after which the non-degradable material loosens after said expansion of the stent in physiologic environment allowing the separation region to form one or more discontinuities and to move in one or more directions, while the non-degradable material continues to contain the separation region.

In yet another preferred example, at least one separation region in at least some rings are contained by at least one degradable material coating and/or sleeve, wherein the degradable material grips the separation region holding it together until after expansion of the stent to the expanded configuration after which the degradable material degrades after said expansion of the stent in physiologic environment, usually degrades from 30 seconds after expansion of the stent to 7 days after expansion of the stent in physiologic environment, allowing the separation region to form one or more discontinuities and to move in one or more directions.

In yet another preferred example, at least one separation region in at least some rings are contained by at least one degradable material coating and/or sleeve and at least one non-degradable material coating and/or sleeve, wherein the non-degradable material and degradable material grip the separation region holding it together until after expansion of the stent to the expanded configuration after which the degradable material degrades after said expansion of the stent in a physiologic environment, usually degrades from 30 seconds after expansion of the stent to one year after expansion of the stent in physiologic environment, more usually degrades from one day after expansion of the stent to nine months after expansion of the stent in physiologic environment, allowing the separation region to form one or more discontinuities and to move in one or more directions, while the separation regions continue to be contained by the at least one non-degradable material after formation of discontinuities.

In another example, the stent or the separation regions have a coating to improve biocompatibility of the stent or separation regions. These coatings can be degradable or non-degradable and applied to the stent on one or more surface regions. Examples of such coating comprise but are not limited to one or more of: Nitric-oxide coating, Titanium nitride-based coatings, Nanoporous layer of aluminum oxide coating, Polyzene-F nano-thin coating, Tantalum-based VisTa coating, Amorphous siliconcarbide coating (proBIO), Polyethylene imine coating, Graphene coating, Polybutene coating, or other.

In another example, a stent prosthesis as in any of the examples of this application comprising one or more circumferential rings, the rings being expandable from a crimped configuration to an expanded configuration, and wherein at least one ring, preferably all rings, have one or more separation regions wherein the separation region comprises a discontinuity or a break in the circumferential ring bisecting said circumferential ring into two or more separate sections, and wherein the separation regions comprise one or more patterns comprising butt junction, male and female junction, parallel junction, key and lock junction, comb junction, hinge type, or other type, and wherein the junctions comprise a material comprised from degradable polymer, non-degradable polymer, degradable metal or metal alloy, non-degradable metal or metal alloy, and wherein the material degrades or deteriorates after expansion of the stent in a physiologic environment to allow the separation regions and/or circumferential rings, and/or portions of the circumferential rings, and/or the structural elements contained within the separation regions (such as struts, portions of struts, crowns, portions of crowns) to move in one or more directions comprising circumferential, radial, longitudinal, or combination thereof. The separation regions may be formed during patterning, after patterning, or before crimping, or before expansion of the stent to the expanded configuration in a physiologic environment.

In another example a stent prosthesis (scaffold) configured to support a graft may be constructed with the scaffolds of the present invention used to support a graft component. The scaffold may have any of the previously described structure such as a plurality of circumferential rings spaced apart over the exterior of a graft sleeve or membrane or inside the interior of a graft sleeve or member, or sandwiched in between an exterior and an interiors graft sleeve or membrane. The graft may comprise any conventional material, typically being a polyester or PTFE, such as an ePTFE, but may also be comprised from other material described in this application including degradable and non-degradable materials such as polymeric materials. The material may be elastic. The stent graft may have a bifurcated construction with legs covered by additional circumferential rings secured over the exterior of the legs. Adjacent rings may be unconnected (that is connected only by attachment to the graft sleeve) or may be joined by axial links or otherwise. The scaffolds may be on the exterior of the graft sleeve, or alternatively may be on the interior, or may be sandwiched or embedded between a coaxial pair of graft sleeves. The scaffold maybe formed from degradable metal or metal alloy, non-degradable metal and metal alloy, degradable polymer, or non-degradable polymer. The scaffold may be balloon expandable or self expandable, and patterned into an open cell design or a closed cell design. The stent may have serpentine ring design, zig zag ring design, closed cell design, helical stent design, or other type stent designs. The stent is configured to have one or more separation regions in one or more rings of the stent, wherein the separation regions are configured to form discontinuities after stent expansion in a physiologic environment and wherein the stent graft is allowed to have pulsatile motion, adaptive remodeling, expand to a larger configuration after implantation, or other benefits described in this application. The graft material is preferably comprised from an elastic material or a material that allows the stent after uncaging (after formation of discontinuities) to exhibit one or more of movement, pulsatile motion, adaptive remodeling, and/or further expansion and contraction, under physiologic environment or conditions. In one example, the stent graft is expanded from a crimped configuration to an expanded configuration, wherein the stent has an initial rigidity, and wherein after formation of discontinuities the stent graft has less rigidity, under physiologic conditions. The graft may cover all the stent, a segment of the stent, a mid segment of the stent, and end segment of the stent, forming the stent graft.

In a preferred example, a stent as described in the present invention is formed from a non-degradable shape memory or spring material as a helical stent, coil stent, or other types of stents with open cells or closed cells, or a combination of open and closed cell designs, wherein one or more of the stent's circumferential turns (rings) have one or more separation regions configured to form one or more discontinuities after expansion of the stent in a physiologic environment. The stent typically is self expanding stent but may also be configured to be balloon expandable, or both. The stent is configured to maintain outward force on the vessel when the stent is implanted in an annulus or body lumen, and wherein after one or more separation regions form one or more discontinuities the ring or stent outward force on the vessel, annulus, or body lumen, decreases. One ring, a part of a ring, or the stent may have a geometry after formation of the discontinuities that contours to the anatomy when the stent is implanted in locations, such as a valve annulus or a body lumen or vessel. As the annulus changes its shape over time, the stent or ring adjacent to the portion of the annulus changing shape and will conform to that shape of the annulus. This minimizes leaks between the stent and annulus for example. In many cases, stent implanted in an annulus will have a graft or a skirt outside the stent, inside the stent, or interwoven between outside and inside the stent to help seal the area between the stent and annulus. The graft or skirt material is configured to be elastic to conform with the shape of the stent as the stent conforms to the change in annulus shape, after formation of discontinuities. The separation region in one example comprises junction and hinges that allow the stent after formation of discontinuities to change shape or move in one or more direction including radial, longitudinal, circumferential, tangential, or combination thereof. Typically even though the stent or rings outward forces decrease after formation of discontinuities allowing hinge motion, the stent and/or skirt (membrane) are typically incorporated into the annulus or body tissue and move in accordance with the body physiologic environment. This minimizes potential excessive damage from the constant excessive outward force of the stent and allows it to accommodate the annulus anatomy better. Although this example is for shape memory or self expanding stents including valve stents, it also applies to balloon expanding stents or valve stents to allow the stent or stent valve to contour to the annulus or bioody lumen after expansion of said stent or stent valve in a body lumen or annulus, such as valve annulus.

In a preferred example, a stent prosthesis comprises at least one segment which contains and/or is contained in a membrane wherein the membrane expands together with the stent from a crimped configuration to an expanded configuration, and wherein the stent comprises one or more circumferential rings, with at least one ring comprising one or more separation regions and/or hinge regions, and wherein the stent after expansion from a crimped configuration has a first substantially cylindrical configuration, and wherein the stent after formation of continuities and/or allowing the one or more hinge junctions to move, has a second configuration wherein the second configuration is one or more of: non cylindrical configuration, contours to an adjacent anatomy configuration, conforms to an adjacent anatomy configuration, contours to an adjacent annulus configuration, contours to a body lumen configuration, contours to an adjacent vessel configuration, or a combination thereof, and wherein the stent and/or sleeve after formation of continuities or hinge movement minimizes or inhibits blood leaks adjacent to the stent and/or stent membrane.

In another example, a stent prosthesis as in any of the examples comprises one or more rings wherein at least one ring has one or more separation regions, wherein the separation regions comprises joined discontinuities or immobilized hinges, and the separation regions are configured to move after expansion under physiologic conditions.

Many or all of the stent or other scaffold designs described herein will be able to accommodate or adapt to most or all forms of annulus and/or vessel geometries, motion, anatomical changes, and distortion over time after deployment. For example, the stents and scaffolds having separation regions and/or hinge junctions as described herein will possess sufficient tensile stress, fracture resistance, and ability to accommodate geometric distortion, such as angulation (bending of the vessel), torsional stress (twisting of the vessel about the vessel axis), longitudinal compression and extension, and the like. Such stresses are experienced, for example, by stents and other scaffolds implanted in annulus, arteries and veins located in the heart, or aorta, or peripheral anatomy such as below the knees, or in the superficial femoral artery, and the like. The stents and scaffolds of the present invention are typically able to dynamically conform and respond to both the pulsation of such blood vessels (radial opening and closing) as well as to torsional deformations about the axes of such blood vessels, and longitudinal compression. In a preferred example, a stent as described in this invention having a plurality of circumferential rings wherein at least some rings have one or more separation regions wherein the stent in the expanded configuration has a flexibility or as called in the art "three point bend test" measured using linear elastic finite element analysis as compression force ranging from 1N-4N, and wherein the stent after formation of discontinuities has a compression force ranging from 0.1N-0.8N, or a reduction in compression force after formation of discontinuities (compared to before formation of discontinuities) ranging from 40% to 90% as measured by finite element analysis or bench testing. The stent has a stress induced by angular bending "also known as the Ormiston Model 2015 test", where the maximum stress after stent expansion and prior to formation of discontinuities in accordance with this test ranges from 200e3 PSI to 800e3 PSI, and wherein the maximum stress after formation of discontinuities ranges from 1e2 PSI to 150e3 PSI, or a reduction in stress after formation of discontinuities (compared to before formation of discontinuities) ranging from 50% to 98% as measured by finite element analysis. The stent in this example has a longitudinal compression maximum stress prior to formation of discontinuities ranging from 400e3 PSI to 800e3 PSI while after formation of discontinuities the maximum stress ranges from 1e3 to 300e3 PSI, or a reduction in stress after formation of discontinuities (compared to before formation of discontinuities) ranging from 50% to 95% as measured by finite element analysis. The stent in the expanded configuration and prior to formation of discontinuities has a torsional maximum stress ranging from 80e3 PSI to 150e3PSI and a maximum torsional stress after formation of discontinuities ranging from 1e3 PSI to 65e3 PSI, or a reduction in stress after formation of discontinuities (compared to before formation of discontinuities) ranging from 40% to 90% as measured by finite element analysis. The stent in this example after expansion in an artery having a bend wherein the bend has an angle as measured in Gyongyosi (2000) using validated QCA system to determine angulation defined by the tangents to the proximal and distal parts of the stenoses/stents at the end-diastolic angiographic frames, which ranges from 30 degrees to 70 degrees and wherein upon expansion of the stent and prior to formation of discontinuities the stent straightens such angle by from 10 degrees to 25 degrees, and wherein the angles after formation of discontinuities reduces the straightening of the artery to less than 9 degrees, or reduces the change in angle by a range from 10% to 90% of the change in angle initially caused by the stent prior to formation of discontinuities.

In another example, a stent prosthesis is patterned from a non-degradable material (or a degradable material) wherein said stent comprises a plurality of circumferential rings, with at least one separation region configured to bisect two or more rings, and the separation regions are held together until after expansion of the stent from a crimped configuration to an expanded configuration. The at least one separation region in one example bisects a crown on one ring and another crown on an adjacent ring and said separation region also bisects a link connecting said two crowns. In another example, the at least one separation region bisects a strut on one ring and another strut on an adjacent ring and said separation region also bisects a link connecting said two struts. In another example, the at least one separation region bisects a strut on one ring and a crown on an adjacent ring and said separation region also bisects a link connecting said strut and crown. In another example, the at least one separation region bisects a crown on one ring and another crown on an adjacent ring wherein the two crowns are fused or joined together. In another example, the at least one separation region bisects a strut on one ring and another strut on an adjacent ring wherein the two struts are fused or joined together. In another example, the at least one separation region bisects a crown on one ring and a strut on an adjacent ring wherein the strut and crown are fused or joined together. In a preferred example of having a separation region circumferentially disconnecting two or more rings, the separation region bisects two or more joined crowns on adjacent rings, or two or more joined struts on adjacent rings, or a crown from one ring and a strut from an adjacent ring that are joined, the two rings become circumferentially separated, typically in an axially connected closed cell rings.

In another example, a stent prosthesis in accordance with this invention, the stent comprises a plurality of rings patterned in an open cell pattern, where the stent has one or more separation regions, with at least some separation regions each bisecting two or more rings forming an axially connected closed cell pattern, and wherein the bisected rings each become circumferentially separated after formation of discontinuities after expansion of the stent in a physiological environment.

Thus, in certain examples or aspects, the present invention provides degradable stents and other scaffolds having one or more separation regions on one or more rings wherein the one or more separation regions form one or more discontinuities after expansion of the stent from a crimped configuration in a physiologic environment. Such stents and other scaffolds may have one or more separation regions configured to form discontinuities prior to degradation of the degradable stent, or prior to substantial degradation of the stent. Such stents and other scaffolds may be configured to degrade by 50% or greater in one year to 3 years or more after expansion of the stent in physiologic environment where one or more separation regions are configured to form one or more discontinuities in one year or less than one year after expansion of the stent in physiologic environment, sometimes one or more separation regions are configured to form one or more discontinuities in 9 months or less than 9 months after expansion of the stent in physiologic environment, in some cases one or more separation regions are configured to form one or more discontinuities from 30 seconds to 9 months after expansion of the stent in physiologic environment. Typically, at least some of the separation regions are configured to form the discontinuities before the stent substantially degrades; usually the stent is configured to have one or more separation regions form one or more discontinuities after expansion of the stent within 9 months of expansion of the stent, and the stent is configured to degrade by at least 50% in six months to five years after expansion of the stent in physiologic environment. Degradable stent and other scaffolds may be patterned or otherwise formed, e.g. from a tube, sheet, or by bending wires, from one or more degradable metal, metal alloy, and/or polymeric material. The separation regions may be formed in a stent or other scaffold during patterning, after patterning, or before expanding the stent from a crimped configuration to an expanded configuration. In some examples, the degradable stent is expanded to an initial stent configuration from a crimped configuration where the stent subsequently expands to a second expanded configuration after recoil from an initial expanded configuration after one or more separation regions have formed one or more discontinuities in physiologic environment and wherein the degradable stent has degraded less than 50%. Often, the second expanded configuration is larger than initial configuration. For example, the stent may be expanded from a crimped configuration to an initial expanded configuration and then one or more materials such as polymeric material, metallic materials, solder, glue, or the like connect and/or hold together the separate ends of the separation region preventing it from forming discontinuities, wherein the one or more material is configured to degrade or deteriorate in physiologic environment to form one or more discontinuities after expansion of the stent in physiologic environment, typically the one or more material comprises different material than the stent material, but can in some cases have the same material as the stent configured, however, to degrade faster than the stent. In particular examples, the one or more separation regions may bisect a circumferential path around the stent formed by the one or more rings. The one or more separation regions on one or more rings may further be configured not to form any discontinuities until after expansion of the stent from a crimped configuration. In other examples, the one or more separation regions may be formed in struts and/or crowns and/or links. Such stents and other scaffolds may be configured to degrade during a period from 1 to 5 years, including at least one year, two years, three years, four years, or five years, after deployment is a physiologic environment and wherein at least some of the separation regions are configured to form discontinuities after expansion in physiologic environment ranging from 2 months to 1 year, including a period of more than one week but less than one month, two months, three months, six months, or one year. Prior to degradation, the degradable stent may be comprised from a polymeric material such as polylactide and poly lactic acid polymers (PLLA's), or PLLA based material, or polycarbonate material which have a strength, typically in the range from 50 to 150 MPa, or alternatively degradable stents, such as metallic material such as magnesium alloys stents having strength ranging from 100 MPa-350 MPa which are typically configured to degrade in a period ranging from 1 year to 3 years, or alternatively other metallic material having strength prior to degradation ranging from 400 MPa to 1000 MPa configured to degrade in a period ranging from 3 years to 7 years. Material degradation may be at least 50% degradation, and/or 75% degradation may be utilized. As with other examples, the one or more separation regions may comprise any one or more junctions selected from a group consisting of butt joints, key and lock junctions, overlapping end regions, male/female connectors such as pins and holes, hinge connections, and the like. The one or more separation regions may bisect the one or more rings to circumferentially disconnect said one or more rings, where some or all circumferentially disconnected ring ends are held together during expansion from a crimped configuration to an expanded configuration by a material comprising one or more of degradable or non-degradable materials and structural designs described throughout the disclosure comprise the separation regions which subsequently form the discontinuities.

Separation regions may be distributed in many or all regions of any stent or other scaffold pattern. In some examples, separation regions may be disposed only in rings or in both rings and axial links or fusion zones. In some instances, separation regions may be provided only in axial links or fusion zones, for example in scaffolds having helical backbones where adjacent turns of the backbone may be connected by axial links or fusion zones having separation regions. In other instances, one, two, three or more but fewer than all links may be formed with separation regions, and the separation regions may have any of the designs and form described elsewhere herein. Separation regions in axial links and fusion zones may in some cases be combined with separation regions in struts, crowns, or any other portions of a scaffold ring or other structure.

In another example, a stent formed in accordance with this invention comprises one or more rings, wherein at least one ring has one or more separation regions, and wherein the separation region forms one or more discontinuities after implantation of the stent in or on one or more of a body lumen, annulus, cavity, vessel, or organ. The stent in this example is formed at an initial configuration or diameter and is implanted at the initial configuration or diameter. The stent in another example is formed at an initial configuration or diameter and is implanted at a first configuration or diameter wherein the first configuration or diameter is smaller than the initial configuration.

In one example, a stent prosthesis comprising a plurality of circumferential rings wherein each ring comprises struts joined by crowns, said stent being expandable from a crimped configuration to an expanded configuration, and wherein at least some rings have two or more separation regions, said two or more separation regions located at one or more of the following: at two struts joined by a crown, at two or more struts wherein each strut is joined to a crown different from the other two or more struts, at two or more crowns, at one strut and one crown. In one example, the said separation regions on at least some rings may have symmetrical pattern or may have non-symmetrical pattern in the crimped or expanded configuration. In another example, the said separation regions on at least some rings may move in the same direction or may move in different directions from one another after the formation of the discontinuities.

In another example, a non-degradable stent prosthesis comprising a plurality of rings, said stent being expandable from a crimped configuration to an expanded configuration, and wherein the stent has three segments along the length of the stent: a proximal segment, a middle segment, and a distal segment, and wherein each segment comprises one or more ring, and wherein the stent is configured to have one of the following: all three segments being expandable to substantially the same configuration, all three segments being expandable to a different configurations from one another, two of the three segments being expandable to substantially the same configuration, and wherein at least some rings along the length of the stent have one or more separation regions, wherein the separation regions form one or more discontinuities after expansion of the stent under physiologic conditions. In one example, all three stent segments have substantially the same crimped configuration. In another example, at least two of the three stent segments have substantially the same crimped configuration. In yet another example, all three stent segments have different crimped configurations. In one example, the stent in the expanded configuration is substantially cylindrical, non-cylindrical, cone shaped, dog bone shaped, hour-glass shaped, elliptical shaped, or other. In another example, the stent in the crimped configuration has a substantially cylindrical configuration.

In another example, a non-degradable implant for use in a body cavity, said implant being expandable from a crimped configuration to an expanded configuration and wherein the implant (or at least one segment) has one or more separation regions configured, after expansion under physiologic conditions, to have one or more of the following: initial expanded configuration, initial strength in the expanded configuration, initial compliance in the expanded configuration, initial contractility in the expanded configuration, and wherein the implant (or at least one said segment) subsequently has one or more of the following: an expanded configuration that is smaller than the initial expanded configuration, an expanded configuration that is larger than initial expanded configuration, a configuration that is the same or smaller than the crimped configuration, strength that is smaller than initial strength, compliance that is larger than initial compliance, compliance that is different than initial compliance, contractility that is larger than the initial contractility, contractility that is different than the initial contractility.

In another example, a non-degradable implant for use in a body cavity, the implant being positioned to replace or support a body part, wherein the implant (or at least one segment) has one or more separation regions configured, after expansion under physiologic conditions, to have one or more of the following: initial configuration, initial strength, initial compliance, initial contractility, and wherein the implant (or at least one said segment) subsequently has one or more of the following: a configuration that is smaller than the initial configuration, a configuration that is larger than initial configuration, a configuration that is different than the initial configuration, strength that is smaller than initial strength, compliance that is larger than initial compliance, compliance that is different than initial compliance, contractility that is larger than the initial contractility, contractility that is different than the initial contractility.

In another example, a stent prosthesis patterned from a non-degradable metal or metal alloy, wherein the stent comprises one or more rings, the stent being expandable from a crimped configuration to an expanded configuration, and wherein at least some rings in the expanded stent configuration have one or more separation regions and wherein the at least some rings containing the one or more separation regions under physiologic conditions are configured to have one or more of the following: an initial contractility in the at least some rings that is smaller than a subsequent contractility of said at least some rings, an initial compliance in the at least some rings that is smaller than a subsequent compliance, an initial expanded configuration that is smaller than a subsequent configuration in said at least some rings. In another example of this example, the at least some rings is composed of the stent.

In another example of any of the examples of this application, a stent as in any of the examples being expandable under physiologic conditions wherein the physiologic conditions comprises one or more of the following: mammalian systole and/or diastole pressure, mammalian heartbeat, mammalian heart muscle expansion and/or contraction, vessel expansion and/or contraction, mammalian muscle contraction and/or expansion, mammalian body lumen, mock mammalian systole and/or diastole pressure, mock mammalian heartbeat, mock mammalian heart muscle expansion and/or contraction, mock mammalian vessel expansion and/or contraction, mock mammalian muscle contraction and/or expansion, mock mammalian body lumen.

In another example of any of the examples of this application, a stent prosthesis being expandable in a body lumen, wherein the stent (or at least some rings) after expansion exhibits one or more of: further expansion of the stent (or the at least some rings) after an inward recoil from said expansion, dynamic expansion and contraction, remodeling, positive remodeling, adaptive remodeling, dynamic remodeling, under physiologic conditions. In one example the magnitude of further expansion, expansion and contraction, or remodeling, ranges from 0.07 mm to 5 mm, preferably ranges from 0.1 mm to 5 mm, more preferably ranges from 0.15 mm to 5 mm. In a preferred example, the stent prosthesis is formed and patterned from non-degradable metal or metal alloy, wherein the stent comprises a plurality of circumferential rings and wherein each ring comprises struts joined by crowns and wherein each ring is axially connected to an adjacent ring. The stent prosthesis in a preferred example is balloon expandable from a crimped configuration to an expanded configuration, formed and patterned from a non-degradable plastically deformable metal or metal alloy, wherein at least some rings have one or more separation regions wherein the stent after stent expansion exhibits one or more of: further expansion of the stent (or the at least some rings) after an inward recoil from said expansion, dynamic expansion and contraction, remodeling, positive remodeling, adaptive remodeling, dynamic remodeling, under physiologic conditions, wherein the further expansion, expansion and contraction, and/or remodeling, taking place after expansion and post procedure. In another example, the further expansion, expansion and contraction, and/or remodeling, are measure by one or more of the following: Intravascular ultrasound, optical coherent tomography, or QCA. In another preferred example, the at least some rings have one or more separation regions in the circumferential rings, wherein the one or more separation regions remain intact during expansion, and wherein the separation regions form one or more discontinuities after expansion under physiologic conditions. In another preferred example, the expandable stent prosthesis comprising a plurality of circumferential rings wherein at least some rings each have one or more paths circumscribing the circumference of said rings in the expanded stent configuration and wherein each said ring has one or more separation regions configured to maintain continuity of each ring circumferentially during stent expansion and to form one or more discontinuities in every path of said each ring circumference after stent expansion under physiologic conditions. In one example, an expandable stent prosthesis comprising a plurality of circumferential rings wherein at least some rings each have one or more paths circumscribing the circumference of each said ring in the expanded stent configuration wherein the at least some circumferential rings of the expandable stent prosthesis each has a number of separation regions ranging from 1 to 6 located such that each said ring has one or more discontinuities in any path of each said ring circumference after stent expansion under physiologic conditions. In one example, an expandable stent prosthesis comprises a plurality of circumferential rings, each ring has one or more paths circumscribing the circumference of the stent in the expanded stent configuration wherein at least one circumferential ring of the expandable stent prosthesis has one or more separation regions located on one or more of struts, crowns, and circumferential connectors, such that said ring has one or more discontinuities in all paths of said ring circumference after stent expansion under physiologic conditions. In one example, an expandable stent prosthesis comprising a plurality of circumferential rings wherein at least some rings each have two or more paths circumscribing the circumference of each said rings in the expanded stent configuration wherein the at least some circumferential rings of the expandable stent prosthesis each have two or more separation regions located on one or more of struts, crowns, and circumferential connectors, such that each said ring has one or more discontinuities in each said two or more paths of each said ring circumference after stent expansion under physiologic conditions. In a preferred example, at least some rings have one or more of: open cell design, closed cell design, hybrid of open and closed cell designs. The stent prosthesis in a preferred example is balloon-expandable formed and patterned from a non-degradable metal or metal alloy.

In another example, a non-degradable plastically deformable stent prosthesis being expandable from a crimped configuration to an expanded configuration, the stent comprises a plurality of circumferential rings, wherein each ring comprises struts joined by crowns, and wherein each ring is axially connected to an adjacent ring, wherein each ring has a continuous circumferential perimeter, and wherein at least some rings each have one or more separation regions which are configured to maintain continuity of each said ring circumferential perimeter during expansion, and wherein the said one or more separation regions are configured to form one or more discontinuities in each said ring circumferential perimeter after stent expansion under physiologic conditions. In a preferred example, the separation regions are configured to maintain said continuous perimeter before expansion of the stent in a body lumen by applying one or more material comprising adhesive, degradable material, or solder, to at least one surface of the one or more separation regions, and wherein the said material degrades after stent expansion under physiologic conditions, forming the said one or more discontinuities in the circumferential perimeter. In one example, the one or more discontinuities after stent expansion form a gap between the separated circumferential ends of said ring ranging from 1 micrometer to 1000 micrometers, wherein said gap is devoid of the stent material and one or more of the degradable material, the adhesive material, or the solder material. In another example, at least some rings further comprise one or more circumferential connectors, wherein at least one connector on each of said rings has one or more separation regions. In yet another example, the one or more separation regions are configured to maintain ring continuity prior to stent expansion by applying one or more non-degradable material to at least one surface of said separation regions (such as non-degradable polymeric material), and wherein the material has sufficient elasticity to stretch allowing the ring ends adjacent to said separation regions in the expanded stent configuration to move apart under physiologic conditions.

In another example, a non-degradable plastically deformable stent prosthesis being expandable from a crimped configuration to an expanded configuration, wherein the stent comprises a plurality of circumferential rings, wherein each ring comprises struts joined by crowns, and wherein each ring is axially connected to an adjacent ring, wherein each ring has at least one continuous circumferential perimeter, and wherein at least some rings each has one or more separation regions which are configured to maintain continuity of the at least one circumferential perimeter of each said ring during expansion, and wherein the said one or more separation regions are configured to form one or more discontinuities in each said ring one or more circumferential perimeters after stent expansion under physiologic conditions. In a preferred example, the separation regions are configured to maintain said continuous one or more perimeters before expansion of the stent in a body lumen by applying one or more material comprising adhesive, degradable material, or solder, to at least one surface of the one or more separation regions, and wherein the said material degrades after stent expansion under physiologic conditions, forming the said one or more discontinuities in each of the one or more of circumferential perimeters. In one example, the one or more discontinuities after stent expansion form a gap between the separated circumferential ends of said ring ranging from 1 micrometer to 1000 micrometers, wherein said gap is void from the stent material and one or more of the degradable material, the adhesive material, or the solder material. In another example, at least some rings further comprise one or more circumferential connectors, wherein at least one connector on each of said rings has one or more separation regions. In yet another example, the one or more separation regions are configured to maintain ring continuity in each of ring one or more circumferential perimeters prior to stent expansion by applying one or more non-degradable material to at least one surface of said separation regions (such as non-degradable polymeric material), and wherein the material has sufficient elasticity to stretch allowing the ring ends adjacent to said separation regions in the expanded stent configuration to move apart under physiologic conditions.

In another example, a non-degradable plastically deformable stent prosthesis being expandable from a crimped configuration to an expanded configuration, wherein the stent comprises a plurality of circumferential rings, wherein each ring comprises struts joined by crowns, and wherein each ring is axially connected to an adjacent ring, and wherein at least some rings each has at least one continuous circumferential perimeter, and each said ring has one or more separation regions which are configured to maintain continuity of the at least one circumferential perimeter of each said ring during expansion, and wherein the said one or more separation regions are configured to form one or more discontinuities in the at least one continuous circumferential perimeter of each said ring after stent expansion under physiologic conditions, wherein each said ring after formation of said one or more discontinuities become circumferentially disconnected. In another example, at least some rings further comprise one or more circumferential connectors, wherein at least one connector on each of said rings has one or more separation regions.

In another example, a non-degradable plastically deformable stent prosthesis being expandable from a crimped configuration to an expanded configuration, wherein the stent comprises a plurality of circumferential rings, wherein each ring comprises struts joined by crowns, and wherein each ring is axially connected to an adjacent ring, and wherein at least some rings each has at least one continuous circumferential perimeter, and each said ring has one or more separation regions, and wherein the said one or more separation regions are configured to form one or more discontinuities in the at least one continuous circumferential perimeter of each said ring after stent expansion under physiologic conditions, wherein each said ring after formation of said one or more discontinuities become circumferentially disconnected. In another example, at least some rings further comprise one or more circumferential connectors, wherein at least one connector on each of said rings has one or more separation regions.

In another example, a non-degradable plastically deformable stent prosthesis being expandable from a crimped configuration to an expanded configuration, wherein the stent comprises a plurality of circumferential rings, wherein at least some rings are composed of a plurality of struts and crowns, and wherein each ring is axially connected to an adjacent ring, and wherein the at least some rings each has at least one continuous circumferential perimeter, and each said ring has one or more separation regions, and wherein the said one or more separation regions after stent expansion under physiologic conditions are configured to form one or more discontinuities in each of said ring wherein each said ring has no continuous circumferential perimeter. In another example, at least some rings further comprise one or more circumferential connectors, wherein at least one connector on each of said rings has one or more separation regions.

In another example, a non-degradable plastically deformable stent prosthesis being expandable from a crimped configuration to an expanded configuration, wherein the stent comprises a plurality of circumferential rings, wherein each ring comprises struts joined by crowns, and wherein each ring is axially connected to an adjacent ring, and wherein at least some rings each has at least one continuous circumferential perimeter, and each said ring has one or more separation regions, and wherein the said one or more separation regions after stent expansion under physiologic conditions are configured to disconnect the at least one continuous circumferential perimeter of each said ring. In another example, at least some rings further comprise one or more circumferential connectors, wherein at least one connector on each of said rings has one or more separation regions.

In another example, a non-degradable plastically deformable stent prosthesis being expandable from a crimped configuration to an expanded configuration, wherein the stent comprises a plurality of circumferential rings, wherein at least some rings are composed of a plurality of struts and crowns, and wherein each ring is axially connected to an adjacent ring, and wherein the at least some rings each has at least one continuous circumferential perimeter, and each said ring has one or more separation regions, and wherein the said one or more separation regions after stent expansion under physiologic conditions are configured to disconnect the at least one continuous circumferential perimeter of each said ring.

In another example, at least some rings further comprise one or more circumferential connectors, wherein at least one connector on each of said rings has one or more separation regions.

In another example of any of the examples of this application, a stent prosthesis being expandable from a crimped configuration to an expanded configuration, wherein the stent comprises a plurality of circumferential rings and wherein each ring comprises low stress regions and high stress regions, and wherein one or more low stress regions on at least some rings have one or more separation regions bisecting each said low stress regions, and wherein the separation regions after expansion of the stent under physiologic conditions undergo one or more of the following: formation of one or more discontinuities, formation of discontinuities after expansion in a period ranging from 30 days to 1 year, disengagement of said separation regions in one or more of radial, circumferential, or axial directions, embedding of the one or more separation regions into the vessel wall, further embedding of the one or more separation regions into the vessel wall, allow rings containing the one or more separation regions have synchronized dynamic movement with the systole and diastole pressure cycles, and wherein the one or more separation regions are held together prior to implantation and configured to allow disengagement after expansion. In a preferred example, the one or more low stress regions are one or more strut regions on the at least some rings.

In another example, a stent prosthesis as in any of the examples of this application, wherein the stent being expandable from a crimped configuration to an expanded configuration, and wherein the stent comprising one or more rings, said stent after expansion under physiologic conditions, exhibit one or more of the following: uncages circumferentially one or more rings, uncages the vessel or body lumen, at least one or more rings exhibit dynamic expansion and contraction, allows a body lumen exhibit vascular remodeling, allows a body lumen in the stented segment exhibit adaptive remodeling, allows the vessel wall in the stented segment to have shear stresses closer to the vessel wall shear stresses in an adjacent unstented segment, allows the vessel wall to have improved endothelial function.

In another preferred example, a discontinuity comprises an opening, gap, joint, elastic junction, bisection, or the like, which forms in the scaffold at the locations of the separation regions after expansion of the scaffold and exposure of the scaffold to a blood vessel or other similar or equivalent physiologic environment or conditions. The discontinuities will increase the radial compliance of the scaffold or at least portions thereof. The discontinuities will be at locations in the expanded scaffold which decrease the hoop strength of the expanded scaffolds after the discontinuities form. For example, discontinuities may be in circumferential rings of a scaffold and will decrease the resistance to circumferential expansion of the ring, thus increasing radial compliance of the ring and of the scaffold as discussed in detail elsewhere in this application. In contrast, a discontinuity or break in an axial link or other axial connection which holds adjacent circumferential rings together typically will not decrease the hoop or radial strength of the expanded rings or scaffolds after the discontinuities form and typically will not increase radial compliance of the rings or scaffold as is an object of the present invention. In particular, a "bisection" occurs when an opening, break, gap, or the like, forms between two adjacent portions or segments of the component which were typically previously joined so that the portions or segments are no longer directly connected to each other in the region of the portions or segments. The two adjacent portions or segments of the component may have been previously joined in any of the ways described elsewhere herein or may have been formed as a continuous structure. In particular, a "bisection" occurs when an opening, break, gap, interruption, or the like, forms between two adjacent portions or segments of the component which were typically previously joined so that the portions or segments are no longer directly connected to each other in the region of the portions or segments. The two adjacent portions or segments of the component may have been previously joined in any of the ways described elsewhere herein or may have been formed as a continuous structure. In some instances, the "bisection" occurs when an opening, break, gap, or the like, is formed in one or more circumferential paths of the stent forming one or more discontinuous circumferential paths.

In another preferred example, the phrase "after all discontinuities are formed," refers to the scaffold when all separation regions in a scaffold have separated and all discontinuities have formed. While discontinuities may not always form in all separation regions in a scaffold after implantation in a blood vessel or other physiology environment, even though the separation regions maybe configured to form discontinuities at each separation region within the scaffold, all of the separation regions can be caused to form during in vitro tests run to determine if a scaffold meets the physical characteristics claimed herein. Thus, for the purposes of determining whether a scaffold meets the requirements of a claim which requires a determination that "all discontinuities are formed," the scaffold may be examined and tested after exposure to in vitro conditions selected to form all discontinuities by mimic in vivo physiologic condition, such as salinity, temperature, pressure, addition of agents or material to cause formation of discontinuities, and the like, which would be expected to result in formation of discontinuities at each separation region within the scaffold. Examples of such in vitro physiologic conditions are provided in the Examples Section hereinbelow.

In another preferred example, the word "pattern" refers to the geometric arrangement of the structural elements of a scaffold. The most common pattern comprises a plurality of "circumferential rings" which are axially joined, either by axial links or by direct attachment of axially adjacent regions on the circumferential rings. The scaffolds of the present invention may also have helical patterns, diamond and other closed or open cell patterns, and other patterns known in the vascular and other stent fabrication arts. The circumferential rings will usually be formed as serpentine or zig-zag structures comprising struts joined by crowns, where the struts will usually be straight (but can be not straight) and the crowns will act as joints or hinges to allow the struts to open and the circumferential ring to expand both circumferentially and radially. That is, the distance around the circumference or perimeter of the circumferential ring will increase as will the radial distance of the ring perimeter from the axial center of the scaffold.

In another preferred example, the individual circumferential rings of a scaffold will usually be "intact" and will usually be "axially joined" when the scaffold is in its crimped configuration prior to expansion or formation of discontinuities. By "intact," it is meant that the circumferential ring will have a continuous serpentine, zig-zag, sinusoidal, or other circumferential structure free from discontinuities. By "axially joined," it is meant that axially adjacent circumferential rings will be joined by axial links, or by direct crown-to-crown attachment by fusing or soldering, for example. After expansion of the scaffold and exposure to a physiologic environment, discontinuities will form in at least some of the rings, typically being gaps, breaks, or bisections in a strut or crown region or other structural component which forms the peripheral path or perimeter of the ring so that the ring structure is no longer continuous. Even though the individual circumferential rings may thus divide into two or more separated portions (partial circumferential rings) after formation of discontinuities, they may also be referred to as "circumferential rings" as that phrase is used herein and in the claims and, in particular, adjacent circumferential rings will be considered to remain "axially joined" (intact) so long as at least one portion of one ring remains connected to at least one portion of an adjacent ring even if the joined portions of a circumferential ring are separated by discontinuities from other portions of the same ring. In another preferred example, "radial compliance" is the composite compliance of the scaffold, stent, prosthesis or other structure measured as a composite compliance in vitro in a mock vessel (or tube) in accordance with ASTM F2477-07R13 which measures compliance at a pressure change of 100 mmHg, or radial strain (compliance measure at other pressure changes such as at about 176 mmHg), but the test can also provide the method for testing compliance at a given change in pressure other than 100 mmHg.

In another preferred example, "segment" and the phrase "segment of a scaffold" refer to a structural component of the scaffold which will remain joined or intact after all discontinuities have formed in the scaffold. For example, a circumferential ring is a segment as well as a closed cell structure. In many instances, two or more segments of the scaffold will remain joined after all discontinuities have formed in the scaffold. Thus, while segments will always remain joined or intact (where intact connotes that the structure is joined without any discontinuities, segments which are initially joined may or may not remain joined after all discontinuities have formed in the scaffold.

In another preferred example, "circumferential ring" refers both to rings with a continuous perimeter or periphery which extends over a full 360° as well as to discontinuous rings which have an offset in their perimeter or periphery. Such discontinuous circumferential rings will often be successively joined end-to-end so that they together form a helical pattern along all or a portion of the length of the scaffold. The individual circumferential rings will thus form successive turns of the helical scaffold. In one example, the circumferential ring pattern may be perpendicular to the longitudinal axis of the stent in the crimped and/or expanded configuration. In another example, the circumferential rings pattern may be at an angle between perpendicular to the stent longitudinal axis in the crimped configuration and/or expanded configuration and the stent longitudinal axis in the crimped and/or expanded configuration.

In another preferred example, "physiologic environment" refers both to natural or endogenous environments, typically a patient vasculature or other luminal environment, as well as to artificial or in vitro environments intended to mimic an endogenous vascular or other natural luminal environment. In particular, the artificial or in vitro environments will have at least some of the same temperature such as 37° C., aqueous solution (water bath), pressure change of about 100 mm Hg or of about 200 mmHg, mock tube having an inner diameter of 3.0 mm and a compliance of about 5%, agents to accelerate formation of discontinuities, and other characteristics of the endogenous environment that can be used to test the scaffolds to see if the separation regions will form discontinuities, stretch, or have enhanced compliance, in accordance with the principles of the present invention. In particular, to determine if a scaffold has separations regions, the scaffold can be examined for such separation regions, and/or be exposed to the physiologic conditions in vitro as described herein and observed to see if discontinuities form, or to test the scaffold for enhanced composite compliance, or to test the scaffold for initial compliance and increased composite compliance, or to test for the scaffold radial initial radial strength, or to test for radial strength after formation of discontinuities, the scaffold can be expanded in a tube "mock vessel" having ID of 3.0 mm, tube compliance of about 5%, in water bath at 37 C, and a pressure change of 100 mmHg, expand the inner scaffold diameter to about 110% of the tube inner diameter to ensure a good fit into the tube, measure initial composite compliance, dissolve the material holding the separation regions together forming discontinuities, and remeasure the composite compliance, the compliance of the stented segment at a mid segment of the stented segment, the compliance in accordance with the present invention increases from initial composite compliance after formation of discontinuities, typically increases by 200%-500% of the initial composite compliance, or usually increases by 200%-300%, or increases by at least 200% of the initial composite compliance, or increases by at least 300%.

In one preferred example, the stent after formation of discontinuities separates into 2, or 3, or 4 separate stent sections along the length of the stent, each section comprising a plurality of partial circumferential rings, where each partial ring remain axially connected (intact) to an adjacent partial ring, where the 2, 3, or 4 separate sections are formed after all the separation regions in each circumferential ring form discontinuities.

In a preferred example, the phrases "stent compliance," "stented segment compliance," and "stent vessel system compliance," all refer to the composite compliance of the stented/scaffolded segment as described in the composite compliance test method.

In a preferred example, the radial strength is measured using the flat plate (10% compression) test as described in the radial test method described in the application.

In a preferred example, at least some rings of the scaffold or stent of the present invention, are preferably which are formed from non-degradable metal or metal alloys, after expansion from a crimped configuration to an expanded configuration in a body lumen (or mock vessel), exhibit one or more of the following after formation of discontinuities compared to before formation of discontinuities: (1) uncage at least some, preferably all circumferential rings (the stent), or the stented segment, (2) display a change in configuration or diameter of at least some rings, preferably all rings of the stented segment, (3) display further expansion of at least some rings of the stented segment, (4) at least some rings of the stented segment, usually all, are able to expand and/or contract in a range from 0.1 mm to 0.5 mm, under physiologic conditions including contractility of the heart and/or change in pressure. Physiologic conditions may also include simulated physiologic conditions. Examples of the above are shown in example 22, showing OCT images of separation regions forming discontinuities in at least some rings uncaging said rings circumferentially, showing the opposite ends of at least some struts(containing the separation region) separate after formation of discontinuities and move radially and/or circumferentially (out of plane compared to each other), and/or showing a change in configuration or diameter of the at least some rings, or the stent further expand to a larger diameter or configuration after expansion and initial inward recoil from expansion of any, as shown in FIG. 100B-D or 101A-B. The above may also be shown in other tests bench, in-vitro, or in-vivo.

In a preferred example of any of the examples of this application, a non-degradable stent comprising at least one circumferential ring, wherein the at least one ring has one or more discontinuities in said at least one ring along a circumferential path of the at least one ring, and wherein the one or more discontinuities are held together to maintain a circumferential continuity of the at least one ring before implantation, and wherein the discontinuities after expansion of the stent in physiologic environment are configured to separate. In one example, the discontinuities are held together using degradable material, wherein the degradable material is configured to degrade after expansion in physiologic environment.

In another preferred example of any of the examples of this application, a stent formed from a non-degradable material is configured to have one or more separation regions on the circumferential stent structural elements that separate (form discontinuities) after expansion in physiologic environment comprise one or more of the following: uncaging of the stent circumferentially, uncaging of the stent circumferentially while the stent remains axially connected by one or more links, forming one or more discontinuities in the circumferential path of at least some circumferential rings, forming one or more discontinuities in the circumferential path of at least one circumferential ring, forming at least two axially connected rings wherein each said ring is circumferentially disconnected (each said ring has one or more discontinuity after expansion in physiologic environment along its circumferential path), forming axially connected rings wherein each said ring is circumferentially disconnected (each said ring has one or more discontinuity after expansion in physiologic environment along its circumferential path).

In another example of any of the examples of this application, a stent comprises one or more circumferential rings, wherein a circumferential ring has one continuous circumferential path, but said ring may also have more than one circumferential path as shown in the various examples and figures. In either case, one or more separation regions are formed in one or more locations on the at least one or more rings to circumferentially separate the one or more rings, such that said one or more rings have no circumferential continuous path after expansion in physiological environment.

In another example of any of the examples in this application, a stent comprising circumferential structural elements, wherein the structural elements are a plurality of rings, wherein at least some rings each have two or more separation regions configured to separate after expansion of the stent in physiologic environment, and wherein at least one separation region in said at least some rings does not separate after expansion of the stent in physiologic environment.

In another example of any of the examples of this application, a non-degradable stent comprising circumferential structural elements composed of a plurality of rings, wherein each ring is connected to an adjacent ring axially, and wherein at least some rings having one or more separation regions and wherein said one or more separation regions after expansion of the stent in physiologic environment are configured to separate, and wherein the separation comprises one or more of: circumferentially separating the at least some rings into two or more sections, circumferentially separating the stent, disengaging the circumferential structural elements adjacent to the separation regions, said at least some rings allow the lumen (including vessel, annulus, etc.) to exhibit positive remodeling, said at least some rings exhibit expansion and contraction in physiologic environment, said at least some rings exhibit positive remodeling in physiologic environment, said at least some rings exhibit dynamic expansion and contraction under physiologic conditions, said stent exhibits dynamic expansion and contraction under physiologic conditions.

In one example of any of the examples in this application, physiologic conditions and physiologic environment are used interchangeably and comprise one or more of: mock mammalian systole and/or diastole pressure, mammalian systole and/or diastole pressure, mock mammalian cardiac electrical, chemical, mechanical, and/or pressure cycle, or mammalian cardiac electrical, chemical, mechanical, and/or pressure cycle, use of vaso-dilator and/or vaso-constrictor, 100 mmHg pressure change, 176 mmHg pressure change, about 37° C., about 37° C. in water bath, in a body lumen or annulus, in a mock vessel (including annulus), use of one or more agents to form discontinuities in the separation regions, mammalian beating heart environment.

In an example of any of the examples in this application, the stent formed from a non-degradable material and patterned into a structure capable of expansion and contraction under physiologic environment, and wherein the stent is composed of a plurality of circumferential rings wherein each ring is axially connected to an adjacent ring, and wherein at least some rings are formed with one or more separation regions configured to separate after expansion of the stent in physiologic environment. The separation regions are configured to separate at about the same time period or separate at different time periods (within each ring or across the at least some rings). In a preferred example, the separation regions are configured to separate after expansion of the stent from a period ranging two weeks to two year, preferably separate from a period ranging from one month to 13 months, more preferably separate from a period ranging from 1 months to 9 months, and most preferably from a period ranging from 1.5 months to 8 months. In one example, the separation regions after forming and before expansion are held together to facilitate the structural integrity of the stent during expansion and to have sufficient strength to support a body lumen. The separation regions are held together by one or more material (such as adhesive, polymer, solder, etc), wherein the material degrades in physiologic environment after expansion of the stent allowing the separation region to separate forming discontinuities. The one or more material may be applied to the separation region, applied within the separation region, applied adjacent to the separation regions, applied to one surface of the at least some rings having the one or more separation regions, applied to all surfaces of the at least some rings having one or more separation region, or combination thereof. The discontinuities formed in this example are configured to allow the structural elements adjacent to the separation region to move in relationship to one another in a radial direction, circumferential direction, axial direction, or combination thereof. In another example, the stent is configured to have the one or more separation regions being held together as formed to facilitate the structural integrity of the stent during expansion and provide sufficient strength to support a body lumen. Examples of such separation region comprise geometrical configuration of structural elements adjacent to separation regions such as lock and key design, the thickness and width of the structural elements adjacent to the separation regions, and orientation of the structural elements adjacent to the separation regions. The separation regions after expansion of the stent in one example allow the structural elements adjacent to the separation region to move relative to one another in a radial direction, followed by circumferential direction or axial direction, or combination thereof. The stent may further be coated with at least one drug, one or more coating, or combination thereof. The stent in yet another example maybe configured to have the structural elements adjacent to the one or more separation regions separate and move relative to one another in radial, axial, circumferential direction, or combination thereof. In yet another example, the stent structural elements are configured to move in one or more direction sequentially or at the same time after expansion in physiologic conditions. In yet another example, the structural elements adjacent to the formed separation regions comprise one or more of the following configurations: embedded into one another, form a male/female configuration, form a butt joint, form a ball and socket configuration, may overlap one another in a parallel configuration, one element may fit into a groove of another element, or combination thereof. The structural elements adjacent to the separation region are in a preferred example held together before expansion, or upon expansion, and form discontinuities after expansion.

In another example of any of the examples in this application, the term radial compliance and radial strain are used interchangeably, and wherein the compliance refers to composite compliance of the at least some circumferential rings having one or more separation regions, and vessel (or mock vessel) together (segment compliance), and wherein the physiologic conditions comprise pressure change of about 100 mmHg. In a preferred example, the segment compliance after initial expansion and inward recoil from the initial expansion is typically less than 1%, usually less than 0.5%. The segment compliance after formation of at least some discontinuities is typically greater than 0.5%, preferably greater than 1%, more preferably greater than 1.5%, and most preferably greater than 2%. The segment stent in this example has inward recoil after an initial expansion typically ranging from 0% to 10%, usually 1% to 7%, and more preferably 1% to 5%, of the initial expansion diameter. The stent (or the at least some rings) in this example has an initial strength (10% crush resistance, after initial expansion and initial inward recoil), and wherein the initial strength decreases after formation of at least some discontinuities in the at least some rings, wherein the strength decreases by a magnitude ranging from 10% to 90% of the initial strength, usually ranging from 20% to 80% of the initial strength. The at least some rings in this example have an initial compliance (segment compliance) and an initial strength, wherein the strength decreases and the compliance increases after formation of at least some discontinuities, preferably after formation of substantially all discontinuities in a physiologic environment. The at least some rings in another example have an initial compliance (segment compliance) and an initial strength, wherein the strength decreases and the compliance increases after formation of at least some discontinuities, preferably after formation of substantially all discontinuities in a physiologic environment, while maintaining or increasing the diameter of the at least some rings after the initial expansion and after the initial inward recoil.

In yet another example, a stent prosthesis comprised of a plurality of circumferential rings, wherein the rings are axially connected, and wherein at least some rings, preferably all rings, have one or more separation regions along one or more circumferential path of each ring, and wherein the separation regions are configured to separate forming discontinuities after expansion of the stent in physiologic environment. The number of separation regions per ring typically ranges from 1 to 6 separation regions. The number of separation regions on at least two adjacent rings may be the same or different, or the separation regions on at least two adjacent rings may have the same orientation or different orientation. In another example, a stent comprised of a plurality of circumferential rings wherein the rings are axially connected. The stent of this example comprises a proximal segment, a middle segment, and a distal segment, along the length of the stent, and wherein each segment comprises one or more rings, wherein at least one segment does not have separation regions, in yet another example at least two segments do not have separation region, yet in another example one or more rings on either end of the stent are free from separation regions.

In one example of any of the examples in this application, the stent prosthesis comprises one or more of the following: an endoluminal stent wherein the stent is placed inside a duct, vessel, lumen, annulus, or organ; and an external stent wherein the stent is placed outside a duct, vessel, lumen, annulus, or organ; and covered stents (such as stent graft or valve stent) wherein the stent has one or more segments (one or more circumferential rings) covered with a different material such as PTFE material, wherein the stent is on the outside of the different material, on the inside of the different material, or wherein the different material is interwoven with the stent, or combination thereof. The stent graft allow the material to further expand and/or contract under physiologic environment after formation of discontinuities in the rings adjacent to the different material as described in various examples of this application; and other stent types.

In yet another example of any of the examples of this application, the non-degradable stent comprises one or more circumferential rings comprising structural elements of crowns and struts, and wherein the structural elements have one or more separation regions configured to separate after expansion of the stent in a physiologic environment, and wherein the structural elements adjacent to each separation region are held together before expansion of the stent in a physiologic environment, and said adjacent structural elements separate after expansion.

In another example of any of the examples of this application, a non-degradable stent is formed from a tube and patterned into a stent wherein the stent comprises a plurality of circumferential rings; each ring is connected axially to an adjacent ring, wherein each ring has one or more separation regions along the circumferential path of said ring. The separation regions are held together to maintain the circumferential structural integrity of each ring and configured to separate after expansion of the stent in a physiologic environment. The non-degradable stent, in a preferred example, further comprises one or more non-degradable axial links that remain intact after expansion. In yet another example, at least one link axially connecting every two adjacent rings remains intact after stent expansion. In yet another example, at least some adjacent rings remain connected by at least one axial link.

In a preferred example of any of the examples of this application, a stent prosthesis formed from a non-degradable metallic alloy material, wherein the stent comprises a plurality of circumferential rings, wherein each ring is connected to an adjacent ring, and wherein the stent being expandable from a crimped configuration to an expanded configuration and have sufficient strength in the expanded configuration to support a body lumen, and wherein at least some rings have one or more separation regions configured to form discontinuities in said circumferential rings after expansion in physiologic environment. In this preferred example, the at least some rings (or the stented segment comprising the at least some rings) after expansion of the stent in a physiologic environment (comprising systole and/or diastole pressure and/or infusion of a vaso-dilator) and before formation of substantially all discontinuities, exhibit one or more of the following: further enlargement of the at least some rings after the initial recoil from the expanded configuration, lumen positive remodeling, further expand and contract from the further expanded configuration of the at least some rings, increased segment compliance from an initial segment compliance after initial expansion and initial expansion inward recoil. In another example, the separation regions are held together by one or more material comprising one or more of polymers and adhesives, and wherein the one or more material are elastic under physiologic conditions, allowing the at least some rings to further expand and contract from further expanded configuration, under physiologic conditions, while substantially maintaining the expanded configuration of the stent (the expanded configuration after the initial inward recoil from the initial expansion of the stent). In a preferred example, the one or more materials are degradable polymer, or an adhesive that degrades in a physiologic environment.

In a preferred example of any of the examples of this application, a stent prosthesis formed from a non-degradable metallic alloy material, wherein the stent comprises a plurality of circumferential rings, wherein each ring is connected to an adjacent ring, and wherein the stent being expandable from a crimped configuration to an expanded configuration and have sufficient strength in the expanded configuration to support a body lumen, and wherein at least some rings have one or more separation regions that are held together, prior to expansion, by one or more non-degradable material wherein said one or more material maintains the structural integrity of the stent during expansion and wherein the stent has sufficient strength after expansion to support a body lumen, and wherein the material exhibit sufficient elasticity to allow movement of the separation regions in one or more of radial direction, axial direction, or circumferential direction, after expansion in physiologic environment. In this preferred example, the at least some rings (or the stented segment comprising the at least some rings) after expansion of the stent in a physiologic environment (comprising systole and/or diastole pressure and/or infusion of a vaso-dilator), exhibit one or more of the following: further expansion of the at least some rings after the initial recoil from the expanded configuration, lumen positive remodeling, further expand and contract from the further expanded configuration of the at least some rings. The one or more non-degradable material in one example comprises one or more polymeric and adhesive material. The stent in this example has sufficient strength to support a body lumen, inward recoil after an initial expansion ranging from 1% to 10%, preferably ranging from 2% to 7%, and a segment compliance ranging from 1% to 5% under pressure change of 100 mmHg. The stent initial strength after initial expansion maybe substantially maintained. The non-degradable material comprises one or more of: polymer, adhesive, or other non-degradable material having sufficient elasticity to allow displacement of the at least some rings adjacent to the separation regions in one or more direction comprising radial direction, circumferential, or axial direction. The material is applied to one or more of the following: inner surface of the separation regions, on at least on surface of the separation regions, adjacent to the separation regions, on at least one surface of the at least some rings, on all surfaces of the at least some rings. The coating thickness in one example ranges from 1 micron to 50 microns, preferably ranges from 3 microns to 25 microns, more preferably ranges from 5 microns to 20 microns. In one example, the separation regions contain non-degradable material holding the separation regions together during expansion and after expansion while allowing the at least some rings to have displacement adjacent to the separation regions in one or more directions, after expansion of the stent in physiologic environment. In one example, the separation regions have no gap, yet in another example, the separation regions have a gap ranging from 1 micron to 500 microns, usually 5 microns to 200 microns, more usually 10 microns to 100 microns, or 10 microns to 50 microns. The stent in the segment of the at least some rings exhibit one or more of the following: further expansion and contraction from said further expansion during mammalian systole and diastole, further expansion and contraction from use of a vaso-dilator, wherein the magnitude of the further expansion and contraction ranges from 0.05 mm to 3 mm, usually ranges from 0.7 mm to 2 mm, more usually ranges from 0.1 mm to 2 mm. In one example, the separation region has In a preferred example of any of the examples of this application, a non-degradable stent patterned from a non-degradable material comprises a plurality of circumferential rings being expandable from a crimped configuration to an expanded configuration, wherein at least some rings have one or more separation region being held together during expansion of the stent and form discontinuities after expansion in a physiologic environment and wherein the stent in the segment of the at least some rings exhibit one or more of the following: further expansion and contraction from said further expansion during mammalian systole and diastole, further expansion and contraction from use of a vaso-dilator, wherein the magnitude of the further expansion and contraction ranges from 0.05 mm to 3 mm, usually ranges from 0.7 mm to 2 mm, more usually ranges from 0.1 mm to 2 mm. In one example, the separation region have no gap, yet in another example, the separation regions have a gap ranging from 1 micron to 500 microns, usually 5 microns to 200 microns, more usually 10 microns to 100 microns, or 10 microns to 50 microns. In one example, the separation regions contain one or more degradable material that degrades under physiologic conditions.

In yet another preferred example of any of the examples of this application, a stent comprises a plurality of rings patterned from a non-degradable material wherein at least three rings have one or more separation regions, and wherein the separation regions within each of said rings contain one or more of the following: non-degradable material different from the stent material, degradable material, or a key and lock type configuration, and wherein the material and/or the key and lock type configuration maintain the structural integrity of the stent during expansion, and allow the stent at least three rings (or the stented segment adjacent to the at least three rings) to further expand and contract under physiologic conditions comprising systole and diastole pressure. In one example, the non-degradable material remains intact after expansion of the stent in physiologic environment. In another example, the degradable material degrades after expansion forming discontinuities in the separation regions. In yet another example, the separation regions are covered with a non-degradable sleeve that remains intact after expansion of the stent in physiologic conditions. The sleeve after expansion of the stent allows the movement of the struts and/or crowns adjacent to the separation regions to move in one or more directions.

In yet another preferred example of any of the examples of this application, a stent comprises a plurality of circumferential rings patterned from a non-degradable material wherein the stent being expandable from a crimped configuration to an expanded configuration, and wherein at least some rings have one or more separation regions, and wherein each separation region form a discontinuity in a strut and/or a crown of said at least some rings, and where said strut opposite ends and/or crown opposite ends adjacent to said discontinuity are held together by one or more comprising degradable material or non-degradable material, and wherein the stent expands substantially uniformly from the crimped configuration to the expanded configuration, and wherein the stent after expansion in physiologic environment is capable to further expand and contract wherein the further expansion and contraction are unaided by an operator or an external device.

In another example of any of the examples of this application, a stent comprising a plurality of circumferential rings, wherein the rings are axially connected along the length of the stent, and wherein at least some rings have one or more separation regions forming one or more discontinuities in the circumferential path of each said rings, and wherein the one or more separation regions are formed on a strut region and/or crown region of said rings. In one example, the at least some rings have the same number of separation regions. In another example, the at least some rings have different number of separation regions. In a third example, the orientation of the separation regions are the same or different. In a forth example, the stent has one or more rings having no separation regions.

In another example of any of the examples in this application, a stent formed from a non-degradable shape memory or springy material, wherein the stent comprises a plurality of circumferential rings patterned in a closed cell or open cell design, and wherein the stent being expandable from a crimped configuration to an expanded configuration and have sufficient strength to support a body lumen or an annulus open, and wherein the stent is pre-programed to expand to a nominal configuration or diameter and typically expanded to a smaller diameter lumen or annulus, and wherein at least some rings are configured to have one or more separation regions as described throughout this application, and wherein the separation regions after expansion of the stent form discontinuities in physiologic environment, allowing the at least some rings to exhibit one or more of the following: being expandable to a smaller configuration or diameter than the pre-programed configuration or diameter, being more accommodative or adaptive to the lumen or annulus adjacent to said at least some rings, increase compliance compared to an initial expanded compliance, strength decrease compared to an initial strength after initial expansion, reduced outward force onto the adjacent lumen or annulus tissue. In one example, the stent is self-expanding stent constrained in the crimped configuration and expanded by removing the constraint. In one example the stent material is NiTi alloy, or spring material such as spring steel.

In another example, a non-degradable stent comprising a plurality of non-degradable circumferential rings, wherein the rings are axially connected along the length of the stent, and wherein at least some rings have one or more separation regions forming one or more discontinuities in the circumferential path of each said rings after stent expansion in a physiologic environment, and wherein the one or more separation regions are formed on a strut region and/or crown region of said rings, and wherein at least some rings have one or more shape memory or springy material reinforcement elements coupled to one or more crowns on said at least some rings, and wherein the shape memory or springy elements span at least partially the crown region, preferably spans the entire crown region and into the adjacent struts regions, and wherein in a preferred example the shape memory or springy elements substantially conforms to the shape of the crown regions the elements are coupled to, and wherein the coupled elements further expand the crowns after stent expansion. In one example, the reinforcement elements are coupled to the same rings where the separation regions are formed, coupled to different rings, or at least some rings have both coupled elements and separation regions. In one example, the elements are coupled to one or more of the following on the crown: embedding the elements in a groove formed within the crown region, or attach the elements on top of the crown region, or attach the element on one or more surface regions of the crown, or embed inside a formed groove of a crown region, or other. In one example, the reinforcement element material is weaker than the stent non-degradable material. In another example, the crown region of the non-degradable material is hollowed out and the reinforcement material is placed in the hollowed out region of the crown. In another example, the separation regions are configured to separate from 30 days to 1 year after expansion of the stent, preferably from 1 month to 9 months after expansion of the stent. In one example, the stent material is NiTi alloy, or spring material such as spring steel.

In still further embodiments and examples of the present invention, separation regions may be provided in axial links between adjacent circumferential rings. Such circumferentially separable axial links will usually have one end located and attached at a circumferentially separable region within one circumferential ring and another end located and attached at another circumferentially separable region within an adjacent circumferential ring. In this way, after the scaffold expands in a physiologic environment, the axial links may circumferentially separate together with the circumferentially separable regions in each of the adjacent circumferential rings, and the two circumferential rings may circumferentially "uncage" while they remain axially linked by the remaining halves of the axial links which are joined to each of the adjacent circumferential rings. As described in greater detail below, the axial links may have a variety of different geometries, including linear, non-linear, S-shaped, ω-shaped, W-shaped, U-shaped, M-shaped, V-shaped, Z-shaped, and the like. The circumferential rings will typically comprise interconnected struts and crowns, as described previously, but may alternatively have other conventional structures, including closed-cell structures, diamond-shaped structures, and the like.

In certain exemplary embodiments, an endoluminal prosthesis comprises a scaffold having a plurality of circumferential rings arranged along an axis and patterned from a non-degradable material. The scaffold will typically be configured to expand from a crimped configuration to an expanded configuration, either by balloon expansion or by self-expansion upon release from constraint. At least some of the circumferential rings will typically be circumferentially separable and be joined by circumferentially separable axial links. The circumferentially separable axial links typically will be configured to circumferentially separate along separation interfaces, e.g. opposed surfaces which have been laser cut or patterned into the links after an initial pattern of the scaffold has been formed from a tubular or other substrate. In these embodiments, at least some of the circumferentially separable axial links will be configured to bend and/or elongate when the scaffold is implanted in a body lumen, e.g. during expansion and implantation of the scaffold. The circumferentially separable regions of the circumferential rings and the axial links will be initially immobilized usually by a biodegradable polymer and/or adhesive which degrades in a body lumen or other physiologic environment in order to release the separable regions so that they can expand in situ. In this way, discontinuities will form in each of the axial links and adjacent regions of the circumferential rings after expansion of the scaffold in such a physiologic environment.

In particular examples, the separation interfaces will have opposed non-linear congruent surfaces which nest together prior to circumferential separation. For example, the separation interfaces may have opposed curve surfaces which nest together prior to separation. The curve surfaces may have one or more S-shaped bends, or more ω-shaped bends, one or more U-shaped bends, one or more M-shaped bends, one or more V-shaped bends, one or more Z-shaped bends, or the like.

Such curved surfaces will typically follow a reversing path. For example, the interfaces may extend from a first circumferential ring in a first generally circumferential direction and turn to extend in an opposite generally circumferential direction, for example displaying or comprising a generally U-shaped geometry. Often, the interfaces may turn at least one more time to extend once again in the first circumferential direction before attaching to the second circumferential ring, for example following a S-shaped or Z-shaped path. Sometimes, the curved surfaces may turn at least one more time before they attach to the second circumferential ring, for example following a W-shaped or ω-shaped path. In still other instances the curved surfaces may turn at least two, three, four or more times prior to attaching to the second circumferential ring, for example following a serpentine or zig-zag path A particular advantage of axial links having non-linear and/or curved interface surfaces is that the lengths of the interfaces may be made longer than the distances between the locations on the circumferential rings which are being held together by the axial links. Often, such curved or other non-linear surfaces will have an end-to-end length when straightened which is at least twice as long as the end-to-end length prior to straightening, often being at least three times as long, frequently being at least four times as long, and optionally being five times, six times, or even ten times as long as the end-to-end length prior to straightening. Often, such curved or other non-linear surfaces will have an end-to-end length when straightened which is at least twice as long as the distance along the axis between the circumferential rings being connected, often being at least three times as long, frequently being at least four times as long, and optionally being five times, six times, or even ten times as long as the distance along the axis between the circumferential rings being connected. Such extended surface lengths provide extended engagement lengths between the opposed interface surfaces prior to separation which, in turn, enhances the ability to immobilize the surfaces with a biodegradable polymer, adhesive, or the like, as described elsewhere herein.

As described thus far, at least one circumferentially separable axial link will be positioned between each adjacent pair of circumferential rings. In many instances and examples, there will be at least two circumferentially separable regions joined respectively by at least two circumferentially separable axial links between at least some of the adjacent circumferential rings. In other instances, separation regions in adjacent circumferential rings may be joined by at least three circumferentially separable axial links, while in still further examples they may be joined by four or more circumferentially separable axial links.

In still other embodiments and examples, the separation interfaces within the axial links may have axial separation gaps, and the gaps may be arranged in different directions and patterns. For example, in some instances, the axial separation gaps may be arranged in a directionally reversing pattern, and in still further examples such axially aligned separation gaps may be aligned in a circumferential direction or may be aligned at an angle oblique to the circumferential direction.

In many specific instances, the circumferential rings which are joined by circumferentially separable axial links will comprise a plurality of struts joined by crowns as described in detail elsewhere herein. In such instances, the circumferentially separable axial links may be connected between separable regions on the crowns of the adjacent circumferential links, on the struts of the adjacent circumferential links, or on both crowns and struts of the adjacent circumferential links. In particular, the separable axial links may be connected peak-to-peak between crowns on adjacent circumferential rings, may be connected peak-to-valley between crowns on adjacent circumferential links, or may be connected valley-to-valley between crowns on adjacent circumferential rings. In still other instances, the circumferentially separable axial links may be connected between struts on adjacent circumferential rings, or between any locations on a crown on one circumferential ring and a strut on another circumferential ring.

In still further embodiments and examples of scaffolds having circumferentially separable axial links, the biodegradable polymer and/or adhesive may cover at least a portion of a luminal and/or abluminal surface of the axial link and at least a portion of a luminal and/or an abluminal surface of the circumferential ring adjacent to the axial link. In many instances, the biodegradable polymer and/or adhesive may cover most or all of an entire luminal and/or abluminal surface of the scaffold, and in some instances may cover substantially the entire scaffold, e.g. if the scaffold has been coated by dipping or other conventional techniques which covers all surfaces.

In still further examples and embodiments, the circumferentially separable axial links may have a first segment extending between a first separable portion of an adjacent circumferential ring and a second segment extending between a second portion of the adjacent circumferential ring. The first and second segments of the separable link may have the same width or in other instances may have different widths. In still other instances, the segments of the axial links may have widths that vary along their lengths. Having different widths, or widths that vary along the length of the interface, assists bending of the link during expansion; helps maintain the bond of the interface during expansion; and assists uncaging of the scaffold by reducing interference between adjacent structural elements during expansion. The inner or outer portions of the interfaces may be wider or narrower than the opposing side. The width of either side may be variable along the length with narrowing occurring at the curves of the interface or at the junction of the axial link with the structural elements. Often, the luminal and abluminal surfaces of the first and the second segments of the axial link are coplanar, i.e. so that the first and second segments have the same thicknesses in a radial direction, typically having coplanar surfaces will result in the axial links having substantially the same thickness as at least adjacent portions of the circumferential ring and typically the scaffold as a whole.

In some instances of the present invention, the circumferentially separable axial links between adjacent circumferential rings may have specific configurations intended to lock the separable regions of the axial link together prior to expansion and exposure in a physiologic environment. For example, the axial links may be formed as a nested wedge typically having a male portion on one segment of the link and a female portion on the apposed segment of the link where the male and female portions have an interference fit prior to expansion of the scaffold. In specific instances, the nested wedges may each have a trapezoidal geometry. Other shapes are possible, particularly those that provide an interference fit between adjacent portions of the axial link at least prior to radial expansion of the scaffold. In still further examples and embodiments of the present invention, the circumferential rings which form a scaffold may all be joined by axial links and all of said axial links may be circumferentially separable. In many instances, the circumferentially separable axial links will be axially aligned along the scaffold so that, after separation of the axial links and the circumferential rings, the scaffolds will separate into at least two unconnected axial segments, frequently separating into at least three circumferentially separate axial segments, and sometimes separating into four or more circumferentially separated axial segments.

In still other particular examples and embodiments, the scaffolds will be arranged so that they do not separate into unattached axial segments after discontinuities form in all separation regions. For example, certain scaffolds will include a plurality of circumferential rings in a "mid-scaffold region" of the scaffold and at least one end circumferential ring located at an end of the scaffold. In such instances, while all of the circumferential rings may separate in the mid-region, at least one of the end circumferential rings will remain attached to the other rings so that the remaining rings may not separate. For example, either or both of the end circumferential rings may have portions which circumferentially bridge axial segments of the scaffold which would otherwise circumferentially separate in the absence of these bridging regions.

In still other examples and embodiments of the present invention, the endoluminal prostheses comprise scaffolds having circumferential rings comprising crowns and struts. Circumferentially separable axial links will extend between a first circumferentially separable location on a first circumferential ring and a second circumferentially separable location on a second circumferential ring. At least the first circumferentially separable location is not located on the peak of a crown of a circumferential ring. The first circumferentially separable location may be on a crown valley, or on a strut. The second circumferentially separable location may be on any of a crown peak, a crown valley, or a strut.

The following numbered clauses describe other examples, aspects, and embodiments of the inventions described herein:

Clause 1. An endoluminal prosthesis comprising:

a scaffold having a plurality of circumferential rings patterned from a non-degradable material, said scaffold being configured to expand from a crimped configuration to an expanded configuration;

wherein the scaffold has at least two end rings and a plurality of mid-scaffold rings between said end rings and wherein at least one of the end rings has one or more separation regions configured to form one or more discontinuities in said at least one end ring after expansion of the scaffold in a physiologic environment.

Clause 2. An endoluminal prosthesis as in clause 1, wherein both of the end rings have one or more separation regions configured to form discontinuities after expansion of the scaffold in a physiologic environment.

Clause 3. An endoluminal prosthesis as in clause 1 or 2, wherein at least some of mid-scaffold rings have fewer separation regions than at least one of the end rings.

Clause 4. An endoluminal prosthesis as in clause 1, wherein at least some of the mid-scaffold rings have no separation regions.

Clause 5. An endoluminal prosthesis as in clause 1, wherein at least some of the circumferential rings comprise a plurality of struts joined by crowns and said separation regions are formed in the crowns, the struts, or both.

Clause 6. A method for reducing a mismatch in vessel compliance between a stented vessel segment and an adjacent unstented vessel, said method comprising implanting an endoluminal prosthesis as in any one of clauses 1 to 5 in a blood vessel, wherein the end rings form a greater number of discontinuities than are formed by adjacent mid-scaffold rings ring after expansion of the scaffold in a physiologic environment.

Clause 7. An endoluminal prosthesis as in clause 1, wherein the at least one end ring is configured to have one or more discontinuities circumferentially separating said end ring into two or more sections before expansion of the scaffold in a physiologic environment.

Clause 8. An endoluminal prosthesis as in clause 1, wherein both end rings are configured to each form one or more discontinuities circumferentially separating said end rings into two or more sections before expansion of the scaffold in a physiologic environment.

Clause 9. An endoluminal prosthesis as in clause 1, wherein at least some rings are configured to form one or more discontinuities circumferentially separating said rings each into two or more sections before expansion of the scaffold in a physiologic environment.

Clause 10. An endoluminal prosthesis as in clause 1, wherein at least some rings have one or more separation regions configured to form one or more discontinuities in said rings after expansion of the scaffold in a physiologic environment within a period ranging from 1 minute to 3 days.

Clause 11. An endoluminal prosthesis as in clause 1, wherein at least some rings are configured to have one or more discontinuities in said rings circumferentially bisecting each said ring into two or more sections before expansion of the scaffold in a physiologic environment, and wherein the two or more sections of each ring are contained in a sleeve, wherein the sleeve is holding said sections together to expand the stent uniformly and wherein the sleeve holding the at least two sections allow said section to move in one or more directions after expansion of the stent in physiologic environment.

Clause 12. An endoluminal prosthesis as in 11, wherein the sleeve comprises at least one non-degradable material that loosens after expansion of the stent in physiologic environment, and wherein the sleeve continues to contain the two or more sections of each ring.

Clause 13. An endoluminal prosthesis as in 11, wherein the sleeve comprises at least one degradable material that degrades after expansion of the stent in physiologic environment.

Clause 14. An endoluminal prosthesis as in clause 1, wherein the at least one end ring is configured to have one or more discontinuities circumferentially separating said end ring into two or more sections before expansion of the scaffold in a physiologic environment, and wherein said separated sections are held together till after expansion of the stent allowing the stent to expand uniformly before separating or moving in one or more directions.

Clause 15. An endoluminal prosthesis as in clause 1, wherein the at least one end ring is configured to have one or more discontinuities circumferentially separating said end ring into two or more sections before expansion of the scaffold in a physiologic environment, and wherein said separated sections are held together during expansion of the stent allowing the stent to expand uniformly before separating or moving in one or more directions.

Clause 16. An endoluminal prosthesis comprising:
a scaffold having a plurality of circumferential rings patterned from a non-degradable material, said scaffold being configured to expand from a crimped configuration to an expanded configuration, wherein at least some of the circumferential rings comprise one or more separation regions configured to form a discontinuity having free ends in said at least one ring after expansion of the scaffold in a physiologic environment; and
a non-degradable protective structure at least partially covering the separation region to protect an adjacent luminal wall from the free ends after formation of the discontinuity.

Clause 17. An endoluminal prosthesis as in clause 16, wherein the non-degradable protective structure comprises a porous, non-degradable material.

Clause 18. An endoluminal prosthesis as in clause 17, wherein the porous, non-degradable material comprises a porous, non-degradable polymer.

Clause 19. An endoluminal prosthesis as in clause 16, wherein the non-degradable protective structure comprises an open lattice formed from a non-degradable material.

Clause 20. An endoluminal prosthesis as in clause 19, wherein the non-degradable material comprises a non-degradable polymer.

Clause 21. An endoluminal prosthesis as in clause 16, wherein at least some struts and/or crowns have one or more separations regions bisecting said struts and/or crowns.

Clause 22. An endoluminal prosthesis as in clause 16, wherein the separation regions further comprise a degradable polymeric material.

Clause 23. An endoluminal prosthesis as in clause 16, wherein the non-degradable material comprises a non-degradable polymer and wherein the non-degradable polymer grips the separation region holding it together until after expansion of the scaffold to the expanded configuration, wherein the non-degradable polymer after expansion loosens allowing movement of the separation region in one or more directions comprising radial, circumferential, longitudinal, or combination thereof.

Clause 24. An endoluminal prosthesis comprising:
a scaffold having a plurality of circumferential rings patterned from a non-degradable material, said scaffold being configured to expand from a crimped configuration to an expanded configuration, at least some of said circumferential rings being joined by axial junctions;
wherein at least some of the axial junctions have at least one separation region configured to form at least one discontinuity between adjacent circumferential rings after expansion of the scaffold in a physiologic environment.

Clause 25. An endoluminal prosthesis as in clause 24, wherein the axial junctions extend between crowns on adjacent turns of the helical backbone.

Clause 26. An endoluminal prosthesis as in clause 24, wherein the axial junctions extend between struts on adjacent turns of the helical backbone.

Clause 27. An endoluminal prosthesis as in clause 24, wherein the axial junctions extend between crowns and struts on adjacent turns of the helical backbone.

Clause 28. An endoluminal prosthesis as in clause 24, wherein the axial junctions comprise axial links.

Clause 29. An endoluminal prosthesis as in clause 24, wherein the axial junctions comprise direct fusion between adjacent circumferential rings.

Clause 30. An endoluminal prosthesis comprising:
a scaffold having a plurality of circumferential rings patterned from a degradable material, said scaffold being configured to expand from a crimped configuration to an expanded configuration;
wherein at least some of the circumferential rings have at least one separation region configured to form at least one discontinuity after expansion of the scaffold in a physiologic environment;
wherein at least some of the separation regions are configured to form discontinuities more rapidly than the degradable material of the scaffold degrades in the in the physiologic environment.

Clause 31. An endoluminal prosthesis as in clause 30, wherein the degradable material comprises a degradable polymer or a degradable metal.

Clause 32. An endoluminal prosthesis as in clause 30, wherein the degradable material comprises a degradable material selected from a group consisting of polylactide, PLLA, PDLA and poly lactic acid polymers and co polymers, polycarbonate polymers and co-polymers, Magnesium alloy, and other metal and metal alloy, or combination thereof.

Clause 33. An endoluminal prosthesis as in clause 30, wherein the degradable polymer will persist in the physiologic environment for a period of at least one year, two years, three years, four years, or five years.

Clause 34. An endoluminal prosthesis as in clause 34, wherein the separation regions form discontinuities in the in a physiologic environment after a period of more than one week but less than one month, two months, three months, six months, or one year.

Clause 35. An endoluminal prosthesis as in clause 34, wherein the separation regions configured to form discontinuities more rapidly than the degradable material degrades in the in the physiologic environment bisect the circumferential path of at least one circumferential ring.

Clause 36. An endoluminal prosthesis comprising:

a helical backbone having a plurality of struts joined by a plurality of crowns, wherein the helical backbone includes a multiplicity of adjacent turns and wherein at least some of the adjacent turns are attached to each other by a separation region.

Clause 37. An endoluminal prosthesis as in clause 36, wherein the separation regions are disposed between immediately adjacent turns of the helical backbone.

Clause 38. An endoluminal prosthesis as in clause 37, wherein the separation region are disposed between adjacent pairs of crowns.

Clause 39. An endoluminal prosthesis as in clause 37, wherein the separation region are disposed on struts between a crown on one turn and strut on an adjacent turn.

Clause 40. An endoluminal prosthesis as in clause 37, wherein the separation region are disposed on struts between adjacent pairs of struts.

Clause 41. An endoluminal prostheses as in clause 36, wherein the helical backbone has a serpentine arrangement.

Clause 42. An endoluminal prosthesis as in clause 36, wherein the helical backbone has a zig-zag arrangement.

Clause 43. An endoluminal prosthesis as in clause 36, wherein the helical backbone is formed from a bent wire.

Clause 44. An endoluminal prosthesis as in clause 36, wherein the helical backbone is formed from a patterned tube Clause 45. An endoluminal prosthesis comprising:
a helically wound serpentine backbone having a multiplicity of adjacent turns, wherein at least some of the adjacent turns are attached to each other by a separation region and/or have separation regions formed therein.

Clause 46. An endoluminal prosthesis as in clause 45, wherein at least some of the separation regions are disposed between immediately adjacent turns of the helical backbone.

Clause 47. An endoluminal prosthesis as in clause 46, wherein the helically wound serpentine backbone comprises a plurality of struts joined by a plurality of crowns Clause 48. An endoluminal prosthesis as in clause 47, wherein at least some the separation region are disposed between adjacent pairs of crowns.

Clause 49. An endoluminal prosthesis as in clause 48, wherein at least some the separation region are disposed on struts between a crown on one turn and strut on an adjacent turn.

Clause 50. An endoluminal prosthesis as in clause 47, wherein at least some the separation region are disposed on struts between adjacent pairs of struts.

Clause 51. An endoluminal prosthesis as in clause 45, wherein at least some of the separation regions are formed in turns of the helical backbone.

Clause 52. An endoluminal prosthesis as in clause 51, wherein the helically wound serpentine backbone comprises a plurality of struts joined by a plurality of crowns.

Clause 53. An endoluminal prosthesis as in clause 52, wherein at least some the separation region are disposed in crowns of the serpentine backbone.

Clause 54. An endoluminal prosthesis as in clause 52, wherein at least some the separation region are disposed in struts of the serpentine backbone.

Clause 55. An endoluminal prosthesis as in clause 45, wherein the helical backbone is formed from a bent wire.

Clause 56. An endoluminal prosthesis as in clause 45, wherein the helical backbone is formed from a patterned tube.

Clause 57. New CLAUSE set for a separation regions bisecting two or more joined crowns on separate rings (turns), and/or two or more joined struts on separate rings (turns), and/or one crown on one ring joined to a strut on another ring.

Clause 58. An endoluminal prosthesis comprising:
a scaffold having a plurality of circumferential rings patterned from a non-degradable material, said scaffold being configured to expand from a crimped configuration to an expanded configuration, wherein at least some of the circumferential rings comprise one or more separation regions wherein at least one separation region is configured to bisect two or more adjacent rings, and wherein said separation region forms one or more discontinuity after expansion of the scaffold in a physiologic environment.

Clause 59. An endoluminal prosthesis as in clause 58, wherein the separation region bisects two crowns on adjacent rings and a link joining said two crowns.

Clause 60. An endoluminal prosthesis as in clause 58, wherein the separation region bisects two struts on adjacent rings and a link joining said two struts.

Clause 61. An endoluminal prosthesis as in clause 58, wherein the separation region bisects a crown on one ring and a strut on an adjacent rings and a link joining said crown and strut.

Clause 62. An endoluminal prosthesis as in clause 58, wherein the separation region bisects two joined or fused crowns on adjacent rings.

Clause 63. An endoluminal prosthesis as in clause 58, wherein the separation region bisects two joined or fused struts on adjacent rings.

Clause 64. An endoluminal prosthesis as in clause 58, wherein the separation region bisects a crown on one ring joined or fused to a strut on an adjacent ring.

Clause 65. An endoluminal prosthesis as in clause 58, wherein the two or more rings after formation of discontinuities circumferentially separate.

Clause 66. An endoluminal prosthesis as in clause 58, wherein the two or more rings after formation of discontinuities circumferentially separate into closed cell pattern.

Clause 67. An endoluminal prosthesis as in clause 58, wherein the two or more rings after formation of discontinuities circumferentially separate and have no free ends after separation.

Clause 68. An endoluminal prosthesis as in clause 58, wherein the two or more rings after formation of discontinuities circumferentially separate into axially connected closed cell pattern.

Clause 69. A stent prosthesis comprising:
a scaffold having one or more circumferential rings patterned from a non-degradable material, said scaffold being configured to expand from a crimped configuration to an expanded configuration, wherein at least one of the circumferential rings comprises one or more separation regions bisecting or cutting said one or more rings wherein the separation regions uncage after expansion of the scaffold in a physiologic environment.

Clause 70. A stent prosthesis as in clause 69, wherein the scaffold is expanded in a heart annulus to replace or repair a heart valve.

Clause 71. A stent prosthesis as in clause 69, wherein the one or more separation regions comprise one or more of hinge junctions, butt junction, male and female junctions, key and lock junction, or other type junctions, or combination thereof, wherein at least some of the junctions are held together during expansion of the stent, and wherein the junctions are configured to separate and/or form discontinuities and/or move in one or more directions after expansion of the stent.

Clause 72. A stent prosthesis as in clause 69, wherein the one or more separation regions are held together by one or more materials.

Clause 73. A stent prosthesis as in clause 69, wherein the one or more separation regions are held together by one or more degradable polymers.

Clause 74. A stent prosthesis as in clause 69, wherein the one or more separation regions are held together by one or more elastic membrane.

Clause 75. A stent prosthesis as in clause 69, wherein the stent comprises an elastic membrane circumferentially covering two or more adjacent rings, and wherein the membrane covers one or more separation regions.

Clause 76. A stent prosthesis as in clause 69, wherein the stent comprises an elastic membrane circumferentially covering two or more adjacent rings, and wherein the membrane is formed from one or more degradable polymeric material, wherein the material degrades after expansion of the stent under physiologic conditions.

Clause 77. A stent prosthesis as in clause 69, wherein the stent comprises an elastic membrane circumferentially covering two or more adjacent rings, and wherein the membrane is formed from one or more non-degradable material.

Clause 78. A stent prosthesis as in clause 69, wherein the stent comprises an elastic membrane circumferentially covering two or more adjacent rings, and wherein the membrane covers one or more separation regions, and wherein the elastic membrane is configured to expand and/or move in one or more directions after the one or more covered separation regions form one or more discontinuities and/or move in one or more directions.

Clause 79. A stent as in clause 69, wherein the one or more separation regions after uncaging move in one or more direction, wherein the one or more directions comprises one or more longitudinal, radial, circumferential, and combination thereof.

Clause 80. A stent prosthesis as in clause 69, wherein the stent comprises an elastic membrane circumferentially covering two or more adjacent rings, and wherein the membrane covers one or more separation regions, and wherein the elastic membrane is configured to expand and/or move in one or more directions in conformance with the one or more covered separation regions forming one or more discontinuities and/or move in one or more directions.

Clause 81. A stent prosthesis as in clause 69, wherein the stent comprises an elastic membrane circumferentially covering two or more adjacent rings, and wherein the membrane covers one or more separation regions, and wherein the elastic membrane is configured to expand and/or move in one or more directions adapting to the one or more covered separation regions forming one or more discontinuities and/or move in one or more directions.

Clause 82. A stent prosthesis as in clause 69, wherein the stent comprises two or more elastic membranes each circumferentially covering two or more adjacent rings and at least one ring in between said two or more elastic membranes, wherein said at least one ring has one or more separation regions not covered by membrane.

Clause 83. A stent prosthesis as in clause 69, wherein the stent comprises two or more elastic membranes each circumferentially covering two or more adjacent rings and at least one ring in between said two or more elastic membranes, wherein said at least one ring has one or more separation regions not covered by membrane, and wherein the two or more membranes are joined on portions of the at least one ring in between.

Clause 84. A stent prosthesis as in clause 69, wherein the stent is balloon expandable, or self-expandable.

Clause 85. A stent prosthesis as in clause 69, wherein the stent comprises an artificial valve contained circumferentially by one or more rings of the stent and wherein the valve is sutured and/or affixed to the stent.

Clause 86. A stent prosthesis as in clause 69, wherein the stent expands to a substantially cylindrical configuration, and wherein the stent after formation of discontinuities and/or allowed to move in one or more directions expand further to a different configuration.

Clause 87. A stent prosthesis as in clause 69, wherein the stent expands to a first configuration, and wherein the stent after formation of discontinuities and/or allowed to move in one or more directions changes to a different configuration.

Clause 88. A stent prosthesis as in clause 69, wherein the stent expands to a first configuration, and wherein the stent after formation of discontinuities and/or allowed to move in one or more directions changes to a second configuration, wherein the second configuration is different than the first configuration.

Clause 89. A stent prosthesis as in clause 69, wherein the stent comprises one or more membranes covering one or more rings circumferentially, covered by one or more rings circumferentially, or sandwiched in between two membranes.

Clause 90. A stent prosthesis as in clause 69, wherein the stent comprises one or more membranes inside, outside, or sandwiching one or more rings like a sleeve.

Clause 91. A stent prosthesis as in clause 69, wherein the stent has a first configuration after expansion of the stent and wherein the stent has a second different configuration after uncaging one or more separation regions, and wherein the second configuration contours to the tissue geometry adjacent to the one or more separation regions.

Clause 92. A stent prosthesis as in clause 69, wherein the stent has a first configuration after expansion of the stent and wherein the stent has a second different configuration after uncaging one or more separation regions, and wherein the second configuration prevents blood leaks between the stent and adjacent tissue.

Clause 93. A stent prosthesis as in clause 69, wherein the stent has a first configuration after expansion of the stent and wherein the stent has a second different configuration adjacent to one or more membranes circumferentially covering two or more rings of the stent, said second configuration is configured after uncaging one or more separation regions, and wherein the second configuration prevents blood leaks between the stent and adjacent tissue.

Clause 94. A stent prosthesis as in clause 69, wherein the stent has one or more separation regions in one or more rings, and wherein said one or more separation regions expand the stent to a second expanded configuration to accommodate changes in tissue geometric configuration, thereby inhibiting blood leaks between the stent and adjacent tissue.

Clause 95. A stent as in clause 69, wherein the stent is configured to have an outward force after expansion of the stent in a heart annulus to maintain contact between the stent and adjacent annulus tissue, and wherein the one or more separation regions outward force is decreased after uncaging while substantially maintaining the contact between the stent and adjacent tissue.

Clause 96. A stent as in clause 69, wherein the stent is configured to contour to the adjacent tissue after uncaging of the one or more separation regions, and wherein the stent exhibits one or more of movement, pulsatility, positive adaptive remodeling, and/or contractility, or combination thereof.

Clause 97. A stent as in clause 69, wherein the uncaging comprises one or more of formation of one or more discontinuities, movement in one or more direction comprising longitudinal, radial, and/or circumferential, or other, or combination thereof.

Clause 98. A stent prosthesis as in clause 69, wherein the stent comprises one or more axial links connecting adjacent rings and wherein at least some axial links remain intact.

Clause 99. A stent as in clause 69, wherein the stent has a first crush resistance force after expansion of the stent and wherein the stent has a second crush resistance force after uncaging and wherein the second crush resistance force is smaller than the first crush resistance.

Clause 100. A stent prosthesis as in clause 69, wherein the stent comprises one or more membranes and wherein the membrane has porosity to allow incorporation with the adjacent tissue.

Clause 101. A stent as in clause 69, wherein the stent has a first compliance after expansion of the stent and wherein the stent has a second compliance after uncaging and wherein the second compliance is larger than the first compliance.

Clause 102. A stent as in clause 69, wherein the stent spans a heart annulus, superior region to heart annulus, and an inferior region to the heart annulus, and wherein the one or more separation regions are located adjacent to the heart annulus, adjacent to said superior region, and/or adjacent to said inferior region to the heart annulus.

Clauses Directed at Separable Flexible Axial Links Between any Type of Circumferentially Separable Circumferential Ring:

Clause 103. An endoluminal prosthesis comprising:

a scaffold having a plurality of circumferential rings arranged along an axis and patterned from a non-degradable material, said scaffold being configured to expand from a crimped configuration to an expanded configuration;

wherein at least some of the circumferential rings are circumferentially separable, joined by circumferentially separable axial links, and configured to circumferentially separate along separation interfaces;

wherein at least some of the circumferentially separable axial links are configured to bend and/or elongate when the scaffold is implanted in a body lumen; and wherein circumferentially separable regions of the circumferential rings and the axial links comprise a biodegradable polymer and/or adhesive configured to form at least one discontinuity in the circumferential ring and the axial link after expansion of the scaffold in a physiologic environment.

Clause 104. An endoluminal prosthesis as in clause 103, wherein at least some of the circumferential rings comprise struts joined by crowns.

Clause 105. An endoluminal prosthesis as in clause 103 or 104, wherein the separation interfaces have opposed, non-linear congruent surfaces which nest together prior to separation.

Clause 106. An endoluminal prosthesis as in any of clauses 103-105, wherein the separation interfaces have opposed, curved surfaces which nest with together prior to separation.

Clause 107. An endoluminal prosthesis as in any of clauses clause 103-106, wherein the separation interfaces have one or more S-shaped bends.

Clause 108. An endoluminal prosthesis as in any of clauses 103-106, wherein the separation interfaces have one or more w-shaped bends.

Clause 109. An endoluminal prosthesis as in any of clauses 103-106, wherein the separation interfaces have one or more m-shaped bends.

Clause 110. An endoluminal prosthesis as in any of clauses 103-106, wherein the separation interfaces have one or more v-shaped bends.

Clause 111. An endoluminal prosthesis as in clauses 103 or 106, wherein the separation interfaces have one or more Z-shaped bends.

Clause 112. An endoluminal prosthesis as in any of clauses 103-106, wherein the separation interfaces extend from a first circumferential ring in a first generally circumferential direction, turn to extend in an opposite generally circumferential direction, and turn again to extend in the first circumferential direction before they attach to a second circumferential ring.

Clause 113. An endoluminal prosthesis as in clause 112, wherein the separation interfaces turn at least one more time to extend in the opposite circumferential direction before they attach to a second circumferential ring.

Clause 114. An endoluminal prosthesis as in clause 112, wherein the separation interfaces turn at least two more times to extend in the opposite circumferential direction before they attach to the second circumferential ring.

Clause 115. An endoluminal prosthesis as in any of clauses 103-114, wherein at least some of the separation interfaces have a length when straightened which is at least twice as long as their length along the axis of the scaffold between adjacent rings prior to straightening.

Clause 116. An endoluminal prosthesis as in any of clauses 103-114, wherein at least some of the separation interfaces have a length when straightened which is at least three times as long as their length along the axis of the scaffold between adjacent rings prior to straightening.

Clause 117. An endoluminal prosthesis as in any of clauses 103-114, wherein at least some of the separation interfaces have a length when straightened which is at least four times as long as their length along the axis of the scaffold between adjacent rings prior to straightening.

Clause 118. An endoluminal prosthesis as in any of clauses 103-117 wherein at least some of the circumferential rings have at least two circumferentially separable regions joined respectively by at least two circumferentially separable axial links to at least two circumferentially separable regions on an adjacent circumferential ring.

Clause 119. An endoluminal prosthesis as in any of clauses 103-118 wherein at least some of the circumferential rings have at least three circumferentially separable regions joined respectively by at least three circumferentially separable axial links to at least three circumferentially separable regions on an adjacent circumferential ring.

Clause 120. An endoluminal prosthesis as in any of clauses 103-119 wherein the separation interfaces have axial separation gaps arranged in a directionally reversing pattern.

Clause 121. An endoluminal prosthesis as in clause 120 wherein the separation gaps are aligned in a circumferential direction.

Clause 122. An endoluminal prosthesis as in clause 120 wherein the separation gaps are aligned at an angle oblique to the circumferential direction.

Clause 123. An endoluminal prosthesis as in any of clauses 103-122, wherein the separable axial links are connected between separable regions on crowns of adjacent circumferential rings.

Clause 124. An endoluminal prosthesis as in clause 123, wherein the separable axial links are connected peak-to-peak.

Clause 125. An endoluminal prosthesis as in clause 123, wherein the separable axial links are connected peak-to-valley.

Clause 126. An endoluminal prosthesis as in clause 123, wherein the separable axial links are connected valley-to-valley.

Clause 127. An endoluminal prosthesis as in any of clauses 103-122, wherein the separable axial links are connected between struts on adjacent circumferential rings.

Clause 128. An endoluminal prosthesis as in any of clauses 103-122, wherein the separable axial links are connected between a crown on one circumferential ring and a strut on an adjacent circumferential ring.

Clause 129. An endoluminal prosthesis as in any of clauses 103-128, wherein the biodegradable polymer and/or adhesive covers at least a luminal and/or an abluminal surface of the axial link.

Clause 130. An endoluminal prosthesis as in clause 129, wherein the biodegradable polymer and/or adhesive covers at least luminal and/or abluminal surfaces of the axial link and luminal and/or abluminal surfaces of the circumferential ring adjacent to the axial link.

Clause 131. An endoluminal prosthesis as in clause 130, wherein the biodegradable polymer and/or adhesive covers at least an entire luminal and/or abluminal surfaces of the scaffold.

Clause 132. An endoluminal prosthesis as in any of clauses 103-131, wherein the separable links have a first segment extending between first separable portions of the adjacent circumferential rings and a second segment extending between second separable portions of the adjacent circumferential rings.

Clause 133. An endoluminal prosthesis as in clause 132, wherein the first segment and the second segment have the same widths.

Clause 134. An endoluminal prosthesis as in clause 132, wherein the first segment and the second segment have different widths.

Clause 135. An endoluminal prosthesis as in clause 132, wherein luminal and abluminal surfaces of the first segment and the second segment are coplanar.

Clause 136. An endoluminal prosthesis as in clause 132, wherein the first segment and the second segment have the same thickness in a radial direction.

Clause Directed at Nested Wedge:

Clause 137. An endoluminal prosthesis comprising:

a scaffold having a plurality of circumferential rings arranged along an axis and patterned from a non-degradable material, said scaffold being configured to expand from a crimped configuration to an expanded configuration;

wherein at least some of the circumferential rings are circumferentially separable, joined by circumferentially separable axial links, and configured to circumferentially separate along separation interfaces;

wherein at least some of the circumferentially separable axial links comprise nested wedges with having a male portion and a female portion with an interference fit prior to expansion of the scaffold; and wherein circumferentially separable regions of the circumferential rings and/or the axial links comprise a biodegradable polymer and/or adhesive configured to form at least one discontinuity in the circumferential ring and the axial link after expansion in of the scaffold in a physiologic environment.

Clause 138. An endoluminal prosthesis as in clause 137, wherein the nested wedges have a trapezoidal geometry.

Clause 139. An endoluminal prosthesis as in clause 137 or 138, wherein at least some of the circumferential rings comprise a plurality of struts joined by crowns.

Clause 140. An endoluminal prosthesis as in any of clauses 103-139, 141, 143, and 144, wherein the non-degradable material comprises one or metal or metal alloy.

Clauses Directed at all Axial Links being Separable:

Clause 141. An endoluminal prosthesis comprising:

a scaffold having a plurality of circumferential rings arranged along an axis and patterned from a non-degradable material, said scaffold being configured to expand from a crimped configuration to an expanded configuration;

wherein all circumferential rings have circumferential separation regions that are joined to circumferential separation regions on adjacent circumferential rings by axial links that are configured to circumferentially separate along separation interfaces which extend through the circumferential separation regions on the adjacent circumferential rings.

Clause 142. An endoluminal prosthesis as in clause 141, wherein at least some of the circumferential rings comprise a plurality of struts joined by crowns.

Clauses Directed at Overlapping End Segments:

Clause 143. An endoluminal prosthesis comprising:

a scaffold having a plurality of circumferential rings arranged along an axis and patterned from a non-degradable material, said scaffold being configured to expand from a crimped configuration to an expanded configuration, wherein the scaffold has two end circumferential rings and a plurality of mid-scaffold circumferential rings between said end circumferential rings;

wherein the circumferential rings comprise a plurality of struts joined by crowns and at least some of the crowns are circumferentially separable in a physiologic environment and joined by axial links that are circumferentially separable in the physiologic environment so that the mid-scaffold region of the scaffold separates into a plurality of axial segments after the separation regions have opened in the physiologic environment; and wherein each of the plurality of separated axial segments remains connected to a circumferentially adjacent axial segment by one of the two end circumferential rings after the separation regions have opened.

Clauses Directed Peak-to-Valley and Valley-to-Valley:

Clause 144. An endoluminal prosthesis comprising:

a scaffold having a plurality of circumferential rings arranged along an axis and patterned from a non-degradable material, said scaffold being configured to expand from a crimped configuration to an expanded configuration;

wherein the circumferential rings comprise a plurality of struts joined by crowns having peaks and valleys and wherein at least some of the circumferential rings have a first circumferentially separable location joined to a second circumferentially separable location on an adjacent circumferential ring by a circumferentially separable axial link;

wherein at least the first circumferentially separable locations is not located on a crown peak.

Clause 145. An endoluminal prosthesis as in clause 144, wherein said circumferentially separable axial link is separable after expansion of thee scaffold in a physiologic environment.

Clause 146. An endoluminal prosthesis as in clause 144 or 145, wherein the first circumferentially separable location is located on a crown valley.

Clause 147. An endoluminal prosthesis as in clause 146, wherein the second circumferentially separable location is located on a crown peak.

Clause 148. An endoluminal prosthesis as in clause 146, wherein the second circumferentially separable location is located on a crown valley.

Clause 149. An endoluminal prosthesis as in clause 146, wherein the second circumferentially separable location is located on a strut.

Clause 150. An endoluminal prosthesis as in clause 144 or 145, wherein the first circumferentially separable location is located on a strut.

Clause 151. An endoluminal prosthesis as in clause 150, wherein the second circumferentially separable location is located on a crown peak.

Clause 152. An endoluminal prosthesis as in clause 150, wherein the second circumferentially separable location is located on a crown valley.

Clause 153. An endoluminal prosthesis as in clause 150, wherein the second circumferentially separable location is located on a strut.

Clause 154. A stent prosthesis as in any of clauses 144-1453, wherein the radial strain is measured at a pressure change of 100 mmHg Clause 155. A stent prosthesis as in any of clauses 144-154, wherein the all rings have one or more separation regions.

Clause 156. A stent prosthesis as in any of clauses 145-155, wherein the physiologic environment comprises mammalian systole and diastole pressure, or a mammalian beating heart environment.

Clause 157. A stent as in any clauses 144-156 or any of the examples, wherein the scaffold further comprises one or more of polymer material or adhesive.

Clause 158. A stent as in any of clauses 144-157 or any of the examples, wherein the non-degradable material comprises one or more of, stainless steel alloys, cobalt chrome alloys, Platinum iridium alloys, or NiTi alloys.

Clause 159. A stent prosthesis as in any of clauses 144-158, wherein the at least some rings have one or more separation regions separating after expansion of the stent in a physiologic environment into two or more circumferential sections, wherein each section comprises one or more of struts and/or crowns, and wherein at least one strut and/or crowns does not have a separation region.

Clause 160. A stent prosthesis as in any of clauses 144-159, wherein the at least some rings have one or more separation regions which separate after expansion of the stent in a physiologic environment into two or more circumferential sections, wherein each section comprises two or more struts and/or crowns.

Clause 161. A stent prosthesis as in any of clauses 144-160, wherein the at least some rings have one or more separation regions which separate after expansion of the stent in a physiologic environment into two to four circumferential sections, wherein each section comprises one or more struts and/or crowns, and wherein at least one strut and/or crown do not have a discontinuity.

Clause 162. A stent as in any of clauses 144-161, wherein the non-degradable stent further comprises one or more axial links connecting adjacent rings, and wherein at least some circumferential sections remain axially connected by at least one intact axial link after expansion of the stent in a physiologic environment.

Clause 163. A stent as in any of clauses 144-162, wherein the at least some rings are axially connected by at least one link formed from the same stent non-degradable material during patterning, and wherein at least one link remains intact after expansion of the stent in a physiologic environment.

Clause 164. A stent as in any of clauses 144-163, wherein all the rings are axially connected by at least one link formed from the same stent non-degradable material during patterning, and wherein at least one link connecting every adjacent rings remains intact after expansion of the stent in a physiologic environment.

Clause 165. A stent as in any of clauses 144-164, wherein all the rings are axially connected by at least one link formed from the same stent non-degradable material during patterning, and wherein at least one link connecting most but not all adjacent rings remains intact after expansion of the stent in a physiologic environment.

Clause 166. A stent as in any of clauses 144-165, wherein the at least some circumferential rings form about a 90 degree angle with the longitudinal axis of the stent, when the stent is in the crimped or expanded configuration.

Clause 167. A stent as in any of clauses 144-166, wherein the at least some circumferential rings form an angle with the longitudinal axis of the stent ranging from 5 degrees to 85 degrees.

Clause 168. A stent as in any of clauses 144-166, wherein the at least some circumferential rings form a variable angles with the longitudinal axis of the stent ranging from 5 degrees to 85 degrees.

Clause 169. A stent as in any of clauses 144-168, wherein the at least some rings form a closed cell ring pattern, an open cell ring pattern, or a combination of a closed cell and an open cell pattern.

Clause 170. A stent as in any of clauses 144-169, wherein the at least some rings are circumferentially disconnected at every separation region.

Clause 171. A stent as in any of clauses 144-170, wherein the at least some rings (or the stented segment comprising the at least some rings) after expansion of the stent in a physiologic environment (comprising systole and/or diastole pressure and/or infusion of a vaso-dilator) and before formation of at least some discontinuities, exhibit one or more of the following: further enlargement of the at least some rings after the initial recoil from the expanded configuration, lumen positive remodeling, expansion and contraction of the at least some rings, increased segment compliance from an initial segment compliance after initial expansion and initial expansion inward recoil.

Clause 172. A stent as in any of clauses 1484-171 wherein the at least some rings (or the stented segment comprising the at least some rings) after expansion of the stent in a physiologic environment (comprising systole and/or diastole pressure and/or infusion of a vasodilator) and before formation of substantially all discontinuities, exhibit one or more of the following: further enlargement of the at least some rings after the initial recoil from the expanded configuration, lumen positive remodeling, expansion and contraction of the at least some rings, increased segment compliance from an initial segment compliance after initial expansion and initial expansion inward recoil.

Clause 173. A stent as in any of clauses 144-172, wherein the circumferentially separable axial links or separation regions are held together by one or more material comprising one or more of polymers and adhesives, and wherein the one or more materials are elastic under physiologic conditions, allowing the at least some rings to further expand and contract from further expansion, under physiologic conditions, while substantially maintaining the expanded configuration of the stent (the expanded configuration after the initial inward recoil from the initial expansion of the stent).

Clause 174. A stent prosthesis comprising: a scaffold having circumferential rings patterned from a non-degradable material, said scaffold being expandable from a crimped configuration to an expanded configuration; wherein at least some of the circumferential rings have at least one separation region in each of said circumferential ring, wherein the at least one separation region is configured to enable said at least some rings to substantially uniformly expand from the crimped configuration to the expanded configuration, and wherein the stent has sufficient strength in the expanded configuration to support a body lumen.

Clause 175. A stent as in clause 174, wherein the at least one separation region contains and/or is contained within one or more degradable material, and wherein the one or more degradable material degrades after expansion of the stent in a physiologic environment forming at least one discontinuity in each of said at least some rings.

Clause 176. A stent as in clause 175, wherein the one or more degradable material forms a continuous circumferential perimeter in each of said at least some rings before degrading and forming the at least one discontinuity.

Clause 177. A stent as in clause 17, wherein the at least one separation region contains and/or is contained within one or more non-degradable material different from the stent material, and wherein the one or more non-degradable material forms a continuous circumferential perimeter in each of said at least some rings that is maintained after expansion of the stent in physiologic environment but said material has sufficient elasticity to enable the at least one separation region to have a displacement in one or more directions comprising radial, circumferential, or axial directions.

Clause 178. A stent as in any of 174 to 177, wherein the separation region comprises one or more junctions comprising, butt type, male/female type, key and lock type, or ball and socket type junctions.

Clause 179. A stent as in clause 175, wherein the one or more degradable material has sufficient elasticity to enable the at least some rings to have a displacement in one or more directions comprising radial, circumferential, or axial directions, prior to degradation of the material or formation of the at least one discontinuity.

Clause 180. A stent as in any of clauses 174-179, wherein the physiologic conditions comprise one or more of: systole and diastole pressure, cardiac beat cycle, annulus lumen, body lumen, mock artery or annulus, mock systole and diastole pressure, 37° C., 37° C. in a water bath, and use of solvents to form discontinuities simulating physiologic conditions to degrade the material.

Clause 181. A stent as in any of the dependent clauses, wherein the stent further comprises at least one drug and at least one polymeric material, wherein the at least one polymeric material contains the drug.

Clause 182. A stent as in any of of clauses 174-181, wherein the at least some rings form an open cell design, a closed cell design, or a combination thereof.

Clause 183. A stent as in any of the clauses, wherein the separation region is formed during or after patterning.

Clause 184. A stent as in any of the clauses, wherein the separation region is formed in a strut region or a crown region, and wherein the strut or the crown opposite ends adjacent to the separation region are configured to have a displacement in one or more directions comprising radial, circumferential, axial, or other direction, after expansion of the stent in physiologic environment.

Clause 185. A stent as in clause 179, wherein the displacement is continuous during systole and diastole pressure cycle.

Clause 186. A stent as in any of clauses 174-185, wherein the separation region is formed on a circumferential connector along the circumferential path of said rings.

Clause 187. A stent as in any of clauses 174-186, wherein the at least one ring has 2 or more separation regions Clause 188. A stent as in any of clauses 174-187, wherein the one or more separation regions form one or more discontinuities in said at least some rings, said discontinuities break the continuous circumferential perimeter of said rings into two or more sections, wherein each section can independently move in one or more axis or direction.

Clause 189. A stent as in clause 188, wherein each section moves in at least one of radial or circumferential directions.

Clause 190. A stent as in any of clauses 174-189, wherein the stent is patterned into a structure being expandable from a crimped configuration to an expanded configuration, and wherein the structure is composed of a plurality of circumferential rings, wherein each ring is connected axially to an adjacent ring, and wherein each ring is composed of struts joined by crowns forming an angle in between, wherein the angle increases as the stent is expanded from a crimped configuration to an expanded configuration.

Clause 191. A stent as in any of the clauses, wherein the separation regions are configured to form discontinuities before the stent degrades.

Clause 192. A stent as in any of the clauses, wherein the stent further expands to a diameter larger than the expanded diameter before said inward recoil.

Clause 193. A stent as in any of the clauses, wherein at least some separation regions have a gap, said gap magnitude ranges from 0.001 mm to 0.5 mm.

Clause 194. A stent as in any of clauses 174-193, wherein at least some rings have an initial contractility in the expanded stent configuration under physiologic conditions comprising systole and diastole pressure, and wherein the at least some rings have a different contractility after said initial phase.

Clause 195. A stent as in any of clauses 174-194, wherein at least some rings have an initial contractility in the expanded stent configuration under physiologic conditions comprising systole and diastole pressure, and wherein the at least some rings have a larger contractility after said initial phase Clause 196. A stent as in any of clauses 174-194, wherein at least some rings have an initial contractility in the expanded stent configuration under physiologic conditions comprising systole and diastole pressure, and wherein the at least some rings have a larger contractility after said initial phase, and wherein the contractility is in sync with the systole and diastole pressure.

Clause 197. A stent as in any of clauses 174-196, wherein at least some rings have an initial compliance in the expanded stent configuration, and wherein the the compliance of said at least some rings increase after said initial expansion.

Clause 198. A stent as in any of clauses 174-197, wherein at least some rings have an initial contractility in the expanded stent configuration under physiologic conditions comprising systole and diastole pressure, and wherein the contractility changes after said initial expansion.

Clause 199. A stent as in any of the clauses, wherein the subsequent contractility (after initial contractility) magnitude ranges from 0.1 mm to 0.5 mm.

Clause 200. An endoluminal prosthesis comprising: a scaffold having a plurality of circumferential rings patterned from a non-degradable material, said scaffold being configured to expand from a crimped configuration to an expanded configuration; wherein at least some of the circumferential rings comprise a plurality of struts joined by crowns wherein the struts and crowns form a continuous circumferential path around the scaffold; wherein at least some of the circumferential rings have at least one separation region configured to form at least one discontinuity in said circumferential rings after expansion in a physiologic environment; wherein at least portions of two of the circumferential rings remain axially joined after all discontinuities are formed; and wherein at least some of the separation regions comprise a biodegradable polymer comprising a sleeve, coating, and/or adhesive.

Clause 201. An endoluminal prosthesis as in clause 200, 217 or 218, wherein all circumferential rings remain axially joined after all discontinuities are formed.

Clause 202. An endoluminal prosthesis as in clause 200 201, 217 or 218, wherein prior to formation of any discontinuity, each circumferential ring has an initial radial compliance, and wherein after formation of discontinuities, at least some circumferential rings have an increased radial compliance.

Clause 203. An endoluminal prosthesis as in any of clauses 200-202, 217 or 218, wherein the scaffold does not separate into segments after all discontinuities are formed.

Clause 204. An endoluminal prosthesis as in any of clauses 200-202, 217 or 218, wherein the scaffold separates into two or more segments after all discontinuities are formed.

Clause 205. An endoluminal prosthesis as in clause 204, wherein at least some of the two or more segments comprise closed cell segments.

Clause 206. An endoluminal prosthesis as in clause 204, wherein at least some of the two or more segments circumferentially separate along separation lines which extend from a first end of the scaffold to a second end of the scaffold.

Clause 207. An endoluminal prosthesis as in clause 206, wherein the separation lines have axial or spiral geometries.

Clause 208. An endoluminal prosthesis as in any of clauses 200-207, 217 or 218, wherein the circumferential rings form a helical scaffold.

Clause 209. An endoluminal prosthesis as in any of clauses 200-208, 217 or 218, wherein at least one separation region is located in a strut of a circumferential ring.

Clause 210. An endoluminal prosthesis as in clause 209, wherein each of the at least some circumferential rings has from one to five struts having a separation region.

Clause 211. An endoluminal prosthesis as in any of clauses 200-210, 217 or 218, wherein at least one separation region is located in a crown of a circumferential ring.

Clause 212. An endoluminal prosthesis as in any of clauses 200-211, 217 or 218, wherein the separation regions comprise an elastic material disposed in, over, and/or adjacent to a gap formed in the ring and wherein the elastic material remains intact after expansion in a physiologic environment.

Clause 213. An endoluminal prosthesis as in any of clauses 200-212, 217 or 218, wherein the separation regions comprise junctions which are immobilized during expansion but are configured to separate after expansion in the physiologic environment.

Clause 214. An endoluminal prosthesis as in clause 213, wherein the junctions allow separation at said junction in circumferential, radial, and/or axial directions.

Clause 215. An endoluminal prosthesis as in any of clauses 200-214, 217 or 218, wherein the separation regions comprise junctions joined by, covered by, or embedded in the biodegradable polymer.

Clause 216. An endoluminal prosthesis as in any of clauses 200-215, 217 or 218, wherein the non-degradable material comprises a metal or a metal alloy material.

Clause 217. An endoluminal prosthesis, comprising: a scaffold having a plurality of circumferential rings patterned from a non-degradable material, said scaffold being configured to expand from a crimped configuration to an initial expanded configuration; wherein at least some of the circumferential rings have at least one separation region configured to form at least one discontinuity in said circumferential rings after expansion in a physiologic environment and at least portions of two of the circumferential rings remain axially joined after all discontinuities are formed; wherein the discontinuities are configured to allow the scaffold to further expand after recoil from the initial expanded configuration.

Clause 218. An endoluminal prosthesis, comprising:
a scaffold having a plurality of circumferential rings patterned from a non-degradable material, said scaffold being configured to expand from a crimped configuration to an initial expanded diameter; wherein at least some of the circumferential rings have at least one separation region configured to form at least one discontinuity in said circumferential rings after expansion in a physiologic environment and at least portions of two of the circumferential rings remain axially joined after all discontinuities are formed; wherein the discontinuities are configured to allow the scaffold to further expand to an expansion diameter larger than the initial expanded diameter.

Clause 219. An endoluminal prosthesis as in clause 218, wherein the circumferential rings are aligned substantially perpendicularly to a longitudinal axis of the scaffold in the crimped configuration.

Clause 220. An endoluminal prosthesis as in clause 218, wherein the circumferential rings are inclined at an angle relative to a longitudinal axis of the scaffold in the crimped configuration.

Clause 221. An endoluminal prosthesis as in any of clauses 217-220, wherein the scaffold is patterned from a tube, flat substrate, or a bent wire.

Clause 222. An endoluminal prosthesis as in any of clauses 217-221, wherein the scaffold further comprises at least one drug comprising an m-TOR inhibitor comprising sirolimus, novolimus, biolimus, everolimus, ridaforolimus, temsirolimus, or zotarolimus.

Clause 223. An endoluminal prosthesis as in any of clauses 217-222, wherein the scaffold further comprises a polymer coating, wherein the polymer coating comprises polylactide, poly-L-lactic acid, poly-DL-lactide, polylactide-co-glycolide, poly(lactic-co-glycolide), poly(n-butylmethacrylate), ethylene vinyl acetate, poly(ethylene-co-vinyl acetate), polyvinyl pyrrolidone, parylene, PVDF-HFP poly(vinylidene fluoride hexafluoropropylene), polystyrene, poly(L-lactide-co-epsilon-caprolactone), and poly(styrene-b-isobutylene-b-styrene).

Clause 224. An endoluminal prosthesis as in any of clauses 217-223, wherein the non-degradable comprises a metal or metal alloy, comprising stainless steel, cobalt alloy, cobalt chrome, platinum, platinum iridium, platinum chromium, platinum rhodium, or nickel titanium.

Clause 225. An endoluminal prosthesis as in any of clauses 217-224, where said scaffold has a pattern comprising serpentine, zigzag, helical, open cell design, or closed cell design.

Clause 226. An endoluminal prosthesis as in any of clauses 217-225, wherein each of the circumferential rings of the scaffold are joined to an adjacent ring by at least one link prior to expansion in a physiologic environment.

Clause 227. An endoluminal prosthesis as in any of clauses 217-226, wherein the scaffold is balloon expandable from the crimped configuration to the expanded configuration.

Clause 228. An endoluminal prosthesis as in any of clauses 217-227, wherein the separation regions comprise a pre-formed break or gap which bisects a strut or a crown and is joined by, covered by, or embedded in the biodegradable polymer.

Clause 229. An endoluminal prosthesis as in clause 228, wherein the biodegradable polymer comprises polylactide, poly-L-lactide, poly-DL-lactide, polylactide-co-glycolide, poly(L-lactic-co-glycolide), poly(ethylene-co-vinyl acetate), poly(L-lactide-co-epsilon-caprolactone), poly(DL-lactide-co-glycolide), poly(lactide-co-caprolactone), poly (D-lactide), polyglycolide, polycaprolactone, polyhydroxyalkanoate, polyvinyl alcohol, polyvinyl acetate or cyanoacrylate.

Clause 230. An endoluminal prosthesis comprising:

a scaffold having a plurality of circumferential rings patterned from a non-degradable material, said scaffold being configured to expand from a crimped configuration to an expanded configuration, wherein attachment points on at least some adjacent circumferential rings are joined by circumferentially separable axial links;

wherein at least some of the axial links comprise a first segment and a second segment, wherein the first and second segments are divided by an axially extending dividing line, are circumferentially interlocked while the scaffold is in the crimped configuration, and are configured to deform to circumferentially unlock when the scaffold is in the expanded configuration; and wherein the circumferential rings separate at the attachment points while each segment of the axial link remains attached to said attachment points after the segments have unlocked.

Clause 231. An endoluminal prosthesis as in clause 230 or 265 or 273, wherein said circumferential rings comprise struts joined by crowns.

Clause 232. An endoluminal prosthesis as in clauses 230, or 265 or 273, wherein said non-degradable material comprises a metal or metal alloy.

Clause 233. An endoluminal prosthesis as in any of clauses 230-231, 265 or 273, wherein the non-degradable material comprises stainless steel, cobalt alloy, cobalt chrome, platinum, platinum iridium, platinum chromium, platinum rhodium, or nickel titanium.

Clause 234. An endoluminal prosthesis as in any of clauses 230-233, 265 or 273, wherein the scaffold is patterned from a tube, flat substrate, or a bent wire.

Clause 235. An endoluminal prosthesis as in any of clauses 230-234, or 265, wherein the circumferentially separable axial links extend between crowns on adjacent circumferential rings.

Clause 236. An endoluminal prosthesis as in any of clauses 230-234 or 265, wherein the circumferentially separable axial links extend between struts on adjacent circumferential rings.

Clause 237. An endoluminal prosthesis as in any of clauses 230-234 or 265, wherein the circumferentially separable axial links extend between a crown on one circumferential rings and a struts on an adjacent circumferential rings.

Clause 238. An endoluminal prosthesis as in any of clauses 230-237 or 265, wherein said at least some axial links are arranged in an axial line along the scaffold.

Clause 239. An endoluminal prosthesis as in any of clauses 230-238 or 265, wherein said at least some axial links are arranged in a helical line along the scaffold.

Clause 240. An endoluminal prosthesis as in any of clauses 230-238 or 265, wherein said at least some axial links are arranged in two lines along the scaffold.

Clause 241. An endoluminal prosthesis as in any of clauses 230-238 or 265, wherein said at least some axial links are arranged in three lines along the scaffold.

Clause 242. An endoluminal prosthesis as in any of clauses 230-241 or 265, wherein the axially extending dividing line, is non-linear.

Clause 243. An endoluminal prosthesis as in any of clauses 230-241 or 265, wherein the axially extending dividing line is non-linear Clause 244. An endoluminal prosthesis as in any of clauses 230-243 or 265, wherein the axially extending dividing line comprises includes a curved section.

Clause 245. An endoluminal prosthesis as in clause 244, wherein the curved section includes regions of different curvature, wherein said curving regions may mirror each other.

Clause 246. An endoluminal prosthesis as in clause 244, wherein the curved section includes regions of reversing curvature.

Clause 247. An endoluminal prosthesis as in any of clauses 230-246 or 265, wherein the scaffold has first and second ends and wherein dividing line extends from the first attachment point in a first axial direction toward the first end and makes a first turn to travel in a second axial direction toward the second end.

Clause 248. An endoluminal prosthesis as in clause 247, wherein the dividing line makes a third turn to travel again in the first axial direction Clause 249. An endoluminal prosthesis as in clause 248, wherein the dividing line makes a fourth turn to travel again in the second axial direction Clause 250. An endoluminal prosthesis as in any of clauses 247-249 or 265, wherein at least some of the turns are 135° or greater.

Clause 251. An endoluminal prosthesis as in any of clauses 247-249 or 265, wherein at least some of the turns are 180° or greater.

Clause 252. An endoluminal prosthesis as in any of clauses 247-249 or 265, wherein at least some of the turns are greater than 180°.

Clause 253. An endoluminal prosthesis as in any of clauses 230-252 or 265, wherein the axially extending dividing line has one or more straight portions joined to one or more curves sections, wherein said straight and curved portions any mirror that shape of each other.

Clause 254. An endoluminal prosthesis as in clause 253, wherein the axially extending dividing line has a curved region attached to the attachments point on one circumferential ring followed by a straight region followed by a curved region attached to the attachment point on the adjacent circumferential ring.

Clause 255. An endoluminal prosthesis as in clause 253, wherein the axially extending dividing line has a curved region attached to the attachments point on one circumferential ring followed by a second curved region having a different direction of curvature that the first region region followed by a third curved region having a different direction of curvature than the second curved region attached to the attachment point on the adjacent circumferential ring.

Clause 256. An endoluminal prosthesis as in any of clauses 230-252 or 265, wherein the axially extending dividing line a an S-shape.

Clause 257. An endoluminal prosthesis as in any of clauses 230-252 or 265, wherein the axially extending dividing line has a W-shape.

Clause 258. An endoluminal prosthesis as in any of clauses 230-252 or 265, wherein the axially extending dividing line has a serpentine shape.

Clause 259. An endoluminal prosthesis as in any of clauses 230-258 or 265, wherein at least some of the circumferentially separable axial links comprise nested curves with having a male portion and a female portion which engage in the interference fit prior to expansion of the scaffold.

Clause 260. An endoluminal prosthesis as in clause 259, wherein at least some of the circumferentially separable axial links comprise nested wedges with having a male portion and a female portion which engage in the interference fit prior to expansion of the scaffold.

Clause 260. An endoluminal prosthesis as in any of clauses 143-259 or 265, wherein the scaffold further comprises at least one drug comprising an m-TOR inhibitor comprising sirolimus, novolimus, biolimus, everolimus, ridaforolimus, temsirolimus, or zotarolimus.

Clause 261. An endoluminal prosthesis as in any of clauses 143-260 or 265, where said scaffold has a pattern comprising serpentine, zigzag, helical, open cell design, or closed cell design.

Clause 262. An endoluminal prosthesis as in any of clauses 143-261 or 265, wherein the scaffold is balloon expandable from the crimped configuration to the expanded configuration Clause 263. An endoluminal prosthesis as in any of clauses 143-262 or 265, wherein the circumferentially separable axial links comprise a pre-formed break or gap joined by, covered by, or embedded in the biodegradable polymer.

Clause 264. An endoluminal prosthesis as in clause 263, wherein the biodegradable polymer comprises polylactide, poly-L-lactide, poly-DL-lactide, polylactide-co-glycolide, poly(L-lactic-co-glycolide), poly(ethylene-co-vinyl acetate), poly(L-lactide-co-epsilon-caprolactone), poly(DL-lactide-co-glycolide), poly(lactide-co-caprolactone), poly (D-lactide), polyglycolide, polycaprolactone, polyhydroxy-alkanoate, polyvinyl alcohol, polyvinyl acetate or cyanoacrylate.

Clause 265. An endoluminal prosthesis comprising:

a scaffold having a plurality of circumferential rings patterned from a non-degradable material, said scaffold being configured to expand from a crimped configuration to an expanded configuration, wherein at least some adjacent circumferential rings are joined by circumferentially separable axial links;

said circumferentially separable axial links are divided along the axial joining line into two portions each having one or more corresponding bends, curves, straight areas, angles, or any combination thereof, wherein said portions are configured to fit together and inhibit separation of the portions during expansion of the scaffold, but are configured to separate along said axial joining line following expansion of said scaffold in a physiologic environment, allowing said adjacent circumferential rings joined by said separable axial links to circumferentially open, while said adjacent rings remain axially attached through said portions.

Clause 266. An endoluminal prosthesis as in clause 265, wherein said portions are aligned along some of, most of, or approximately all of the length of said joining line.

Clause 267. An endoluminal prosthesis as in clause 265, wherein said portions comprise a series of curves and at least some aligned straight sections between said curves.

Clause 268. An endoluminal prosthesis as in clauses 265, wherein the portions comprise a section with a series of interlocking curves which curves are aligned at an angle from 0 up to 45 degrees relative to the axial axis of the scaffold.

Clause 269. An endoluminal prosthesis as in any of clauses 230-268, wherein said scaffold has an even number of circumferential rings and upon expansion in a physiologic environment, said separable axial links separate and the scaffold opens and separates into two, three four or more units, with axial links joining the rings within each unit.

Clause 270. An endoluminal prosthesis as in any of clauses 230-268, wherein said scaffold has an uneven number of circumferential rings and upon expansion in a physiologic environment, said separable axial links separate and the scaffold opens with the scaffold being connected as a single, unitary piece of non-degradable material.

Clause 271. An endoluminal prosthesis as in any of clauses 230-270, wherein the majority of said circumferential rings in said scaffold are joined by separable axial links.

Clause 272. An endoluminal prosthesis as in any of clauses 230-270, wherein all of said circumferential rings in said scaffold are joined by separable axial links to adjacent circumferential rings.

Clause 273. An endoluminal prosthesis comprising a scaffold having a plurality of circumferential rings comprising struts and crowns, said rings patterned from a non-degradable material, said scaffold being configured to expand from a crimped configuration to an expanded configuration, wherein at least some circumferential rings comprise one or more sections of two aligned struts, each strut joined to an adjacent circumferential ring through a link or connector, said two aligned struts held together during expansion of said scaffold but configured to separate after expansion of the scaffold under physiologic conditions.

Clause 274. An endoluminal prosthesis as in clause 273, wherein said aligned struts are held together through geometry of the struts or with a biodegradable or non-degradable polymer or adhesive.

Clause 275. An endoluminal prosthesis as in clauses 273 or 274, wherein said aligned struts comprise a series of corresponding curves to provide a mechanical locking of the struts during expansion of the scaffold.

Clause 276. An endoluminal prosthesis as in clause 275, wherein the curves further comprise a straight portion between curves.

Clause 277. An endoluminal prosthesis as in clause 275 or 276, wherein the curved section includes regions of reversing curvature.

Clause 278. An endoluminal prosthesis as in clause 276, wherein said aligned struts have corresponding S-shape, W-shape, serpentine shape or combinations thereof.

Clause 279. An endoluminal prosthesis as in any of clauses 273-278, wherein said aligned struts comprise a biodegradable polymer or adhesive over or between said aligned struts to hold them together during expansion of said stent.

Clause 280. An endoluminal prosthesis as in any of clauses 273-279, wherein said aligned struts are arranged in two lines along the scaffold.

Clause 281. An endoluminal prosthesis as in any of clauses 273-279, wherein said aligned struts are arranged in three lines along the scaffold.

Clause 282. An endoluminal prosthesis as in any of clauses 143, 144, 173, 174, 230, 265-281, wherein said axial links or aligned struts are configured to elongate, compress or rotate circumferentially, radially or axially during expansion to counteract, offset or counterbalance the forces of expansion so the axial links or aligned struts do not separate until after expansion in a physiologic environment.

Clause 283. An endoluminal prosthesis as in any of clauses 230-272, further comprising one or more partial circumferential rings connected to adjacent whole or adjacent partial circumferential rings through one or more separable axial links.

Clause 284. An endoluminal prosthesis as in any of clauses 143, 144, 173, 174, 230, 265-281, wherein said prosthesis is formed from nondegradable material and having circumferential rings comprising struts joined by crowns with separation regions configured to form discontinuities after expansion of the prosthesis under physiologic conditions has stresses induced by longitudinal compression or extension of the expanded prosthesis prior to the separation regions forming discontinuities; n some cases, the maximum stresses induced by longitudinal compression or extension of the expanded prosthesis prior to separation regions forming discontinuities decreases after formation of discontinuities by at least 10%, 15%, 25%, 50%, 75%, 85%, or 90%; in some cases, the maximum stresses induced by longitudinal compression or extension of the expanded prosthesis prior to separation regions forming discontinuities decreases after formation of discontinuities by 15%-95%, preferably by 50% to 95%, more preferably by 70%-95%; in some cases, the maximum stresses as measured by linear elastic finite element analysis induced by 5-7% longitudinal compression or extension of the expanded prosthesis prior to separation regions forming discontinuities ranges from 400e3 to 800e3 PSI, and after formation of discontinuities ranges from 1e3-300e3 PSI; sometimes the maximum stresses as measured by linear elastic finite element analysis induced by 5-7% longitudinal compression or extension of the expanded prosthesis prior to separation regions forming discontinuities ranges from 300e3 to 1000e3 PSI, and after formation of discontinuities ranges from 1e3-250e3 PSI; in some examples, the maximum stresses induced by torsion applied to the expanded prosthesis prior to separation regions forming discontinuities decreases after formation of discontinuities by at least 10%, 15%, 25%, 50%, 75%, 85%, or 90%; alternatively, the maximum stresses induced by torsion applied to the expanded prosthesis prior to separation regions forming discontinuities decreases after formation of discontinuities by 15%-95%, preferably by 50% to 95%, more preferably by 70%-95%; in some examples, the maximum stresses as measured by linear elastic finite element analysis induced by torsional displacement of 3.5°/cm of prosthesis length applied to the expanded prosthesis prior to separation regions forming discontinuities ranges from 80e3 to 150e3 PSI, and after formation of discontinuities ranges from 1e3-65e3 PSI; alternatively, the maximum stresses as measured by linear elastic finite element analysis induced by torsional displacement of 3.5°/cm of prosthesis length applied to the expanded prosthesis prior to separation regions forming discontinuities ranges from 65e3 to 150e3 PSI, and after formation of discontinuities ranges from 1e3-50e3 PSI; sometimes, the force required to bend the prosthesis by a specified amount in a 3-point bend configuration prior to separation regions forming discontinuities decreases after formation of discontinuities by at least 10%, 15%, 25%, 50%, 75%, 85%, or 90%; alternatively, the force required to bend the prosthesis by a specified amount in a 3-point bend configuration prior to separation regions forming discontinuities decreases after formation of discontinuities by 15%-95%, preferably by 50% to 95%, more preferably by 70%-95%; in some cases, the force required to bend the center of the prosthesis by approximately 1 mm in a 3-point bend configuration with supports approximately 11 mm apart prior to separation regions forming discontinuities ranges from 1 to 4N, and after formation of discontinuities ranges from 0.1 to 0.8N; alternatively, the force required to bend the center of the prosthesis by approximately 1 mm in a 3-point bend configuration with supports approximately 11 mm apart prior to separation regions forming discontinuities ranges from 0.7 to 4N, and after formation of discontinuities ranges from 0.01 to 0.5N; in some examples, the maximum stresses induced by bending the expanded prosthesis to a target radius prior to separation regions forming discontinuities decreases after formation of discontinuities by at least 10%, 15%, 25%, 50%, 75%, 85%, or 90%; alternatively, the maximum stresses induced by bending the expanded prosthesis to a target radius prior to separation regions forming discontinuities decreases after formation of discontinuities by 15%-95%, preferably by 50% to 95%, more preferably by 70%-95%; sometimes, the maximum stresses as measured by linear elastic finite element analysis bending the expanded prosthesis to a target radius of 70 mm prior to separation regions forming discontinuities ranges from 100e3 to 800e3 PSI, and after formation of discontinuities ranges from 10e3-90e3 PSI. for 6 mm expanded stent diameter; sometimes, the change in angulation of a curved vessel with an expanded physiologic implant placed within prior to separation regions forming discontinuities decreases after formation of discontinuities by at least 10%, 15%, 25%, 50%, 75%, 85%, or 90%; alternatively, the change in angulation of a curved vessel with an expanded physiologic implant placed within prior to separation regions forming discontinuities decreases after formation of discontinuities by 15%-95%, preferably by 50% to 95%, more preferably by 70%-95%; in some instances, the change in angulation of a curved vessel with an expanded physiologic implant placed within prior to separation regions forming discontinuities ranges from 30 to 70 degrees, and after formation of discontinuities ranges from 10 to 25 degrees; in some examples, the maximum stresses induced by bending the expanded prosthesis by a given angle prior to separation regions forming discontinuities decreases after formation of discontinuities by at least 10%, 15%, 25%, 50%, 75%, 85%, or 90%; the maximum stresses induced by bending the expanded prosthesis by a given angle prior to separation regions forming discontinuities decreases after formation of discontinuities by 15%-95%, preferably by 50% to 95%, more preferably by 70%-95%; or in some examples, the maximum stresses as measured by linear elastic finite element analysis bending the expanded prosthesis to 3.0 mm diameter by a given angle of approximately 7 degrees prior to separation regions forming discontinuities ranges from 100e3 to 800e3 PSI, and after formation of discontinuities ranges from 10e3-90e3 PSI.

BRIEF DESCRIPTION OF THE DRAWINGS

FIGS. 35A-35C illustrate a scaffold having a plurality of circumferential rings joined by circumferentially separable axial links having a U-shape.

FIGS. 36A-36C illustrate a scaffold comprising a plurality of circumferential rings joined by a circumferentially separable axial links having an S-shape.

FIGS. 38A through 38C illustrate a scaffold having circumferentially separable axial links having a S-shape with separation gaps which are inclined at an oblique angle relative to the circumferential direction in the crimped state (FIG. 38B) and may change to become aligned to the circumferential direction upon expansion (FIG. 38C).

FIGS. 39A through 39C illustrate a scaffold comprising a plurality of circumferential rings having circumferentially separable axial links with a w-shaped.

FIG. 50 shows the link in its initial configuration prior to deformation and circumferential separation. FIG. 51 shows the link in both partial separation and full separation configurations.

DETAILED DESCRIPTION OF THE INVENTION

Figure 1:
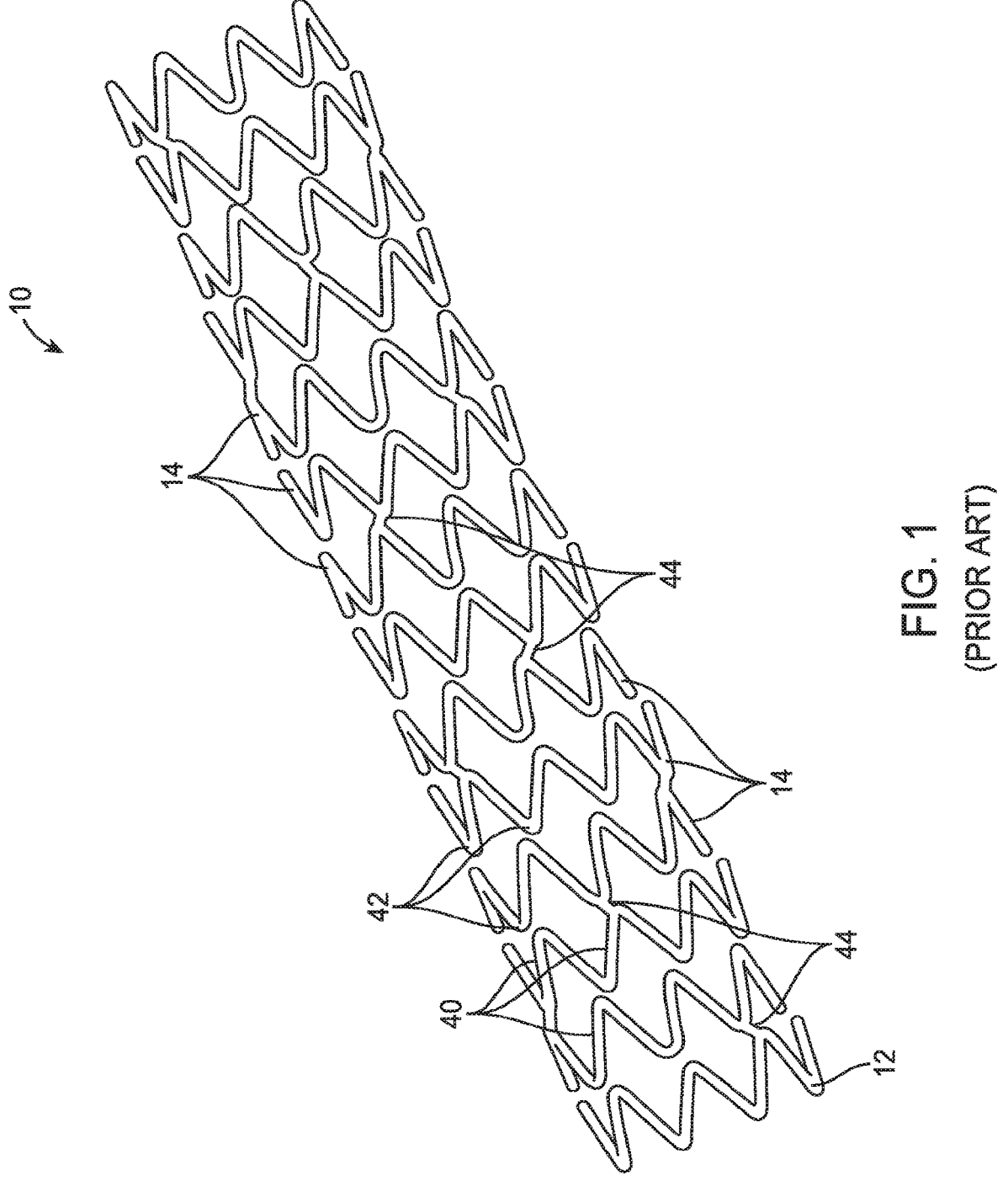
FIG. 1 illustrates a prior art endoluminal prostheses comprising a circumferential scaffold having a plurality of expansible rings.
Figure 2A:
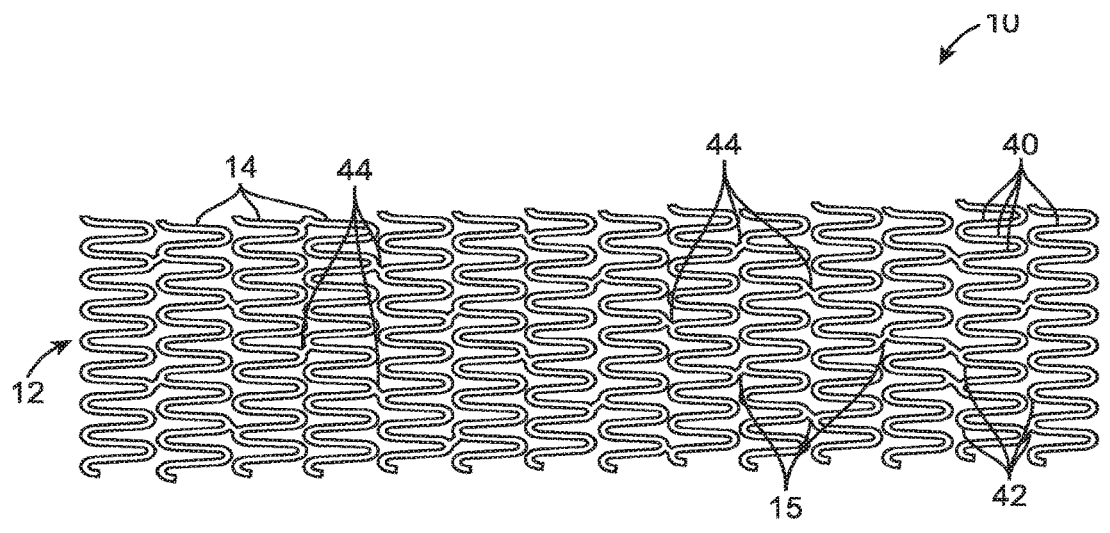
FIGS. 2A and 2B are "rolled-out" illustrations of the endoluminal prosthesis of FIG. 1.
Figure 2B:
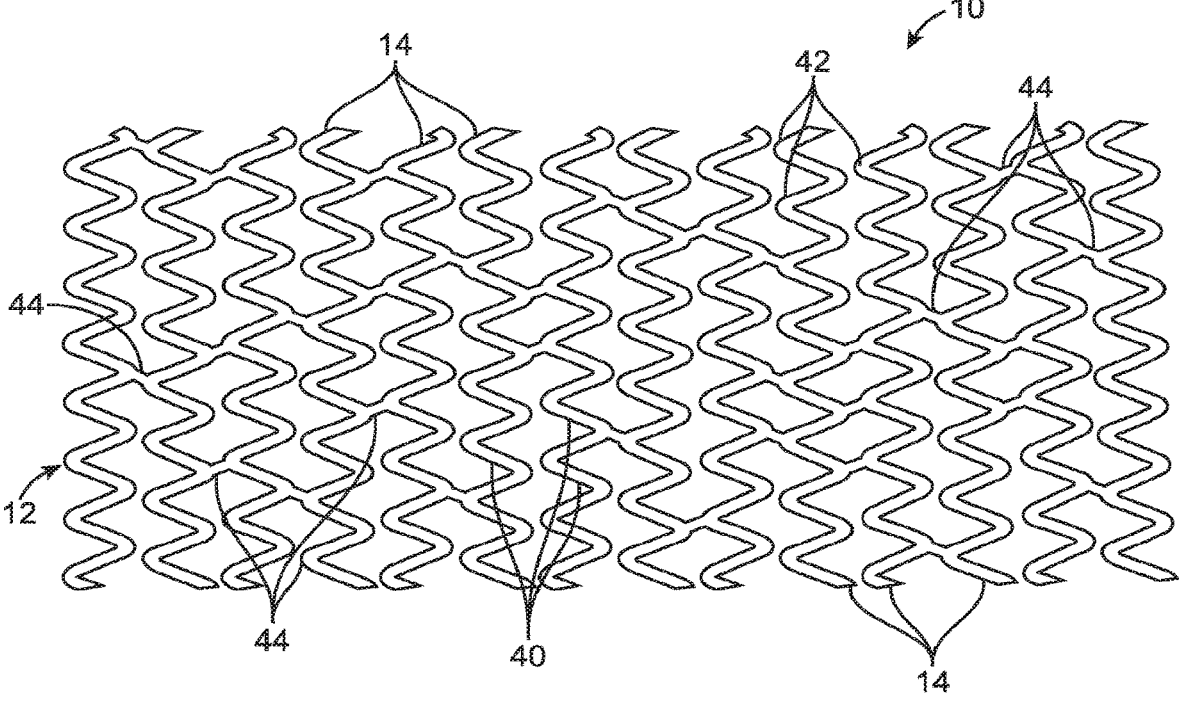

Referring to FIGS. 1-3, a conventional endoluminal prosthesis 10 comprises a generally tubular scaffold 12 including zig-zag rings 14. Each zig-zag ring 14 includes a plurality of generally straight struts 40 joined by curved hinges (expansion regions) 42. As shown in FIG. 2A, where the prosthesis 10 is in a "rolled-out" configuration, the hinges 42 are relatively close together and the diameter of the prosthesis is at a small diameter or at a minimum, typically referred to as non-expanded or "crimped." As shown in FIG. 2B, in contrast, the stent has been radially expanded so that the hinges 42 have opened and the struts 40 have moved circumferentially apart. Such zig-zag stent constructions are well known in the art in both metallic and polymeric materials.

Figure 3A:
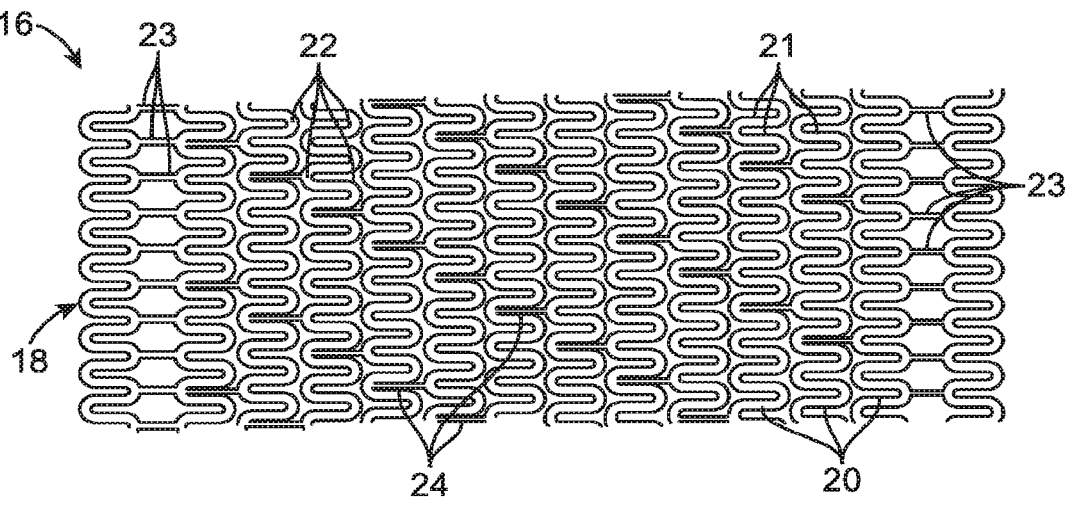
FIGS. 3A and 3B are "rolled-out" illustrations of a prior art endoluminal prosthesis similar to that of FIGS. 1, 2A and 2B, except that the rings are serpentine rings rather than zig-zag rings.
Figure 3B:
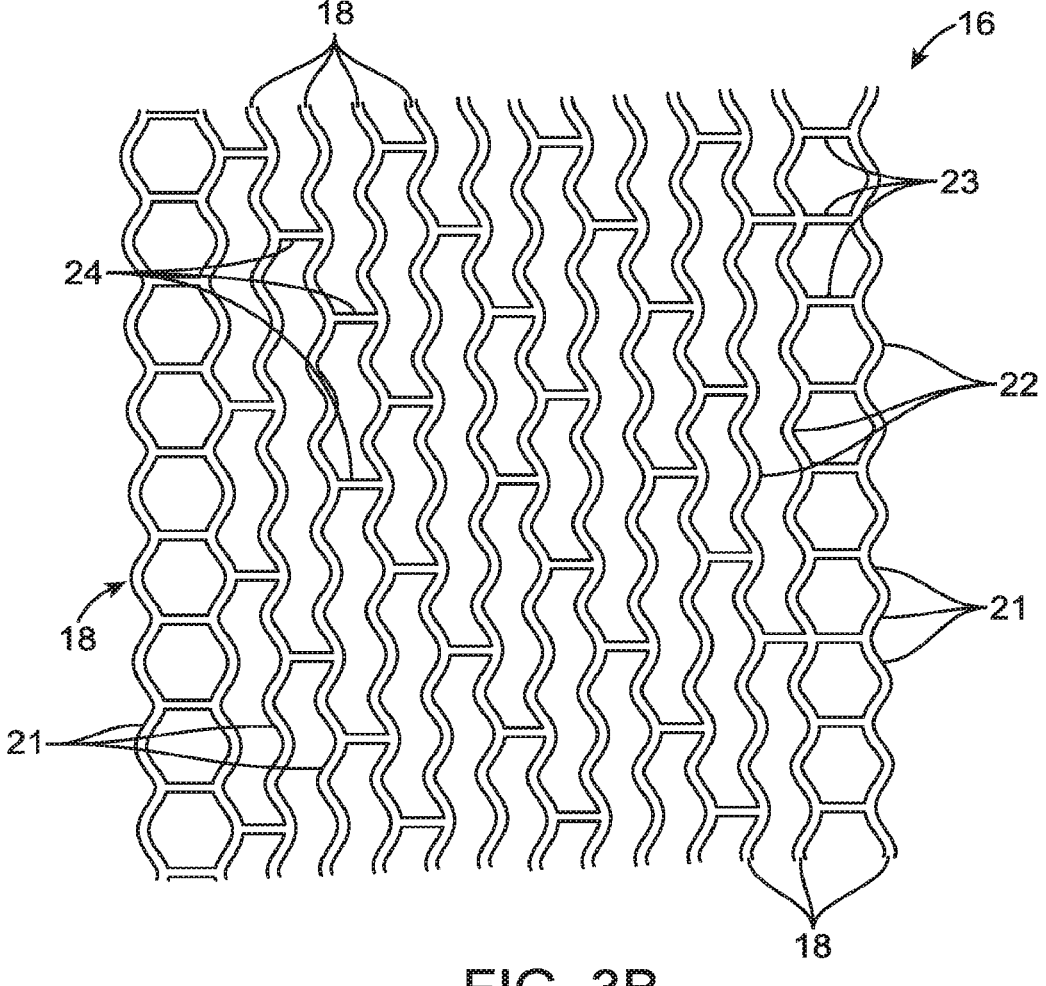

FIGS. 3A and 3B illustrate a second type of conventional endoluminal prosthesis commonly referred to as a "serpentine" stent. The serpentine stent or endoluminal prosthesis 16 comprises a circumferential scaffold 18 with a plurality of serpentine rings 20. Each ring 20 includes a plurality of generally linear struts 21 joined by curved or bent hinges 22. The hinges 22 generally have a larger diameter than those of the hinges 42 in the zig-zag stents, and the struts 21 will generally lie parallel to each other in the non-expanded or crimped configuration of FIG. 3A, as opposed to slightly offset or the non-parallel orientation of the struts 40 of the zig-zag stent. The serpentine stent 16 further includes a first type of axial link 23 which joins the outermost serpentine rings to the adjacent main body of the circumferential scaffold. The axial links 23 join the outer diameters of adjacent hinges 22 so that the hinges are spaced apart by the full length of the link. Within the main body of the circumferential scaffold 18, however, the links 24 are joined from the outer diameter of a first serpentine ring 20 to the inner diameter of an adjacent serpentine ring 20. In this way, the hinges 22 are spaced close together but out of phase when the stent is in its crimped or small diameter configuration, as shown in FIG. 3A. When the serpentine stent 16 is balloon or otherwise expanded, as shown in FIG. 3B, the hinges 22 open up and the struts 21 diverge much more greatly than shown with the struts 40 in the zig-zag endoluminal prosthesis 10. In one example, the angle between two adjacent struts joined by an expansion region can range from sub-stantially zero in the crimped configuration to about 160° or more in the fully expanded configuration.

The present invention is directed at methods and structural modifications for many types of balloon-expandable and self-expanding endoluminal prosthesis including but not limited to prostheses with zig-zag structures and serpentine structures as just described. The methods and structural modification are also directed to the various types of stents such as closed ring type, closed cell type, open cell type, helical coil or wire type, wire mesh type, balloon expandable type, self-expanding type, to name a few, whether formed from wire(s), sheet, or a tube, or other. It is an object of the present invention to provide prostheses which will, upon implantation or after implantation and/or over time, uncage the body lumen, have a radial strain (compliance) ranging between 1% and 5%, expands and/or contracts in the deployed configuration ranging from 0.05 mm to 1 mm while having sufficient strength in the deployed configuration to support a body lumen, further expand to a larger diameter after inward recoil from initial expansion, exhibit vaso-constriction and/or vaso-dilation in response to a therapeutic agent, decrease resistance to circumferential expansion of the stent in order to accommodate luminal remodeling in blood vessels and other body lumens. In some specific embodiments or examples, the prostheses of the present invention will comprise or be composed primarily of biodegradable (degradable) polymers, or degradable metal, which will substantially degrade over time so that they no longer inhibit vessel expansion and remodeling. In such biodegradable stents, the present invention will provide modifications which increase the strength, or initial strength of the stents so that they can provide adequate structural support for the body lumen during the deployment, or after deployment, or healing process but limit interference with subsequent remodeling of the lumen during later stages of the healing process. In other examples or embodiments of the present invention, the endoluminal prosthesis will comprise a circumferential scaffold which is formed or fabricated from a high-strength material, such as a metal or hard plastic, which is non-degradable or slowly degradable in the luminal environment. With prostheses having inherently high strength, the present invention will provide for modifications which enable the stent to, break into pieces, or break into segments, or break into patterned structures, or have separation regions forming discontinuities upon deployment, or after deployment, such as during the later stages of the healing process so that there is minimum interference with vessel remodeling. In still other embodiments or examples, the endoluminal prostheses of the present invention may be provided with joints such as active joints which remain intact and provide resistance to vessel compression while allowing vessel expansion after deployment. In yet other examples or embodiments, the prosthesis of the present invention may comprise non-degradable material that provides high radial strength (crush resistance) upon expansion of the stent and the material weakens after implantation lowering the resistance of the stent to further expand in response to vessel or lumen remodeling.

Stents tend to have low radial strain (compliance) in the expanded configuration specially ones that are plastically deformable, such as non-degradable metals and metal alloys, such as stainless steel alloys, cobalt chrome alloys, and platinum iridium alloys. This may be harmful to the anatomy the stent is implanted in as it can cause irritation to the lumen or vessel, it can cause fatigue of the stent or of the lumen or vessel over time as a result of having a substantially rigid structure in a dynamically (or constantly) moving environment, and can result in adverse events over time. Typical % radial strain (compliance) approximation for coronary artery ranges from 3% to 5%. Stent technologies, when expanded in a lumen (or mock tube), tend to have % radial strain (composite compliance) usually between 0.1% and 0.5%, typically in the range from 0.1% to 0.3%. It is an objective of this invention to configure a stent, in accordance with the the present invention, to having % radial strain (or composite compliance) ranging from 0.5% to 5%, preferably ranging from 1% to 5%, more preferably ranging between 1% and 5%, most preferably from 1.2% to 5%, or from 1.5% to 5%, after expansion of the stent prosthesis from a crimped configuration to an expanded configuration, or after formation of circumferential discontinuities, when the inner stent diameter is expanded within a lumen (or mock tube) to approximately 110% the inner diameter of the lumen (or mock tube) under physiologic condition, and where the lumen (or mock tube) has a compliance ranging from 4% to 5%, or the stent of the present invention after expansion in a body lumen (or mock tube) would have a substantially similar radial strain (or composite compliance) to that of the anatomy the stent is implanted in, or the stent of the present invention is configured to have a composite compliance of at least 25% of that of the radial strain (compliance) of the anatomy the stent is implanted in after expansion of the stent in such anatomy (such as lumen or mock vessel) or after formation of discontinuities, or the stent of the present invention is configured to have a composite compliance of at least one-third of that of the radial strain (compliance) of the anatomy the stent is implanted in after expansion of the stent in such anatomy (such as lumen or mock vessel) or after formation of discontinuities, or the expanded stent may have a composite compliance of at least 50% of the radial strain (compliance) of the anatomy the stent is implanted in, or a composite compliance of at least 65% of the radial strain (compliance) of the anatomy the stent is implanted in, under physiologic conditions. In a preferred example, the stent of the present invention is configured to have a composite compliance after expansion in a body lumen (or a mock tube), or after formation of discontinuities, ranging from 0.7% to 4%, or ranging from 0.9% to 4%, or ranging from 1% to 4%, or ranging from 1.1% to 4%, or ranging from 1.2% to 4%, or ranging from 1.5% to 4%, or ranging from 2% to 4%, wherein the lumen (or mock tube) has a compliance of about 5%, under physiological conditions. In another preferred examples, the stent of the present invention is configured to have an initial composite compliance after expansion in a body lumen (or mock tube), ranging from 0.1% to 0.5%, and has a second composite compliance after the initial compliance, or after formation of discontinuities, ranging from 0.7% to 4%, or the stent is configured to have an initial composite compliance after expansion in a body lumen (or mock tube), ranging from 0.1% to 0.7%, and has a second composite compliance after the initial compliance, or after formation of discontinuities, ranging from 1% to 4%, or the stent is configured to have an initial composite compliance after expansion in a body lumen (or mock tube), ranging from 0.1% to 1%, and has a second composite compliance after the initial compliance, or after formation of discontinuities, ranging from 1.2% to 4%, or ranging from 1.5% to 4%, or ranging from 2% to 4%, and wherein the lumen (or mock tube) compliance is about 5%. In another preferred example, the stent of the present invention is configured to have an initial composite compliance magnitude after expansion in a body lumen (or mock tube) where the lumen diameter ranges from 2.5 mm to 3.5 mm and the lumen (or mock tube) has a compliance of about 5%, and wherein the initial stent composite compliance magnitude after expansion ranges from 0.01 mm to 0.05 mm, or ranges from 0.01 mm to 0.06 mm, or ranges from 0.01 mm to 0.07 mm, and where the stent has a second composite compliance magnitude after the initial compliance, or after formation of discontinuities, ranging from 0.07 mm to 0.15 mm, or ranging from 0.08 to 0.15 mm, or ranging from 0.1 mm to 0.15 mm, under physiologic conditions. Scaffolds in accordance with this invention are configured to circumferentially uncage allowing the stent and the lumen to have % radial compliance as described above. Scaffolds may also be formed to have differing regions of radial compliance (radial strain) along their lengths assuming that all other characteristics of the circumferential rings are similar. The stent may have a substantially similar radial strain (compliance) along the entire stent ring segments or can have a variable radial strain (compliance) among various ring segments or regions of the stent. Radial strain (compliance) may be increased or decreased by configuring for example one or more of the following: The number of separation regions per ring, the type of stent design or pattern, the location of the separation regions on each ring, the length, width, and/or thickness of the structural element where the separation region is located on the ring, the pattern of the separation regions along the stent length or segment, to name a few. The magnitude of displacement (expansion and/or contraction) in the expanded stent configuration, in physiological environment, of the stent of this invention, in one example, having the desired % radial compliance, ranges from 0.1 mm to 1 mm, preferably ranges from 0.15 mm to 0.5 mm, more preferably ranges from 0.2 mm to 0.5 mm. The displacement (contraction and/or expansion) magnitude and rate are typically coupled (or synchronized with or corresponding to) with the beating of the heart, the pressure or mean pressure adjacent to the stented segment, and/or contractility of the heart muscle, or other physiologic conditions. It is desirable to have a stent having high initial strength sufficient to support a body lumen in the expanded stent configuration, and at the same time said stent is configured to have one or more % radial strain (compliance) values or ranges along the length (or segments or regions) of the stent rings. Shape memory stents tend to have weaker strength (or crush force) due to the properties and processing of the material. Stent formed from shape memory alloy tend to have closed cell designs to compensate for such weakness in strength. However, it is desirable to have stents formed from shape memory alloys having strength in the expanded configuration and having separation region on at least some rings to uncaging the rings (forming one or more discontinuities in the circumferential ring path sufficient to uncage said rings). The stent formed from shape memory alloy can thus be configured to have high crush resistance in the expanded configuration and the desired displacement or radial strain (compliance) along various segments of the stent rings as described above to accommodate the radial strain (compliance) of the anatomy where the stent is implanted in, or the stent is configured to have the desired radial strain (or compliance). In some cases, it is desirable to have a stent having high crush strength in the expanded configuration, and have radial strain (compliance) or radial displacement magnitude (larger or smaller) by forming separation regions or breaking sections along the circumferential path of the stent rings, uncaging the stent or one or more stent segments and achieving the desired level or range of displacement or radial strain (compliance) for the stent ring or stent segment. In other or same cases, it is desirable to have a stent having high crush strength in the expanded configuration, and have radial strain or radial displacement magnitude (larger or smaller) and/or have contraction magnitude being different from expansion magnitude, by forming separation regions or breaking sections along the circumferential path of the stent rings uncaging the stent or stent segment and achieving the desired level or range of displacement or radial strain for the stent rings or stent segment. In addition to other stent design configurations such as supporting features described in In some cases the stent of this invention can be configured to have high crush resistance in some segments of the stent in the expanded configuration and having substantially low % radial strain in such segments, while achieving certain desired radial strain value or displacement magnitude in other segments of the stent (while having similar crush resistance or lower crush resistance to the other segments of the stent). This can be specially suited for heart valves stents where certain segments require anchoring of the stent and therefore require high crush resistance, while other segments of the stent require higher % radial strain (compliance) or contractility magnitude usually in stent ring segments adjacent to or the segment containing the stent valve. Stents formed with separation regions configured to uncage in the circumferential ring path can have an advantage by accommodating the contractility of the annulus or lumen where it is necessary and have strength and low radial strain (compliance) in areas or segments where it is not necessary, or where it is important to anchor or affix the implant structure.

Typically, In one example, the non-degradable materials will comprise, or formed from, metals and metal alloy, such as stainless steel, such as 304V, 304L, and 316LV stainless steel; steel alloy such as mild steel; cobalt based alloy such as cobalt chrome; L605, Elgiloy, Phynox; platinum based alloy such as platinum chromium, platinum iridium, and platinum rhodium; tin based alloys; rhodium; rhodium based alloy; palladium; palladium base alloy; aluminum based alloy; titanium or their alloy; rhenium based alloy such 50:50 rhenium molybdenum; molybdenum based alloy; tantalum; gold or their alloy; shape memory metal or alloy; chromium based alloy; nickel-titanium alloy such as linear-elastic and/or super-elastic nitinol; nickel alloy such as nickel-chromium-molybdenum alloys (e.g., INCONEL 625, Hastelloy C-22, Hastelloy C276, Monel 400, Nickelvac 400, and the like); nickel-cobalt-chromium-molybdenum alloy such as MP35-N; nickel-molybdenum alloy; platinum enriched stainless steel; combination thereof; or the like, and other malleable metals, or plastically deformable when expanded from a crimped configuration to an expanded configuration, of a type commonly employed in stent and prosthesis manufacture. In other examples, however, the non-degradable material may comprise a non-degradable polymer, such as polyaryletherketone; polyetheretherketone; polyimide, polyethylene such as UHMW, HDPE, LDPE, or others; polypropylene; polyester; polyethylene terephthalate; polycarbonate; polysulfone; polyphenylsulfone; polyethersulpone, Ultem; polyetherimide; polyurethane; polyamide; nylon such as nylon 12, nylon 6, nylon 6-6, or others; polyvinylchloride; PTFE; FEP; ETFE; PFA; PVDF; polyvinylchloride; acrylobutadiene styrene; Delrin; polymethylmethacrylate; polystyrene; polyacrylamide, polyphenylsufide; PEBAX; or other materials. In still other examples, the non-degradable material may comprise an elastic metal, such as a shape or heat memory alloy, shape memory polymer, or superelastic materials, typically a nickel-titanium alloy; a spring stainless steel; Ni50-Mn28-Ga22; copper-aluminium-nickel; alloys of zinc, copper, gold and iron; iron-based alloy such as Fe—Mn—Si; copper-based alloy such as Cu—Zn—Al and Cu—Al—Ni; poly(E-caprolactone)dimethacrylate; PVDF/PMMA; PVDF/PVA; PLA/PVAc; or other, or the like.

In an example of metal and metal alloy comprise, or composed from: as stainless steel, such as 304V, 304L, and 316LV stainless steel; steel alloy such as mild steel; cobalt based alloy such as cobalt chrome; L605, Elgiloy, Phynox; platinum based alloy such as platinum chromium platinum iridium, and platinum rhodium; tin based alloys; rhodium; rhodium based alloy; palladium; palladium base alloy; aluminum based alloy; titanium or their alloy; rhenium based alloy such 50:50 rhenium molybdenum; molybdenum based alloy; tantalum; gold or their alloy; silver or their alloy; shape memory metal or alloy; chromium based alloy; nickel-titanium alloy such as linear-elastic and/or super-elastic nitinol; nickel alloy such as nickel-chromium-molybdenum alloys (e.g., INCONEL 625, Hastelloy C-22, Hastelloy C276, Monel 400, Nickelvac 400, and the like); nickel-cobalt-chromium-molybdenum alloy such as MP35-N; nickel-molybdenum alloy; tungsten or their alloy; platinum enriched stainless steel; magnesium; magnesium alloy with less than 20% zinc or aluminum by weight, without or with one or more impurities of less than 3% iron, silicone, manganese, cobalt, nickel, yttrium, scandium or other rare earth metal; zinc or its alloy; bismuth or its alloy; indium or its alloy, tin or its alloy such as tin-lead; silver or its alloy such as silver-tin alloy; cobalt-iron alloy; iron; iron containing alloys such as 80-55-06 grade cast ductile iron, other cast ductile irons, AISI 1010 steel, AISI 1015 steel, AISI 1430 steel, AISI 8620 steel, AISI 5140 steel, or other steels; melt fusible alloys (such as 40% bismuth-60% tin, 58% bismuth-42% tin, bismuth-tin-indium alloys; alloys comprising one or more of bismuth, indium, cobalt, tungsten, bismuth, silver, copper, iron, zinc, magnesium, zirconium, molybdenum, indium, tin; or other material; or the like.

In an example of polymeric material comprises, or composed from: polyaryletherketone; polyetheretherketone; polyimide, polyethylene such as UHMW, HDPE, LDPE, or others; polypropylene; polyester; polyethylene terephthalate; polycarbonate; polysulfone; polyphenylsulfone; polyethersulpone, Ultem; polyetherimide; polyurethane; polyamide; nylon such as nylon 12, nylon 6, nylon 6-6, or others; polyvinylchloride; PTFE; FEP; ETFE; PFA; PVDF; polyvinylchloride; acrylobutadiene styrene; Delrin; polymethylmethacrylate; polystyrene; polyacrylamide, polyphenylsufide; PEBAX; terpolymer, blends, mixes, or combination thereof of lactides, caprolactones, trimethylene carbonate, and or glycolides such as polylactide, poly(L-lactide), poly-DL-Lactide, polylactide-co-glycolide (e.g., poly(L-lactide-co-glycolide) with 85% L-lactide to 15% glycolide), copolymer of poly(L-lactide-co-epsilon-caprolactone (e.g., weight ratio of from around 50 to around 95% L-lactide to about 50 to about 5% caprolactone; poly(L-lactide-co-trimethylene carbonate), polytrimethylene carbonate, poly(glycolide-trimethylene carbonate), poly(lactide-glycolide-trimethylene carbonate) or the like; polyhydroxybutyrate such as poly(3-hydroxybutyrate) and poly(4-hydroxybutyrate); polyhydroxyvalerate; polyhydroxybutyrate/polyhydroxyvalerate copolymers (PHV/PHB); polyhydroxyalkanoate; poly orthoesters; poly anhydride; polyiminocarbonate; tyrosine-derived polycarbonate; tyrosine-derived polyacrylate; iodinated and/or brominated tyrosine-derived polycarbonate; iodinated and/or brominated tyrosine-derived polyacrylates polyesteramide; polycarbonate copolymer, lactone based polymers such as poly (propylene fumarate-co-ethylene glycol) copolymer (aka fumarate anhydride); polyanhydride esters; polyorthesters; silk-elastin polymer; polyphosphazene; aliphatic polyurethane; polyhydroxy acid; polyether ester; polyester; polydepsidpetide; poly(alkylene oxalates); polyaspartimic acid; polyglutarunic acid polymer; poly-p-dioxanone; poly-beta-dioxanone; asymmetrically 3,6-substituted poly-1,4-dioxane-2,5-diones; polyalkyl-2-cyanoacrylates; polydepsipeptides (glycine-DL-lactide copolymer); polydihydropyranes; polyalkyl-2-cyanoacrylates; poly-beta-maleic acid (PMLA); polyalkanotes; poly-beta-alkanoic acids; protein such as elastin, fibrin, collagen, glycoproteins, gelatin, or pectin; poly-serine; polycaprolactam; cyclodextrins; polysaccharides such as chitosan, and hyaluronan; alginate; polyketals; fatty acid-based polyanhydrides, amino acid-based polyanhydrides; poly(ester anhydride); combination thereof.

In some examples or embodiments, the scaffolds and other components of the stents and endoluminal prostheses may be coated for various purposes, including coating to prevent sharp metal edges, as described throughout this application, and/or where coating material comprises, or composed from: polyaryletherketone; polyetheretherketone; polyimide, polyethylene such as UHMW, HDPE, LDPE, or others; polypropylene; polyester; polyethylene terephthalate; polycarbonate; polysulfone; polyphenylsulfone; polyethersulpone, Ultem; polyetherimide; polyurethane; polyamide; nylon such as nylon 12, nylon 6, nylon 6-6, or others; polyvinylchloride; PTFE; FEP; ETFE; PFA; PVDF; polyvinylchloride; acrylobutadiene styrene; Delrin; polymethylmethacrylate; polystyrene; polyacrylamide, polyphenylsufide; PEBAX; terpolymer, blends, mixes, or combination thereof of lactides, caprolactones, trimethylene carbonate, and or glycolides such as polylactide, poly(L-lactide), poly-DL-Lactide, polylactide-co-glycolide (e.g., poly(L-lactide-co-glycolide) with 85% L-lactide to 15% glycolide), copolymer of poly(L-lactide-co-epsilon-caprolactone (e.g., weight ratio of from around 50 to around 95% L-lactide to about 50 to about 5% caprolactone; poly(L-lactide-co-trimethylene carbonate), polytrimethylene carbonate, poly(glycolide-trimethylene carbonate), poly(lactide-glycolide-trimethylene carbonate) or the like; polyhydroxybutyrate such as poly(3-hydroxybutyrate) and poly(4-hydroxybutyrate); polyhydroxyvalerate; polyhydroxybutyrate/polyhydroxyvalerate copolymers (PHV/ PHB); polyhydroxyalkanoate; poly orthoesters; poly anhydride; polyiminocarbonate; tyrosine-derived polycarbonate; tyrosine-derived polyacrylate; iodinated and/or brominated tyrosine-derived polycarbonate; iodinated and/or brominated tyrosine-derived polyacrylates polyesteramide; poly-carbonate copolymer, lactone based polymers such as poly (propylene fumarate-co-ethylene glycol) copolymer (aka fumarate anhydride); polyanhydride esters; polyorthesters; silk-elastin polymer; polyphosphazene; aliphatic polyurethane; polyhydroxy acid; polyether ester; polyester; polydepsidpetide; poly(alkylene oxalates); polyaspartimic acid; polyglutarunic acid polymer; poly-p-dioxanone; poly-beta-dioxanone; asymmetrically 3,6-substituted poly-1,4-dioxane-2,5-diones; polyalkyl-2-cyanoacrylates; polydepsi-peptides (glycine-DL-lactide copolymer); polydihydropyranes; polyalkyl-2-cyanoacrylates; poly-beta-maleic acid (PMLA); polyalkanotes; poly-beta-alkanoic acids; protein such as elastin, fibrin, collagen, glycoproteins, gelatin, or pectin; poly-serine; polycaprolactam; cyclodextrins; polysaccharides such as chitosan, and hyaluronan; alginate; polyketals; fatty acid-based polyanhydrides, amino acid-based polyanhydrides; poly(ester anhydride); combination thereof, or the like.

In one example, corrodible or degradable metallic or metallic alloy material comprising metal or metal alloy of Nickel; Cobalt; Tungsten and Tungsten alloys; Tungsten alloys of rhenium, cobalt, iron, zirconium, zinc, titanium; Magnesium, Magnesium alloy AZ31, magnesium alloy with less than 20% zinc or aluminum by weight, without or with one or more impurities of less than 3% iron, silicone, manganese, cobalt, nickel, yttrium, scandium or other rare earth metal; zinc or its alloy; bismuth or its alloy; indium or its alloy, tin or its alloy such as tin-lead; silver or its alloy such as silver-tin alloy; cobalt-iron alloy; iron; iron containing alloys such as 80-55-06 grade cast ductile iron, other cast ductile irons, AISI 1010 steel, AISI 1015 steel, AISI 1430 steel, AISI 8620 steel, AISI 5140 steel, or other steels; melt fusible alloys (such as 40% bismuth-60% tin, 58% bismuth-42% tin, bismuth-tin-indium alloys; alloys comprising one or more of bismuth, indium, cobalt, tungsten, bismuth, silver, copper, iron, zinc, magnesium, zirconium, molybdenum, indium, tin; or other material; or the like.

In another example, materials suitable for holding together the separation regions may be formed as a coating on or over the separation regions, and/or as a coating on or over one or more surfaces of the stent, and such coatings may carry a drug agent, including suitable stent material including polymeric and metallic (degradable or non-degradable), Suitable materials comprise adhesives, coatings, solder, sleeves, sealants, sealants, potting compounds, fixation materials, cement, energy fixation, elastomers and other materials suitable for incorporation into the stent. Some examples comprise but are not limited to: adhesives such as cyanoacrylate such as polyalkyl-2-cyanoacrylate, methyl-2-cyanoacrylate, ethyl-2-acrylate; n-butyl cyanoacrylate, 2-octyl cyanoacrylate, or others; gorilla glue; lysine based adhesive such as cyanoacrylate such as polyalkyl-2-cyano-acrylate, methyl-2-cyanoacrylate, ethyl-2-acrylate; n-butyl cyanoacrylate, 2-octyl cyanoacrylate, or others; gorilla glue; lysine based adhesive such TissueGlu, Sylys Surgical Sealant, or others; fibrin glue; beeswax. Non-degradable adhesives, sealants, and potting compounds such as epoxy; epoxamine; UV-curable from Loctite, Dymax, Master Bond, or other; acrylic; silicone; hot melt; polyurethane; Degradable sleeve materials, stent material, and coatings such as polyester; polylactide and their copolymers and blends; copolymers of lactide, caprolactone, trimethylene carbonate, glycolide; poly(L-lactide), poly-DL-Lactide, polylactide-co-glycolide (e.g., poly(L-lactide-co-glycolide); copolymer of poly(L-lactide-co-epsilon-caprolactone (e.g., weight ratio of from around 50 to around 95% L-lactide to about 50 to about 5% caprolactone; poly(L-lactide-co-trimethylene carbonate); polytrimethylene carbonate; poly-caprolactone; poly(glycolide-trimethylene carbonate); poly(lactide-glycolide-trimethylene carbonate) or the like; polyhydroxybutyrate such as poly(3-hydroxybutyrate) and poly(4-hydroxybutyrate); polyhydroxyvalerate; polyhydroxybutyrate/polyhydroxyvalerate copolymers (PHV/PHB); polyhydroxyalkanoate; poly orthoesters; poly anhydride; polyiminocarbonate; tyrosine-derived polycarbonate; tyrosine-derived polyacrylate; iodinated and/or brominated tyrosine-derived polycarbonate; iodinated and/or brominated tyrosine-derived polyacrylates polyesteramide; polycarbonate copolymer, lactone based polymers such as poly(propylene fumarate-co-ethylene glycol) copolymer (aka fumarate anhydride); polyanhydride esters; polyorthesters; silk-elastin polymer; polyphosphazene; aliphatic polyurethane; polyhydroxy acid; polyether ester; polyester; polydepsidpetide; poly(alkylene oxalates); polyaspartimic acid; polyglutarunic acid polymer; poly-p-dioxanone; poly-beta-dioxanone; asymmetrically 3,6-substituted poly-1,4-dioxane-2,5-diones; polyalkyl-2-cyanoacrylates; polydepsipeptides (glycine-DL-lactide copolymer); polydihydropyranes; polyalkyl-2-cyanoacrylates; poly-beta-maleic acid (PMLA); polyalkanotes; poly-beta-alkanoic acids; protein such as elastin, fibrin, collagen, glycoproteins, gelatin, or pectin; poly-serine; polycaprolactam; cyclodextrins; polysaccharides such as chitosan, and hyaluronan; alginate; polyketals; fatty acid-based polyanhydrides, amino acid-based polyanhydrides; poly(ester anhydride); polymer blends; and/or co-polymers; or combination thereof; or the like. Corrodible solder or fusible alloy such as Sn97Cu3, Sn50Zn49Cu1, Sn95.5Cu4Ag0.5, Sn90Zn7Cu3, Sn98Ag2, Sn96.5Ag3Cu0.5, Sn91Zn9, Sn85Zn15, Sn70Zn30, Sn89Zn8Bi3, Sn83.6Zn7.6In8.8, Sn86.9In10Ag3.1, Sn95Ag3.5Zn1Cu0.5, Sn86.5Zn5.5In4.5Bi3.5, Sn95Sb5, Sn96.2Ag2.5Cu0.8Sb0.6, Sn90Au10, or others; Indium or its alloy such as In97Ag3, In90Ag10, In50Sn50, In52Sn48, or others; zinc or its alloy such as Zn95Al5, Zn60Sn40, Zn95Sn5, or others; bismuth or its alloy such as Bi57Sn42Ag1, Bi58Sn52, or others. Non-corrodible solder or fusible alloy such as gold or its alloy such as Au80Sn20, Au98Si2, Au87.5Ge12.5, Au82In18. Degradable and non-degradable polymers include: polyester; polylactide and their copolymers and blends; copolymers of lactide, capro-lactone, trimethylene carbonate, glycolide; poly(L-lactide), poly-DL-Lactide, polylactide-co-glycolide (e.g., poly(L-lac-tide-co-glycolide); copolymer of poly(L-lactide-co-epsilon-caprolactone (e.g., weight ratio of from around 50 to around 95% L-lactide to about 50 to about 5% caprolactone; poly (L-lactide-co-trimethylene carbonate; polytrimethylene car-bonate; poly-caprolactone; poly(glycolide-trimethylene car-bonate); poly(lactide-glycolide-trimethylene carbonate) or the like; polyhydroxybutyrate such as poly(3-hydroxybu-tyrate) and poly(4-hydroxybutyrate); polyhydroxyvalerate; polyhydroxybutyrate/polyhydroxyvalerate copolymers (PHV/PHB); polyhydroxyalkanoate; poly orthoesters; poly anhydride; polyiminocarbonate; tyrosine-derived polycar-bonate; tyrosine-derived polyacrylate; iodinated and/or bro-minated tyrosine-derived polycarbonate; iodinated and/or brominated tyrosine-derived polyacrylates polyesteramide; polycarbonate copolymer, lactone based polymers such as poly(propylene fumarate-co-ethylene glycol) copolymer (aka fumarate anhydride); polyanhydride esters; polyorth-esters; silk-elastin polymer; polyphosphazene; aliphatic polyurethane; polyhydroxy acid; polyether ester; polyester; polydepsidpetide; poly(alkylene oxalates); polyaspartimic acid; polyglutarunic acid polymer; poly-p-dioxanone; poly-beta-dioxanone; asymmetrically 3,6-substituted poly-1,4-dioxane-2,5-diones; polyalkyl-2-cyanoacrylates; polydepsi-peptides (glycine-DL-lactide copolymer); polydihydropyranes; polyalkyl-2-cyanoacrylates; poly-beta-maleic acid (PMLA); polyalkanotes; poly-beta-alkanoic acids; protein such as elastin, fibrin, collagen, glycoproteins, gelatin, or pectin; poly-serine; polycaprolactam; cyclodex-trins; polysaccharides such as chitosan, and hyaluronan; alginate; polyketals; fatty acid-based polyanhydrides, amino acid-based polyanhydrides; poly(ester anhydride); polymer blends; and/or co-polymers; or combination thereof; or the like. polyvinyl alcohol; polyvinyl acetate; ethylene-vinyl acetate (a hot-melt glue); phenol formaldehyde resin; poly-amide such as nylon 12, nylon 6, nylon 6-6, or others; polyester resins; polyethylene (a hot-melt glue), UHMW, HDPE, LDPE, or others; polychloroprene; polyaryletherke-tone; polyetheretherketone; polypropylene; polystyrene; polyester; polyethylene terephthalate; polycarbonate; poly-sulfone; polyphenylsulfone; polyethersulpone, Ultem; polyetherimide; polyurethane; polyvinylchloride; PTFE; FEP; ETFE; PFA; PVDF; polyvinylchloride; acrylobutadi-ene styrene; polyacetal such as Delrin; polymethylmethacry-late; polystyrene; polyacrylamide, polyphenylsufide; PEBAX; and/or co-polymers, and/or combination thereof. Elastic non-absorbable polymeric or elastomers such as silicone rubber; C-flex; poly(n-butylmethacrylate); poly(n-butylmethacrylate) blended with poly(methamethacrylate), Poly(hexyl methacrylate), and polyvinylpyrrolidone; Kra-ton; poly(styrene-ethylene/butylene-styrene) (SEBS); poly (styrene-ethylene/propylene-styrene) (SEPS), poly(acrylic acid-b-styrene-b-isobutylene-b-styrene-b-acrylic acid; poly (styrene-b-isobutylene-b-styrene); polybutadiene; PVDF-HFP poly(vinylidene fluoride-hexafluorpropylene); polyvi-nylpyrrolidone; poly(ethylene-co-vinyl acetate); phosphorylcholine; PEBAX; polyurethane elastomers; Tecoflex; Biomer; Pellethane; corethane; silicone rubber; rubbers; elastomers; blends; copolymers; combination thereof or the like. Non-corrodible elastic metal or metal alloys such as shape or heat memory alloy, shape memory polymer, or superelastic materials, typically a nickel-tita-nium alloy; a spring stainless steel; Ni50-Mn28-Ga22; cop-per-aluminium-nickel; alloys of zinc, copper, gold and iron; iron-based alloy such as Fe—Mn—Si; copper-based alloy such as Cu—Zn—Al and Cu—Al—Ni; or the like. Metals or metal alloys that have high initial strength and weaken over time include Ti6Al4V, Ti5Al2.5Sn, or Ti-10V-Fe-3Al; stainless steel such as SAF2507; zinc alloys such as Zn5al, Zn10Al, Zn18Al, Zn30Al, platinum metal and its alloys; tin alloys such as Sn3.9Ag0.6Cu, Sn-3.8Ag-0.7Cu, SnPb, or SnPbAt; aluminum alloys such as Al1.7Fe, Al0.7Cu, A1.5MgScZr, Al6Mg0.2Sc0.15Zr, 3004, 8090, 7075, 6061, or 5056; zirconium alloy such as Zr55Al10Ni5Cu30; mag-nesium alloy such as AZ31B or MG11li5Al1Zn0.034Sc (LAZ1151); iron alloy such as Fe29.7Mn8.7Al1C, 30HGSA alloy steel, 4140, C45 steel, Fe36Ni, or low carbon steel; Nickel Alloys such as Ni21Cr17Mo or Haynes 230. Non-corrodible (non-degradable) metals or metal alloys such as conventional titanium alloys such as Ti6Al4V, Ti5Al2.5Sn, or Ti-10V-Fe-3Al; stainless steel such as SAF2507; plati-num metal and its alloys; aluminum alloys such as Al1.7Fe, Al0.7Cu, A1.5MgScZr, Al6Mg0.2Sc0.15Zr, 3004, 8090, 7075, 6061, or 5056; zirconium alloy such as Zr55Al10Ni5Cu30; 304V, 304L, and 316LV stainless steel; steel alloy such as mild steel; cobalt based alloy such as cobalt chrome; L605, Elgiloy, Phynox; platinum based alloy such as platinum chromium, platinum iridium, and platinum rhodium; tin based alloys; rhodium; rhodium based alloy; palladium; palladium base alloy; aluminum based alloy; titanium or their alloy; rhenium based alloy such 50:50 rhenium molybdenum; molybdenum based alloy; tantalum; gold or their alloy; silver or their alloy; shape memory metal or alloy; chromium based alloy; nickel-titanium alloy such as linear-elastic and/or super-elastic nitinol; nickel alloy such as nickel-chromium-molybdenum alloys (e.g., INC-ONEL 625, Hastelloy C-22, Hatelloy C276, Monel 400, Nickelvac 400, and the like); nickel-cobalt-chromium-mo-lybdenum alloy such as MP35-N; Nickel Alloys such as Ni21Cr17Mo or Haynes 230; or other; nickel-molybdenum alloy; platinum enriched stainless steel; combination thereof; or the like. Corrodible metals or metal alloys (degradable) include nickel, cobalt, tungsten; tungsten alloys of rhenium, cobalt, iron, zirconium, zinc, titanium; magnesium, magnesium alloys, magnesium alloy AZ31, magnesium alloy with less than 20% zinc or aluminum by weight, without or with one or more impurities of less than 3% iron, silicone, manganese, cobalt, nickel, yttrium, scan-dium or other rare earth metal, AZ31B or MG11li5Al1Zn0.034Sc (LAZ1151); zinc or its alloy such as zinc alloys such as Zn5al, Zn10Al, Zn18Al, Zn30Al; bis-muth or its alloy; indium or its alloy, tin or its alloy such as tin-lead, Sn3.9Ag0.6Cu, Sn-3.8Ag-0.7Cu, SnPb, or SnPbAt; silver or its alloy such as silver-tin alloy; cobalt-iron alloy; iron or its alloys such as 80-55-06 grade cast ductile iron, other cast ductile irons, AISI 1010 steel, AISI 1015 steel, AISI 1430 steel, AISI 8620 steel, AISI 5140 steel, Fe29.7Mn8.7Al1C, 30HGSA alloy steel, 4140, C45 steel, Fe36Ni, low carbon steel or other steels; melt fusible alloys (such as 40% bismuth-60% tin, 58% bismuth-42% tin, bismuth-tin-indium alloys; alloys comprising one or more of bismuth, indium, cobalt, tungsten, bismuth, silver, copper, iron, zinc, magnesium, zirconium, molybdenum, indium, tin; or other material; or the like. Other non-degradable polymeric material includes Parylene, and C-flex.

In further examples or embodiments, the body of the device, or the stent, or the material comprising the body of the device, or the material comprising one or more layers of the body of the device, comprises one or more biologically active agents. In some embodiments, the biologically active agent(s) are selected from the group consisting of anti-proliferative agents, anti-mitotic agents, cytostatic agents, anti-migratory agents, immunomodulators, immunosuppressants, anti-inflammatory agents, anticoagulants, anti-thrombotic agents, thrombolytic agents, anti-thrombin agents, anti-fibrin agents, anti-platelet agents, anti-ischemia agents, anti-hypertensive agents, anti-hyperlipidemia agents, anti-diabetic agents, anti-cancer agents, anti-tumor agents, anti-angiogenic agents, angiogenic agents, anti-bacterial agents, anti-fungal agents, anti-chemokine agents, and healing-promoting agents. In certain embodiments, the body of the device comprises an anti-proliferative agent, anti-mitotic agent, cytostatic agent or anti-migratory agent. In further embodiments, the body of the device comprises an anticoagulant, anti-thrombotic agent, thrombolytic agent, anti-thrombin agent, anti-fibrin agent or anti-platelet agent in addition to an anti-proliferative agent, anti-mitotic agent, cytostatic agent or anti-x migratory agent. It is appreciated that specific examples of biologically active agents disclosed herein may exert more than one biological effect.

Examples of anti-proliferative agents, anti-mitotic agents, cytostatic agents and anti-migratory agents include without limitation inhibitors of mammalian target of rapamycin (mTOR), rapamycin (also called sirolimus), deuterated rapamycin, TAFA93, 40-O-alkyl-rapamycin derivatives, 40-O-hydroxyalkyl-rapamycin derivatives, everolimus {40-O-(2-hydroxyethyl)-rapamycin}, 40-O-(3-hydroxy)propyl-rapamycin, 40-O-12-(2-hydroxy)ethoxylethyl-rapamycin, 40-O-alkoxyalkyl-rapamycin derivatives, biolimus {-40-O-(2-ethoxyethyl)-rapamycin}, 40 acyl-rapamycin derivatives, temsirolimus {-40-(3-hydroxy-2-hydroxymethyl methylpropanoate)-rapamycin, or CCI-779}, 40-O-phospho-containing rapamycin derivatives, ridaforolimus (40-dimethylphosphinate-rapamycin, or AP23573), 40(R or S)-heterocyclyl- or heteroaryl-containing rapamycin derivatives, zotarolimus {-40-epi-(N1-tetrazolyl)-rapamycin, or ABT-578}, 40-epi-(N2-tetrazolyl)-rapamycin, 32(R or S)-hydroxy-rapamycin, myolimus (32-deoxo-rapamycin), novolimus (16-O-desmethyl-rapamycin), AP20840, AP23464, AP23675, AP23841, taxanes, paclitaxel, docetaxel, cytochalasins, cytochalasins A through J, latrunculins, and salts, isomers, analogs, derivatives, metabolites, prodrugs and fragments thereof. The IUPAC numbering system for rapamycin is used herein. In certain embodiments, the body of the device comprises myolimus or novolimus. Other drugs include vasoactive agents including vas-dilators and vaso-constrictors, comprising for example, Methergin, acetylcholine, and Nitro-glycerine, their analogues, derivatives, and metabolite, to name a few.

Other specific drugs suitable for use on the scaffolds and in the methods of the present invention are described in commonly assigned U.S. Pat. No. 9,119,905, the full disclosure of which is incorporated herein by reference.

Figure 4A:
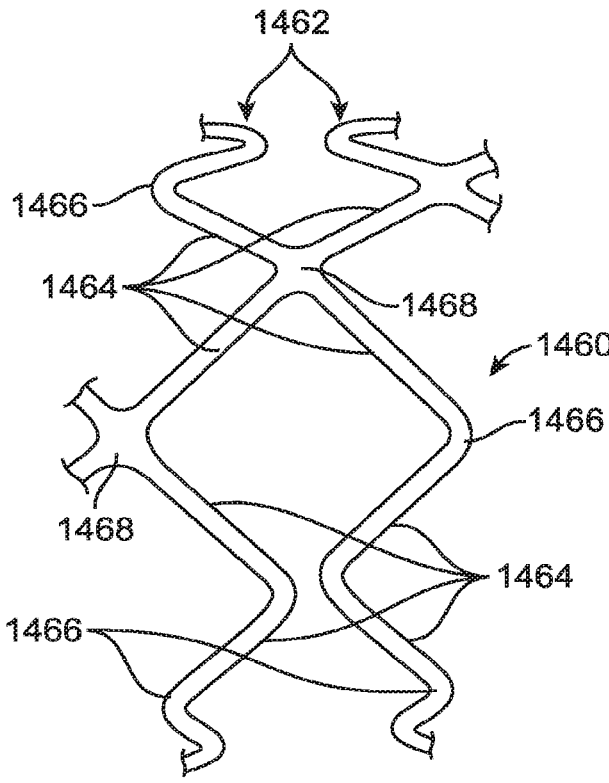
FIGS. 4A and 4B show a stent scaffold comprising zig-zag, serpentine or other circumferential rings which are formed by struts which are joined at crowns.
Figure 4B:
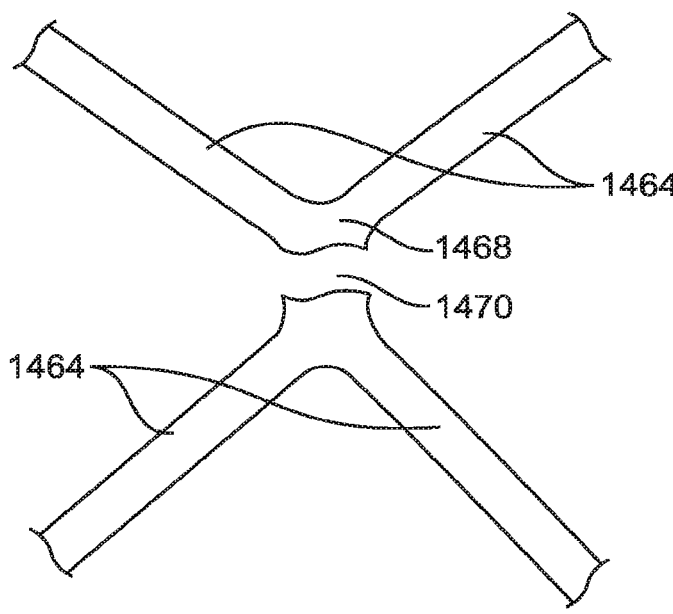

In a still further example as shown in FIGS. 4A and 4B, a stent scaffold 1460 comprises zig-zag, serpentine or other circumferential rings which are formed by struts 1464 which are joined at crowns 1466. Some, but not all axially adjacent crown 1464 in axially adjacent rings 1462 are joined into four-way junctions that join the adjacent rings. The junctions 1468 may be or have separation regions which form discontinuities, break or bisect at locations 1470 to allow circumferential separation of the rings, as shown in FIG. 4B. In this way, adjacent rings 1462 will remain axially joined by the portions of the junctions 1468 which remain intact while the rings are circumferentially released to increase circumferential compliance as described elsewhere herein. The junctions 1468 may be formed as separation regions in any of the ways described previously, e.g. having preformed breaks joined by degradable sleeves or adhesives, being weakened regions which break in response to fatigue caused by luminal pulsation, or other, or the like. Although this example shows at least one separation region bisecting two joined crowns on axially adjacent rings, other configurations such as a crown on one ring joined to a strut on another adjacent ring maybe bisected as described, or a strut on one ring joined to a strut on an adjacent ring maybe bisected as described. In this way, adjacent rings will remain axially joined by the axial links 1468 which are bisected but remain intact while the rings are circumferentially released (separated) to increase circumferential compliance as described elsewhere herein. In other examples, more than one separation regions maybe formed to bisect joined rings and/or struts on adjacent rings. The separation region at 1468 may divide, separate, break or sever the axial link into approximately equal halves, or it may separate the axial link into unequal portions. In each case, the adjacent circumferential rings remain attached through the separated axial link. The bisection, splitting, or division of the axial links circumferentially does not necessarily create equal halves. In still other instances, axial links 1468 can be configured to separate in the circumferential direction so that axially adjacent rings may separate while the rings remain circumferentially intact at that particular junction while optionally circumferentially separating at other locations on the ring. These four-way junctions may include any type of separation region described herein, including key and lock junction that may be oriented to separate axially or circumferentially.

Figure 5A:
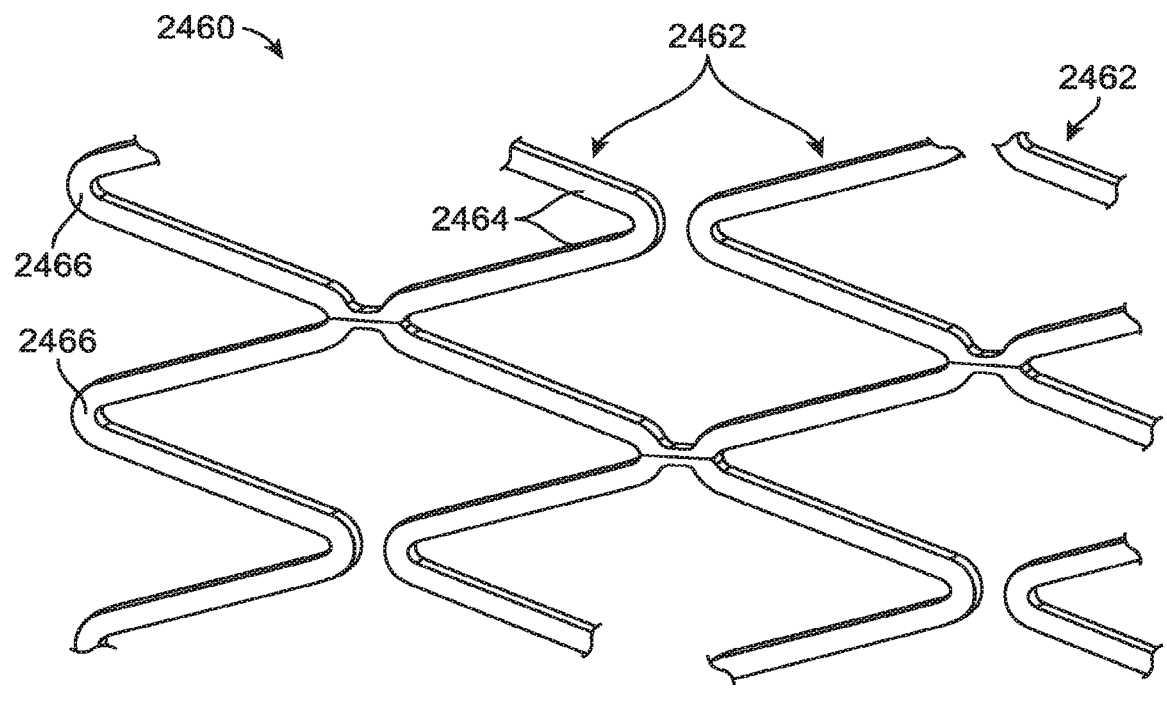
FIGS. 5A, 5B, 6, 7, and 8A-C illustrate examples of stents (scaffolds) having circumferential rings which are axially joined by separation regions formed as bisecting joined crowns and/or struts.
Figure 5B:
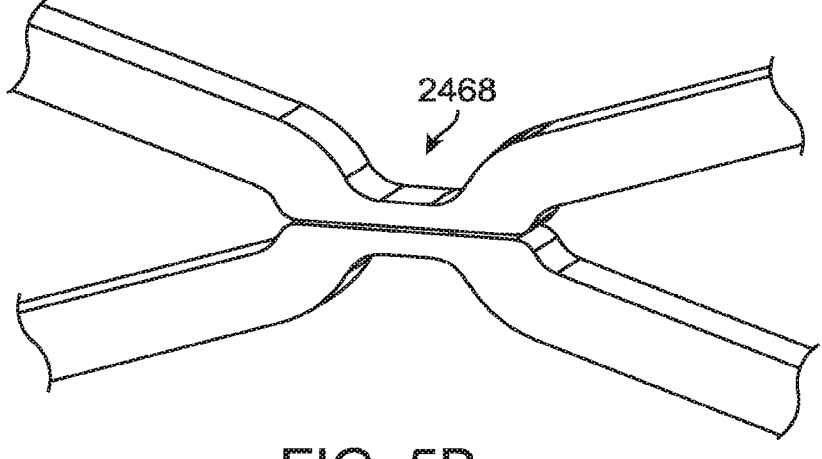
Figure 6:
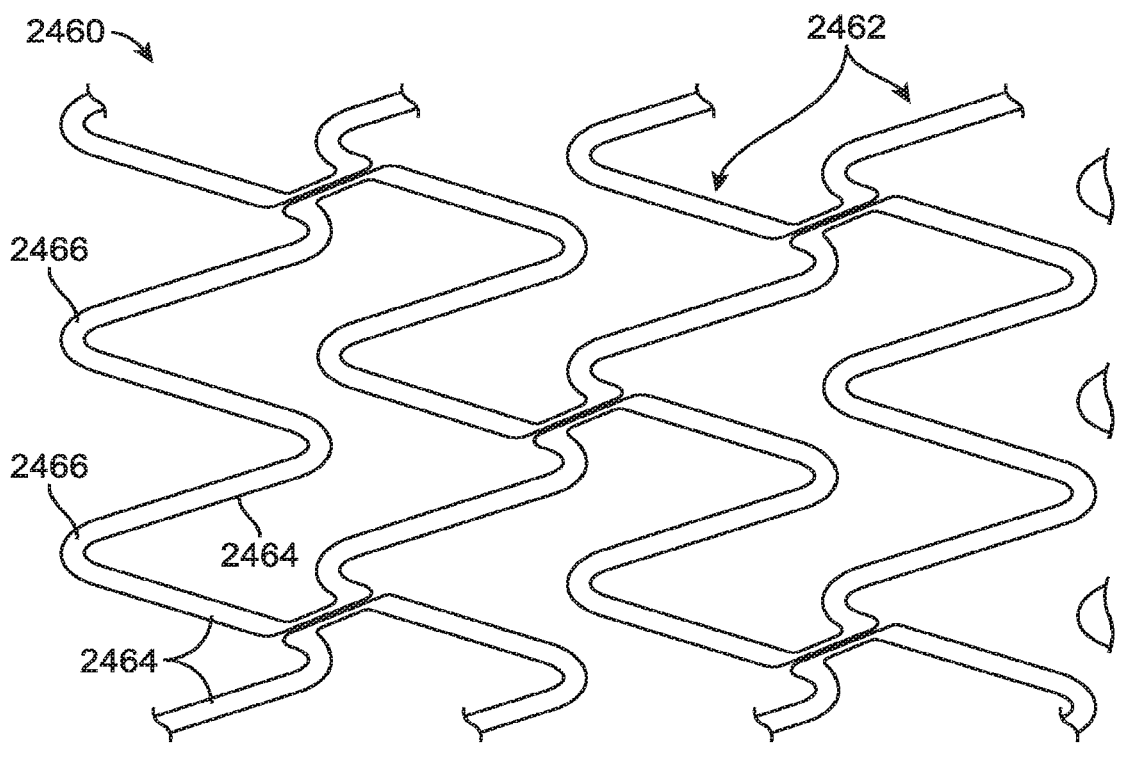
Figure 7:
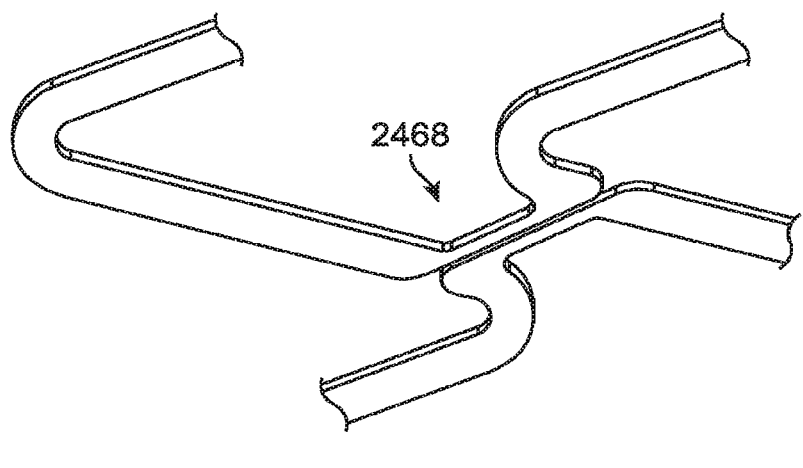

As in FIGS. 5A to 8C, a stent scaffold 2460 comprises zig-zag, serpentine or other circumferential rings 2462 which are formed comprising struts 2464 which are joined by crowns 2466. Some, but not all axially adjacent crowns 2466 in axially adjacent rings 2462 are joined by axial links 2468. The axial links 2468 may have at least one separation region which bisects the link and both adjacent crowns forming at least one discontinuity, breaks or bisect at locations 2470 to allow circumferential separation of the rings, as shown in FIGS. 6A and 6B. In this way, adjacent rings 2462 will remain axially joined by the axial links 2468 which are bisected but remain intact while the rings are circumferentially released (separated) to increase circumferential compliance as described elsewhere herein. In this case, at least one separation region bisects both the links 2468 and two crowns on adjacent rings joined by said link, or bisects a link and one crown on one ring and a strut on an adjacent ring joined by the link, or bisects a link and one strut on one rings and another strut on an adjacent ring joined by the link, and may be formed in any of the ways described previously, e.g. having formed (pre-formed) breaks joined by degradable material, adhesives, being weakened regions which break in response to fatigue caused by luminal pulsation, or other, or the like. Links can have a variety of shapes as described in this application including straight links, wavy links, curved links, offset links, U shaped links, S shaped links, V shaped links, or other shaped links. In other examples, one or more separation regions maybe formed to bisect joined rings and/or struts on adjacent rings, where in addition to circumferentially separating the ring, the link connecting both rings is also separated. Links can also be directly connecting the crowns of a ring, as shown in FIGS. 5A and 5B, or may connect adjacent struts, as shown in FIGS. 6 and 7.

Figure 8A:
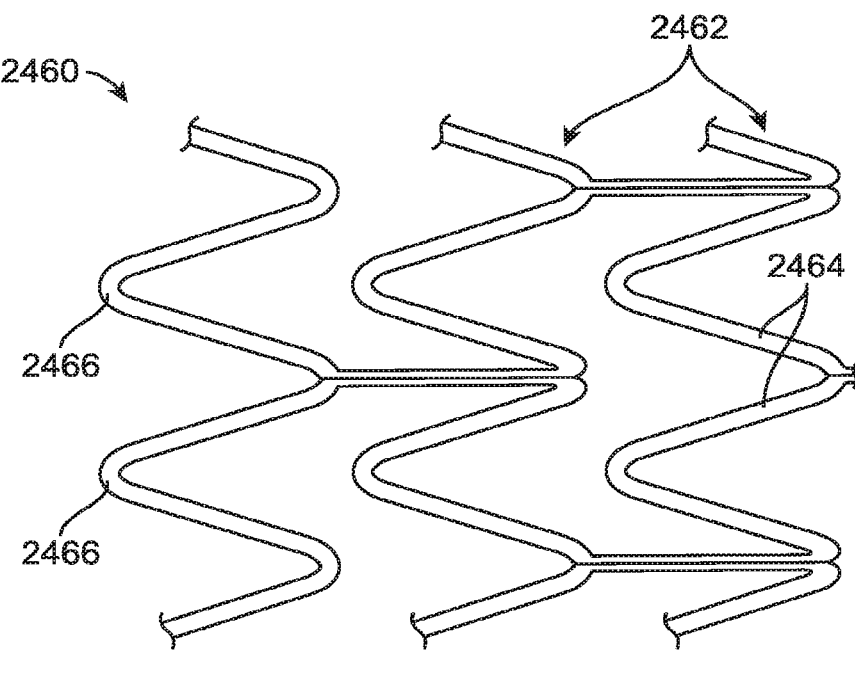
Figure 8B:
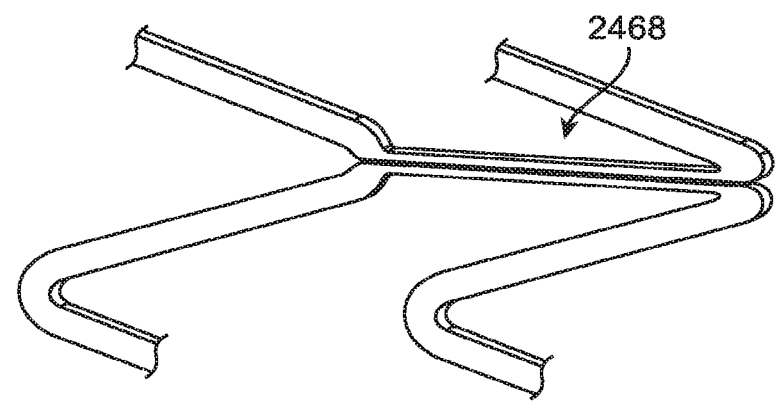
Figure 8C:
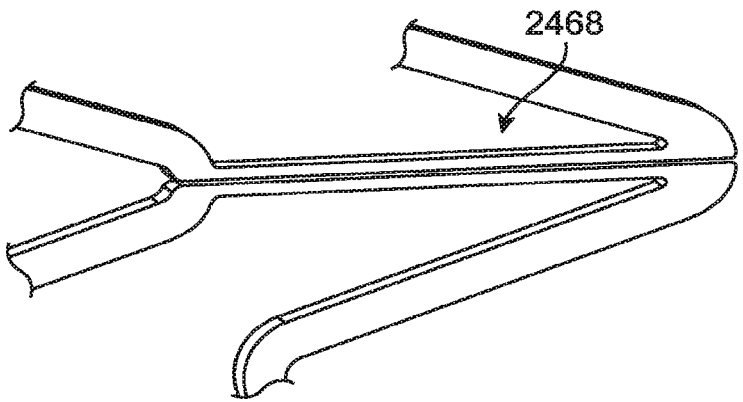
Figure 9:
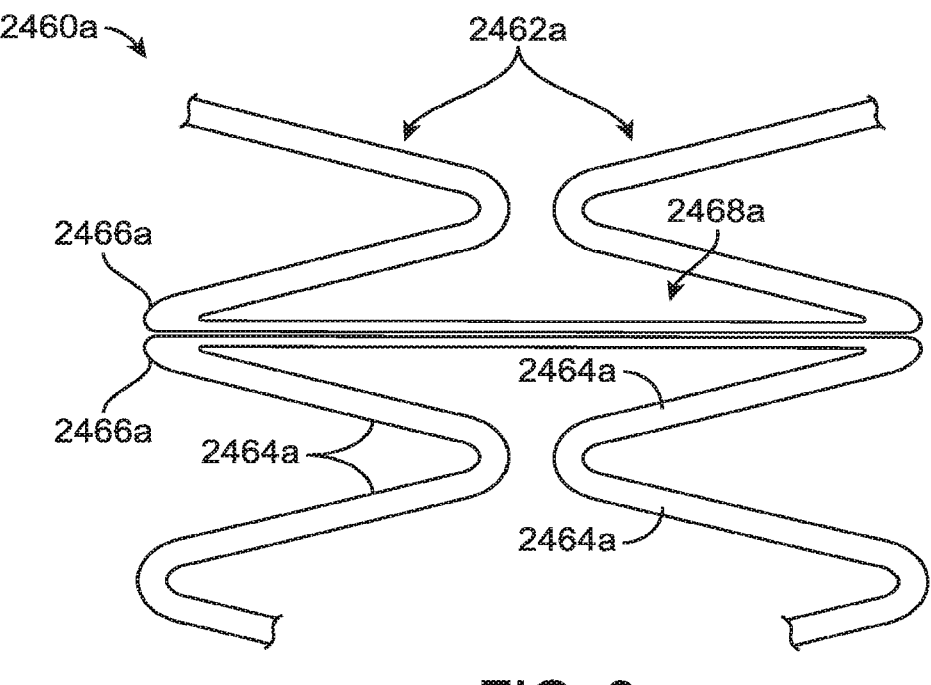
FIGS. 9-12 illustrate alternative locations for positioning a circumferentially separable axial link between location on adjacent circumferential rings, including peak-to-peak (FIG. 9), peak-to-strut (FIG. 10), and strut-to-strut (FIG. 11), and valley-to-valley with an elongate axial link having an S-shaped region at its center (FIG. 12).
Figure 10:
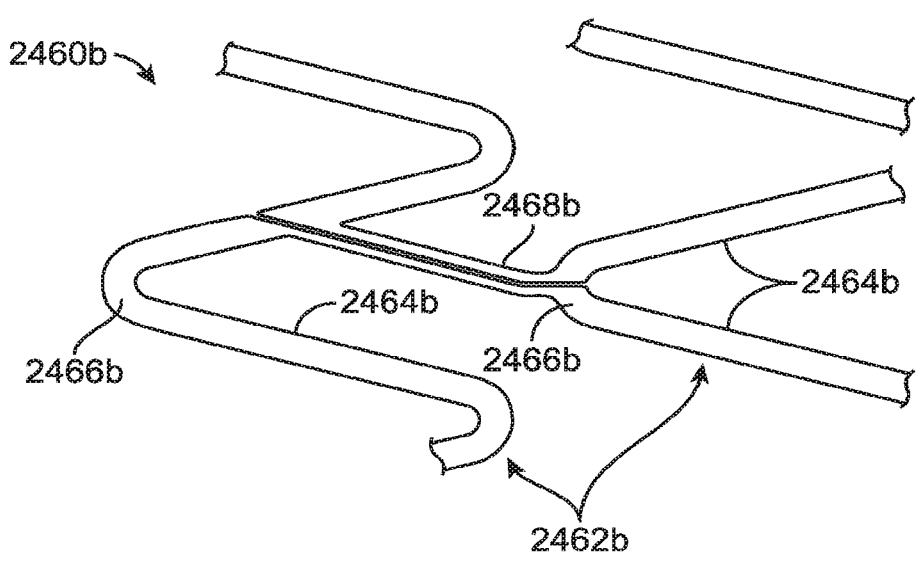
Figure 11:
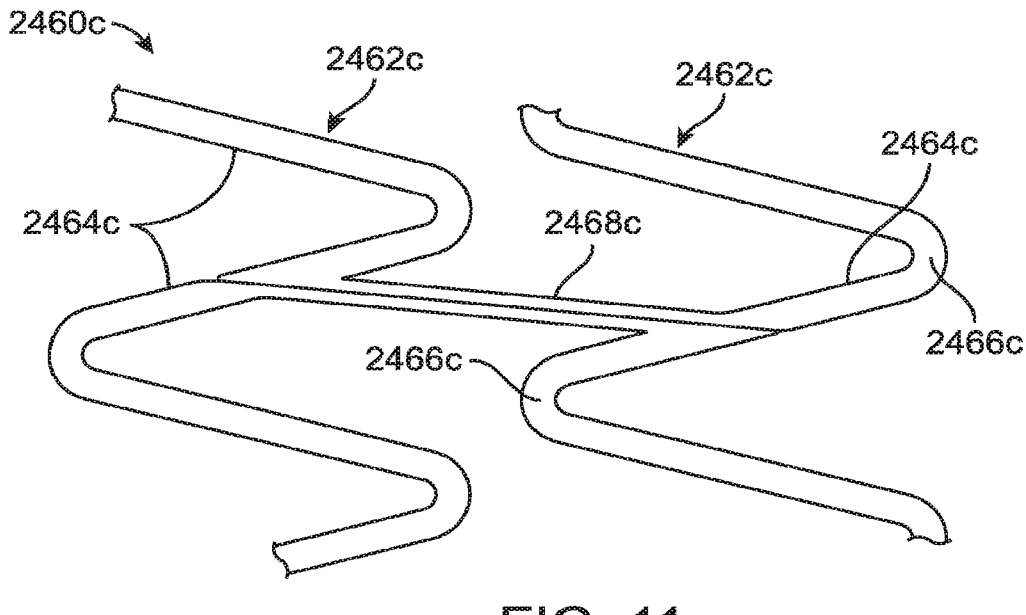
Figure 12:
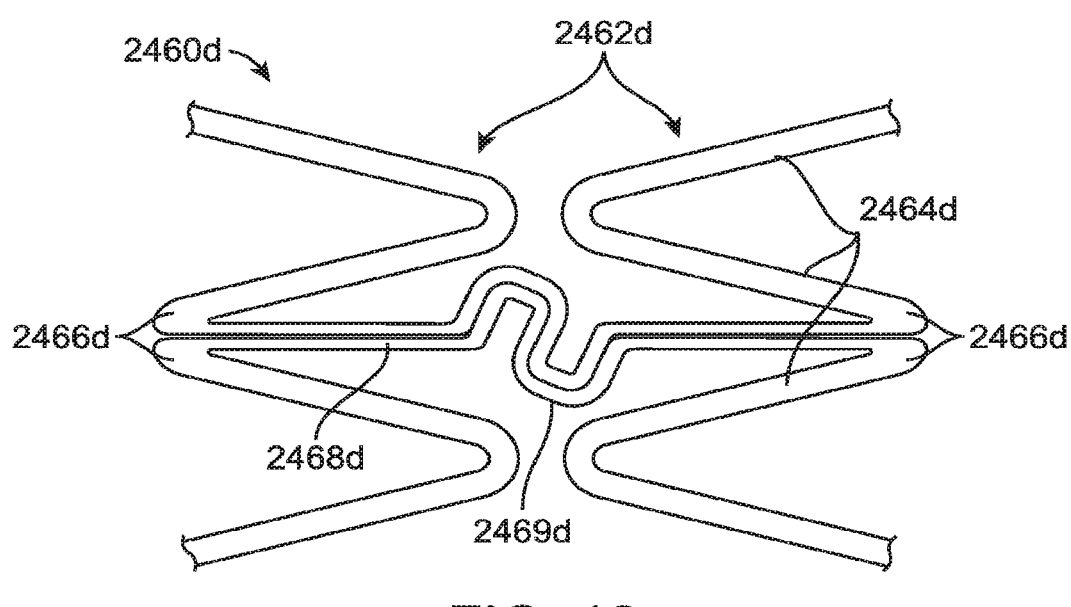

As shown in FIGS. 8A to 8C, the circumferentially separable axial links 2468 extend between a peak on one crown to a valley on a crown on an adjacent circumferential ring. Such circumferentially separable axial links may extend between other regions on adjacent circumferential rings. For example, as shown in FIG. 9 a circumferentially separable axial link 2468*a* may extend between a valley on a crown 2466*a* on a first circumferential ring 2462*a* to a valley on a crown 2466*a* on an adjacent circumferential ring 2462*a*. Alternatively, shown in FIG. 10, a circumferentially separable axial link 2468*b* can extend between a peak on a crown 2466*b* of a first circumferential ring 2462*b* to a strut 2464*b* on the adjacent circumferential ring 2462*b*. Alternatively, as shown in FIG. 11, a circumferentially separable axial link 2468*c* may extend between a strut 2464*c* on a first circumferential ring 2462*c* to a strut 2464*c* on a second circumferential ring 2462*c*. Additionally, as shown in FIG. 12, a circumferentially separable axial link 2468*d* may extend between a valley on a crown 2466*d* on a first circumferential ring 2462*d* to a valley on a crown 2466*d* on an adjacent circumferential ring 2462*d*, similarly to FIG. 9, except that an axial link 2468*d* comprises an S-shaped region 2469*d* near its center to provide a degree of bendability and axial extendibility beyond that provided by a straight axial link. Such a modified link incorporating an S-shaped or other bendable, extendable region may be substituted into any of the other circumferentially separable axial link designs shown in FIGS. 8A to 12. Moreover, such circumferentially separable axial links may extend between virtually any circumferentially separable locations on a first circumferential ring to any circumferentially separable locations on an adjacent circumferential ring within the principles of the present invention.

Figure 13:
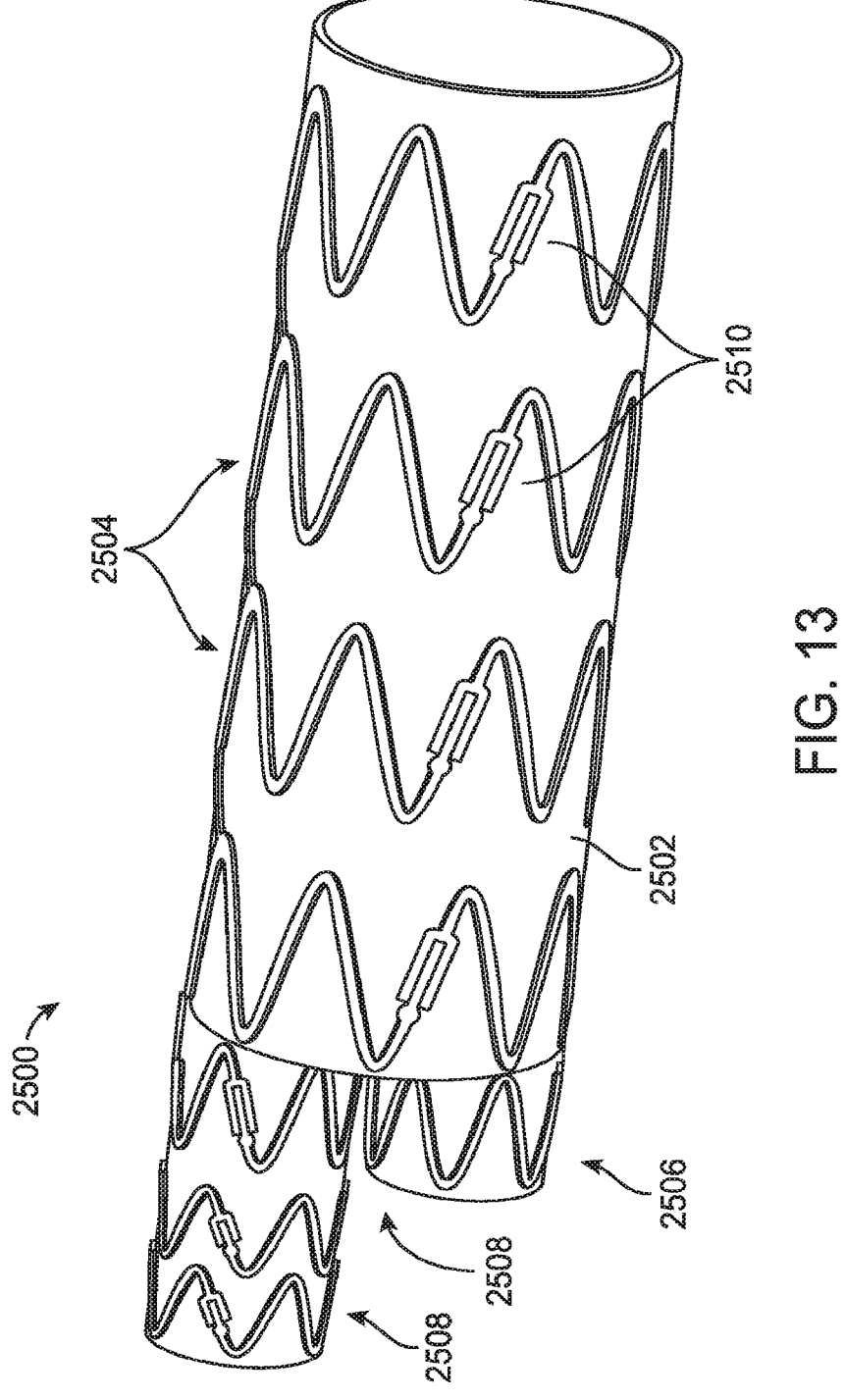
FIG. 13 illustrates supporting scaffolds of the present invention incorporated into a stent-graft.

Referring now to FIG. 13, a stent graft 2500 may be constructed with the scaffolds of the present invention used to support a graft component. The scaffold may have any of the previously described structure and is shown to have a plurality of circumferential rings 25404 spaced apart over the exterior of a graft sleeve or membrane 2502. The graft may comprise any conventional material, typically being a polyester or PTFE, such as an ePTFE. Stent graft 2500 may have a bifurcated construction with legs covered by additional circumferential rings 2506 and 2508 secured over the exterior of the legs. Adjacent rings may be unconnected (that is connected only by attachment to the graft sleeve) or may be joined by axial links or otherwise. The scaffolds may me be on the exterior of the graft sleeve as illustrated, or alternatively may be on the interior, or may be sandwiched or embedded between a coaxial pair of graft sleeves. The graft may have an initial compliance after deployment and wherein the compliance increases after the separation regions form discontinuities under physiologic conditions. Alternatively, the graft may substantially be rigid upon expansion (deployment), and wherein the graft becomes less rigid after the separation regions form discontinuities under physiologic conditions. The separation regions may be aligned axially as shown or may have any configuration along the length of the graft. The number of separation regions may vary from one ring to an adjacent ring. The number of separation regions may vary from 1 separation region per ring to 5 separation regions per ring. Alternatively, one or more rings may not have any separation regions. In a preferred example, physiologic conditions comprises pressure gradient of 40-150 mmHg.

EXAMPLES

The following Examples are offered by way of illustration, not by way of limitation:

Example 1: Vasomotion evaluation by IVUS: A porcine animal having a control non-degradable plastically deformable stent (DESyne, Elixir Medical Inc. n=2) and a test stent of (PR153RG, n=4) having a 6-crown 3-link non-degradable plastically deformable stent patterned to have three evenly spaced separation regions per ring, with the S shaped axial links connecting adjacent rings was tested and followed up at the 3 month time point. The test devices were coated with a fast degrading (from 1-3 months) lactide copolymer covering the separation regions (including the inner, sides, and outer surfaces of the separation regions and the space within the separation regions) and covering the stent surfaces (luminal, abluminal and two side surface). The stents were further coated with a top coat of Novolimus and a lactide copolymer drug matrix. The abluminal and luminal coating thickness was about 10 microns. The test stents and the control stents (DESyne, Elixir Medical Inc.) were implanted in the coronary arteries of domestic pig following which they were serially imaged by angiography and Optical Coherence Tomography (OCT) at 3 months from baseline (after stent expansion). At the 3 month time point, the test and control devices were further evaluated for vasomotion (dynamic expansion and contraction) using Intra Vascular Ultra Sound (IVUS) imaging in the absence and presence of nitroglycerin. The images captured the device and vessel movements during systole and diastole pressures. Using still images from the IVUS video, the device and lumen area in the test and control devices implanted segments were measured during the systole and diastole pressure cycles for the same still images.

Vasomotion of the stented vessels were performed as follows. An IVUS catheter was introduced into the stented coronary artery and positioned at approximately the mid portion of the device implanted vessel segment. An IVUS video was captured in the absence of nitroglycerin. Without disturbing the position of the IVUS catheter, a bolus dose of nitroglycerin (1 mL of 0.5 mg/mL) was injected and IVUS video was captured at approximately 3 minutes post-nitro injection. Still images of systolic and diastolic cycles of the vessel and device were used to measure each of the device and lumen area at the two pressure cycles of the vessel in the absence and presence of nitroglycerin.

Figure 14:
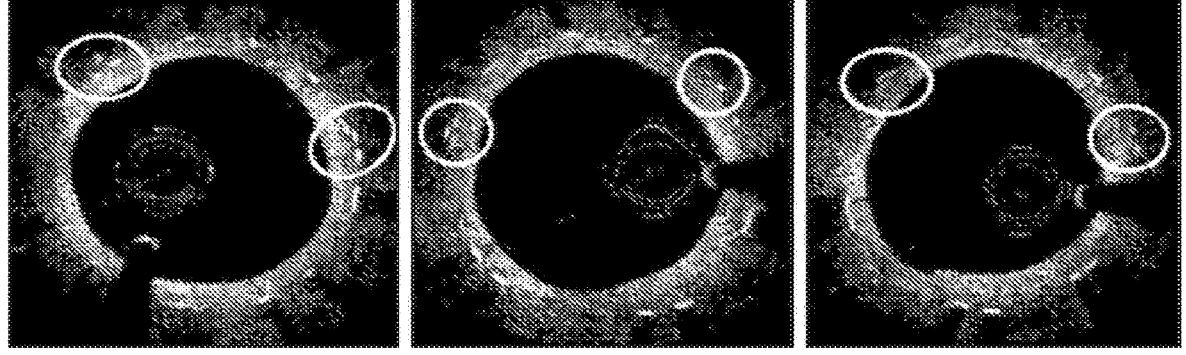
FIG. 14 shows three OCT still images taken at the 3-month time point of Example 1 (test PR153RG). Discontinuities within rings of stented segment are shown inside the circles.

Tables 1 and 2 show the mean device area and mean lumen area of the stented segment respectively of the test (PR153RG) and control (DESyne) stents during the diastole and systole pressure cycles as evaluated at 3 month post device implantation. Based on these measurements the mean percent change for the device and lumen area of the stented segment between diastole and systole was then calculated for the test and control device. Table 7 showed an increase in the mean device area for test devices PR153RG of 15% between the two pressure cycles in both the pre-nitro and post-nitro state. Mean device area for control stents showed increases of 2% pre-nitro, and 4% post-nitro. Table 8 shows the mean lumen area for the test devices PR153RG and control devices DESyne stented segments. The test device stented segment shows mean lumen area increase of 11% pre-nitro, and 16% post-nitro, while the control device stented segment showed no to minimal mean lumen area increase of 0% pre-nitro and 2% post-nitro. FIG. 14 shows OCT images of the discontinuities formed within rings in the test PR153RG stented segment. The discontinuities in the OCT frames are within the circled areas in the figure. The control stents (not shown in the figure) had no separation regions or discontinuities within the rings.

TABLE 1

Mean Device Area of the test (PR153RG) and control (DESyne)
stents during diastole and systole pressure cycles
3 month
Mean Device Area (mm²)

| | Diastole | Systole | % Change |
|---|---|---|---|
| DESyne (n = 2) | | | |
| Pre Nitro | 8.37 | 8.55 | 2% |
| Post Nitro | 9.02 | 9.34 | 4% |
| PR153RG (n = 4) | | | |
| Pre Nitro | 8.05 | 9.22 | 15% |
| Post Nitro | 8.03 | 9.26 | 15% |

TABLE 2

Mean Lumen Area of the test (PR153RG) and control (DESyne) stented
segment during the diastole and systole pressure cycles
3 month
Mean Lumen Area (mm²)

| | Diastole | Systole | % Change |
|---|---|---|---|
| DESyne (n = 2) | | | |
| Pre Nitro | 6.78 | 6.75 | 0% |
| Post Nitro | 6.98 | 7.1 | 2% |
| PR153RG (n = 4) | | | |
| Pre Nitro | 6.36 | 7.05 | 11% |
| Post Nitro | 6.28 | 7.24 | 15% |

Example 2. Finite Element Analysis Model testing for the different Tests listed below were conducted on the stent of the present invention. The mock artery had a wall thickness of 0.010", regardless of diameter, and an inner diameter match the outer diameter of the stent. The artery wall material was modeled as a linear elastic material with a Poisson's ratio of 0.45, and exhibits a 5% diametric compliance when pressurized with 100 mmHg on the inner surface of the artery. The Young's modulus varied between 300 and 700 PSI, depending on the arterial diameter. The Stent material was a linear elastic material having a Young's modulus of between 36,000,000 and 39,000,000 PSI (36e6 to 39e6 PSI) and a Poisson's ratio of 0.3. FEA model used FEMAP and Nastran software and consisted of arrangements of 10 node modified Tet elements at a density shown to give results accurate to less than +/−5%. The minimum mesh density used in this analysis had 1 layer of elements through the thickness of the artery, and 2 layers of elements through the thickness of the stent.

Figure 15:
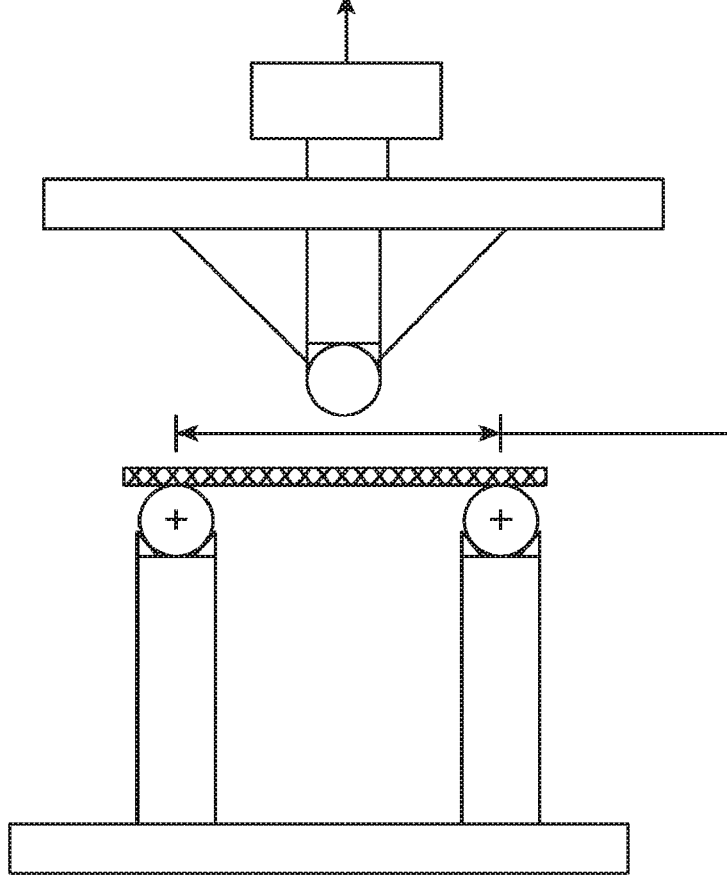
FIGS. 15-18 illustrate tests for determining scaffold flexibility, geometric distortion, and stress characteristics before and after separation regions open (form discontinuities) in the scaffold.

Example 3: Three point Bend Test FIG. 15: A stent was patterned from Stent Material having a thickness of 75 microns, having a serpentine ring with each ring having 3 separation regions. The stent was in an expanded configuration of diameter 3.5 mm and is connected to a mock artery. Fixtures were connected at each end and in the middle. The minimum separation between the end connectors was 11 mm. The fixture at one end of the model was allowed to pivot along a line as shown below, but was otherwise fixed against movement. The fixture at the opposite end could pivot and move relative to the first end in the direction of the axis of the stent. The fixture on top in the middle was then displaced by 1 mm toward the stent, bending the stent and mock artery. Linear elastic analysis was used, resulting in an estimated Force of 1.4N prior to the formation of discontinuities, which dropped to 0.4N after formation of discontinuities. The stent of the current invention with discontinuities in the separation regions resulted in a 70% reduction in bending forces.

Figure 16:
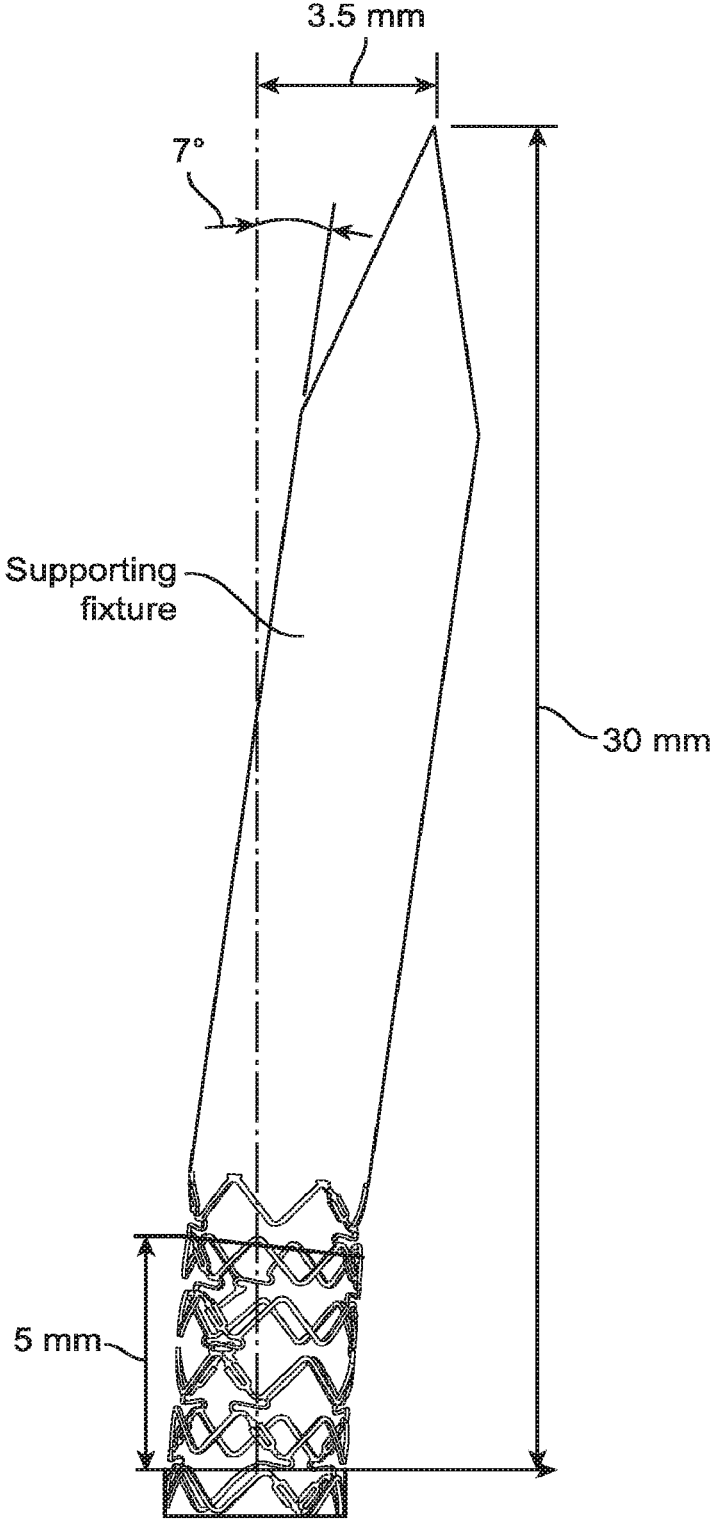

"Ormiston" Test: Angular Bend Test FIG. 16: A stent was patterned from Stent Material having a thickness of 75 microns, having a serpentine ring with each ring having 3 separation regions. The stent was in an expanded configuration of diameter 3.5 mm and was connected to a base fixture and a lever (with an unsupported distance of 5 mm between them). The lever length was 25 mm, so that the tip of the lever was 30 mm from the base fixture. The base fixture was fixed rigidly against all motion and rotation on its bottom surface. The point on the lever farthest from the base fixture was deflected 3.5 mm perpendicular to the axis of the stent. Linear elastic analysis was used, resulting in an estimated stress prior to formation of discontinuities of 308e3 PSI, which dropped to 30.7e3 PSI after formation of discontinuities. The stent of the current invention with discontinuities in the separation regions resulted in a 90% reduction in bending forces.

Figure 17A:
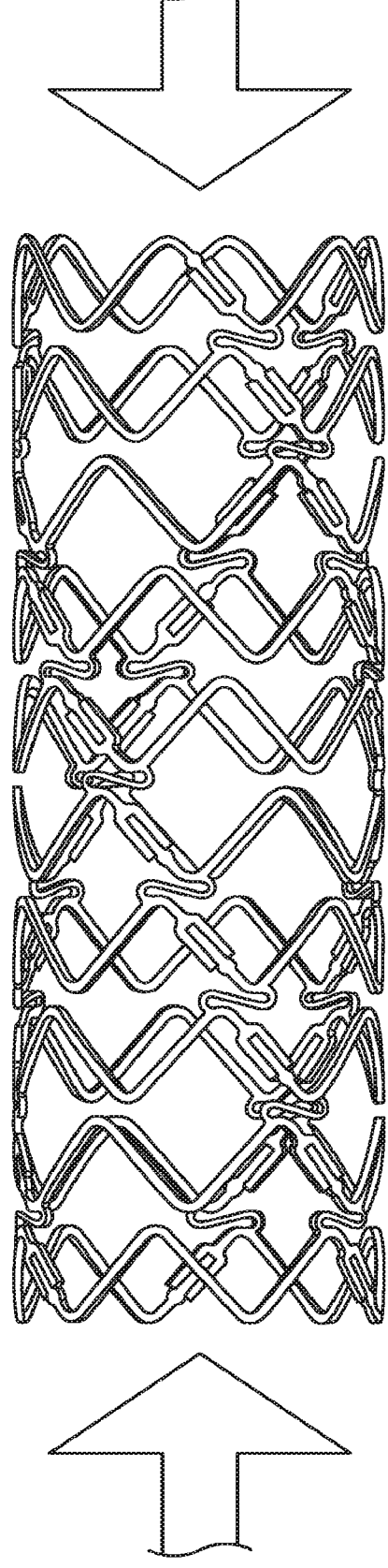
Figure 17B:
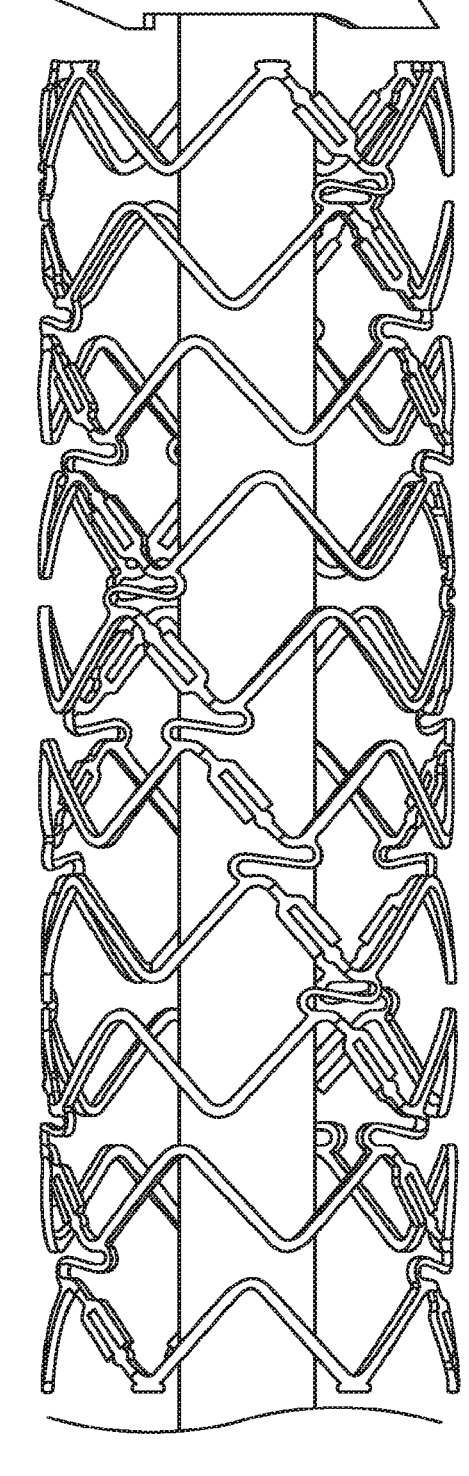

Test: Longitudinal Compression Test FIGS. 17A and 17B: A stent was patterned from Stent Material having a thickness of 107 microns, having a serpentine ring with each ring having 3 separation regions. The stent was in an expanded configuration of diameter 6.0 mm and was connected to a mock artery. One point near the middle of each of the stent segments was constrained against rotational and longitudinal motion, and each end of the artery was displaced toward the middle by 3.5% of the artery length (7% length reduction total). In addition, the inner surface of the mock artery had a pressure of 100 mmHg applied to it. Linear elastic analysis was used, resulting in an estimated stress prior to formation of discontinuities of 566e3 PSI, which dropped to 81e3 PSI after formation of discontinuities. The stent of the current invention with discontinuities in the separation regions resulted in an 86% reduction in bending forces.

Test: Torsion Test FIG. 18: A stent was patterned from Stent Material having a thickness of 107 microns, having a serpentine ring with each ring having 3 separation regions. The stent was in an expanded configuration of diameter 6.0 mm and was connected to a mock artery, with both ends fixed axially and radially. One end of the stent fixed against rotation, while the free-to-rotate end of the stent was twisted by 3.5 degrees for every cm of stent length. In addition, the inner surface of the mock artery had a pressure of 100 mmHg applied to it. Linear elastic analysis was used, resulting in an estimated stress prior to formation of discontinuities of 110e3 PSI, which dropped to 32e3 PSI after formation of discontinuities. The stent of the current invention with discontinuities in the separation regions resulted in a 70% reduction in bending forces.

Figure 18:
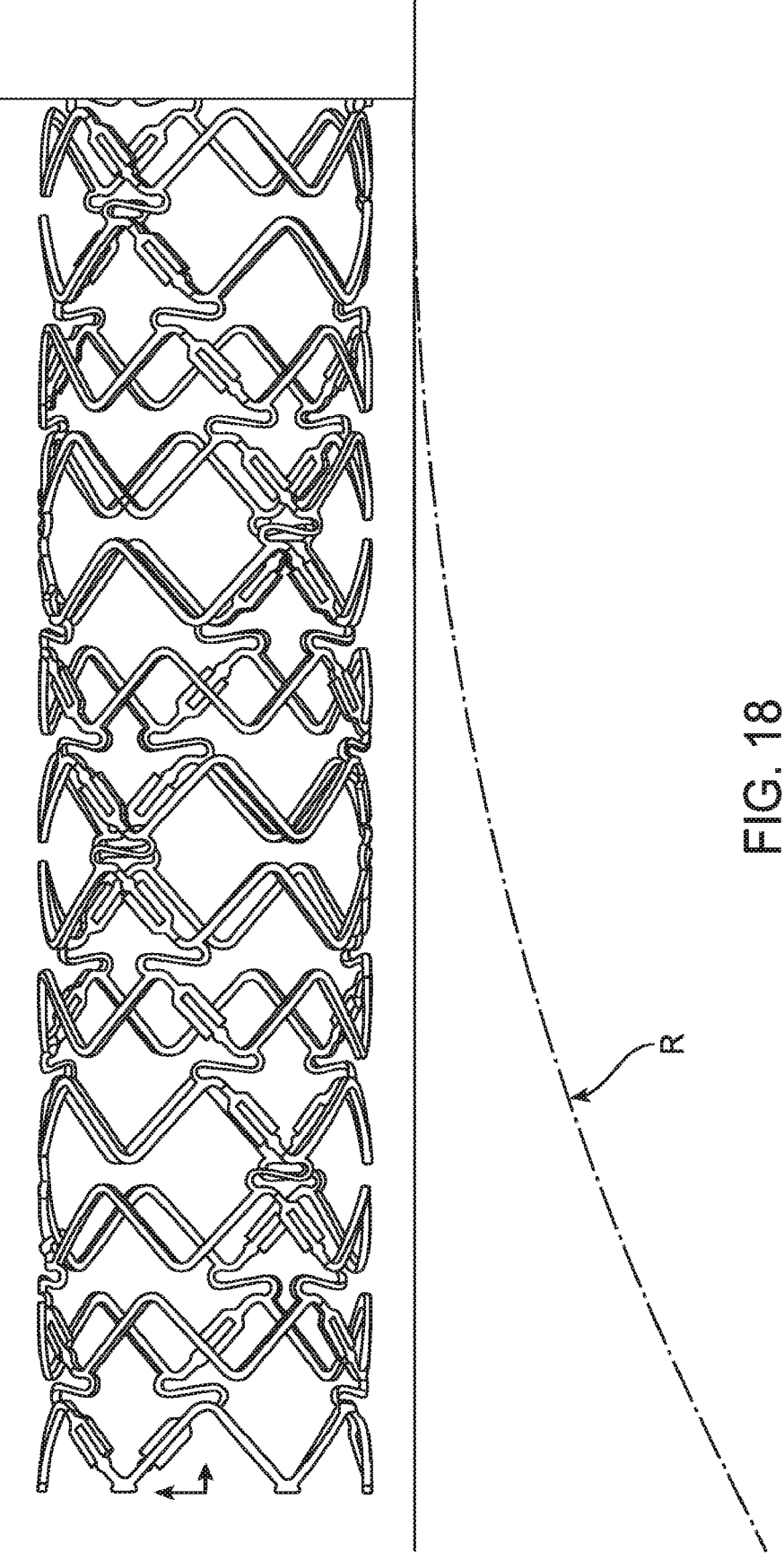
Figure 19:
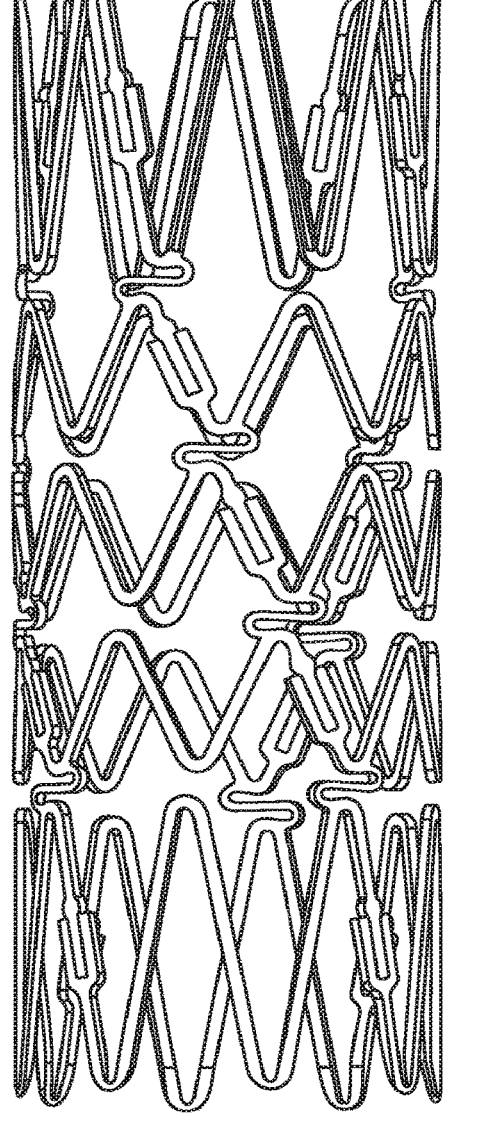
FIGS. 19-28 illustrate incorporation of separation region of the present invention in different scaffold geometries where the scaffold geometries are as expanded or after uncaging (separation regions formed discontinuities).

Test: Bending Test FIG. 18: A stent was patterned from Stent Material having a thickness of 107 microns, having a serpentine ring with each ring having 3 separation regions. The stent was in an expanded configuration of diameter 6.0 mm and was connected to a mock artery, with both stent and artery divided in half at a symmetry plane. The remaining half of the mock artery was attached to a fixture that surrounded it at the end farthest from the symmetry plane, and formed a flexible spine along the bottom (used to enforce the radius of bending). In addition, the inner surface of the mock artery had a pressure of 100 mmHg applied to it. All points of the artery and stent on the symmetry plane were confined to that plane. The spine was fixed against vertical displacement as shown in FIG. 17. Points on the spine were displaced to a point on the target radius, as shown in FIG. 18. Large deformation nonlinear elastic analysis was used, resulting in an estimated stress prior to formation of discontinuities of 486e3 PSI, which dropped to 69e3 PSI after formation of discontinuities. The stent of the current invention with discontinuities in the separation regions resulted in an 86% reduction in bending forces.

Figure 20:
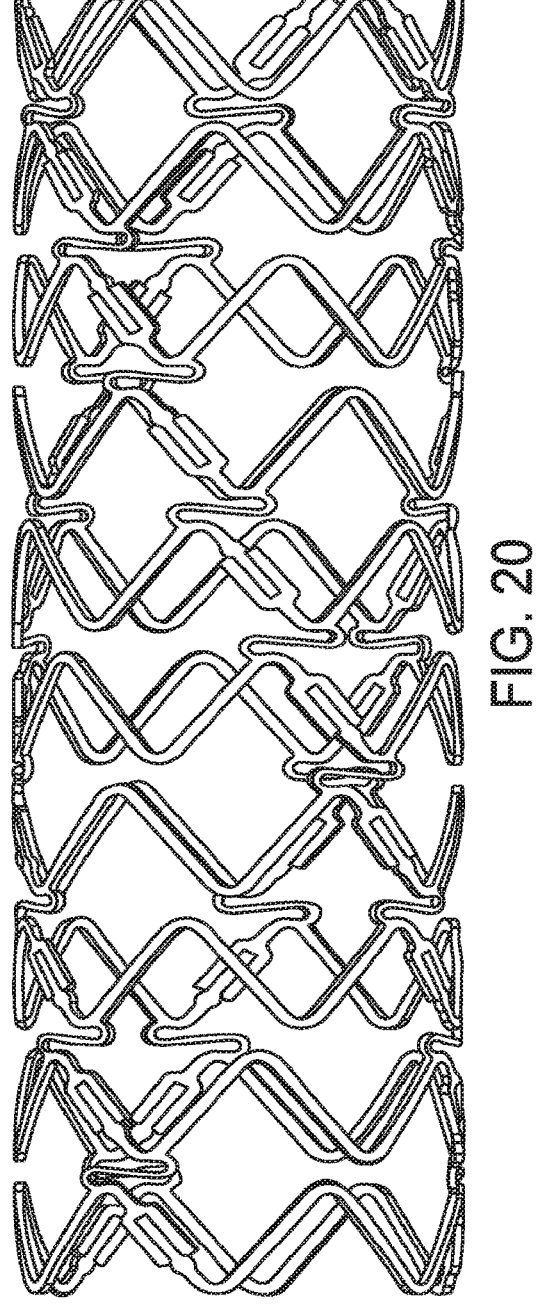
Figure 21:
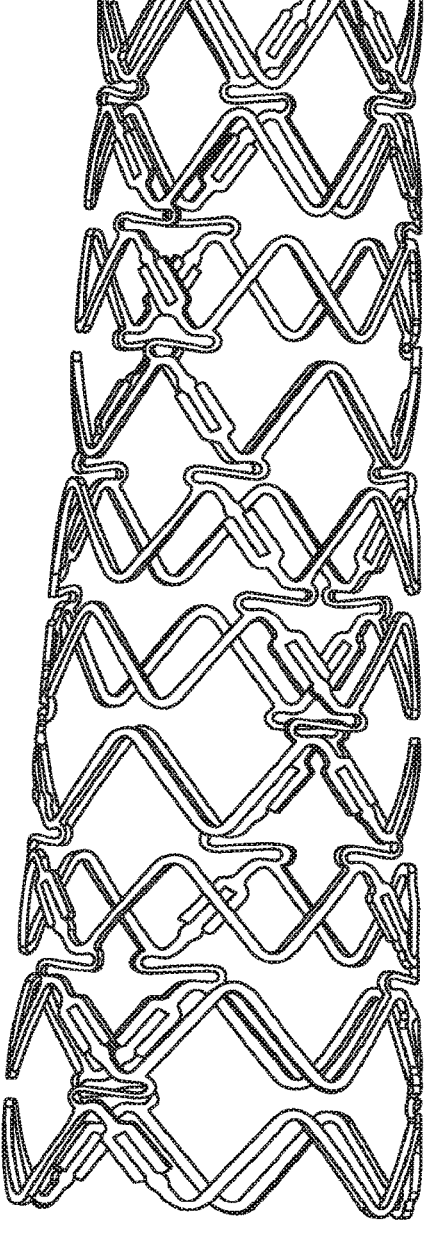
Figure 22:
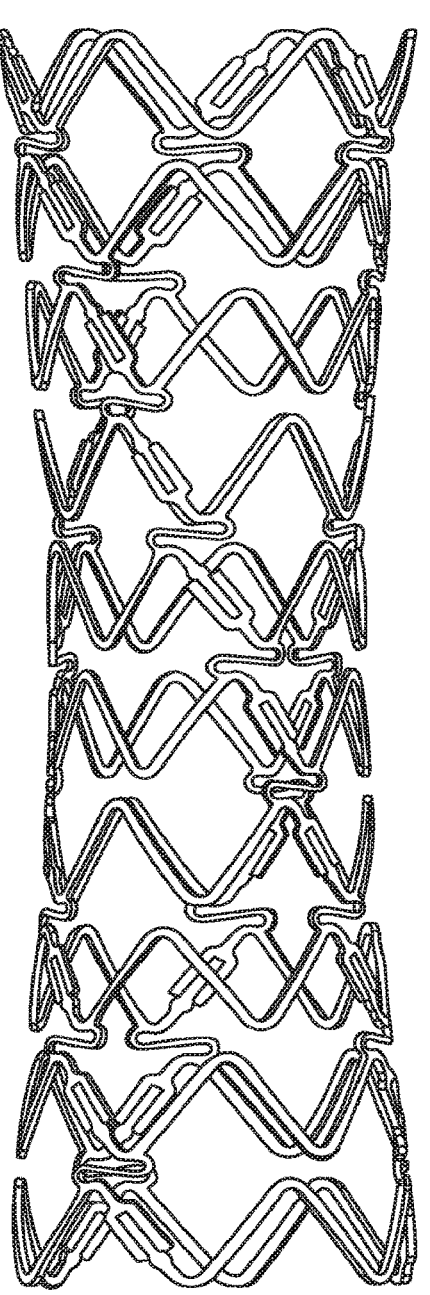
Figures 23, 24:
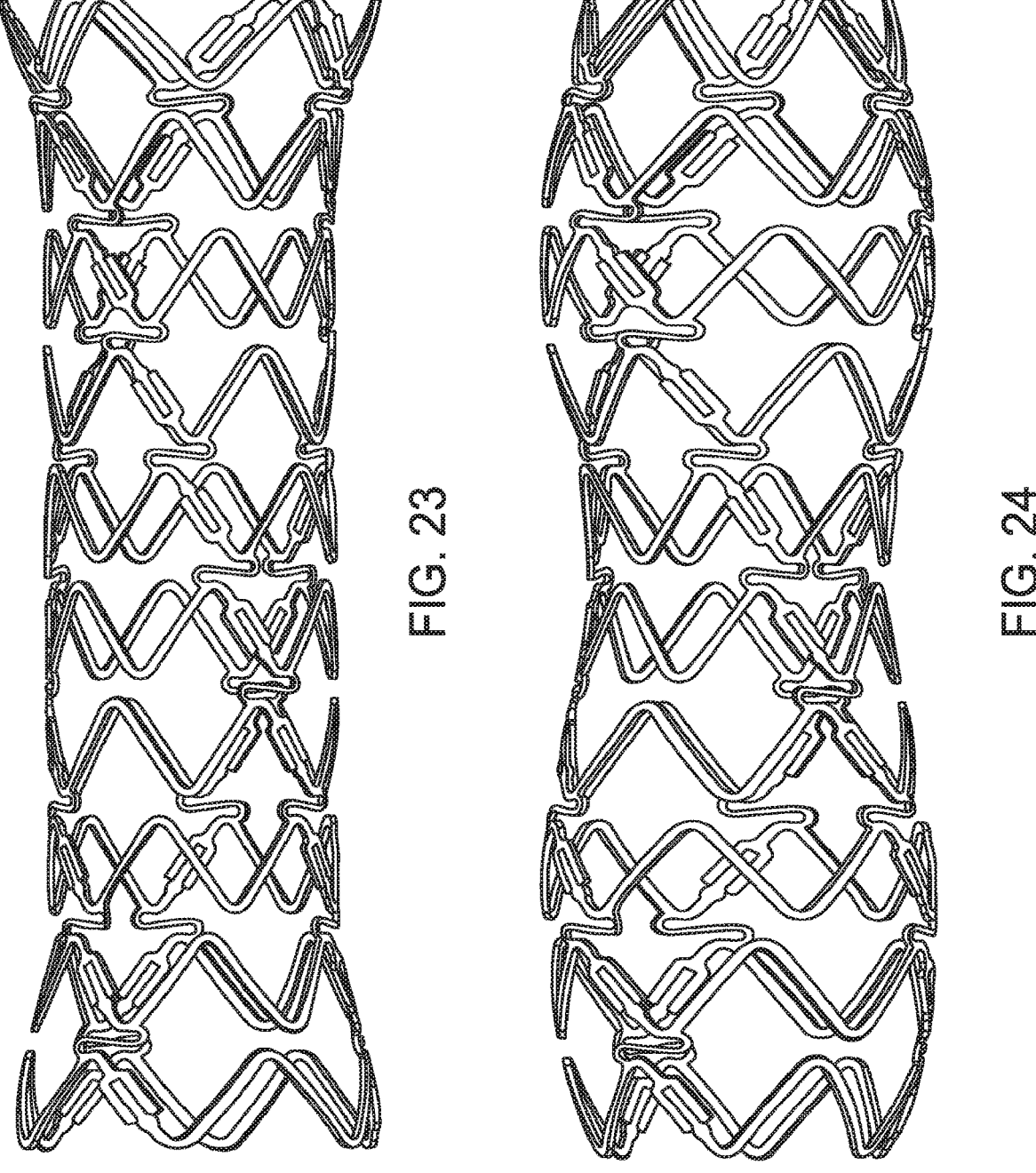
Figures 25, 26:
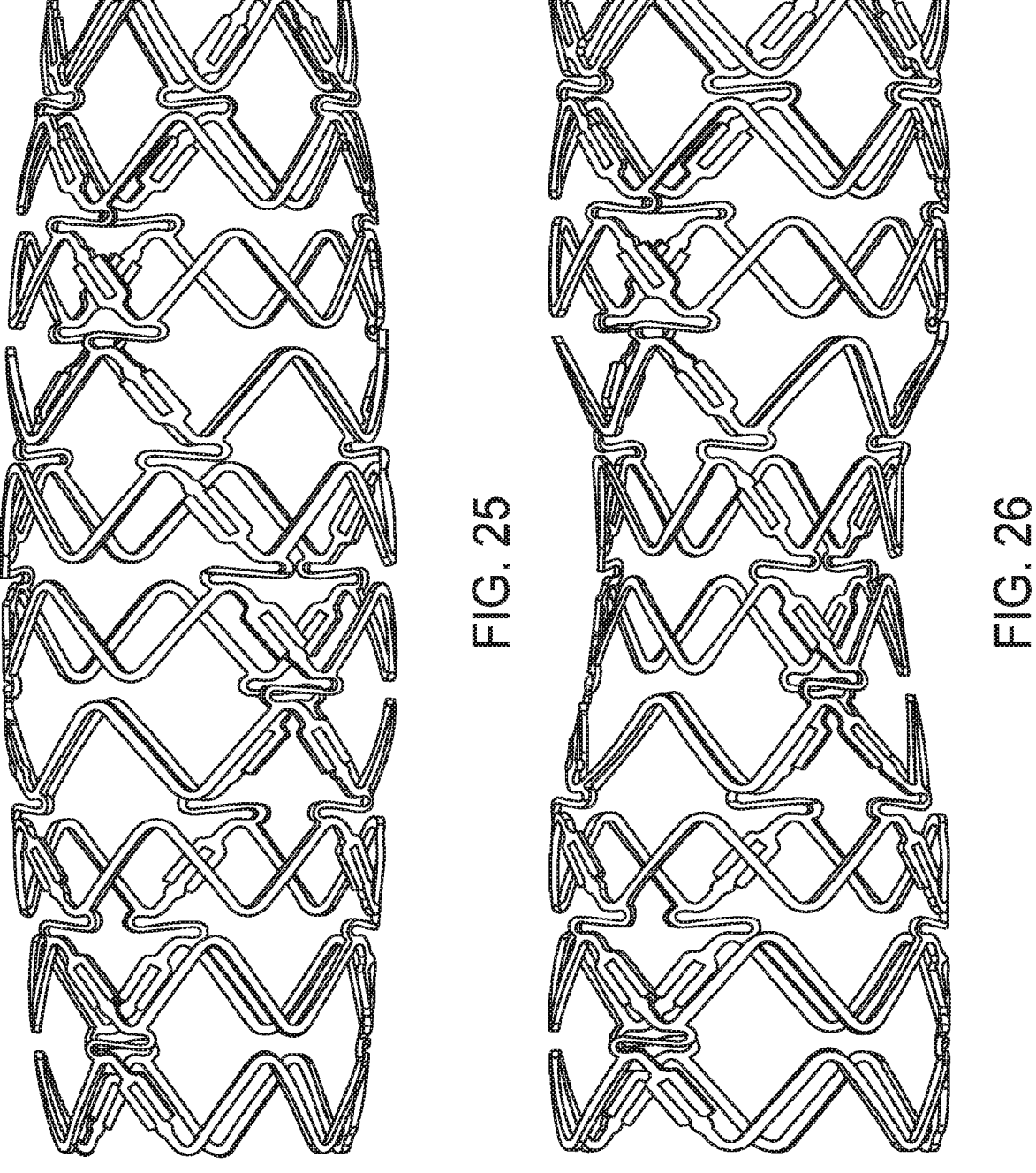
Figure 27:
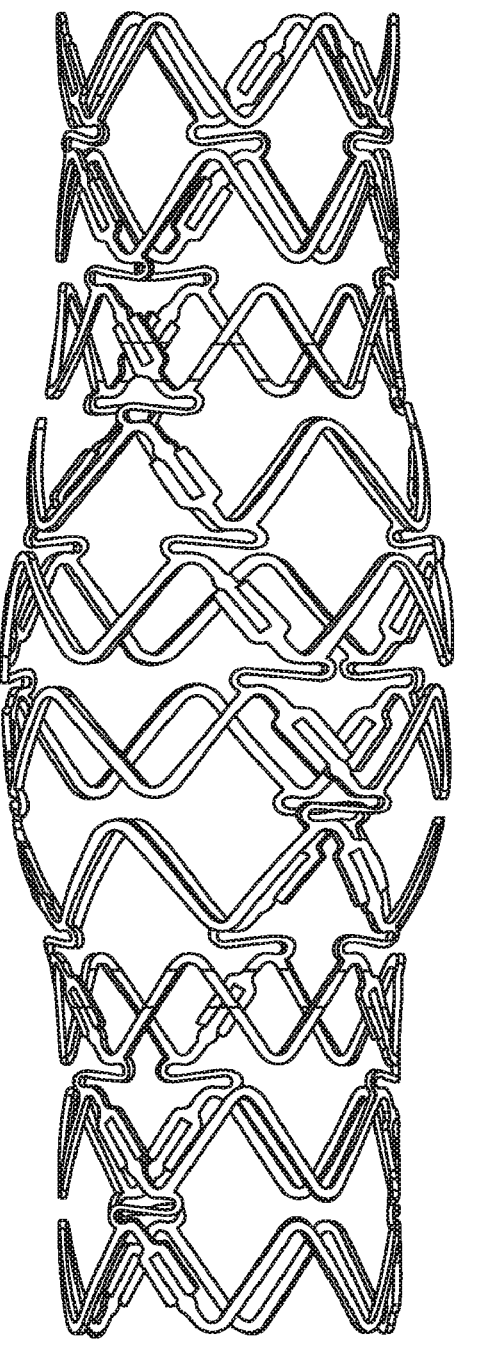
Figure 28:
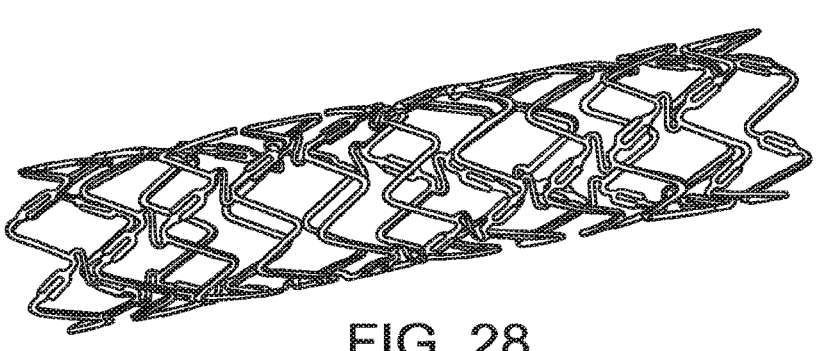

FIGS. 19-28 illustrate different scaffold geometries which can incorporate the separation regions of the present invention. The scaffold of FIG. 19 has end rings which incorporate both a lengthened strut (compared to inner rings between the two end rings) and separation regions. It also shows end ring crowns having width and thickness smaller than about mid ring crowns. Such modified end rings reduce the stiffness of the ends after deployment to reduce the abrupt change in compliance as discussed previously. FIG. 20 illustrates a straight scaffold with the separation regions arranged heli-cally about the cylindrical surface of the scaffold. FIG. 21 illustrates a tapered stent which incorporates the separation regions of the present invention. FIG. 22 illustrates a full curve neck scaffold which incorporates the separation regions of the present invention. FIG. 23 illustrates a flat neck scaffold which incorporates the separation regions of the present invention. FIG. 24 illustrates an undulated or "coke bottle" scaffold which incorporates the separation regions of the present invention. FIG. 25 illustrates a scaf-fold having a cylindrical convex or "outwardly bowed" surface which incorporates the separation regions of the present invention. FIG. 26 illustrates a scaffold having an inwardly tapered waist and straight cylindrical ends which incorporates the separation regions of the present invention. FIG. 27 illustrates a scaffold having an outwardly expanded waist and straight cylindrical ends which incorporates the separation regions of the present invention. The scaffold of FIG. 28 has a structure similar to that FIG. 20 with two additional scaffold rings. FIGS. 18-28 show variations of stent geometries providing separation regions located on each side of an axial link joining adjacent circumferential rings. These examples show the line of separation regions positioned in a spiral around the stent with all axial links having a separation region flanking each side. Such con-figuration provides stability to the stent by decreasing the stress in the axial links as the stent expands from a crimped configuration to an expanded configuration, contributing to more uniform expansion of the stent. The axial links still connect adjacent circumferential rings following expansion and the formation of the discontinuities.

Figure 29:
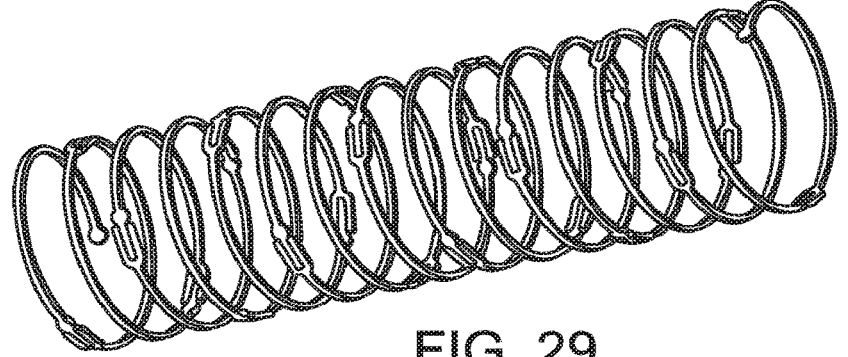
FIGS. 29 and 30 illustrate helical wire stents which can incorporate the separation regions of the present invention.
Figure 30:
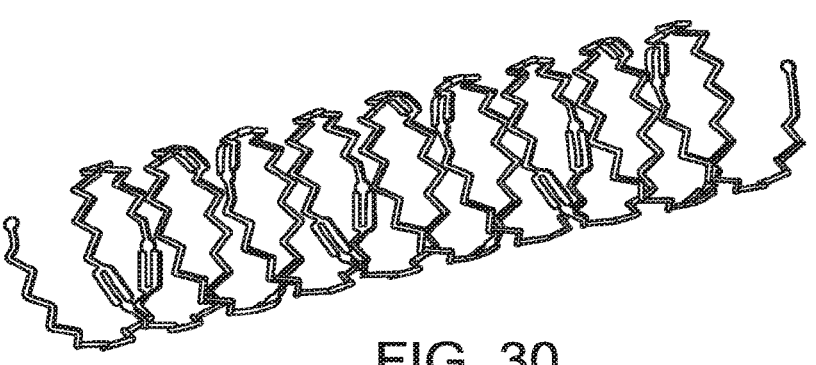

FIGS. 29 and 30 illustrate helical wire stents which can incorporate the separation regions of the present invention. FIG. 29 shows a helical wire stent and FIG. 30 shows a zig-zag wire would into a helix. Such helical wire stent will typically be formed from an elastic metal, such as spring, a shape memory alloy, and will typically be self-expanding.

Figure 31:
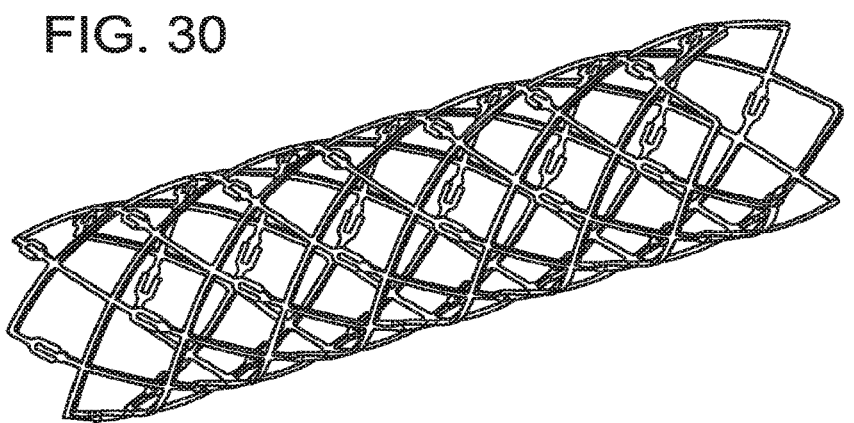
FIG. 31 illustrates a closed cell, counter wound helical scaffold which incorporates the separation regions of the present invention.

FIG. 31 illustrates a closed cell, counter-wound helical scaffold which incorporates the separation regions of the present invention. Such counter-wound stent will typically be formed from an elastic metal wire or tube, such as a shape memory alloy, and will be self-expanding. Alternatively, such scaffolds may be patterned from metal tubes and later expanded into their deployment dimensions.

Figure 32:
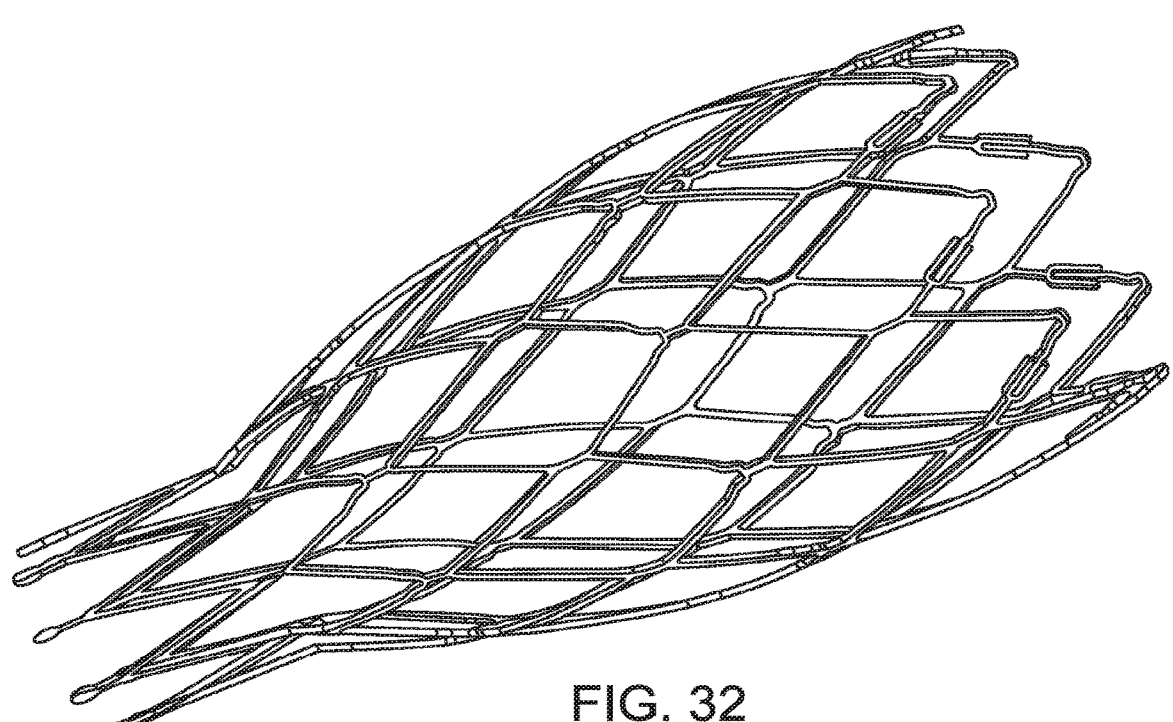
FIGS. 32-34 illustrate a funnel-shaped scaffold suitable for some anatomies such as annulus, left atrial appendage closure, and other purposes which incorporates the separation regions of the present invention.
Figure 33:
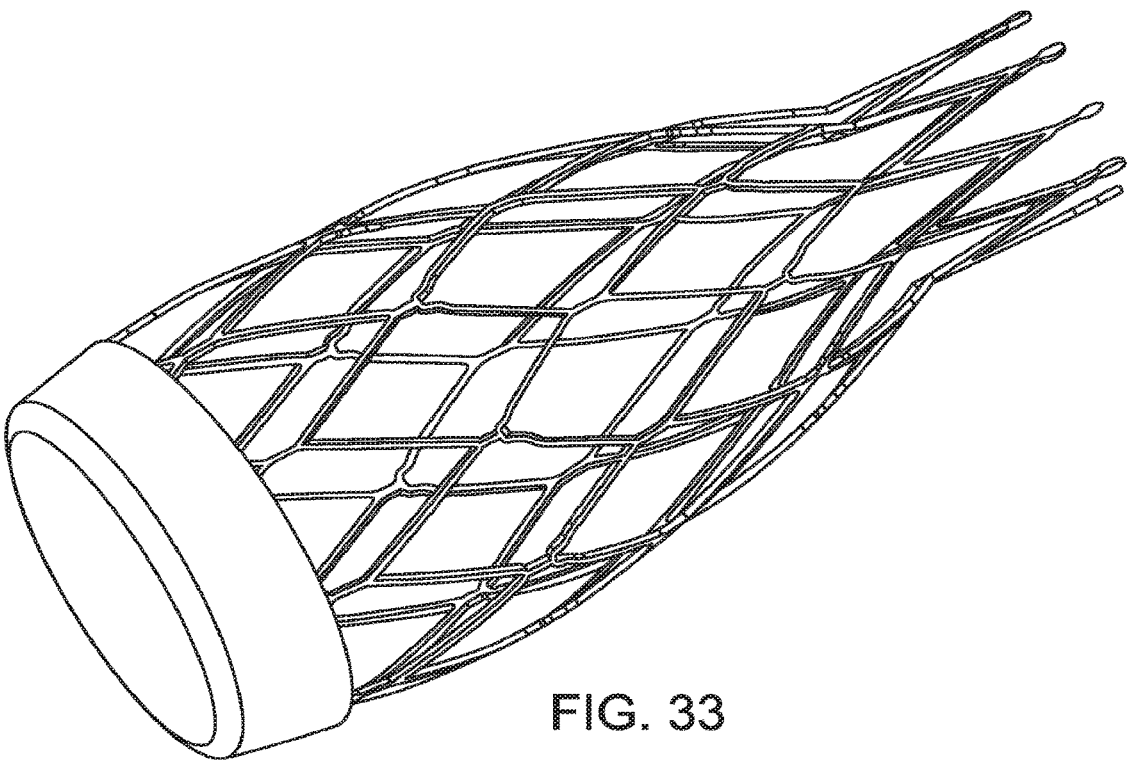
Figure 34:
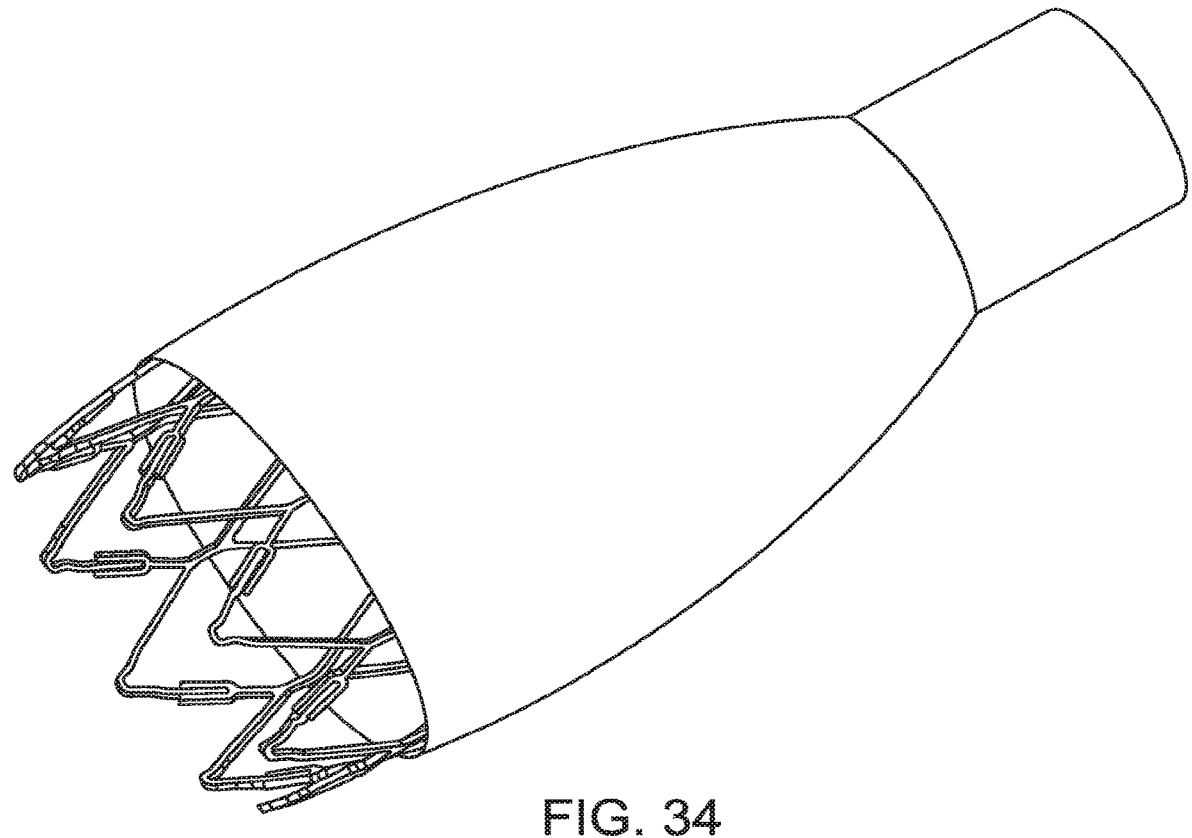

FIGS. 32-34 illustrate a funnel-shaped scaffold suitable for certain anatomies such as annulus, left atrial appendage (LAA) closure and other purposes which incorporates the separation regions of the present invention. In these designs, only the larger end of the scaffold has separation regions about its circumference, however, one can appreciate that such separation regions can be configured in various regions of the scaffold to achieve various objectives as described in this application. It is this enlarged end that is positioned at the opening of the LAA with the tapered end ending into the LAA. As shown in FIG. 33, a covering may be formed over the enlarged end to inhibit blood flow between the left atrium and the LAA (where emboli may form). Alterna-tively, the cover could be over the tapered end as shown in FIG. 34. The various scaffold geometries shown in FIGS. 19 to 28 illustrate the incorporation of separation regions in one or more of the scaffold segments of the scaffold to achieve certain geometries for the scaffold after uncaging (formation of discontinuities in scaffold rings). The illustrations are of the scaffold in the expanded configuration and before uncag-ing, or as a result of uncaging of the separation regions which are configured to give such geometries under physi-ologic conditions. In a preferred example, the scaffold are expanded from a crimped configuration to an expanded configuration, wherein the scaffold in the expanded configu-ration is substantially cylindrical and wherein the scaffold after formation of discontinuities conform to the anatomy and form the various geometries as described in FIGS. 21-27 and 32-34 examples. In FIGS. 21-34 examples, the stent prosthesis configurations are expanded configuration typi-cally having a uniform crimped configuration, but may have such configurations in the crimped state, or may have such configuration after said separation regions form discontinui-ties.

Referring now to FIGS. 35A-35C, a scaffold 2600 includes a plurality of circumferential rings 2602 including struts 2604 joined by crowns 2606. Each of the adjacent circumferential rings 2602 is joined by circumferentially separable axial links 2608 which have a U-shaped geometry and which are joined between crowns on adjacent circum-ferential rings 2602. The crowns are also circumferentially separable at the locations where joined by the axial links 2608 so that both the axial links and the crowns may separate together when the scaffold is expanded in a physi-ologic environment, as shown in FIG. 35B. Note that FIG. 35B shows a transition state where some of the axial links 2608 have not yet separated while the majority have. As shown in FIG. 35C, each circumferentially separable axial link 2608 includes an outer U-shaped segment 2610 and an inner U-shaped segment 2612. The outer segment is wider than the inner segment, and each of the segments is capable of bending and axially elongating when still together or after separation. The interface surfaces or gaps between the outer and inner segments have a length which is significantly greater than the distance between the adjacent crowns. As illustrated, the length of this interface surface or gap region is about three times that of the distance between the adjacent crowns in the stent before expansion. The increase in interspace length may vary depending on the particular circumstances and geometries.

Referring now to FIGS. 36A through 36C, a scaffold 2620 comprising a plurality of circumferential rings 2622 includ-ing struts 2624 and crowns 2626 will be described. Adjacent circumferential rings 2622 are joined by circumferentially separable axial links 2628 having a generally S-shape. The S-shaped axial links are also capable of bending and axially elongating in response to implantation and exposure in the physiologic environment. The scaffold is shown prior to separation of the links 2628 in FIG. 36A, while the scaffold is shown partially separated in FIG. 36B. The S-shaped axial links 2628 include a first segment 2610 having both wider and narrower portions and a second congruent segment 2612 having similar wider and narrower portions. Each of the segments joins a pair of struts 2624 on adjacent circumfer-ential rings prior to separation, and the segments remain intact after separation to continue to hold portions of the adjacent circumferential rings together even after all separation rings have separated.

Figure 36D:
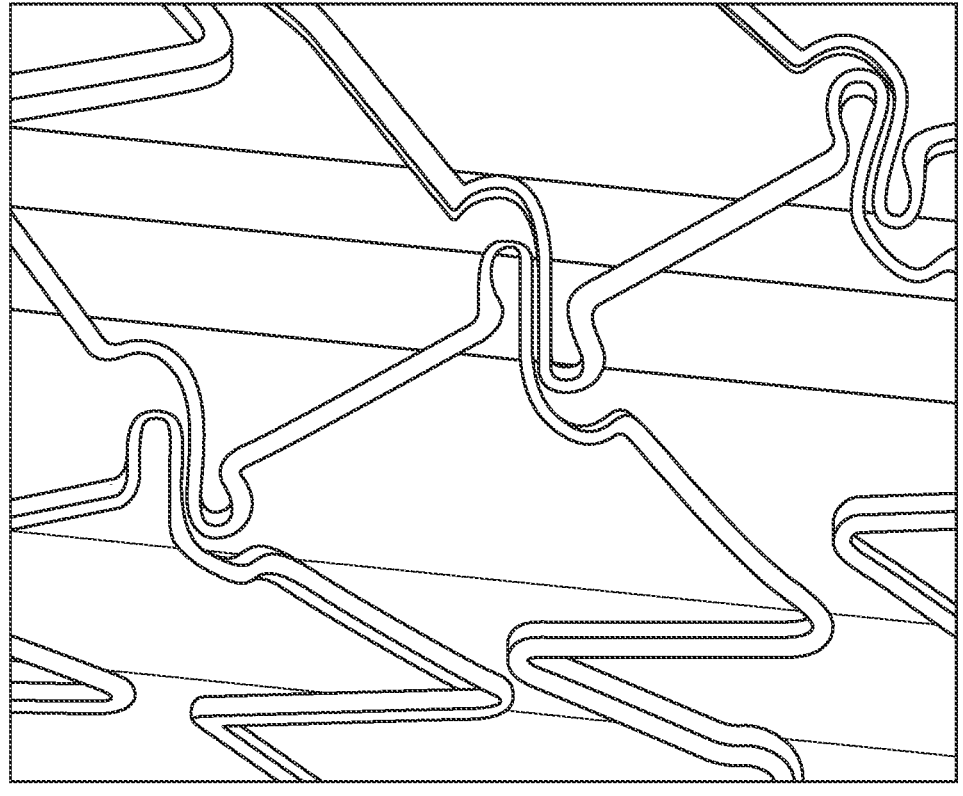
FIG. 36D is a photograph showing a scaffold fabricated with the pattern shown in FIGS. 36A through 36C after it has been radially expanded and the axial links have partially circumferentially separated.

FIG. 36D is a photograph showing a scaffold fabricated with the pattern shown in FIGS. 36A through 36C after it has been radially expanded and the axial links have partially circumferentially separated.

Figure 37A:
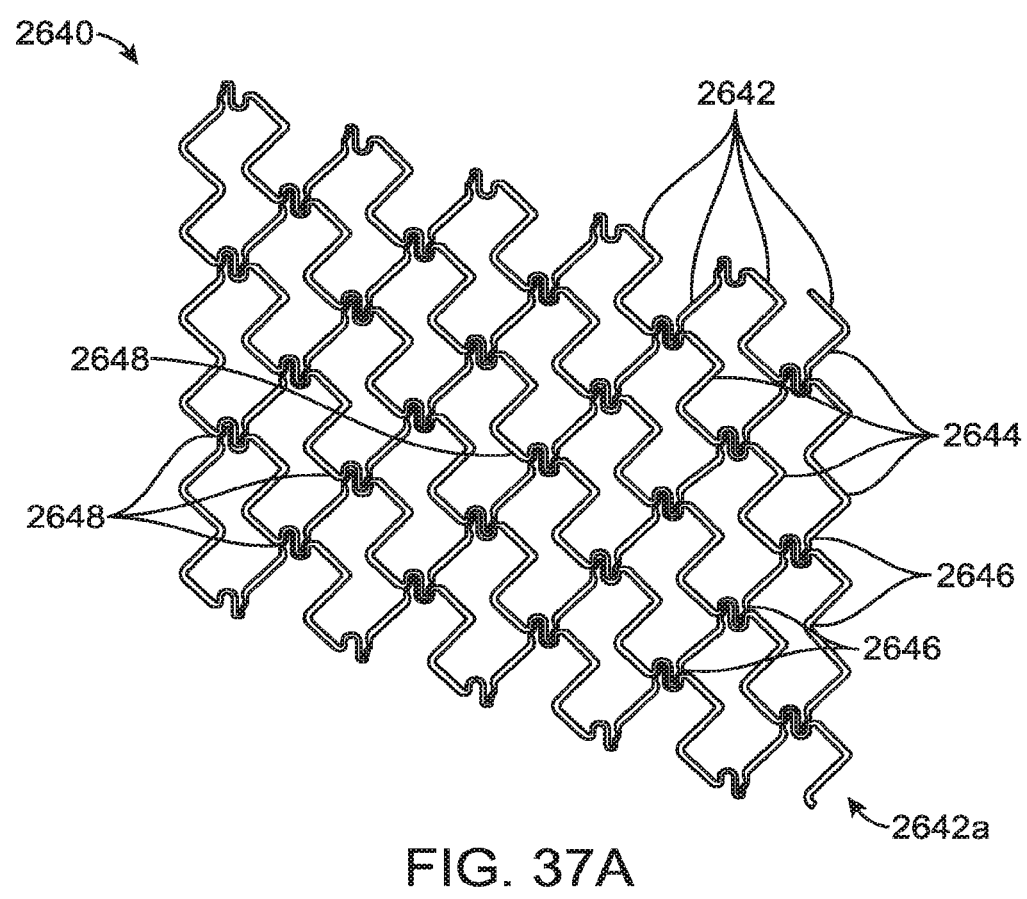
FIGS. 37A and 37B illustrate a scaffold having a plurality of circumferential rings joined by S-shaped circumferentially separable axial links where an end ring of the scaffold is configured to prevent complete separation of the scaffold into axial segments after expansion.
Figure 37B:
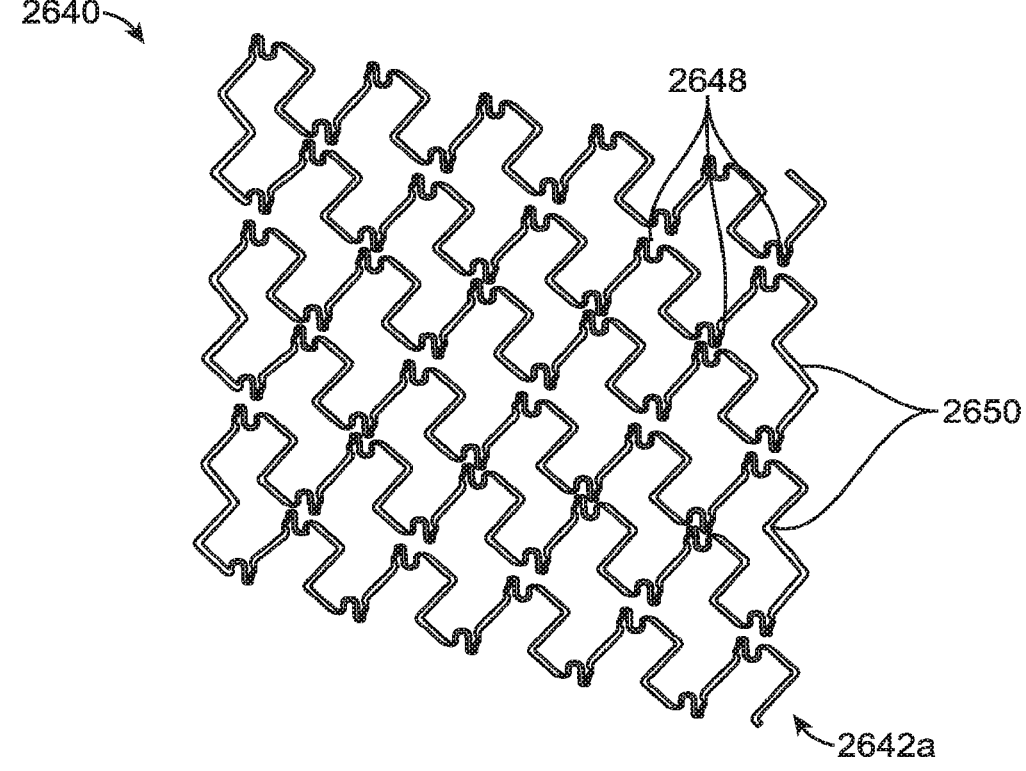

Referring now to FIGS. 37A and 37B, a scaffold 2640 constructed in accordance with the principles of the present invention comprises a plurality of circumferential rings 2642 each including a plurality of struts 2644 joined by crowns 2646. Crowns on adjacent circumferential rings are joined by circumferentially separable axial links 2648 which are shown in their non-separated configuration in FIG. 37A and in their separated configurations in FIG. 37B. Of particular note, an end-most circumferential ring 2642*a* separates so that certain regions or portions 2650 thereof span or bridge otherwise separated axial regions of the scaffold which would completely separate were it not for these remaining bridges 2650. Putting it another way, after full separation of the axial links 2648, the remaining assembly of struts and crowns forms a continuous length which loops back and forth as viewed in FIG. 37B. Such continuing separation can be advantageous to reduce the likelihood that any portion of the scaffold will be inadvertently released after separation of the separation regions.

Referring now to FIGS. 38A through 38C, a scaffold 2660 constructed in accordance with the principles of the present invention includes a plurality of circumferential rings 2662, where each ring includes individual struts 2664 joined by crowns 2666. Each circumferential ring is joined to at least one adjacent circumferential ring by three circumferentially separable axial links 2668, where the axial links are shown to have generally S-shaped geometries. As shown in FIGS. 38A and B, the circumferentially separable axial link 2668 has a separation interface or gap 2670 which is oriented at an oblique angle relative to the circumferential direction. As shown in FIG. 38C, the orientation of the separation interface may change upon expansion, such that it becomes aligned approximately parallel to the circumferential direction around the stent upon full expansion. Orienting the direction of the separation gap away from the circumferential direction can help immobilize or maintain the stability of the separation region as the stent is being regularly expanded during deployment. After deployment, of course, the biodegradable polymer or other adhesive material holding the segments of the circumferentially separable axial links together will degrade and allow the links to circumferentially open. The length of the axial link along the length of the axis may be 0.10 mm to 1.4 mm, preferably 0.2 mm to 1.1 mm, more preferably 0.2 mm to 0.7 mm. The length along the length of the axis of the axial link may be 10% to 150% compared to the length of the adjacent struts, preferably 20% to 110% compared to the length of the adjacent struts, more preferably 20% to 70% compared to the length of the adjacent struts. The bond line itself has a length and thickness, and is for example 0.5 to 7 mm in length, preferably 0.9-5.5 mm in length, more preferably 1.4 to 3.7 mm in length, and 60-90 microns in thickness, or 0.03 to 0.7 mm² in surface area on each side of the bond.

Referring now to FIGS. 39A through 39C, a scaffold 2680 constructed in accordance with the principles of the present invention includes a plurality of circumferential rings 2682 each including a plurality of struts 2684 joined by crowns 2686. Adjacent circumferential rings are held together by three circumferentially separable axial links 2688 having a w-shaped geometry. As shown in FIG. 39B, each end of the w-shaped circumferentially separable axial link may be joined in a strut of the adjacent circumferential ring, while as shown in FIG. 39C, the ends of the axial link 2688 may be joined in the crowns 2686 of each circumferential link. In particular, as shown in FIG. 39C, the ends of the axial link 2688 are joined at the side of each crown. In alternative embodiments (illustrated) any of the circumferentially axial links illustrated herein could be joined at the apex of the crown or at any point between the apex and the lateral portion of the crown where it joins the adjacent strut.

Figures 40, 41:
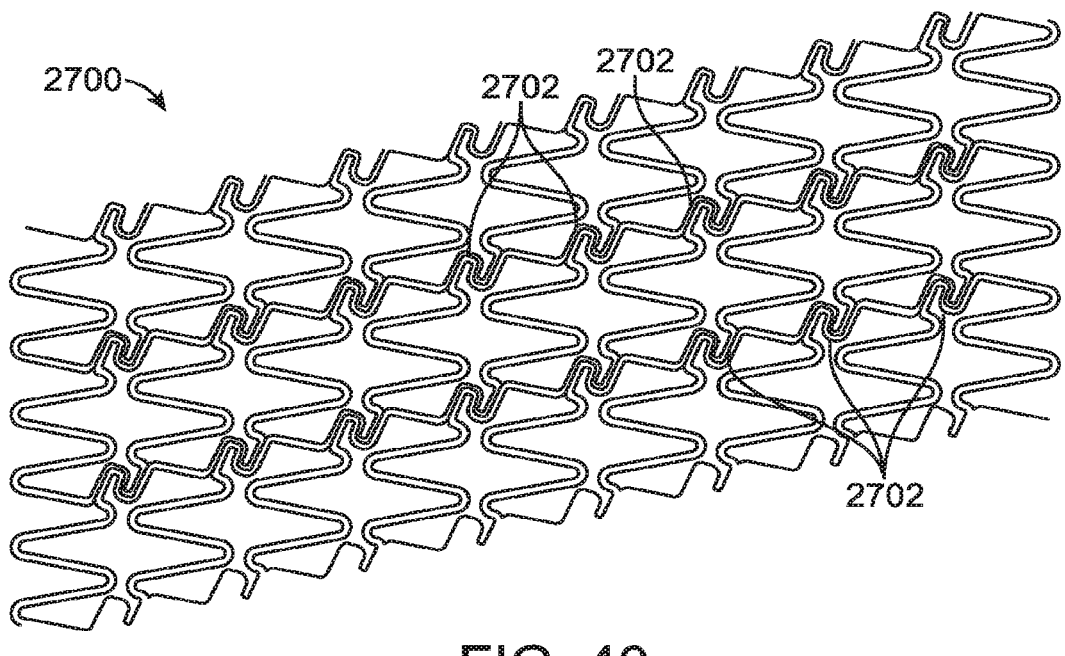
FIG. 40 illustrates a scaffold comprising a plurality of circumferential rings having generally S-shaped circumferentially separable axial links connected between struts on adjacent circumferential rings.
FIG. 41 illustrates a scaffold similar to that shown in FIG. 40 except that the circumferentially separable axial links are connected between crown regions on adjacent circumferential rings.

As shown now in FIG. 40, a scaffold 2700 constructed in accordance with the principles of the present invention includes a plurality of S-shaped circumferentially separable axial links 2702 which are distributed helically around the stent. In contrast, as shown in FIG. 41, a scaffold 2704 was a plurality of circumferentially separable axial links 2706 which are arranged axially along the scaffold. The scaffold 2700 has three helical arrangements of the circumferentially separable axial links 2702, while the scaffold 2704 has two linear arrangements of the circumferentially separable axial links 2706. In this example, the S-shaped links are angled differently than some other examples. Here the "take-off" angle of the S-shaped link is at 90 degrees to each of the struts to which the link is attached.

Figure 42A:
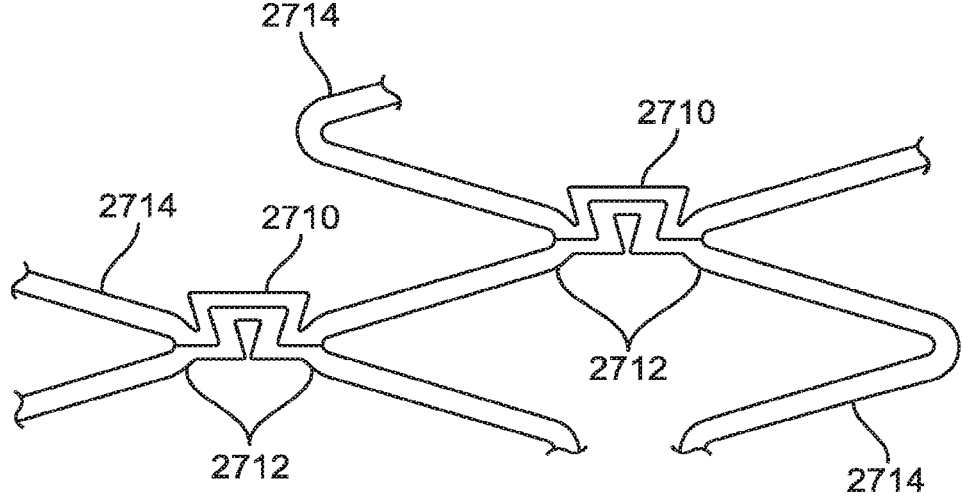
FIGS. 42A and 42B illustrate circumferentially separable axial links having a wedge-shaped geometry.
Figure 42B:
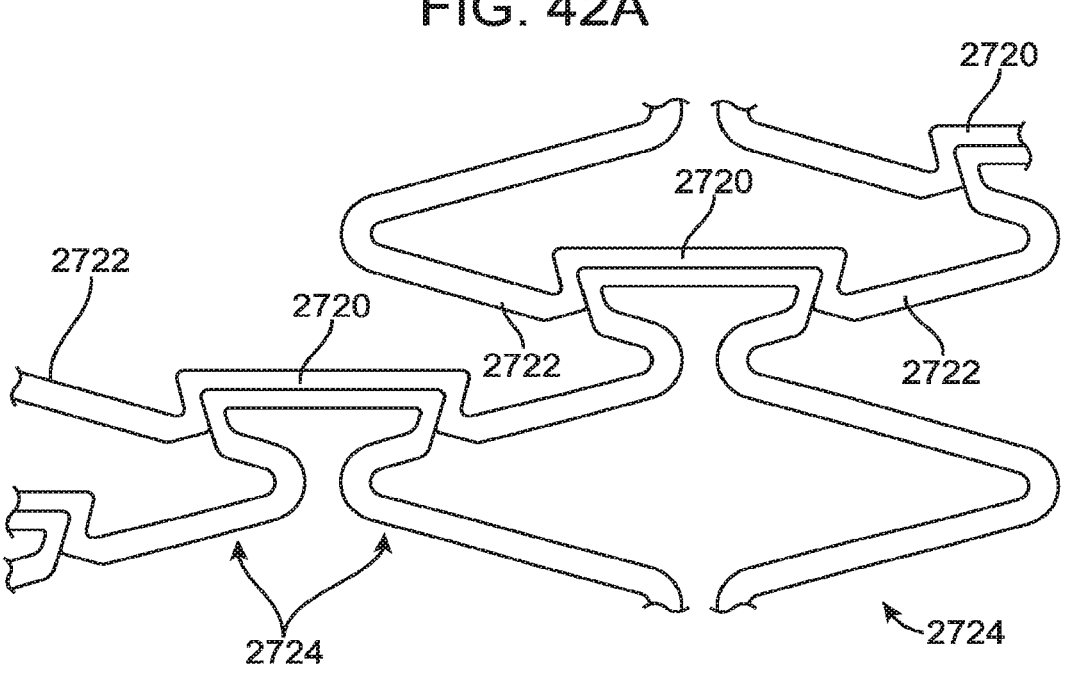

Referring now to FIGS. 42A and 42B, circumferentially separable axial links according to the present invention may take a variety of forms. In previous figures, the links have generally been shown as being curved, but other geometries are also possible, such as wedge-shapes. As shown in FIG. 42A, a wedge-shaped link 2710 extends between the apex on a pair of opposed crowns 2712 on adjacent circumferential rings 2714. Alternatively, a wedge-shaped circumferentially separable axial link 2720 may extend between struts 2722 on adjacent circumferential rings 2724.

Figure 43:
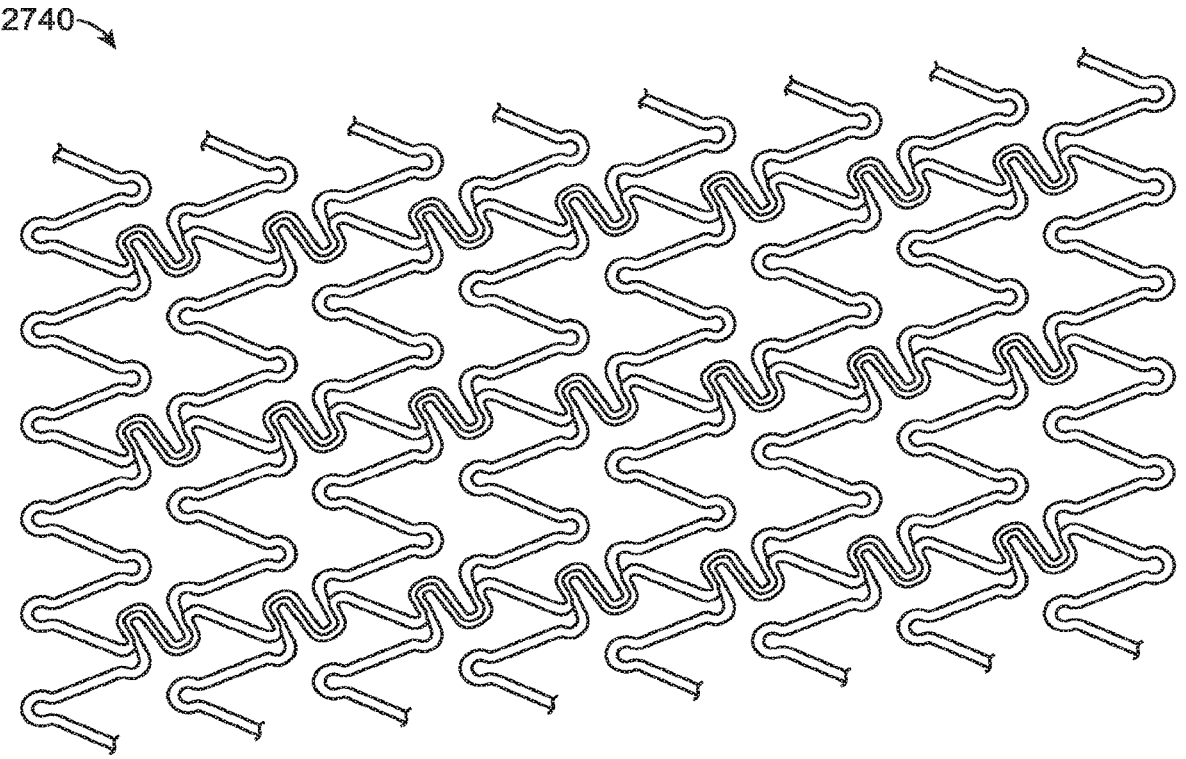
FIG. 43 illustrates a scaffold comprising of plurality of circumferential rings having circumferentially separable axial links between the keyhole crown regions on adjacent circumferential rings.

Referring now to FIG. 43, a scaffold 2740 comprising a plurality of circumferential rings 2742 each including struts 2744 and crowns 2746 has S-shaped circumferentially separable axial links 2748 joining adjacent circumferential rings. Crowns are "keyhole" crowns and the axial links 2748 are joined to open portions of the keyhole crowns as illustrated.

Figure 44:
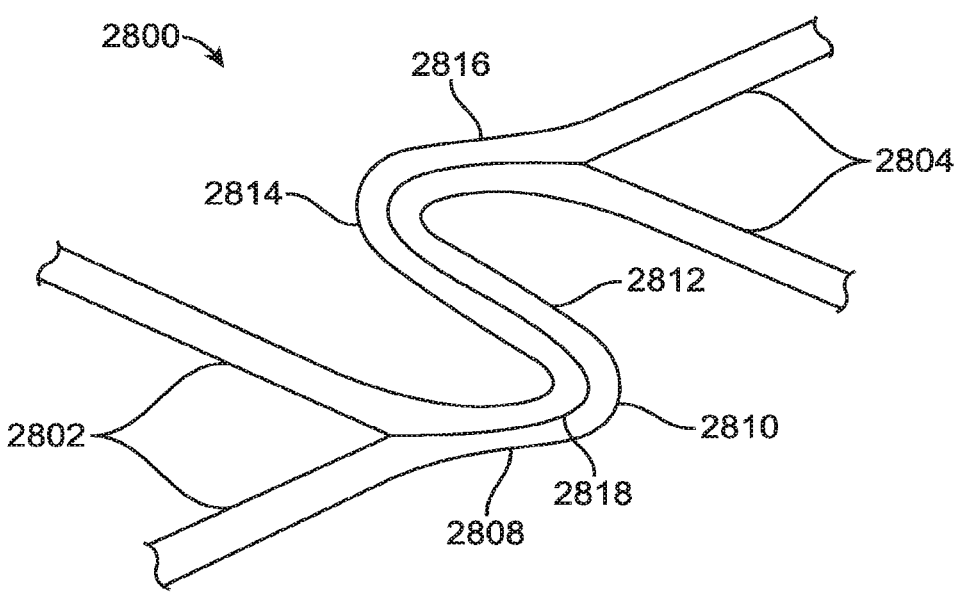
FIG. 44 illustrates a first exemplary embodiment of a curved, circumferentially separable axial link constructed in accordance with the principles of the present invention.

An exemplary axial link structure 2800 is illustrated in FIG. 44 and includes a pair of left struts 2802 and a pair of right struts 2804. The pairs of struts are joined by an S-shaped axial link region having a first straight section 2808 extending in the right direction from an attachment point at the base of the left struts 2802. The axial link extends rightwardly to a first bend or curve 2802 where the link region makes a transition to a straight region 2812. The curve is greater than 90°, and shown as about 135°, so that the direction of the transition region 12 is back toward the left side of the strut. A second curved or bent region 2014 then takes the direction of the link region back to the rightward direction and terminates in a second straight or axially aligned portion 2816. The S-shaped axial link region has a dividing line 2818 running through its center and is held together by the reversing curve of the link region. In particular, the interface between the segments on either side of the dividing line in the first straight or axial section 2808 and the second straight or axial section 2816 are directly opposed so that they resist circumferential separation of the axial link when a circumferential expansion force is applied to the scaffold.

Figure 45:
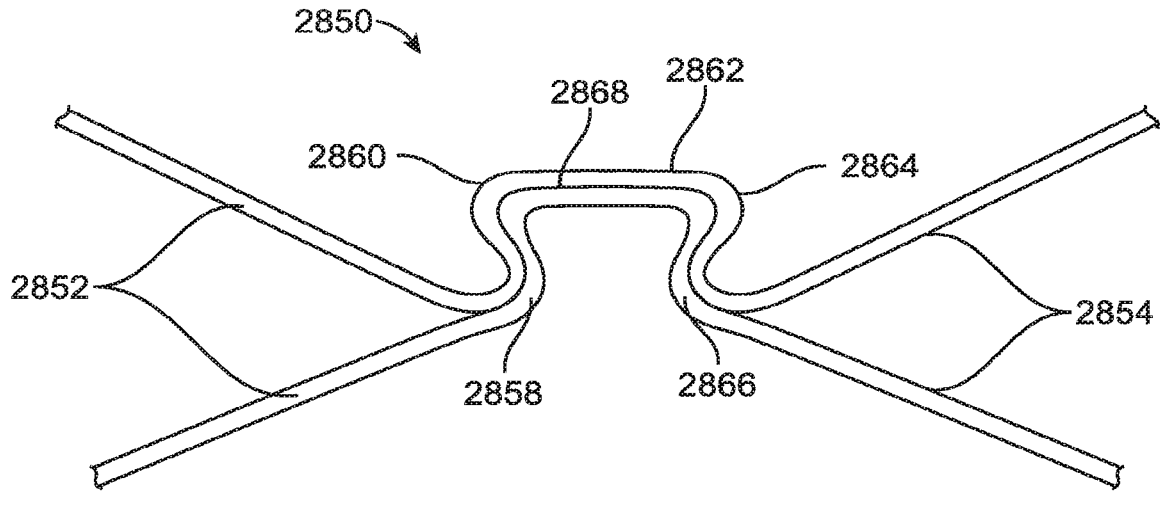
FIG. 45 illustrates a second exemplary circumferentially separable axial link constructed in accordance with the principles of the present invention.

Referring now to FIG. 45, an alternative axial link structure 2850 is illustrated. The axial link structure 2850 also has a pair of left struts 2852 and right struts 2854. The left struts 2852 merge in a rightwardly direction immediately to a first curved section 2858 and then to a second curved region 2860. A straight, axially aligned region 2868 then extends in the rightward direction toward a third bent or curved region 2864 and immediately into a fourth curved region 2866 which joins to the base of the right strut pair 2854. The axial link 2850 is divided into first and second segments by dividing line 2868. The two segments are initially held together so long as the shape of the axial link 2850 remains as illustrated in FIG. 45. As the scaffold expands, however, the axial link will deform and allow the axial link to circumferentially separate. For example, the attachment points of the axial link to the left and right struts 2852 and 2854 will be drawn axially apart allowing the lower segment of the axial link to slip out of the constraint of the upper segment of the axial link.

Figure 46A:
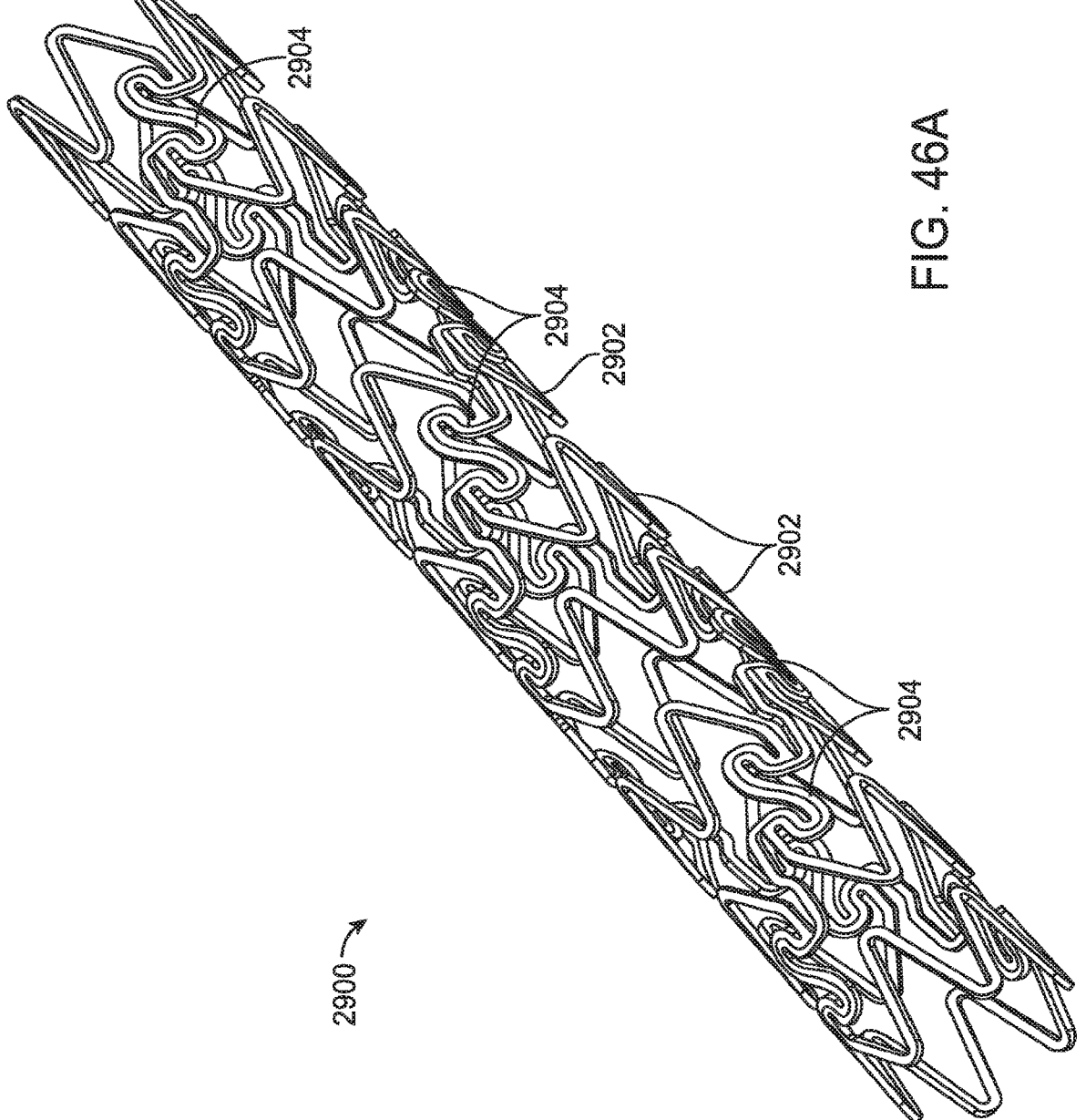
FIGS. 46A-46B illustrate a stent scaffold comprising a plurality of rings joined by curved, circumferentially separable axial links in accordance with the principles of the present invention.
Figure 46B:
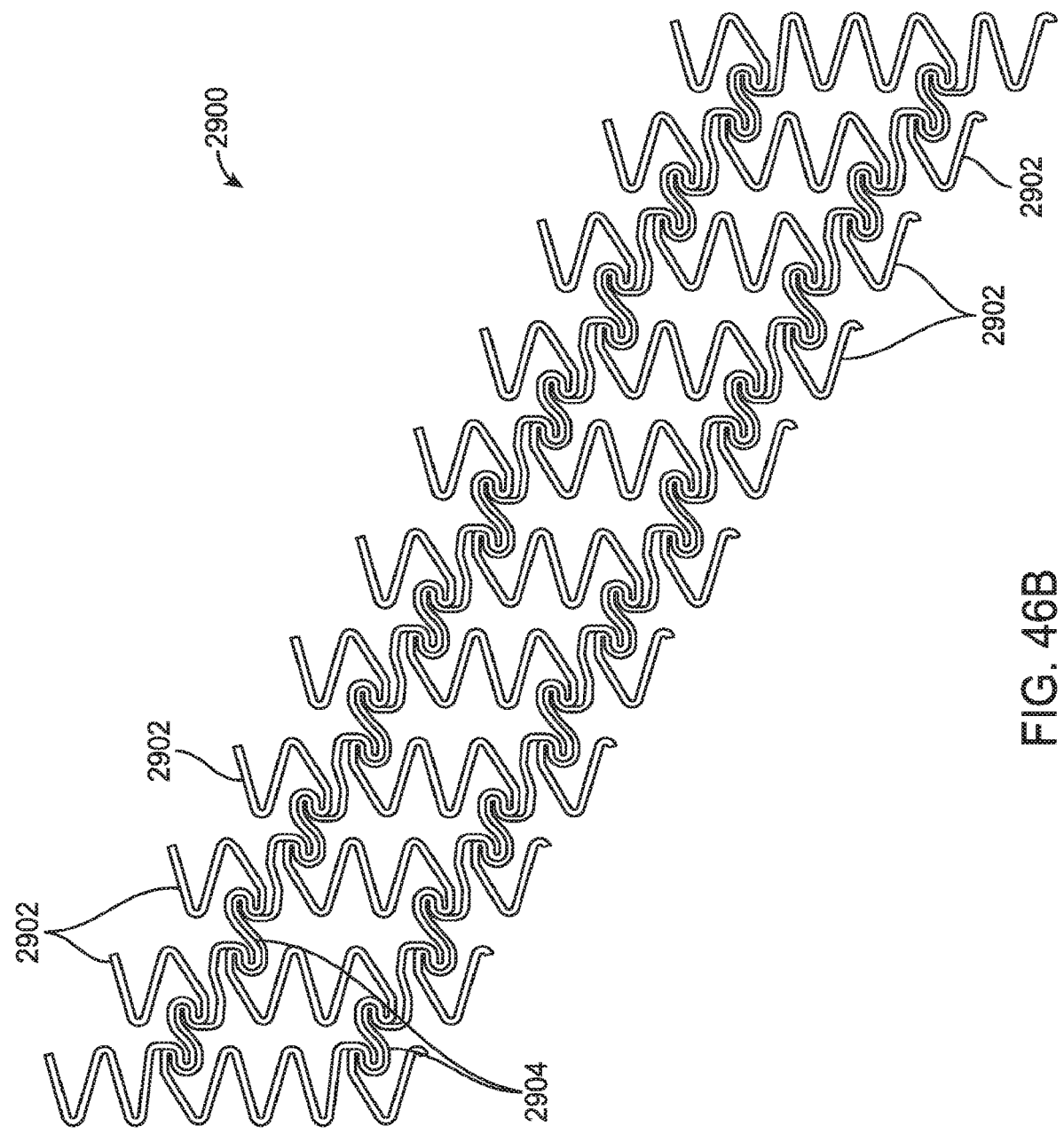
Figure 47A:
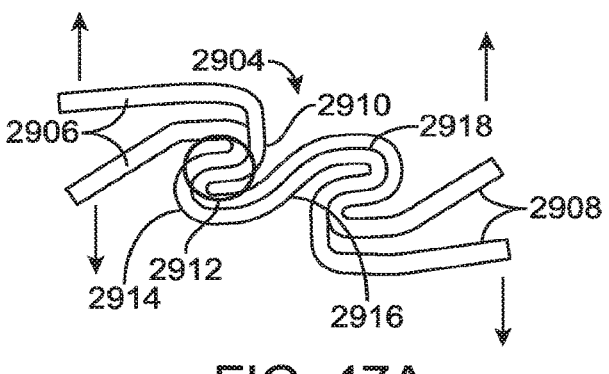
FIGS. 47A and 47B illustrate the circumferentially separable axial link that is used in the stent scaffold of FIG. 46A having axially aligned interlocking regions.
Figure 47B:
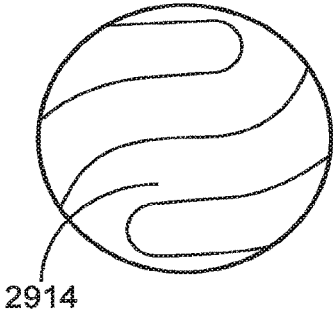

A further exemplary stent scaffold 2900 is illustrated in FIGS. 46A and 46B. FIG. 46B illustrates the stent or scaffold in a rolled-out view. The stent scaffold includes a plurality of circumferential rings 2902 joined by circumferentially separable axial links 2904. The axial links 2904 are arranged in a pair of parallel, helical lines around the cylindrical body of the stent. In this way, the stent can separate into a pair of helical ribbons which are completely unconnected after all the axial links have separated. Axial link 2904 is illustrated in greater detail in FIGS. 47A and 47B. Left struts 2906 join in a first curved region 2910 which turns from a generally axial direction to a circumferentially aligned direction. The turn continues until a short, straight region 2912 is directed back in the leftward direction and is oriented parallel to the axis of the stent scaffold. After extending a short distance in the leftward direction, the axial link enters a second curve which turns approximately 180° and enters a transition region 2916. The transition region 2916 continues the curve and makes a generally S-shaped transition into a symmetrically shaped region which is attached to the right-hand struts 2908. It will be appreciated that the straight interface region of the link segments shown at 2912 provides significant resistance to circumferential separation as the stent scaffold itself is being circumferentially expanded.

Figure 48A:
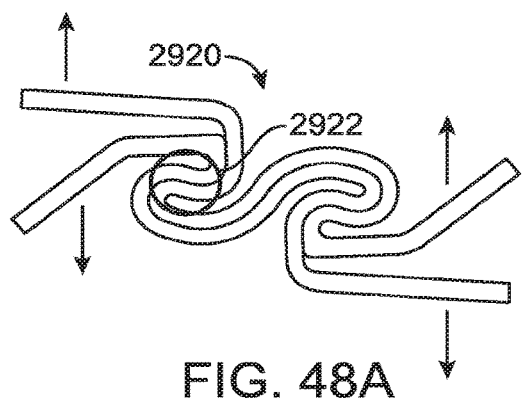
FIGS. 48A and 48B illustrate a circumferentially separable axial link similar to that of FIGS. 47A and 47B, where the interlocking segment has a curve which increases resistance to axial separation.
Figure 48B:
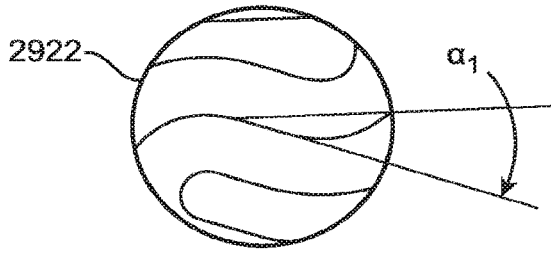
Figure 49A:
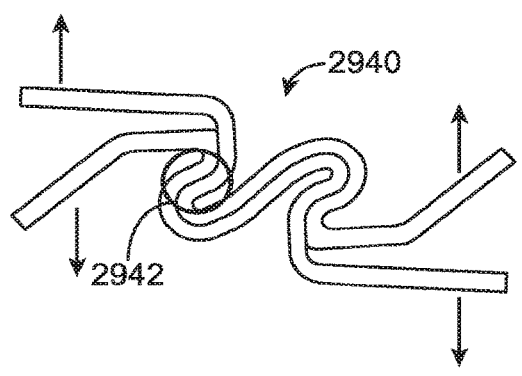
FIGS. 49A and 49B illustrate a circumferentially separable axial link having an interlocking segment which decreases the force necessary for circumferential separation.
Figure 49B:
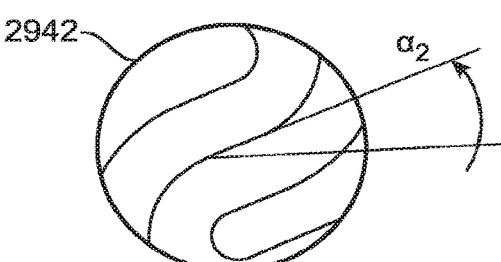

The degree of resistance to circumferential expansion and separation can be adjusted by changing the angle of the short, flat segment in the axial link 2904. For example, as shown in FIGS. 48A and 48B, the flat region can be tilted downward (when viewed relative to the rightward direction) so that the resistance to separation along the dividing line 2918 is increased. Alternatively, the resistance to circumferential separation of the axial link can be decreased by turning the direction of the dividing line in the short segment upward in the rightward direction, as shown at 2942 in FIGS. 49A and 49B. The angle of downward inclination $\alpha_1$ and/or angle of upward inclination $\alpha_2$ can be increased or decreased in order to adjust the resistance to circumferential separation.

Figure 50:
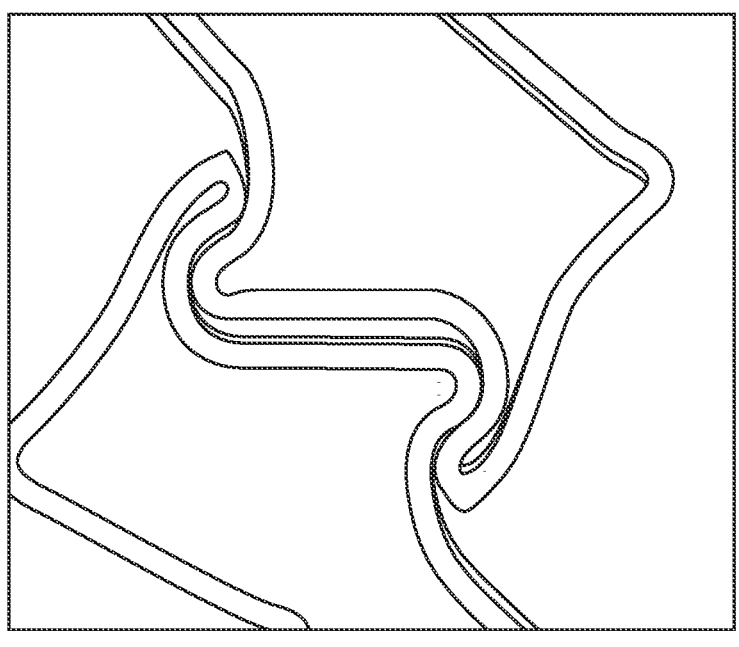
FIGS. 50 and 51 are photographs of a circumferentially separable axial link of a type similar to those illustrated in FIGS. 46A and 46B.
Figure 51:
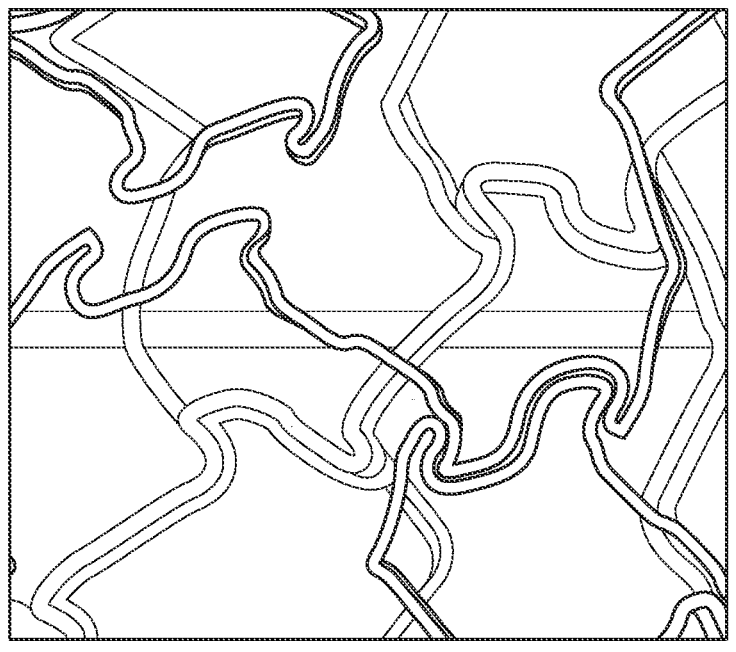

FIGS. 50 and 51 are photographs showing circumferentially separable axial links similar to those in FIGS. 46A-46B and 47A-49B in their initially locked configuration (FIG. 50) and in a partially released and fully released configuration (FIG. 51).

Figure 52:
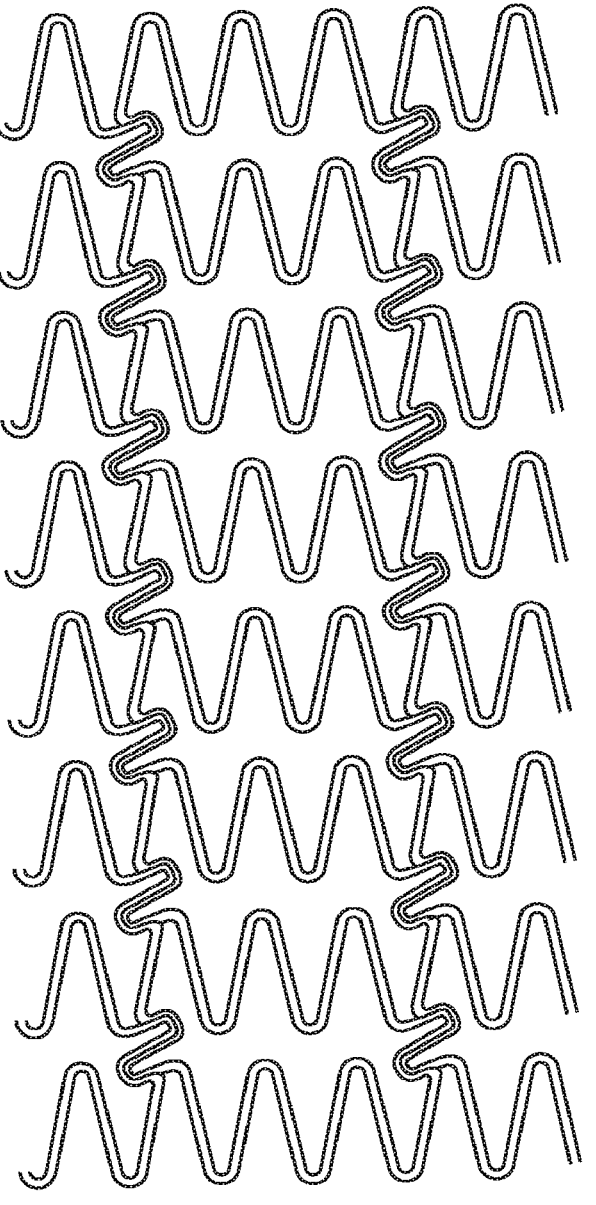
FIG. 52 shows an alternative stent scaffold pattern having circumferentially separable axial links arranged in a pair of parallel axial lines along the length of the scaffold.
Figure 53:
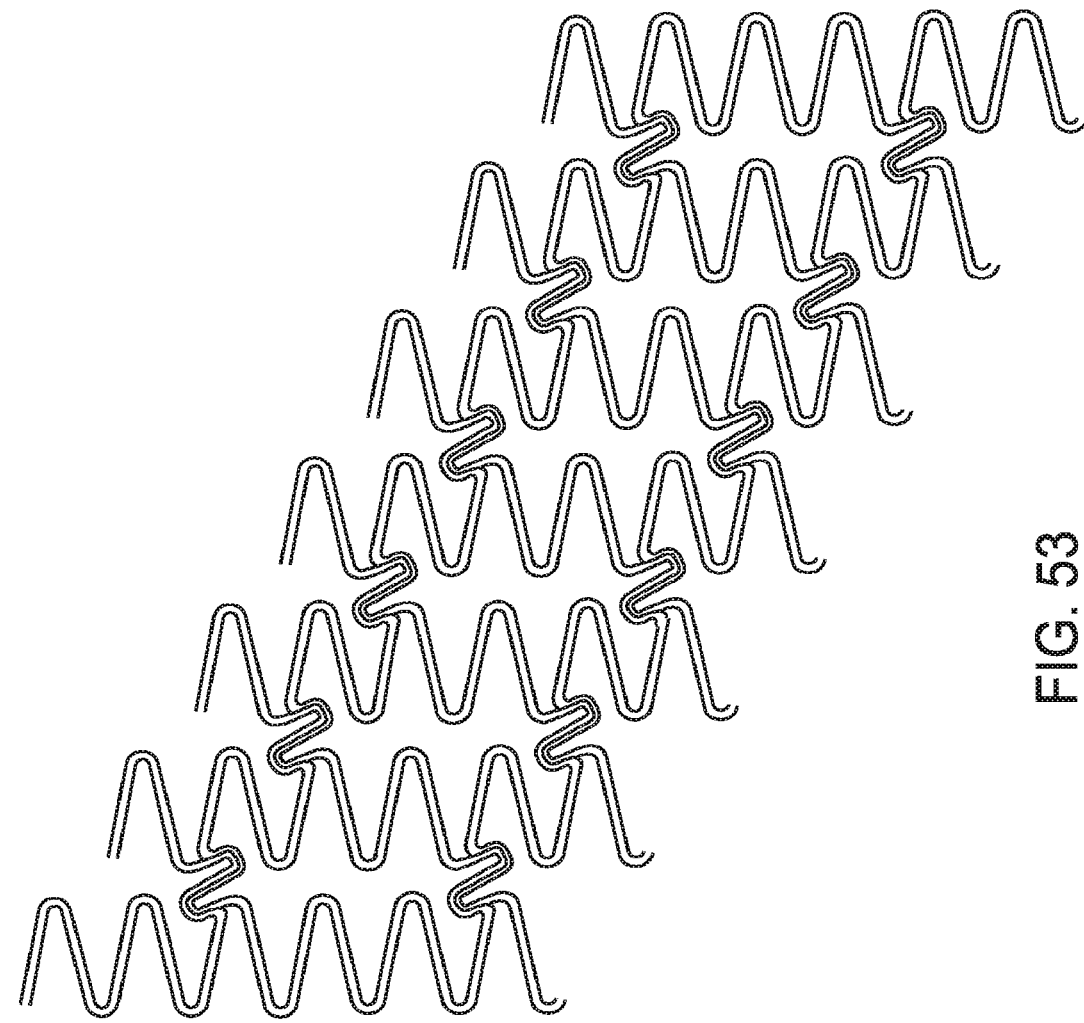
FIG. 53 illustrates a stent scaffold pattern having a pair of lines of axial links arranged helically around the stent.

FIGS. 52 and 53 illustrate further exemplary embodiments of stent scaffolds having S-shaped links arranged along a pair of axial lines (FIG. 52) or a pair of helical lines (FIG. 53). In both cases, the stents will completely separate through the separation lines in each of the circumferentially separable axial links.

Figures 54A, 54B:
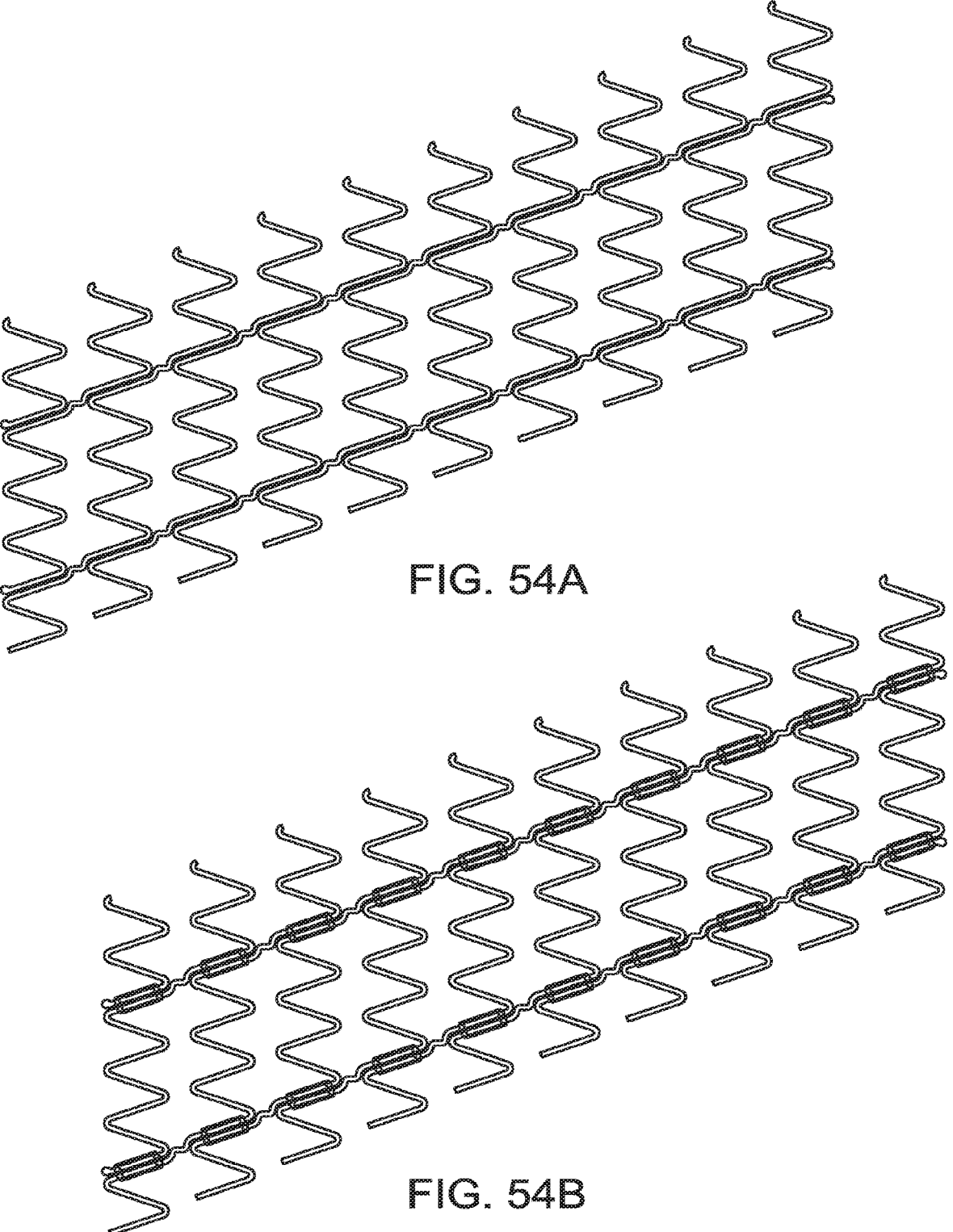
FIGS. 54A-54C illustrate alternative scaffold structures with partial ring separation.
Figure 54C:
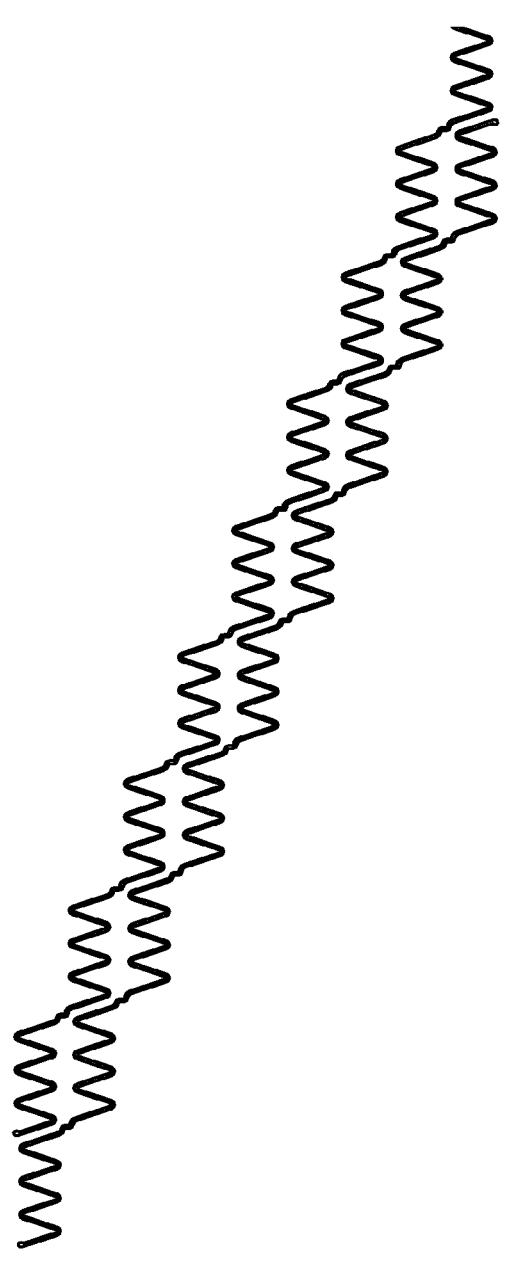

FIGS. 54A-54C illustrate alternative scaffold structures with partial ring separations. Separation lines run through struts of the stent scaffold as shown in FIG. 54A so that the stent can separate along parallel lines as shown in FIG. 54C.

Usually, the "split" struts having separation lines formed therethrough will be initially held together by biodegradable sleeves (as illustrated in FIG. 54B) or by any of the other immobilization means described herein.

Although certain embodiments or examples of the disclosure have been described in detail, variations and modifications will be apparent to those skilled in the art, including embodiments or examples that may not provide all the features and benefits described herein. It will be understood by those skilled in the art that the present disclosure extends beyond the specifically disclosed embodiments or examples to other alternative or additional examples or embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or sub-combinations of the specific features and aspects of the embodiments and examples may be made and still fall within the scope of the present disclosure. Accordingly, it should be understood that various features and aspects of the disclosed embodiments can be combined with or substituted for one another in order to form varying modes or examples of the present disclosure. Thus, it is intended that the scope of the present disclosure herein disclosed should not be limited by the particular disclosed embodiments or examples described above. For all of the embodiments and examples described above, the steps of any methods for example need not be performed sequentially.

What is claimed is:

1. An endoluminal prosthesis comprising:
a scaffold patterned from a tubular body comprising a non-degradable material formed into a plurality of circumferential rings, the scaffold being configured to expand from a crimped configuration to an expanded configuration;
wherein at least some of the plurality of circumferential rings comprise structural elements comprising struts joined by crowns, the structural elements comprising abluminal surfaces, luminal surfaces, and two side surfaces;
wherein at least some of the plurality of circumferential rings are axially joined to adjacent circumferential rings;
wherein at least some of the plurality of circumferential rings comprise at least one separation region comprising a pre-formed break in at least some circumferential rings, the preformed break providing a first segment having a first non-degradable free end on one side of the break in the circumferential ring and a second segment having a second non-degradable free end on the other side of the break in the same circumferential ring, wherein prior to expansion the second free end fits into the first free end when the scaffold is in a crimped configuration; the first and second free ends lying adjacent to each other along side surfaces of the first and second free ends when the scaffold is in its crimped configuration; and
wherein the separation region is held together during expansion in a physiologic environment and is configured to separate at the break to form at least one discontinuity in the plurality of circumferential rings after expansion of the scaffold in the physiologic environment, wherein the at least one discontinuity is configured to allow the scaffold to further expand after inward recoil from an initial expansion in a physiologic environment, and wherein the at least one discontinuity allows a movement of the first and second free ends relative to each other in an axial direction, a radial direction, a circumferential direction, or combinations thereof.

2. The endoluminal prosthesis as in claim 1, wherein the at least one separation region is joined by, covered by, or embedded in a biodegradable material comprising a polymer and/or adhesive formed as a coating, a sleeve, or a solder, the biodegradable material holding the separation region together during expansion and which biodegradable material degrades in a physiologic environment, allowing the separation region to separate after expansion.

3. The endoluminal prosthesis as in claim 2, wherein the biodegradable polymer and/or adhesive comprises polylactide, poly-L-lactide, poly-DL-lactide, polylactide-co-glycolide, poly(L-lactic-co-glycolide), poly(ethylene-co-vinyl acetate), poly(L-lactide-co-epsilon-caprolactone), poly(DL-lactide-co-glycolide), poly(lactide-co-caprolactone), poly(D-lactide), polyglycolide, polycaprolactone, polyhydroxyalkanoate, polyvinyl alcohol, polyvinyl acetate, or cyanoacrylate.

4. The endoluminal prosthesis as in claim 1, wherein all circumferential rings are axially joined by one or more axial links, and wherein at least some the circumferential rings remain axially joined after all discontinuities are formed.

5. The endoluminal prosthesis as in claim 4, wherein all axial links remain substantially intact after expansion in a physiologic environment.

6. The endoluminal prosthesis as in claim 1, wherein the first free end comprises a lock and the second free end comprises a key.

7. The endoluminal prosthesis as in claim 6, wherein the lock and key comprises male and female portions, wherein the male portion fits into a slot or channel between two arms of the female portion.

8. The endoluminal prosthesis as in claim 7, wherein the length of the male portion and the slot or channel of the female portion are longer than the width of the strut containing the male and female portions.

9. The endoluminal prosthesis as in claim 1, wherein the at least one separation region is in a strut which joins two crowns on one circumferential ring.

10. The endoluminal prosthesis of claim 1, wherein the scaffold separates into two or more axially joined segments after all discontinuities are formed.

11. The endoluminal prosthesis as in claim 10, wherein at least some of the two or more axially joined segments circumferentially separate along separation lines which extend from a first end of the scaffold to a second end of the scaffold.

12. The endoluminal prosthesis as in claim 11, wherein the separation lines have axial or spiral geometries along the length of the scaffold.

13. The endoluminal prosthesis as in claim 1, wherein the struts, crowns, and the held-together separation region of the at least some of the circumferential rings provide a continuous perimeter around the scaffold, and wherein adjacent rings are axially joined.

14. The endoluminal prosthesis as in claim 1, wherein at least some of the circumferential rings have a discontinuous perimeter with end regions which join to form a helical scaffold.

15. The endoluminal prosthesis as in claim 1, wherein the prosthesis has an open cell, closed cell, or helical backbone design.

16. The endoluminal prosthesis as in claim 1, wherein each circumferential ring has from one to five struts having a separation region.

17. The endoluminal prosthesis as in claim 1, wherein all crowns of at least some circumferential rings are free from separation regions.

18. The endoluminal prosthesis as in claim 1, wherein the struts and the crowns of at least some of the circumferential rings form a continuous circumferential path in each of the plurality of circumferential rings, and wherein the separation regions, located within at least some of the circumferential rings, form discontinuities in each of the paths after expansion in a physiologic environment providing a discontinuous circumferential path in each of the at least some circumferential rings.

19. The endoluminal prosthesis as in claim 1, wherein the prosthesis comprises at least one coating on at least one surface of the prosthesis.

20. The endoluminal prosthesis as in claim 1, wherein the prosthesis comprises at least one drug on at least one surface of the prosthesis.

21. The endoluminal prosthesis as in claim 20, wherein the at least one drug comprising an m-TOR inhibitor comprising sirolimus, novolimus, biolimus, everolimus, ridaforolimus, temsirolimus, or zotarolimus.

22. The endoluminal prosthesis as in claim 1, wherein at least two adjacent rings are connected though an axial link between a crown on one of the at least two adjacent rings and a crown on the other of the at least two adjacent rings, and wherein none of the struts connected to the crowns comprises a separation region.

23. The endoluminal prosthesis as in claim 1, wherein at least two adjacent rings are connected though an axial link between a crown on one of the two adjacent rings and a crown on the other of the at two adjacent rings, wherein at least one of the struts connected to the crowns comprises a separation region.

24. The endoluminal prosthesis as in claim 1, wherein the free ends comprise a male portion and a female portion, a ball and socket, disc and cap, interlocking combs, interlocking teeth, or wavy or undulating interlocking surfaces.

25. The endoluminal prosthesis as in claim 1, wherein the separation regions of the circumferential rings have a random pattern or are rotationally offset between circumferential rings.

26. The endoluminal prosthesis as in claim 1, wherein the non-degradable materials comprise a metal or metal alloy.

27. The endoluminal prosthesis as in claim 26, wherein the metal or metal alloy comprises stainless steel, cobalt alloy, cobalt chrome, platinum, platinum iridium, platinum chromium, platinum rhodium, or nickel titanium.

*   *   *   *   *